US011365447B2

(12) United States Patent
Jensen et al.

(10) Patent No.: US 11,365,447 B2
(45) Date of Patent: Jun. 21, 2022

(54) METHODS AND PROCESSES FOR NON-INVASIVE ASSESSMENT OF GENETIC VARIATIONS

(71) Applicant: SEQUENOM, INC., San Diego, CA (US)

(72) Inventors: Taylor Jacob Jensen, San Diego, CA (US); Jennifer Geis, San Diego, CA (US); Sung Kyun Kim, San Diego, CA (US); Cosmin Deciu, San Diego, CA (US); Mathias Ehrich, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 15/124,324

(22) PCT Filed: Mar. 12, 2015

(86) PCT No.: PCT/US2015/020250
§ 371 (c)(1),
(2) Date: Sep. 7, 2016

(87) PCT Pub. No.: WO2015/138774
PCT Pub. Date: Sep. 17, 2015

(65) Prior Publication Data
US 2017/0073756 A1    Mar. 16, 2017

Related U.S. Application Data

(60) Provisional application No. 61/952,135, filed on Mar. 13, 2014.

(51) Int. Cl.
*C12Q 1/6883* (2018.01)
*G16B 25/00* (2019.01)
*G16B 45/00* (2019.01)
*G16B 25/10* (2019.01)
*G16B 25/20* (2019.01)
*H01J 49/16* (2006.01)

(52) U.S. Cl.
CPC .......... *C12Q 1/6883* (2013.01); *G16B 25/00* (2019.02); *G16B 25/10* (2019.02); *G16B 25/20* (2019.02); *G16B 45/00* (2019.02); *C12Q 2537/143* (2013.01); *C12Q 2565/627* (2013.01); *C12Q 2600/106* (2013.01); *C12Q 2600/158* (2013.01); *C12Q 2600/16* (2013.01); *H01J 49/164* (2013.01)

(58) Field of Classification Search
None
See application file for complete search history.

(56) References Cited

U.S. PATENT DOCUMENTS

| 4,109,496 | A | 8/1978 | Allemann et al. |
| 4,179,337 | A | 12/1979 | Davis et al. |
| 4,458,066 | A | 7/1984 | Caruthers et al. |
| 4,469,863 | A | 9/1984 | Ts'o et al. |
| 4,522,811 | A | 6/1985 | Eppstein et al. |
| 4,656,127 | A | 4/1987 | Mundy |
| 4,676,980 | A | 6/1987 | Segal et al. |
| 4,683,195 | A | 7/1987 | Mullis et al. |
| 4,683,202 | A | 7/1987 | Mullis |
| 4,851,331 | A | 7/1989 | Vary et al. |
| 4,868,103 | A | 9/1989 | Stavrianopoulos et al. |
| 4,873,316 | A | 10/1989 | Meade et al. |
| 4,965,188 | A | 10/1990 | Mullis et al. |
| 5,048,530 | A | 9/1991 | Hurwitz et al. |
| 5,075,212 | A | 12/1991 | Rotbart |
| 5,118,937 | A | 6/1992 | Hillenkamp et al. |
| 5,210,015 | A | 5/1993 | Gelfand et al. |
| 5,272,071 | A | 12/1993 | Chappel |
| 5,283,317 | A | 2/1994 | Saifer et al. |
| 5,487,972 | A | 1/1996 | Gelfand et al. |
| 5,492,806 | A | 2/1996 | Drmanac et al. |
| 5,525,464 | A | 6/1996 | Drmanac et al. |
| 5,536,821 | A | 7/1996 | Agrawal et al. |
| 5,541,306 | A | 7/1996 | Agrawal et al. |
| 5,547,835 | A | 8/1996 | Koster et al. |
| 5,589,330 | A | 12/1996 | Shuber |
| 5,605,798 | A | 2/1997 | Koester et al. |
| 5,614,622 | A | 3/1997 | Iyer et al. |
| 5,631,169 | A | 5/1997 | Lakowicz et al. |
| 5,637,683 | A | 6/1997 | Usher et al. |
| 5,637,684 | A | 6/1997 | Cook et al. |
| 5,656,493 | A | 8/1997 | Mullis et al. |
| 5,679,524 | A | 10/1997 | Nikiforov et al. |
| 5,691,141 | A | 11/1997 | Koester et al. |
| 5,695,940 | A | 12/1997 | Drmanac et al. |
| 5,700,922 | A | 12/1997 | Cook |

(Continued)

FOREIGN PATENT DOCUMENTS

| AU | 2009293232 | 9/2015 |
| AU | 2010295968 | 12/2015 |
| AU | 2015252141 | 12/2015 |
| AU | 2013290102 | 2/2019 |
| AU | 2017251674 | 11/2019 |

(Continued)

OTHER PUBLICATIONS

U.S. Appl. No. 12/401,493, Final Office Action dated Jul. 19, 2011, 49 pages.

(Continued)

*Primary Examiner* — Katherine D Salmon
(74) *Attorney, Agent, or Firm* — Kilpatrick Townsend & Stockton LLP

(57) ABSTRACT

Technology provided herein relates in part to methods, processes and apparatuses for non-invasive assessment of genetic variations. In particular the invention relates to methods and kits for detecting aneuploidy of a fetal chromosome by determining the amounts of differentially methylated regions in each of chromosomes 13, 18 and 21 in circulating cell-free nucleic acid from a human pregnant female.

15 Claims, 3 Drawing Sheets
Specification includes a Sequence Listing.

(56) References Cited

U.S. PATENT DOCUMENTS

| | | |
|---|---|---|
| 5,717,083 A | 2/1998 | Cook et al. |
| 5,719,262 A | 2/1998 | Buchardt et al. |
| 5,720,928 A | 2/1998 | Schwartz |
| 5,739,308 A | 4/1998 | Kandimalla et al. |
| 5,739,314 A | 4/1998 | Roy et al. |
| 5,766,849 A | 6/1998 | McDonough et al. |
| 5,773,601 A | 6/1998 | Agrawal |
| 5,786,146 A | 7/1998 | Herman et al. |
| 5,834,189 A | 11/1998 | Stevens et al. |
| 5,849,483 A | 12/1998 | Shuber |
| 5,849,497 A | 12/1998 | Steinman |
| 5,849,542 A | 12/1998 | Reeve et al. |
| 5,849,546 A | 12/1998 | Sousa et al. |
| 5,851,770 A | 12/1998 | Babon et al. |
| 5,869,242 A | 2/1999 | Kamb et al. |
| 5,876,934 A | 3/1999 | Duthie et al. |
| 5,886,165 A | 3/1999 | Kandimalla et al. |
| 5,891,625 A | 4/1999 | Buchardt et al. |
| 5,908,755 A | 6/1999 | Kumar et al. |
| 5,912,118 A | 6/1999 | Ansorge et al. |
| 5,928,906 A | 7/1999 | Koester et al. |
| 5,929,226 A | 7/1999 | Padmapriya et al. |
| 5,952,174 A | 9/1999 | Nikiforov et al. |
| 5,955,599 A | 9/1999 | Iyer et al. |
| 5,958,692 A | 9/1999 | Cotton et al. |
| 5,962,674 A | 10/1999 | Iyer et al. |
| 5,976,802 A | 11/1999 | Ansorge et al. |
| 5,977,296 A | 11/1999 | Nielsen et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Soederlund et al. |
| 6,013,499 A | 1/2000 | Narumiya et al. |
| 6,017,702 A | 1/2000 | Lee et al. |
| 6,018,041 A | 1/2000 | Drmanac et al. |
| 6,024,925 A | 2/2000 | Little et al. |
| 6,029,041 A | 2/2000 | Takano et al. |
| 6,043,031 A | 3/2000 | Koester et al. |
| 6,045,996 A | 4/2000 | Cronin et al. |
| 6,046,005 A | 4/2000 | Ju et al. |
| 6,057,134 A | 5/2000 | Lader et al. |
| 6,057,143 A | 5/2000 | Meyer et al. |
| 6,087,095 A | 7/2000 | Rosenthal et al. |
| 6,107,037 A | 8/2000 | Sousa et al. |
| 6,110,684 A | 8/2000 | Kemper et al. |
| 6,117,992 A | 9/2000 | Iyer et al. |
| 6,136,541 A | 10/2000 | Gulati |
| 6,140,053 A | 10/2000 | Koester |
| 6,140,054 A | 10/2000 | Wittwer et al. |
| 6,140,482 A | 10/2000 | Iyer et al. |
| 6,142,681 A | 11/2000 | Gulati |
| 6,143,496 A | 11/2000 | Brown et al. |
| 6,156,501 A | 12/2000 | Mcgall et al. |
| 6,183,958 B1 | 2/2001 | Stanton et al. |
| 6,194,144 B1 | 2/2001 | Koester |
| 6,194,180 B1 | 2/2001 | Joyce et al. |
| 6,197,506 B1 | 3/2001 | Fodor et al. |
| 6,210,574 B1 | 4/2001 | Sammons et al. |
| 6,210,891 B1 | 4/2001 | Nyren et al. |
| 6,214,556 B1 | 4/2001 | Olek et al. |
| 6,214,560 B1 | 4/2001 | Yguerabide et al. |
| 6,223,127 B1 | 4/2001 | Berno et al. |
| 6,225,625 B1 | 5/2001 | Pirrung et al. |
| 6,229,911 B1 | 5/2001 | Balaban et al. |
| 6,239,273 B1 | 5/2001 | Pease et al. |
| 6,251,638 B1 | 6/2001 | Umansky et al. |
| 6,258,538 B1 | 7/2001 | Koester et al. |
| 6,258,540 B1 | 7/2001 | Lo et al. |
| 6,297,028 B1 | 10/2001 | Taniguchi et al. |
| 6,326,174 B1 | 12/2001 | Joyce et al. |
| 6,368,834 B1 | 4/2002 | Senapathy et al. |
| 6,440,706 B1 | 8/2002 | Vogelstein et al. |
| 6,468,748 B1 | 10/2002 | Monforte et al. |
| 6,610,492 B1 | 8/2003 | Stanton, Jr. et al. |
| 6,664,056 B2 | 12/2003 | Lo et al. |
| 6,723,513 B2 | 4/2004 | Lexow |
| 6,759,217 B2 | 7/2004 | Kopreski |
| 6,794,142 B2 | 9/2004 | Laird et al. |
| 6,818,394 B1 | 11/2004 | O'Donnell-Maloney et al. |
| 6,884,586 B2 | 4/2005 | Van Ness et al. |
| 6,916,634 B2 | 7/2005 | Kopreski |
| 6,927,028 B2 | 8/2005 | Dennis et al. |
| 6,929,911 B2 | 8/2005 | Oefner et al. |
| 7,081,339 B2 | 7/2006 | Slepnev et al. |
| 7,169,314 B2 | 1/2007 | Unger et al. |
| 7,244,567 B2 | 7/2007 | Chen et al. |
| 7,253,259 B2 | 8/2007 | Otagiri et al. |
| 7,285,422 B1 | 10/2007 | Little et al. |
| 7,468,249 B2 | 12/2008 | Xie et al. |
| 7,655,399 B2 | 2/2010 | Cantor et al. |
| 7,709,194 B2 | 5/2010 | Lo et al. |
| 7,709,262 B2 | 5/2010 | Cantor et al. |
| 7,754,428 B2 | 7/2010 | Lo et al. |
| 7,785,798 B2 | 8/2010 | Cantor et al. |
| 7,820,378 B2 | 10/2010 | Van Den Boom et al. |
| 7,901,884 B2 | 3/2011 | Lo et al. |
| 8,034,567 B2 | 10/2011 | Cantor et al. |
| 8,048,627 B2 | 11/2011 | Dressman et al. |
| 8,195,415 B2 | 6/2012 | Fan et al. |
| 8,206,926 B2 | 6/2012 | Ehrich et al. |
| 8,450,061 B2 | 5/2013 | Nygren |
| 8,455,221 B2 | 6/2013 | Nygren |
| 8,460,872 B2 | 6/2013 | Nygren |
| 8,476,013 B2 | 7/2013 | Ehrich et al. |
| 8,518,228 B2 | 8/2013 | Thompson et al. |
| 8,706,422 B2 | 4/2014 | Chan et al. |
| 8,962,247 B2 | 2/2015 | Ehrich et al. |
| 9,074,013 B2 | 7/2015 | Rehli |
| 9,139,874 B2 | 9/2015 | Myers et al. |
| 9,187,780 B2 | 11/2015 | Micallef et al. |
| 9,189,086 B2 | 11/2015 | McGibney et al. |
| 9,222,937 B2 | 12/2015 | Micallef |
| 9,249,464 B2 | 2/2016 | Rehli |
| 9,400,276 B2 | 7/2016 | Micallef |
| 9,709,569 B2 | 7/2017 | Micallef et al. |
| 9,926,593 B2 | 3/2018 | Ehrich et al. |
| 10,612,086 B2 | 4/2020 | Ehrich et al. |
| 10,738,358 B2 | 8/2020 | Ehrich et al. |
| 10,738,359 B2 | 8/2020 | Cantor et al. |
| 10,892,035 B2 | 1/2021 | Deciu et al. |
| 11,060,145 B2 | 7/2021 | Jensen et al. |
| 2001/0008615 A1 | 7/2001 | Little et al. |
| 2001/0051341 A1 | 12/2001 | Lo et al. |
| 2002/0006621 A1 | 1/2002 | Bianchi et al. |
| 2003/0022207 A1 | 1/2003 | Balasubramanian et al. |
| 2003/0082600 A1 | 5/2003 | Olek et al. |
| 2003/0087276 A1 | 5/2003 | Kopreski et al. |
| 2003/0096426 A1 | 5/2003 | Little et al. |
| 2003/0180748 A1 | 9/2003 | Braun et al. |
| 2003/0180779 A1 | 9/2003 | Lofton-Day et al. |
| 2003/0211483 A1 | 11/2003 | Schroeder et al. |
| 2003/0211522 A1 | 11/2003 | Landes et al. |
| 2004/0014105 A1 | 1/2004 | Schroeder et al. |
| 2004/0081993 A1 | 4/2004 | Cantor et al. |
| 2004/0115684 A1 | 6/2004 | Costa et al. |
| 2004/0137470 A1 | 7/2004 | Dhallan |
| 2004/0203037 A1 | 10/2004 | Lo et al. |
| 2005/0009059 A1 | 1/2005 | Shapero et al. |
| 2005/0019762 A1 | 1/2005 | Olek et al. |
| 2005/0037388 A1 | 2/2005 | Antonarakis et al. |
| 2005/0059003 A1 | 3/2005 | Enoki et al. |
| 2005/0064406 A1 | 3/2005 | Zabarovsky et al. |
| 2005/0064428 A1 | 3/2005 | Berlin et al. |
| 2005/0069879 A1 | 3/2005 | Berlin et al. |
| 2005/0069931 A1 | 3/2005 | Allis |
| 2005/0079521 A1 | 4/2005 | Beaulieu et al. |
| 2005/0112590 A1 | 5/2005 | Boom et al. |
| 2005/0153316 A1 | 7/2005 | Jeddeloh et al. |
| 2005/0153347 A1 | 7/2005 | Shapero et al. |
| 2005/0164241 A1 | 7/2005 | Hahn et al. |
| 2005/0266473 A1 | 12/2005 | Zhang et al. |
| 2005/0272070 A1 | 12/2005 | Ehrich et al. |
| 2005/0287592 A1 | 12/2005 | Kless et al. |
| 2006/0019278 A1 | 1/2006 | Lo et al. |

(56) References Cited

U.S. PATENT DOCUMENTS

| | | |
|---|---|---|
| 2006/0094039 A1 | 5/2006 | Rosenfeld et al. |
| 2006/0136142 A1 | 6/2006 | Berlin et al. |
| 2006/0160105 A1 | 7/2006 | Dhallan et al. |
| 2006/0166228 A1 | 7/2006 | Page et al. |
| 2006/0210992 A1 | 9/2006 | van den Boom et al. |
| 2006/0252068 A1 | 11/2006 | Lo et al. |
| 2006/0252071 A1 | 11/2006 | Lo et al. |
| 2007/0048755 A1 | 3/2007 | Di Fiore |
| 2007/0059707 A1 | 3/2007 | Cantor et al. |
| 2007/0065823 A1 | 3/2007 | Dressman et al. |
| 2007/0011123 A1 | 5/2007 | Bianchi et al. |
| 2007/0202525 A1 | 8/2007 | Quake et al. |
| 2007/0207466 A1 | 9/2007 | Cantor et al. |
| 2007/0212689 A1 | 9/2007 | Bianchi et al. |
| 2007/0243549 A1 | 10/2007 | Bischoff et al. |
| 2007/0275402 A1 | 11/2007 | Lo et al. |
| 2008/0020390 A1 | 1/2008 | Mitchell |
| 2008/0026390 A1 | 1/2008 | Stoughton et al. |
| 2008/0070792 A1 | 3/2008 | Stoughton et al. |
| 2008/0096766 A1 | 4/2008 | Lee |
| 2008/0299562 A1 | 12/2008 | Oeth et al. |
| 2008/0305479 A1 | 12/2008 | Van Den Boom et al. |
| 2009/0026082 A1 | 1/2009 | Rothberg et al. |
| 2009/0029377 A1 | 1/2009 | Lo et al. |
| 2009/0053719 A1* | 2/2009 | Lo .................. C12Q 1/6851 |
| | | 435/6.11 |
| 2009/0061425 A1 | 3/2009 | Lo et al. |
| 2009/0111712 A1 | 4/2009 | Van Den Boom et al. |
| 2009/0142755 A1 | 6/2009 | Albitar et al. |
| 2009/0202984 A1 | 8/2009 | Cantor et al. |
| 2009/0317817 A1 | 12/2009 | Oeth et al. |
| 2009/0317818 A1 | 12/2009 | Ehrich et al. |
| 2010/0105049 A1* | 4/2010 | Ehrich ............... C12Q 1/6804 |
| | | 435/6.12 |
| 2010/0184046 A1 | 7/2010 | Klass et al. |
| 2010/0203529 A1 | 8/2010 | Kuslich et al. |
| 2010/0216153 A1 | 8/2010 | Lapidus et al. |
| 2010/0227320 A1 | 9/2010 | Fu et al. |
| 2010/0240054 A1 | 9/2010 | Bischoff et al. |
| 2010/0273165 A1 | 10/2010 | Ehrich et al. |
| 2010/0279295 A1 | 11/2010 | Roy et al. |
| 2011/0033851 A1 | 2/2011 | Rand et al. |
| 2011/0039724 A1 | 2/2011 | Lo et al. |
| 2011/0105353 A1 | 5/2011 | Lo et al. |
| 2011/0151460 A1 | 6/2011 | Klass et al. |
| 2011/0177517 A1 | 7/2011 | Rava et al. |
| 2011/0178719 A1 | 7/2011 | Rabinowitz et al. |
| 2011/0201507 A1 | 8/2011 | Rava et al. |
| 2011/0212846 A1 | 9/2011 | Spier |
| 2011/0224087 A1 | 9/2011 | Quake et al. |
| 2011/0244451 A1 | 10/2011 | Cantor et al. |
| 2011/0266780 A1 | 11/2011 | Komoll et al. |
| 2011/0276277 A1 | 11/2011 | Lo et al. |
| 2011/0288780 A1 | 11/2011 | Rabinowitz et al. |
| 2012/0028613 A1 | 2/2012 | Lewis et al. |
| 2012/0065076 A1 | 3/2012 | Peters et al. |
| 2012/0184449 A1 | 7/2012 | Hixson et al. |
| 2012/0196754 A1* | 8/2012 | Quake ............... C12Q 1/6806 |
| | | 506/2 |
| 2012/0264618 A1 | 10/2012 | Nygren |
| 2012/0276542 A1 | 11/2012 | Nygren |
| 2012/0277119 A1 | 11/2012 | Ehrich et al. |
| 2012/0282613 A1 | 11/2012 | Patsalis et al. |
| 2012/0322072 A1* | 12/2012 | Nygren ............... C12Q 1/6881 |
| | | 435/6.12 |
| 2013/0012399 A1 | 1/2013 | Myers et al. |
| 2013/0022974 A1 | 1/2013 | Chinnaiyan et al. |
| 2013/0065254 A1 | 3/2013 | Lunyak |
| 2013/0085681 A1 | 4/2013 | Deciu et al. |
| 2013/0130923 A1 | 5/2013 | Ehrich et al. |
| 2013/0143211 A1 | 6/2013 | Ehrich et al. |
| 2013/0150249 A1 | 6/2013 | Ehrich et al. |
| 2013/0230858 A1 | 9/2013 | Cantor et al. |
| 2013/0237431 A1 | 9/2013 | Lo et al. |
| 2013/0295564 A1 | 11/2013 | Ehrich et al. |
| 2013/0296180 A1 | 11/2013 | Ehrich et al. |
| 2013/0310260 A1 | 11/2013 | Kim et al. |
| 2014/0093873 A1 | 4/2014 | Tynan et al. |
| 2014/0180594 A1 | 6/2014 | Kim et al. |
| 2015/0267263 A1 | 9/2015 | Rehli |
| 2015/0275304 A1 | 10/2015 | Ehrich et al. |
| 2016/0201113 A1 | 7/2016 | Rehli |
| 2017/0316150 A1 | 11/2017 | Deciu et al. |
| 2017/0321276 A1 | 11/2017 | Cantor et al. |

FOREIGN PATENT DOCUMENTS

| | | |
|---|---|---|
| CA | 2737200 | 3/2010 |
| CA | 2774342 | 1/2019 |
| EP | 0264166 A1 | 4/1988 |
| EP | 0401384 A1 | 12/1990 |
| EP | 1435394 | 7/2004 |
| EP | 1524321 | 4/2005 |
| EP | 1373561 B1 | 2/2009 |
| EP | 1524321 B1 | 7/2009 |
| EP | 2271772 | 7/2014 |
| EP | 2872648 | 5/2015 |
| EP | 2329021 | 8/2016 |
| EP | 3103871 | 12/2016 |
| EP | 2478119 | 7/2017 |
| EP | 3330382 | 6/2018 |
| EP | 2872648 | 9/2019 |
| JP | 2005-514956 A | 5/2005 |
| JP | 2006508632 | 3/2006 |
| JP | 2007-505641 A | 3/2007 |
| JP | 2007508017 | 4/2007 |
| JP | 2008-521389 A | 6/2008 |
| JP | 2008518639 | 6/2008 |
| JP | 2009-529330 A | 8/2009 |
| JP | 2010534068 | 11/2010 |
| JP | 5727375 B2 | 6/2015 |
| JP | 2015-126748 A | 7/2015 |
| JP | 5923571 B2 | 5/2016 |
| JP | 6039034 | 11/2016 |
| JP | 2017000165 | 1/2017 |
| JP | 5873434 B2 | 3/2017 |
| JP | 6447765 | 3/2018 |
| JP | 6513622 | 4/2019 |
| JP | 6513522 | 5/2019 |
| JP | 6634105 | 1/2020 |
| WO | 91/06667 A1 | 5/1991 |
| WO | 94/10300 A1 | 5/1994 |
| WO | 97/12058 A1 | 4/1997 |
| WO | 97/35589 A1 | 10/1997 |
| WO | 97/37041 A2 | 10/1997 |
| WO | 98/20020 A2 | 5/1998 |
| WO | 98/22489 A1 | 5/1998 |
| WO | 98/39352 A1 | 9/1998 |
| WO | 98/39474 A1 | 9/1998 |
| WO | 9839474 A1 | 9/1998 |
| WO | 98/54364 A1 | 12/1998 |
| WO | 99/57318 A2 | 11/1999 |
| WO | 00/41147 A1 | 7/2000 |
| WO | 0039352 | 7/2000 |
| WO | 00/52625 A2 | 9/2000 |
| WO | 00/56746 A2 | 9/2000 |
| WO | 00/66771 A2 | 11/2000 |
| WO | 00/75372 A1 | 12/2000 |
| WO | 01/14398 A1 | 3/2001 |
| WO | 01/20039 A2 | 3/2001 |
| WO | 01/25485 A2 | 4/2001 |
| WO | 01/27326 A2 | 4/2001 |
| WO | 01/27327 A2 | 4/2001 |
| WO | 01/27329 A2 | 4/2001 |
| WO | 01/29259 A2 | 4/2001 |
| WO | 02/18616 A1 | 3/2002 |
| WO | 2002/086163 A1 | 10/2002 |
| WO | 03/000919 A2 | 1/2003 |
| WO | 03/020974 A2 | 3/2003 |
| WO | 03/057909 A2 | 7/2003 |
| WO | 03/062441 A1 | 7/2003 |
| WO | 03/070894 A2 | 8/2003 |
| WO | 03074723 | 9/2003 |
| WO | 03/080863 A1 | 10/2003 |

(56) References Cited

FOREIGN PATENT DOCUMENTS

| | | |
|---|---|---|
| WO | 2004/013284 A2 | 2/2004 |
| WO | 2004/076653 A1 | 9/2004 |
| WO | 2004/078999 A1 | 9/2004 |
| WO | 2004/079011 A1 | 9/2004 |
| WO | 2005/012578 A1 | 2/2005 |
| WO | 2005/021793 A1 | 3/2005 |
| WO | 2005/023091 A2 | 3/2005 |
| WO | 2005023091 | 3/2005 |
| WO | 2005/035725 A2 | 4/2005 |
| WO | 2005/040399 A2 | 5/2005 |
| WO | 2005/098050 A2 | 10/2005 |
| WO | 2005/118852 A2 | 12/2005 |
| WO | 2006/056480 A2 | 6/2006 |
| WO | 2006/097049 A1 | 9/2006 |
| WO | 2006/097051 A1 | 9/2006 |
| WO | 2007/016668 A2 | 2/2007 |
| WO | 2007/028155 A2 | 3/2007 |
| WO | 2007/092473 A2 | 8/2007 |
| WO | 2007/100911 A2 | 9/2007 |
| WO | 2007103910 | 9/2007 |
| WO | 2007/121276 A2 | 10/2007 |
| WO | 2007/132166 A2 | 11/2007 |
| WO | 2007/132167 | 11/2007 |
| WO | 2007/132167 A2 | 11/2007 |
| WO | 2007/140417 A2 | 12/2007 |
| WO | 2007/147063 A2 | 12/2007 |
| WO | 2008/098142 A2 | 8/2008 |
| WO | 2008/103761 A2 | 8/2008 |
| WO | 2008/103763 A2 | 8/2008 |
| WO | 2008/118988 A1 | 10/2008 |
| WO | 2008/157264 A2 | 12/2008 |
| WO | 2009/030100 A1 | 3/2009 |
| WO | 2009/032779 A2 | 3/2009 |
| WO | 2009/032781 A2 | 3/2009 |
| WO | 2009/039507 A2 | 3/2009 |
| WO | 2009/046445 A1 | 4/2009 |
| WO | 2009/091934 A1 | 7/2009 |
| WO | 2009/114543 A2 | 9/2009 |
| WO | 2010/004265 A1 | 1/2010 |
| WO | 2010/033639 A2 | 3/2010 |
| WO | 2010/065470 A2 | 6/2010 |
| WO | 2010/115016 A2 | 10/2010 |
| WO | 2010/033639 A9 | 2/2011 |
| WO | 2011/018600 A1 | 2/2011 |
| WO | 2011/034631 A1 | 3/2011 |
| WO | 2011/051283 A1 | 5/2011 |
| WO | 2011054936 | 5/2011 |
| WO | 2011057094 | 5/2011 |
| WO | 2011/087760 A2 | 7/2011 |
| WO | 2011/091063 A1 | 7/2011 |
| WO | 2011/092592 A2 | 8/2011 |
| WO | 2011/142836 A2 | 11/2011 |
| WO | 2011/143659 A2 | 11/2011 |
| WO | 2011150974 | 12/2011 |
| WO | 2011/142836 A9 | 1/2012 |
| WO | 2012012703 | 1/2012 |
| WO | 2012/071621 | 6/2012 |
| WO | 2012/118745 A1 | 9/2012 |
| WO | 2012/149339 A2 | 11/2012 |
| WO | 2013/052907 | 4/2013 |
| WO | 2013/052913 A2 | 4/2013 |
| WO | 2013/055817 A1 | 4/2013 |
| WO | 2013/109981 A1 | 7/2013 |
| WO | 2013/131021 A1 | 9/2013 |
| WO | 2013/177086 A1 | 11/2013 |
| WO | 2013176958 | 11/2013 |
| WO | 2013/192562 | 12/2013 |
| WO | 2014/011928 A1 | 1/2014 |
| WO | 2014/055774 | 4/2014 |
| WO | 2014/116598 | 7/2014 |
| WO | 2014/168711 A1 | 10/2014 |
| WO | 2014/190286 | 11/2014 |
| WO | 2014/205401 | 12/2014 |
| WO | 2015/040591 | 3/2015 |
| WO | 2015/051163 | 4/2015 |
| WO | 2015/061359 A1 | 4/2015 |
| WO | 2015/138774 A1 | 9/2015 |
| WO | 2016/019042 | 2/2016 |
| WO | 2016/057901 A1 | 4/2016 |
| WO | 2016/067029 A1 | 5/2016 |
| WO | 2017045654 | 3/2017 |
| WO | 2017/068371 A1 | 4/2017 |

OTHER PUBLICATIONS

U.S. Appl. No. 12/401,493, Non-Final Office Action dated Oct. 28, 2010, 25 pages.
U.S. Appl. No. 12/401,493, Non-Final Office Action dated Mar. 18, 2013, 37 pages.
U.S. Appl. No. 12/561,241, Non-Final Office Action dated Jun. 15, 2012, 8 pages.
U.S. Appl. No. 12/727,198, Non-Final Office Action dated Apr. 12, 2013, 5 pages.
U.S. Appl. No. 12/727,198, Non-Final Office Action dated Dec. 31, 2013, 8 pages.
U.S. Appl. No. 13/457,978, Non-Final Office Action dated Sep. 17, 2012, 8 pages.
U.S. Appl. No. 13/458,036, Non-Final Office Action dated Sep. 24, 2012, 9 pages.
U.S. Appl. No. 13/458,341, Non-Final Office Action dated Sep. 17, 2012, 8 pages.
U.S. Appl. No. 13/495,975, Final Office Action dated Sep. 24, 2013, 18 pages.
U.S. Appl. No. 13/495,975, Non-Final Office Action dated Apr. 5, 2013, 20 pages.
U.S. Appl. No. 13/507,508, Notice of Abandonment dated Dec. 18, 2014, 3 pages.
U.S. Appl. No. 13/517,508, Final Office Action dated Jan. 7, 2014, 14 pages.
U.S. Appl. No. 13/517,508, Final Office Action dated Feb. 5, 2014, 15 pages.
U.S. Appl. No. 13/517,508, Non-Final Office Action dated Aug. 13, 2013, 11 pages.
U.S. Appl. No. 13/517,508, Non-Final Office Action dated Dec. 18, 2014, 7 pages.
U.S. Appl. No. 13/517,532, Final Office Action dated Sep. 20, 2013, 20 pages.
U.S. Appl. No. 13/517,532, Non-Final Office Action dated Apr. 5, 2013, 18 pages.
U.S. Appl. No. 13/518,368, Non-Final Office Action dated Jan. 30, 2015, 16 pages.
U.S. Appl. No. 13/782,857, Non-Final Office Action, dated Jun. 26, 2014, 12 pages.
U.S. Appl. No. 13/782,901, Final Office Action dated May 28, 2015, 15 pages.
U.S. Appl. No. 13/782,901, Non-Final Office Action dated Aug. 8, 2014, 13 pages.
U.S. Appl. No. 13/782,901, Non-Final Office Action dated Nov. 17, 2015, 8 pages.
U.S. Appl. No. 13/782,901, Non-Final Office Action dated May 12, 2016, 9 pages.
U.S. Appl. No. 13/791,466, Final Office Action dated Aug. 12, 2016, 10 pages.
U.S. Appl. No. 13/791,466, Final Office Action dated Aug. 3, 2015, 10 pages.
U.S. Appl. No. 13/791,466, Non-Final Office Action dated Nov. 7, 2014, 8 pages.
U.S. Appl. No. 13/801,384, Final Office Action dated Dec. 22, 2014, 9 pages.
U.S. Appl. No. 13/801,384, Non-Final Office Action dated Mar. 7, 2014, 11 pages.
U.S. Appl. No. 13/940,162, Final Office Action dated Mar. 17, 2016, 17 pages.
U.S. Appl. No. 13/940,162, Non-Final Office Action dated Aug. 20, 2015, 12 pages.
U.S. Appl. No. 14/772,544, Non-Final Office Action dated Jul. 24, 2018, 16 pages.

(56) References Cited

OTHER PUBLICATIONS

U.S. Appl. No. 14/772,544, Restriction Requirement dated Dec. 11, 2018, 6 pages.
U.S. Appl. No. 14/772,544, Restriction Requirement dated Dec. 18, 2017, 6 pages.
U.S. Appl. No. 15/443,051, Final Office Action dated Mar. 28, 2019, 12 pages.
U.S. Appl. No. 15/443,051, Non-Final Office Action dated Aug. 2, 2018, 13 pages.
Abyzov et al., CNVnator: An Approach to Discover, Genotype, and Characterize Typical and Atypical CNVs from Family and Population Genome Sequencing, Genome Research, vol. 21, No. 6, Feb. 7, 2011, pp. 974-984.
Adinolfi et al., Rapid Detection of Aneuploidies by Microsatellite and the Quantitative Fluorescent Polymerase Chain Reaction, Prenatal Diagnosis, vol. 17, No. 13, Dec. 1997, pp. 1299-1311.
Agresti, Categorical Data Analysis, Wiley-Interscience, 2nd Edition, Jan. 2002, 13 pages.
Altschul et al., Basic Local Alignment Search Tool, J Mol Biol., vol. 215, No. 3, Oct. 5, 1990, pp. 403-410.
Altschul et al., Gapped BLAST and PSI-BLAST: A New Generation of Protein Database Search Programs, Nucleic Acids Research, vol. 25, No. 17, Sep. 1, 1997, pp. 3389-3402.
Amicucci et al., Prenatal Diagnosis of Myotonic Dystrophy Using Fetal DNA Obtained from Maternal Plasma, Clinical Chemistry, vol. 46, No. 2, Feb. 2000, pp. 301-302.
Amir et al., Rett Syndrome is Caused by Mutations in X-Linked Mecp2, Encoding Methyl-Cpg-Binding Protein 2, Nature Genetics, vol. 23, No. 2, Oct. 1999, pp. 185-188.
Anantha et al., Porphyrin Binding to Quadruplexed T4G4, Biochemistry, vol. 37, No. 9, Mar. 3, 1998, pp. 2709-2714.
Anderson, Shotgun DNA Sequencing Using Closed DNASE I-Generated Fragments, Nucleic Acids Research, vol. 9, No. 13, Jul. 1981, pp. 3015-3027.
Antonarakis et al., Mitotic Errors in Somatic Cells Cause Trisomy 21 in About 4.5% Of Cases and are not Associated with Advanced Maternal Age, Nature Genetics, vol. 3, No. 2, Feb. 1993, pp. 146-150.
Antonarakis et al., The Meiotic Stage of Nondisjunction in Trisomy 21: Determination by Using DNA Polymorphisms, American Journal of Human Genetics, vol. 50, No. 3, Mar. 1992, pp. 544-550.
Aoki et al., Methylation Status of the P15 Ink4b Gene in Hematopoietic Progenitors and Peripheral Blood Cells in Myelodysplastic Syndromes, Leukemia, vol. 14, No. 4, Apr. 2000, pp. 586-593.
Armour et al., Measurement of Locus Copy Number by Hybridization with Amplifiable Probes, Nucleic Acids Research, vol. 28, No. 2, Jan. 15, 2000, pp. 605-609.
Armour et al., The Detection of Large Deletions or Duplications in Genomic DNA, Human Mutation, vol. 20, No. 5, Nov. 2002, pp. 325-337.
Asimakopoulos et al., ABL 1 Methylation is a Distinct Molecular Event Associated with Clonal Evolution of Chronic Myeloid Leukemia, Blood, vol. 94, No. 7, Oct. 1999, pp. 2452-2460.
Assis et al., Halofuginone Inhibits Phosphorylation of SMAD-2 Reducing Angiogenesis and Leukemia Burden in an Acute Promyelocytic Leukemia Mouse Model, Journal of Experimental and Clinical Cancer Research, vol. 34, No. 65, Jun. 23, 2015, pp. 1-11.
Aston et al., Optical Mapping: An Approach for Fine Mapping, Methods in Enzymology vol. 303, 1999, pp. 55-73.
Aston et al., Optical Mapping and its Potential for Large-scale Sequencing Projects, Trends in Biotechnology, vol. 17, No. 7, Jul. 1999, pp. 297-302.
Ausubel et al., Current Protocols in Molecular Biology, vol. 1, 1994, 18 pages.
Banerji et al., A Lymphocyte-Specific Cellular Enhancer is Located Downstream of the Joining Region in Immunoglobulin Heavy Chain Genes, Cell, vol. 33, No. 3, Jul. 1983, pp. 729-740.
Bartel et al., Elimination of False Positives that Arise in Using the Two-Hybrid System, BioTechniques, vol. 14, No. 6, Jun. 1993, pp. 920-924.
Batey et al., Improved Large Scale Culture of Methylophilus Methylotrophus for 13C/15N Labeling and Random Fractional Deuteration of Ribonucleotides, Nucleic Acids Research, vol. 24, No. 23, Dec. 1996, pp. 4836-4837.
Batey et al., Preparation of Isotopically Labeled Ribonucleotides for Multidimensional NMR Spectroscopy of RNA, Nucleic Acids Research, vol. 20, No. 17, Sep. 11, 1992, pp. 4515-4523.
Batzer et al., Enhanced Evolutionary PCR Using Oligonucleotides with Inosine at the 3'-Terminus, Nucleic Acids Research, vol. 19, No. 18, Sep. 1991, p. 5081.
Beaucage et al., Deoxynucleoside Phosphoramidites—A New Class of Key Intermediates for Deoxypolynucleotide Synthesis, Tetrahedron Letters, vol. 22, No. 20, Dec. 1981, pp. 1859-1862.
Beaudet, Progress Toward Noninvasive Prenatal Diagnosis, Clinical Chemistry, vol. 57, No. 6, Jun. 2011, pp. 802-804.
Benson, Tandem Repeats Finder: A Program to Analyze DNA Sequences, Nucleic Acids Research, vol. 27, No. 2, Jan. 15, 1999, pp. 573-580.
Bianchi, Fetal Cells in the Mother: from Genetic Diagnosis to Diseases Associated with Fetal Cell Microchimerism, European Journal of Obstetrics & Gynecology and Reproductive Biology, vol. 92, No. 1, Sep. 2000, pp. 103-108.
Bock et al., CpG Island Methylation in Human Lymphocytes is Highly Correlated with DNA Sequence, Repeats, and Predicted DNA Structure, PLOS Genetics, vol. 2, No. 3, e26, Mar. 2006, pp. 0243-0252.
Boguski et al., Identification of a Cytidine-Specific Ribonuclease from Chicken Liver, The Journal Biological Chemistry, vol. 255, No. 5, Mar. 10, 1980, pp. 2160-2163.
Boom et al., Rapid and Simple Method for Purification of Nucleic Acids, Journal Of Clinical Microbiology, vol. 28, No. 3, Mar. 1990, pp. 495-503.
Boom et al., Rapid Purification of Hepatitis B Virus DNA from Serum, Journal of Clinical Microbiology, vol. 29, No. 9, Sep. 1991, pp. 1804-1811.
Boyer et al., Polycomb Complexes Repress Developmental Regulators in Murine Embryonic Stem Cells, Nature, vol. 441, May 18, 2006, pp. 349-353.
Braslavsky et al., Sequence Information can be Obtained from Single DNA Molecules, PNAS, vol. 100, No. 7, Apr. 1, 2003, pp. 3960-3964.
Brizot et al., Maternal Serum HCG and Fetal Nuchal Translucency Thickness for the Prediction of Fetal Trisomies in the First Trimester of Pregnancy, British Journal of Obstetrics Gynaecology, vol. 102, No. 2, Feb. 1995, pp. 127-132.
Bullinger et al., Use of Gene-Expression Profiling to Identifying Prognostic Subclasses in Adult Acute Myeloid Leukemia, New England Journal of Medicine, vol. 350, No. 16, Apr. 15, 2004, pp. 1605-1616.
Burlingame et al., Mass Spectrometry, Analytical Chemistry, vol. 70, No. 16, Jul. 9, 1998, pp. 647-716.
Burnier et al., Cell-Derived Microparticles in Haemostasis and Vascular Medicine, Thromb Haemost, vol. 101, No. 3, Mar. 2009, pp. 439-451.
Byrne et al., Multiplex Gene Regulation: A Two-Tiered Approach to Transgene Regulation in Transgenic Mice, Proc National Academy Science USA, vol. 86, No. 14, Jul. 1989, pp. 5473-5477.
Calame et al., Transcriptional Controlling Elements in The Immunoglobulin and T Cell Receptor Loci, Advance Immunology, vol. 43, 1988, pp. 235-275.
Camper et al., Postnatal Repression of the Alpha-fetoprotein Gene is Enhancer Independent, Genes & Development, vol. 3, No. 4, Apr. 1989, pp. 537-546.
Cell Death Detection ELISA PLUS, Cat. No. 11 774 425 001, Version 11.0, Roche, Content Version: Sep. 2010, pp. 1-19.
Chan et al., CPG Island Methylation in Carcinoid and Pancreatic Endocrine Tumors, Oncogene, vol. 22, Feb. 2003, pp. 924-934.

(56) References Cited

OTHER PUBLICATIONS

Chan et al., Hypermethylated RASSFIA in Maternal Plasma: A Universal Fetal DNA Marker that Improves the Reliability of Noninvasive Prenatal Diagnosis, Clinical Chemistry, vol. 52, No. 12, Dec. 31, 2006, pp. 2211-2218.
Chan et al., Size Distributions of Maternal and Fetal DNA in Maternal Plasma, Clinical Chemistry, vol. 50, No. 1, Jan. 2004, pp. 88-92.
Chang et al., LIBSVM: A Library for Support Vector Machines, Available on internet at: https://www.csie.ntu.edu.tw/~cjlin/libsvm/, 2001, 39 pages.
Chen et al., A Method for Noninvasive Detection of Fetal Large Deletions/Duplications by Low Coverage Massively Parallel Sequencing, Prenatal Diagnosis, vol. 33, No. 6, Jun. 17, 2013, pp. 584-590.
Chen et al., Fluorescence Energy Transfer Detection as a Homogeneous DNA Diagnostic Method, Proceedings of National Academy Science USA, vol. 94, No. 20., Sep. 30, 1997, pp. 10756-10761.
Chen et al., Noninvasive Prenatal Diagnosis of Fetal Trisomy 18 and Trisomy 13 by Maternal Plasma DNA Sequencing, PLoS ONE, vol. 6, No. 7, e21791, Jul. 6, 2011, pp. 1-7.
Chen et al., Template-Directed Dye-Terminator Incorporation (TDI) Assay: A Homogeneous DNA Diagnostic Method Based on Fluorescence Energy Transfer, Nucleic Acids Research, vol. 25, No. 2, Jan. 15, 1997, pp. 347-353.
Cheson et al., Report of the National Cancer Institute-sponsored workshop on definitions of diagnosis and response in acute myeloid leukemia, J. Clinical Oncology, vol. 8, No. 5, May 1990, pp. 813-819.
Cheung et al., Rapid and Sensitive Method for Detection of Hepatitis C Virus RNA by Using Silica Particles, J. Clinical Microbiology, vol. 32, No. 10, Oct. 1994, pp. 2593-2597.
Chirgwin et al., Isolation of Biologically Active Ribonucleic Acid from Sources Enriched in Ribonuclease, Biochemistry, vol. 18, No. 24, Nov. 1979, pp. 5294-5299.
Chitty, Prenatal Screening for Chromosome Abnormalities, British Medical Bulletin, vol. 54, No. 4, 1998, pp. 839-856.
Chiu et al., Effects of Blood-Processing Protocols on Fetal and Total DNA Quantification in Maternal Plasma, Clinical Chemistry, vol. 47, No. 9, Sep. 2001, pp. 1607-1613.
Chiu et al., Prenatal Exclusion of Thalassemia Major by Examination of Maternal Plasma, Lancet, vol. 360, Sep. 28, 2002, pp. 998-1000.
Chomczynski , A Reagent for the Single-Step Simultaneous Isolation of RNA, DNA and Proteins from Cell and Tissue Samples, Biotechnology, vol. 15, No. 3, Sep. 1993, pp. 532-537.
Chomczynski et al., Single-Step Method of RNA Isolation by Acid Guanidinium Thiocyanate-Phenol-Chloroform Extraction, Analytical Biochemistry, vol. 162, No. 1, Apr. 1987, pp. 156-159.
Chomczynski et al., Substitution of Chloroform by Bromochloropropane in the Single-Step Method of RNA Isolation, Analytical Biochemistry, vol. 225, 1995, pp. 163-164.
Chow et al., Mass Spectrometric Detection of an SNP Panel as an Internal Positive Control for Fetal DNA Analysis in Maternal Plasma, Clinical Chemistry, vol. 53, No. 1, Jan. 2007, pp. 141-142.
Chu et al., A Novel Approach Toward the Challenge of Accurately Quantifying Fetal DNA in Maternal Plasma, Prenatal Diagnosis vol. 30, No. 12-13, Dec. 2010, pp. 1226-1229.
Colella et al., Sensitive and Quantitative Universal Pyrosequencing Methylation Analysis of CPG Sites, Biotechniques, vol. 35, No. 1, Jul. 2003, pp. 146-150.
Costa et al., New Strategy for Prenatal Diagnosis of X-linked Disorders, New England Journal of Medicine, vol. 346, No. 19, May 9, 2002, p. 1502.
Costello et al., Restriction Landmark Genomic Scanning (RLGS): Analysis of CpG Islands in Genomes by 2D Gel Electrophoresis, Methods in Molecular Biology, DNA Methylation: Methods and Protocols, (Tost ed.), vol. 507, 2nd eds, 2009, pp. 131-148.

Coulter, Introduction to Capillary Electrophoresis, 1991, 47 pages.
Cross et al., Purification of CpG Islands Using A Methylated DNA Biding Column, Nature Genetics, vol. 6, No. 3, 1994, pp. 236-244.
Cruikshank et al., A Lipidated Anti-Tat Antibody Enters Living Cells and Blocks HIV-1 Viral Replication, J. Acquired Immune Deficiency Syndromes and Human Retrovirology, vol. 14, No. 3, Mar. 1, 1997, pp. 193-203.
D' Alton, Prenatal Diagnostic Procedures, Semin Perinatol; vol. 18, No. 3, Jun. 1994, pp. 140-162.
Dai et al., Detection of Post-translational Modifications on Native Intact Nucleosomes by ELISA, Journal of Visualized Experiments, vol. 50, 2011, 4 pages.
Das et al., Computational Prediction of Methylation Status in Human Genomic Sequences, Proc National Academy of Science USA, vol. 103, No. 28, Jul. 11, 2006, pp. 10713-10716.
Davison, Sedimentation of Deoxyribonucleic Acid Isolated Under Low Hydrodynamic Shear, Nature, vol. 26, No. 185, Mar. 26, 1960, pp. 918-920.
Davison, The Effect of Hydrodynamic Shear on the Deoxyribonucleic Acid from T(2) and T(4) Bacteriophages, Proc National Academy of Science USA, vol. 45, No. 11, Sep. 28, 1959, pp. 1560-1568.
Dayie et al., 3D C(CC)H TOCSY Experiment for Assigning Protons and Carbons in Uniformly 13C- and Selectively 2H-Labeled RNA, J. Mag. Reson, vol. 130, 1998, pp. 97-101.
Dear, One by One: Single Molecule Tools for Genomics, Briefings in Functional Genomics and Proteomics, vol. 1, No. 4, Jan. 2003, pp. 397-416.
Deininger, Random Subcloning of Sonicated DNA: Application to Shotgun DNA Sequence Analysis, Anal. Biochem, vol. 129, No. 1, Feb. 15, 1983, pp. 216-223.
Deligezer et al., "Sequence-Specific Histone Methylation is Detectable on Circulating Nucleosomes in Plasma", Clinical Chemistry, vol. 54, No. 7, Jul. 2008, pp. 1125-1131.
Dembo, Limit Distribution of Maximal Non-Aligned Two-Sequence Segmental Score, The Annals of Probability, vol. 22, No. 4, Jan. 1, 1994, pp. 2022-2039.
Ding et al., A High-Throughput Gene Expression Analysis Technique Using Competitive PCR and Matrix-Assisted Laser Desorption Ionization Time-of-flight MS, PNAS, vol. 100, No. 6, Mar. 18, 2003, pp. 3059-3064.
Donis-Keller et al., Mapping Adenines, Guanines, and Pyrimidines in RNA, Nucleic Acids Research, vol. 4, No. 8, Aug. 1977, pp. 2527-2538.
Donis-Keller, Phy M: An RNase Activity Specific for U and A Residues Useful in RNA Sequence Analysis, Nucleic Acids Research, vol. 8, No. 14, Jul. 25, 1980, pp. 3133-3142.
Dupont et al., De Novo Quantitative Bisulfite Sequencing Using The Pyrosequencing Technology, Analytical Biochemistry, vol. 333, No. 1, Oct. 2004, pp. 119-127.
Eads et al., CPG Island Hypermethylation in Human Colorectal Tumors is not Associated with DNA Methyltransferase Overexpression, Cancer Research, vol. 59, No. 10, May 15, 1999, pp. 2302-2306.
Eckhardt et al., DNA Methylation Profiling of Human Chromosomes 6, 20 and 22, Nature Genetics, vol. 38, No. 12, Dec. 2006, pp. 1378-1385.
Eckstein, Oligonucleotides and Analogues: A Practical Approach, IRL Press, Oxford, Dec. 1991, 147 pages.
Edlund et al., Cell-Specific Expression of the Rat Insulin Gene: Evidence for Role of Two Distinct 5' Flanking Elements, Science, vol. 230, No. 4728, Nov. 22, 1985, pp. 912-916.
Egger et al., Reverse Transcription Multiplex PCR for Differentiation Between Polio-and Enteroviruses from Clinical and Environmental Samples, Journal of Clinical Microbiology, vol. 33, No. 6, Jun. 1995, pp. 1442-1447.
Ehrich et al., A New Method for Accurate Assessment of DNA Quality After Bisulfite Treatment, Nucleic Acids Research, vol. 35, No. 5, e29, Mar. 2007, pp. 1-8.
Ehrich et al., Cytosine Methylation Profiling of Cancer Cell Lines, PNAS, vol. 105, No. 12, Mar. 25, 2008, pp. 4844-4849.

(56) References Cited

OTHER PUBLICATIONS

Ehrich et al., Noninvasive Detection of Fetal Trisomy 21 by Sequencing of DNA In Maternal Blood: A Study in a Clinical Setting, Reports of Major Impact, American Journal of Obstetrics and Gynecology, vol. 204, No. 3, Mar. 2011, pp. 205.e1-205.e11.
Ehrich et al., Quantitative High-throughput Analysis of DNA Methylation Patters by Base Specific Cleavage and Mass Spectrometry, PNAS, vol. 102, No. 44, Nov. 1, 2005, pp. 15785-15790.
Eiben et al., First-Trimester Screening: An Overview, J Histochem Cytochem, vol. 53, No. 3, Mar. 2005, pp. 281-283.
Ellinger et al., "CpG Island Hypermethylation of Cell-Free Circulating Serum DNA in Patients with Testicular Cancer", The Journal of Urology, vol. 182, Issue 1, 2009, pp. 324-329.
European Application No. 09720284.0, Supplementary European Search Report dated Jul. 14, 2011, 11 pages.
European Application No. 09815148.3, Extended European Search Report dated Apr. 19, 2012, 7 pages.
European Application No. 10817598.5, Extended European Search Report dated Jan. 4, 2013, 8 pages.
European Application No. 10843520.7, Extended European Search Report dated Apr. 22, 2013, 11 pages.
European Application No. 13709696.2, Office Action dated Sep. 25, 2015, 3 pages.
European Application No. 13709696.2, Office Action dated Feb. 16, 2016, 4 pages.
European Application No. 13709696.2, Office Action dated Apr. 5, 2017, 5 pages.
European Application No. 15714069.0, Office Action dated Apr. 17, 2018, 4 pages.
European Application No. 15714069.0, Summons to Attend Oral Proceedings mailed on Feb. 26, 2019, 7 pages.
European Application No. 15753247.4, Office Action dated Oct. 17, 2018, 6 pages.
European Application No. 15785002.5, Office Action dated Oct. 10, 2018, 4 pages.
European Application No. 16173137.7, Extended European Search Report dated Nov. 14, 2016, 8 pages.
European Application No. 18174047.3, Extended European Search Report dated Aug. 13, 2018, 8 pages.
European Application No. 18174047.3, Office Action dated Jul. 5, 2019, 4 pages.
Ernani et al., Agilent's SureSelect Target Enrichment System: Bringing Cost and Process Efficiency to Next-Generation Sequencing Product Note, Agilent Technologies, Mar. 16, 2009, 8 pages.
Eva et al., Isolation of a New Human Oncogene from a Diffuse B-cell Lymphoma, Nature, vol. 316, Jul. 1985, pp. 273-275.
Fajkusova et al., Detailed Mapping of Methylcytosine Positions at the CpG Island Surrounding the Pa Promoter at the bcr-abl Locus in CML Patients and in Two Cell Lines, K562 and BV173, Blood Cells, Molecules, and Diseases, vol. 26, No. 3, Jun. 2000, pp. 193-204.
Fan et al., Analysis of the Size Distributions of Fetal and Maternal Cell-Free DNA by Paired-End Sequencing, Clinical Chemistry, vol. 56, No. 8, Aug. 1, 2010, pp. 1279-1286.
Fan et al., Molecular Counting: From Noninvasive Prenatal Diagnostics to Whole-Genome Haplotyping, Dissertation, Stanford University, Nov. 2010.
Fan et al., Noninvasive Diagnosis of Fetal Aneuploidy by Shotgun Sequencing DNA from Maternal Blood, PNAS, vol. 105, No. 42, Oct. 21, 2008, pp. 16266-16271.
Fan et al., Working Set Selection Using Second Order Information for Training Support Vector Machines, Journal of Machine Learning Research, vol. 6, 2005, pp. 1889-1918.
Feinberg, Methylation Meets Genomics, Nature Genetics, vol. 27, No. 1, Jan. 2001, pp. 9-10.
Ferguson-Smith, Placental MRNA in Maternal Plasma: Prospects for Fetal Screening, Proceedings National Academy of Sciences, vol. 100, No. 8, Apr. 15, 2003, pp. 4360-4362.

Finney et al., Molecular Cloning of PCR Products, Current Protocols in Molecular Biology, Supplement 56, Nov. 2001, pp. 15.4.1-15.4.11.
Fournie et al., Recovery of Nanogram Quantities of DNA from Plasma and Quantitative Measurement Using Labeling by Nick Translation, Analytical Biochemistry, vol. 158, Nov. 1, 1986, pp. 250-256.
Frommer et al., A Genomic Sequencing Protocol that Yields a Positive Display of 5-Methylcytosine Residues in Individual DNA Strands, Proc. National Academy Science USA, vol. 89, Mar. 1992, pp. 1827-1831.
Futreal et al., A Census of Human Cancer Genes, Nature Reviews Cancer, vol. 4, No. 3, Mar. 2004, pp. 177-183.
Gardiner-Garden et al., Cpg Islands in Vertebrate Genomes, J Mol Biol., vol. 196, No. 2, Jul. 20, 1987, pp. 261-282.
Gebhard et al., Genomewide Profiling of CpG Methylation Identifies Novel Targets of Aberrant Hypermthylation in Myeloid Leukemia, Cancer Research, vol. 66, No. 12, Jun. 15, 2006, pp. 6118-6128.
Gebhard et al., Rapid and Sensitive Detection of Cpg-Methylation Using Methyl-Binding (MB)-PCR, Nucleic Acids Research, vol. 34, No. 11, e82, Jul. 5, 2006, 9 pages.
Genbank, "*Homo sapiens* chromosome 5 clone CTC-553D6, complete sequence," GenBank Accession No. AC008575.7, Jul. 20, 2001, Available Online at: https://www.ncbi.nlm.nih.gov/nuccore/ac008575.7, Accessed from Internet on Jul. 24, 2019, 37 pages.
Genbank, "*Homo sapiens* prostaglandin-endoperoxide synthase 2 (PTGS2), RefSeqGene on chromosome 1," GenBank Accession No. NG_028206.2, Dec. 2, 2018, Available Online at https://www.ncbi.nlm.nih.gov/nuccore/ng_028206.2, Accessed from Internet on Jul. 24, 2019, 6 pages.
Giles et al., Acute Myeloid Leukemia, Hematology American Society Hematology Education Program, Jan. 1, 2002, pp. 73-110.
Go et al., 44 Single-Nucleotide Polymorphisms Expressed by Placental RNA: Assessment for Use in Noninvasive Prenatal Diagnosis of Trisomy 21, Clinical Chemistry, vol. 53, No. 12, Dec. 2007, pp. 2223-2224.
Go et al., Non-Invasive Aneuploidy Detection Using Free Fetal DNA and RNA in Maternal Plasma: Recent Progress and Future Possibilities, Human Reproduction Update, vol. 17, No. 3, May-Jun. 2011, pp. 372-382.
Goeddel, Systems for Heterologous Gene Expression, Gene Expression Technology: Methods in Enzymology, Academic Press, San Diego, CA, vol. 185, 1990, pp. 3-7.
Gonzalgo et al., Rapid Quantitation Of Methylation Differences At Specific Sites Using Methylation-Sensitive Single Nucleotide Primer Extension (Ms-SNuPE), Nucleic Acids Research, vol. 25, No. 12, Jun. 15, 1997, pp. 2529-2531.
Gottesmann, Commentary: GABA Mechanisms and Sleep, Neuroscience, vol. 111, No. 2, 2002, pp. 231-239.
Grompe et al., Scanning Detection of Mutations in Human Ornithine Transcarbamoylase by Chemical Mismatch Cleavage, Proc. National Academy Science USA, vol. 86, No. 15, Aug. 1989, pp. 5888-5892.
Grompe, The Rapid Detection of Unknown Mutations in Nucleic Acids, Nature Genetics, vol. 5, No. 2, Oct. 1993, pp. 111-117.
Grunau et al., Bisulfite Genomic Sequencing: Systematic Investigation of Critical Experimental Parameters, Nucleic Acids Research, vol. 29, No. 13, e65, Jul. 1, 2001, 7 pages.
Gupta et al., Use of Specific Endonuclease Cleavage in RNA Sequencing, Nucleic Acids Research, vol. 4, No. 6, Jun. 1977, pp. 1957-1978.
H1FOO antibody (K-14) data sheet: SC-99918, www.scbt.com/datasheet-99918-h1foo-k-14-antibody.html, Santa Cruz Biotechnology, 2007-2015.
Haase et al., Detection of Viral Nucleic Acids by in Situ Hybridization, Methods in Virology, vol. VII, 1984, pp. 189-226.
Haddow et al., Screening of Maternal Serum for Fetal Down's Syndrome in the First Trimester, The New England Journal of Medicine, vol. 338, No. 14, Apr. 2, 1998, pp. 955-961.
Hage et al., Recent Advances in Chromatographic and Electrophoretic Methods for the Study of Drug-Protein Interactions, Journal of Chromatography B: Biomedical Sciences and Applications, vol. 699, Nos. 1-2., Oct. 10, 1997, pp. 499-525.

(56) References Cited

OTHER PUBLICATIONS

Hahn et al., Cell-Free Nucleic Acids as Potential Markers for Preeclampsia, Placenta, vol. 32, Feb. 2011, pp. SI7-S20.
Hahner et al., Matrix-Assisted Laser Desorption/Ionization Mass Spectrometry (Maldi) of Endonuclease Digests of RNA, Nucleic Acids Research, vol. 25, No. 10, May 15, 1997, pp. 1957-1964.
Hames et al., Nucleic Acid Hybridization: A Practical Approach, IRL Press Limited, 1985, 16 pages.
Hanish et al., Activity of DNA Modification and Restriction Enzymes in KGB, A Potassium Glutamate Buffer, Gene Analysis Techniques, vol. 5, No. 5, Sep.-Oct. 1988, pp. 105-107.
Harris et al., Single-Molecule DNA Sequencing of a Viral Genome, Science, vol. 320, No. 5872, Apr. 4, 2008, pp. 106-109.
Hart et al., Cellular Transformation and Guanine Nucleotide Exchange Activity are Catalyzed by a Common Domain on the DBL Oncogene Product, The Journal Biological Chemistry, vol. 269, No. 1, Jan. 1994, pp. 62-65.
Hasan et al., Base-boronated Dinucleotides: Synthesis and Effect of n7-cyanoborane Substitution on the Base Protons, Nucleic Acids Research, vol. 24, No. 11, Jun. 1996, pp. 2150-2157.
Heegaard, Capillary Electrophoresis for the Study of Affinity Interactions, Journal of Molecular Recognition, vol. 11, Nos. 1-6, 1998, pp. 141-148.
Hennig et al., Synthesis of 5-Fluoropyrimidine Nucleotides as Sensitive NMR Probes of RNA Structure, Journal of the American Chemical Society, vol. 129, No. 48, Dec. 5, 2007, pp. 14911-14921.
Herman et al., Methylation-Specific PCR: A Novel Pcr Assay for Methylation Status of CPG Islands, Proceedings of the National Academy of Sciences of the United States of America, vol. 93, No. 18, Sep. 1996, pp. 9821-9826.
Hershey et al., Molceular Homogeneity of the Deoxyribonucleic Acid of Phage T2, Journal of Molecular Biology, vol. 2, 1960, pp. 143-152.
Hill, Gen-Probe Transcription-Mediated Amplification: System Principles, Gen-Probe Incorporated, San Diego, USA, Jan. 1996, 4 pages.
HiSeq 2000 Sequencing System Specification Sheet, Illumina Inc., 2010, 4 pages.
Holdenrieder, "Circulating Nucleosomes: A New Addition to the Personalized Medicine Toolkit", Personalized Medicine, vol. 11, No. 6, 2014, pp. 565-568.
Holdenrieder et al., "Circulating Nucleosomes Predict the Response to Chemotherapy in Patients with Advanced Non-Small Cell Lung Cancer", Clinical Cancer Research, vol. 10, No. 18, Sep. 15, 2004, pp. 5981-5987.
Homer et al., Residual Risk for Cytogenetic Abnormalities After Prenatal Diagnosis by Interphase Fluorescence in Situ Hybridization (Fish), Prenatal Diagnosis, vol. 23, 2003, pp. 566-571.
Hook, Prevalence of Chromosome Abnormalities During Human Gestation and Implications for Studies of Environmental Mutagens, The Lancet, vol. 2, Jul. 25, 1981, pp. 169-172.
Hromadnikova et al., Quantification of Fetal and Total Circulatory DNA in Maternal Plasma Samples Before and After Size Fractionation by Agarose Gel Electrophoresis, DNA and Cell Biology, vol. 25, No. 11, Nov. 2006, pp. 635-640.
Hu et al., Aneuploidy Detection in Single Cells Using DNA Array-Based Comparative Genomic Hybridization, Molecular Human Reproduction, vol. 10, No. 4, Apr. 2004, pp. 283-289.
Hua et al., Quantitative Methylation Analysis of Multiples Genes using Methylationsensitive Restriction Enzymebased Quantitative PCR for the Detection of Hepatocellular Carcinoma, Experimental and Molecular Pathology, vol. 91, No. 1, Aug. 2011, pp. 455-460.
Huang et al., Mechanism of Ribose 2'-Group Discrimination by an RNA Polymerase, Biochemistry, vol. 36, No. 27, Jul. 8, 1997, pp. 8231-8242.
Hulten et al., Rapid and Simple Prenatal Diagnosis of Common Chromosome Disorders: Advantages and Disadvantages of the Molecular Methods FISH and QF-PCR, Reproduction, vol. 126, No. 3, Sep. 2003, pp. 279-297.
Hunkapiller et al., A Microchemical Facility for the Analysis And Synthesis of Genes and Proteins, Nature, vol. 310, No. 5973, Jul. 12, 1984, pp. 105-111.
Hyrup et al., Peptide Nucleic Acids (PNA): Synthesis, Properties and Potential Applications, Bioorganic & Medicinal Chemistry, vol. 4, No. 1, Jan. 1996, pp. 5-23.
Imai et al., Detection of HIV-1 RNA in Heparinized Plasma of HIV-1 Seropositive Individuals, Journal of Virological Methods, vol. 36, No. 2, Feb. 1992, pp. 181-184.
Imamura et al., Prenatal Diagnosis of Adrenoleukodystrophy by Means of Mutation Analysis, Prenatal Diagnosis, vol. 16, No. 3, Mar. 1996, pp. 259-261.
Innis et al., PCR Protocols: A Guide to Methods and Applications, Academic Press, Inc., 1990, 7 pages.
Issa, CPG Island Methylator Phenotype in Cancer, Nature Reviews Cancer, vol. 4, No. 12, Dec. 2004, pp. 988-993.
Iverson et al., Detection and Isolation of Fetal Cells From Maternal Blood Using The Flourescence-activated Cell Sorter (Facs), Prenatal Diagnosis, vol. 1, No. 1, Jan. 1981, pp. 61-73.
Iwabuchi et al., Use of the Two-Hybrid System to Identify the Domain of p53 Involved in Oligomerization, Oncogene, vol. 8, No. 6, Jun. 1993, pp. 1693-1696.
Jensen et al., Detection of Microdeletion 22q11.2 In a Fetus by Next-Generation Sequencing of Maternal Plasma, Clinical Chemistry, vol. 58, No. 7, Jul. 2012, pp. 1148-1151.
Jensen et al., High-Throughput Massively Parallel Sequencing for Fetal Aneuploidy Detection from Maternal Plasma, PLOS ONE, vol. 8, No. 3, e57381, 2013, 8 pages.
Jing et al., Automated High Resolution Optical Mapping Using Arrayed, Fluid-Fixed DNA Molecules, Proceedings of the National Academy of Sciences of the USA, vol. 95, No. 14, Jul. 1998, pp. 8046-8051.
Johansen et al., An Investigation of Methods for Enriching Trophoblast from Maternal Blood, Prenatal Diagnosis, vol. 15, No. 10, Oct. 1995, pp. 921-931.
Jurinke et al., Maldi-TOF Mass Spectrometry: A Versatile Tool for High-Performance DNA Analysis, Molecular Biotechnology, vol. 26, Feb. 2004, pp. 147-163.
Kalinina et al., Nanoliter Scale PCR with TaqMan Detection, Nucleic Acids Research, Oxford University Press, Oxford, United Kingdom, vol. 25, No. 10, May 15, 1997, pp. 1999-2004.
Kaneko et al., Distinct methylated profiles in Helicobacter pylori dependent and independent gastric MALT lymphomas, Gut, vol. 52, No. 5, May 2003, pp. 641-646.
Karlin et al., Methods for Assessing The Statistical Significance of Molecular Sequence Features by Using General Scoring Schemes, Proceedings of the National Academy of Sciences of the USA, vol. 87, No. 6, Mar. 1990, pp. 2264-2268.
Kent, BLAT—The BLAST-Like Alignment Tool, Genome Research, vol. 12, No. 4, Apr. 2002, pp. 656-664.
Kessel et al., Murine Developmental Control Genes, Science, vol. 249, No. 4967, Jul. 27, 1990, pp. 374-379.
Kidd et al., Mapping and Sequencing of Structural Variation from Eight Human Genomes, Nature, vol. 453, No. 7191, May 1, 2008, pp. 56-64.
Kitzman et al., Noninvasive Whole-Genome Sequencing of a Human Fetus, Science Translational Medicine, vol. 4, No. 137, Jun. 2012, pp. 115-122.
Kriegler, Gene Transfer and Expression: A Laboratory Manual, Stockton Press, New York, NY, 1990, 6 pages.
Kristensen et al., PCR-Based Methods for Detecting Single-Locus DNA Methylation Biomarkers in Cancer Diagnostics, Prognostics, and Response to Treatment, Clinical Chemistry, vol. 55, No. 8, Aug. 1, 2009, pp. 1471-1483.
Krueger et al., Bismark: A Flexible Aligner and Methylation Caller for Bisulfite-Seq Applications, Bioinformatics, vol. 27, No. 11, Jun. 1, 2011, pp. 1571-1572.
Kuchino et al., Enzymatic RNA Sequencing, Methods in Enzymology, vol. 180, 1989, pp. 154-163.
Kuhn et al., DNA Helicases, Cold Spring Harbor Symposia Quantitative Biology, vol. 43, No. 1, 1979, pp. 63-67.

(56) References Cited

OTHER PUBLICATIONS

Kulkarni et al., Global DNA Methylation Patterns in Placenta and its Association with Maternal Hypertension in Pre-Eclampsia, DNA and Cell Biology, vol. 30, No. 2, Feb. 2011, pp. 79-84.
Kumps et al., Multiplex Amplicon Quantification (MAQ), a Fast and Efficient Method for the Simultaneous Detection of Copy Number Alterations in Neuroblastoma, BMC Genomics, vol. 11, No. 298, 2010, pp. 1-8.
Labchip, Caliper Life Sciences, Products and Contract Services, LabChip GX, http://www.caliperl.com/products/labchip-gx.htm, Retrieved from Internet on Mar. 15, 2011.
Lai et al., A Shotgun Optical Map of the Entire Plasmodium Falciparum Genome, Nature Genetics, vol. 23, No. 3, Nov. 1999, pp. 309-313.
Laird, The Power and the Promise of DNA Methylation Markers, Nature Reviews Cancer, vol. 3, No. 4, Apr. 1, 2003, pp. 253-266.
Langmead et al., Ultrafast and Memory-Efficient Alignment of Short DNA Sequences to the Human Genome, Genome Biology, vol. 10, No. 3, R25, Mar. 4, 2009, 10 pages.
Larkin et al., Clustal W and Clustal X Version 2.0, Bioinformatics, vol. 23, No. 21, Nov. 1, 2007, pp. 2947-2948.
Lee et al., Control of Developmental Regulators by Polycomb in Human Embryonic Stem Cells, Cell, vol. 125, Apr. 21, 2006, pp. 301-313.
Lee et al., Fetal Nucleic Acids in Maternal Plasma, Fetal and Maternal Medicine Review, vol. 17, No. 2, 2006, pp. 125-137.
Leung et al., An Efficient Algorithm for Identifying Matches with Errors in Multiple Long Molecular Sequences, Journal of Molecular Biology, vol. 221, No. 4, Oct. 20, 1991, pp. 1367-1378.
Li et al., Boron-Containing Oligodeoxyribonucleotide 14mer Duplexes: Enzymatic Synthesis and Melting Studies, Nucleic Acids Research, vol. 23, No. 21, Nov. 1995, pp. 4495-4501.
Li et al., Dynamic Distribution of Linker Histone H1.5 in Cellular Differentiation, PLOS Genetics, vol. 8 No. 8, e1002879., Aug. 2012, pp. 1-13.
Li et al., Genotyping Fetal Paternally Inherited SNPs by MALDI-TOF MS Using Cell-Free Fetal DNA in Maternal Plasma: Influence of Size Fractionation, Electrophoresis, vol. 27, 2006, pp. 3889-3896.
Li et al., Mapping Short DNA Sequencing Reads and Calling Variants Using Mapping Quality Scores, Genome Research, vol. 18, Nov. 2008, pp. 1851-1858.
Li et al., Size Separation of Circulatory DNA in Maternal Plasma Permits Ready Detection of Fetal DNA Polymorphisms, Clinical Chemistry, vol. 50, No. 6, Apr. 8, 2004, pp. 1002-1011.
Li et al., Targeted Mutation of the DNA Methyltransferase Gene Results in Embryonic Lethality, Cell, vol. 69, No. 6, Jun. 12, 1992, pp. 915-926.
Little et al., Mass Spectrometry from Miniaturized Arrays for Full Comparative DNA Analysis, Nature Medicine, vol. 3, No. 12, Dec. 1997, pp. 1413-1416.
Litz et al., Methylation Status of the Major Breakpoint Cluster Region in Philadelphia Chromosome Negative Leukemias, Leukemia, vol. 6, No. 1, Jan. 1992, pp. 35-41.
Liu et al., Quantification of Regional DNA Methylation by Liquid Chromatography/Tandem Mass Spectrometry, Analytical Biochemistry, vol. 391, No. 2, Aug. 15, 2009, pp. 106-113.
Liu et al., The Ribosomal Small-Subunit Protein S28 Gene from Helianthus Annuus (Asteraceae) is Down-Regulated in Response to Drought, High Salinity, and Abscisic Acid, American Journal of Botany, vol. 90, No. 4, Apr. 1, 2003, pp. 526-531.
Lo et al., Increased Fetal DNA Concentrations in the Plasma of Pregnant Women Carrying Fetuses with Trisomy 21, Clin. Chem. vol. 45, No. 10, Oct. 1999, pp. 1747-1751.
Lo et al., Maternal Plasma DNA Sequencing Reveals the Genome-Wide Genetic and Mutational Profile of the Fetus, Science Translational Medicine, vol. 2, No. 61, 61ra91, Dec. 8, 2010, pp. 1-13.
Lo et al., Plasma Placental RNA Allelic Ratio Permits Noninvasive Prenatal Chromosomal Aneuploidy Detection, Nature Medicine, vol. 13, No. 2, Feb. 2007, pp. 218-223.
Lo et al., Prenatal Diagnosis of Fetal RhD Status by Molecular Analysis of Maternal Plasma, The New England Journal of Medicine, vol. 339, No. 24, Dec. 10, 1998, pp. 1734-1738.
Lo et al., Prenatal Diagnosis: Progress Through Plasma Nucleic Acids, Nature Reviews Genetics, vol. 8, No. 1, Jan. 2007, pp. 71-77.
Lo et al., Presence of Fetal DNA in Maternal Plasma and Serum, The Lancet, vol. 350, No. 9076, Aug. 16, 1997, pp. 485-487.
Lo et al., Quantitative Abnormalities of Fetal DNA in Maternal Serum in Preeclampsia, Clinical Chemistry, vol. 45, No. 2, Feb. 1999, pp. 184-188.
Lo et al., Quantitative Analysis of Fetal DNA in Maternal Plasma ad Serum: Implications for Noninvasive Prenatal Diagnosis, Am. J. Hum. Genet., The American Society Of Human Genetics, vol. 62, No. 4, Apr. 1, 1998, pp. 768-775.
Lo et al., RAPIDR: An Analysis Package for Non-Invasive Prenatal Testing of Aneuploidy, Bioinformatics, vol. 30, No. 20, Jul. 1, 2014, pp. 2965-2967.
Lo, Recent Advances in Fetal Nucleic Acids in Maternal Plasma, The Journal of Histochemistry & Cytochemistry, vol. 53, No. 3, Mar. 2005, pp. 293-296.
Lun et al., Microfluidics Digital PCR Reveals a Higher than Expected Fraction of Fetal DNA in Maternal Plasma, Clinical Chemistry, vol. 54, No. 10, Oct. 2008, pp. 1664-1672.
Lun et al., Noninvasive Prenatal Diagnosis of Monogenic Diseases by Digital Size Selection and Relative Mutation Dosage on DNA in Maternal Plasma, PNAS, vol. 105, No. 50, Dec. 16, 2008, pp. 19920-19925.
Madura et al., N-Recognin/Ubc2 Interactions in the N-End Rule Pathway, The Journal of Biological Chemistry, vol. 268, No. 16, Jun. 5, 1993, pp. 12046-12054.
Majlessi et al., Advantages of 2'-O-Methyl Oligoribonucleotide Probes for Detecting RNA Targets, Nucleic Acids Research, vol. 26, No. 9, May 1, 1998, pp. 2224-2229.
Malik et al., Polyethylene Glycol (PEG)-modified Granulocyte-Macrophage Colony-Stimulating Factor (GM-CSF) with Conserved Biological Activity, Experimental Hematology, vol. 20, No. 8, Sep. 1992, pp. 1028-1035.
Mann et al., Development and Implementation of a New Rapid Aneuploidy Diagnostic Service Within the UK National Health Service and Implications for the Future of Prenatal Diagnosis, The Lancet, vol. 358, No. 9287, Sep. 29, 2001, pp. 1057-1061.
Mann, Prenatal Detection of Chromosome Aneuploidy by Quantitative Fluorescence-PCR, Methods in Molecular Medicine, vol. 92, 2004, pp. 141-156.
Mao et al., Assignment of the L30-mRNA Complex Using Selective Isotopic Labeling and RNA Mutants, Nucleic Acids Research, vol. 27, No. 20, 1999, pp. 4059-4070.
Marais et al., Differential Regulation of Raf-1, A-Raf, and B-Raf by Oncogenic Ras and Tyrosine Kinases, The Journal of Biological Chemistry, vol. 272, No. 7, Feb. 14, 1997, pp. 4378-4383.
Marais et al., Ras Recruits Raf-1 to the Plasma Membrane for Activation by Tyrosine Phosphorylation, The EMBO Journal, vol. 14, No. 13, Jul. 3, 1995, pp. 3136-3145.
Margulies et al., Genome Sequencing in Microfabricated High-density Picolitre Reactors, Nature, vol. 437, No. 7057, Sep. 15, 2005, pp. 376-380.
Mason et al., Serine and Tyrosine Phosphorylations Cooperate in Raf-1, but not B-Raf Activation, The EMBO Journal, vol. 18, No. 8, Apr. 15, 1999, pp. 2137-2148.
McClelland et al., KGB: A Single Buffer for All Restriction Endonucleases, Nucleic Acids Research, vol. 16, No. 1, Jan. 1988, p. 364.
McConnell et al., The Cytosensor Microphysiometer: Biological Applications of Silicon Technology, Science, vol. 257, No. 5078, Sep. 25, 1992, pp. 1906-1912.
Metzker, Sequencing Technologies—the Next Generation, Nature Review, vol. 11, No. 1, Jan. 2010, pp. 31-46.
Meyers et al., Optimal Alignments in Linear Space, CABIOS, vol. 4, No. 1, Mar. 1, 1988, pp. 11-17.
Miller et al., ReadDepth: A Parallel R Package for Detecting Copy Number Alterations from Short Sequencing Reads, PLoS ONE, vol. 6, No. 1, e16327, Jan. 31, 2011, pp. 1-7.

(56) References Cited

OTHER PUBLICATIONS

Millipore, QIA25 Nucleosome ELISA Kit, Information Brochure, Calbiochem, Feb. 26, 2013, 2 pages.
Mito et al., Genome-Scale Profiling of Histone H3.3 Replacement Patterns, Nature Genetics, vol. 37, No. 10, Oct. 2005, pp. 1090-1097.
Moudrianakis et al., Base Sequence Determination in Nucleic Acids with the Electron Microscope, III. Chemistry and Microscopy of Guanine-Labeled DNA, Proc. N. A. S., vol. 53, No. 3, Mar. 1965, pp. 564-571.
Mouliere et al., High Fragmentation Characterizes Tumour-Derived Circulating DNA, PLoS ONE, vol. 6, No. 9, e23418, Sep. 6, 2011, pp. 1-10.
Nakamaye et al., Direct Sequencing of Polymerase Chain Reaction Amplified DNA Fragments Through the Incorporation of Deoxynucleoside Alpha-Thiotriphosphates, Nucleic Acids Research, vol. 16, No. 21, Nov. 11, 1988, pp. 9947-9959.
Nakano et al., Single-Molecule PCR Using Water-in-Oil Emulsion, Journal of Biotechnology, vol. 102, No. 2, Apr. 24, 2003, pp. 117-124.
NCBI dbSNP Cluster Report Record for rs16139, Available online at: https://www.ncbi.nlm.nih.gov/projects/SNP/snp_ref.cgi?rs=16139, Sep. 16, 2013, 4 pages.
Needham-Vandevanter et al., Characterization of an Adduct Between CC-1065 and a Defined Oligodeoxynucleotide Duplex, Nucleic Acids Research, vol. 12, No. 15, Aug. 10, 1984, pp. 6159-6168.
Needleman et al., A General Method Applicable to the Search for Similarities in the Amino Acid Sequence of Two Proteins, Journal of Molecular Biology, vol. 48, No. 3, Mar. 1970, pp. 443-453.
Ng et al., "MRNA of Placental Origin is Readily Detectible in Maternal Plasma", PNAS, vol. 100, No. 8, 2003, pp. 4748-4753.
Ng et al., Presence of Filterable and Nonfilterable mRNA in the Plasma of Cancer Patients and Healthy Individuals, Clinical Chemistry, vol. 48, No. 8, Aug. 1, 2002, pp. 1212-1217.
Nicolaides et al., Increased Fetal Nuchal Translucency at 11-14 Weeks, Prenatal Diagnosis, vol. 22, No. 4, Apr. 2002, pp. 308-315.
Nicolaides et al., One-Stop Clinic for Assessment of Risk of Chromosomal Defects at 12 Weeks of Gestation, The Journal of Maternal-Fetal and Neonatal Medicine, vol. 12, No. 1, Jul. 2002, pp. 9-18.
Nicolaidis et al., Origin and Mechanisms of Non-disjunction in Human Autosomal Trisomies, Human Reproduction, vol. 13, No. 2, Feb. 1, 1998, pp. 313-319.
Nishizuka et al., Proteomic Profiling of the NCI-60 Cancer Cell Lines Using New High-Density Reverse-Phase Lysate Microarrays, PNAS, vol. 100, No. 24, Nov. 25, 2003, pp. 14229-14234.
Nolte, Branched DNA Signal Amplification for Direct Quantitation of Nucleic Acid Sequences in Clinical Specimens, Advances in Clinical Chemistry, vol. 33, 1998, pp. 201-235.
Nosaka et al., Increasing Methylation of the CDKN2A Gene is Associated with the Progression of Adult T-Cell Leukemia, Cancer Research, vol. 60, No. 4, Feb. 15, 2000, pp. 1043-1048.
Nygren et al., Quantification of Fetal DNA by Use of Methylation-Based DNA Discrimination, Clinical Chemistry vol. 56, No. 10, Oct. 2010, pp. 1627-1635.
Oefner et al., Efficient Random Subcloning of DNA Sheared in a Recirculating Point-Sink Flow System, Nucleic Acids Res. vol. 24, No. 20, Oct. 15, 1996, pp. 3879-3886.
Oeth et al., iPLEX™ Assay: Increased Plexing Efficiency and Flexibility for Massarray® System through Single Base Primer Extension with Mass-Modified Terminators, Sequenom Application Note, Apr. 28, 2005, 12 pages.
Oeth et al., Qualitative and Quantitative Genotyping Using Single Base Primer Extension Coupled with Matrix-assisted Laser Desorption/Ionization Time-of-Flight Mass Spectrometry (Massarray), Methods in Molecular Biology, vol. 578, 2009, pp. 307-343.
Ohm et al., A Stem Cell-Like Chromatin Pattern May Predispose Tumor Suppressor Genes to DNA Hypermethylation And Heritable Silencing, Nature Genetics, vol. 39, No. 2, Feb. 2007, pp. 237-242.
Ohtsuka et al., An Alternative Approach to Deoxyoligonucleotides as Hybridization Probes by Insertion of Deoxyinosine at Ambiguous Codon Positions, The Journal of Biological Chemistry, vol. 260, No. 5, Mar. 10, 1985, pp. 2605-2608.
Okano et al., DNA Methyltransferases Dumt3a and Dumt3b are Essential for De Novo Methylation and Mammalian Development, Cell, vol. 99, No. 3, Oct. 29, 1999, pp. 247-257.
Old et al., Candidate Epigenetic Biomarkers for Non-invasive Prenatal Diagnosis of Down Syndrome, Reproductive BioMedicine Online, vol. 15, No. 2, Aug. 2007, pp. 227-235.
Olek et al., A Modified and Improved Method for Bisulphite Based Cytosine Methylation Analysis, Nucleic Acids Research, vol. 24, No. 24, Dec. 15, 1996, pp. 5064-5066.
Orita et al., Detection of Polymorphisms of Human DNA by Gel Electrophoresis as Singlestrand Conformation Polymorphisms, Proceedings of the National Academy of Sciences USA, vol. 86, Apr. 1989, pp. 2766-2770.
Osborne et al., Aptamers as Therapeutic and Diagnostic Reagents: Problems and Prospects, Current Opinion in Chemical Biology, vol. 1, No. 1, Jun. 1997, pp. 5-9.
Oudejans et al., Circulating Trophoblast in Maternal Blood, Prenatal Diagnosis, vol. 23, Issue 2, Jan. 15, 2003, pp. 111-116.
Padilla et al., Efficient Synthesis of Nucleic Acids Heavily Modified with Non-Canonical Ribose 2'-Groups Using a Mutant T7 RNA Polymerase (RNAP), Nucleic Acids Research, vol. 27, No. 6, Mar. 15, 1999, pp. 1561-1563.
Palomaki et al., DNA Sequencing of Maternal Plasma to Detect Down Syndrome: An International Clinical Validation Study, Genetics in Medicine, vol. 13, No. 11, Nov. 2011, pp. 913-920.
Palomaki et al., Maternal Serum Screening for Down Syndrome in the United States: A 1995 Survey, American Journal of Obstetrics & Gynecology, vol. 176, No. 5, May 1997, pp. 1046-1051.
Pandya et al., Screening for Fetal Trisomies by Maternal Age and Fetal Nuchal Translucency Thickness at 10 To 14 Weeks of Gestation, British Journal of Obstetrics and Gynaecology, vol. 102, No. 12, Dec. 1995, pp. 957-962.
Papageorgiou et al., Fetal-Specific DNA Methylation Ratio Permits Noninvasive Prenatal Diagnosis of Trisomy 21, Nature Medicine, vol. 17, No. 4, 2011, pp. 510-513.
Papageorgiou et al., Sites of Differential DNA Methylation Between Placenta and Peripheral Blood: Molecular Markers for Noninvasive Prenatal Diagnosis of Aneuploidies, The American Journal of Pathology, vol. 174, No. 5, 2009, pp. 1609-1618.
Patel, Structural Analysis of Nucleic Acid Aptamers, Current Opinion in Chemical Biology, vol. 1, No. 1, Jun. 1997, pp. 32-46.
Paulin et al., Urea Improves Efficiency of Bisulphite-Mediated Sequencing of 5'-Methylcytosine in Genomic DNA, Nucleic Acids Research, vol. 26, No. 21, Nov. 1, 1998, pp. 5009-5010.
International Application No. PCT/US2008/066791, International Preliminary Report on Patentability dated Dec. 30, 2009, 5 pages.
International Application No. PCT/US2008/066791, International Search Report and Written Opinion dated Dec. 22, 2008, 8 pages.
International Application No. PCT/US2008/054468, International Preliminary Report on Patentability dated Sep. 3, 2009, 7 pages.
International Application No. PCT/US2008/054468, International Search Report and Written Opinion dated Sep. 23, 2008, 9 pages.
International Application No. PCT/US2008/054470, International Preliminary Report on Patentability dated Feb. 18, 2010, 6 pages.
International Application No. PCT/US2008/054470, International Search Report and Written Opinion dated Aug. 18, 2008, 9 pages.
International Application No. PCT/US2009/036683, International Preliminary Report on Patentability dated Sep. 23, 2010, 9 pages.
International Application No. PCT/US2009/036683, International Search Report and Written Opinion dated Feb. 24, 2010, 14 pages.
International Application No. PCT/US2009/036683, Invitation to Pay Additional Fees and Partial International Search Report dated Dec. 28, 2009, 4 pages.
International Application No. PCT/US2009/057215, International Preliminary Report on Patentability dated Mar. 31, 2011, 6 pages.
International Application No. PCT/US2009/057215, International Search Report and Written Opinion dated Dec. 29, 2010, 6 pages.
International Application No. PCT/US2010/027879, International Preliminary Report on Patentability dated Mar. 29, 2012, 6 pages.

(56) References Cited

OTHER PUBLICATIONS

International Application No. PCT/US2010/027879, International Search Report and Written Opinion dated Dec. 30, 2010, 12 pages.
International Application No. PCT/US2010/061319, International Preliminary Report on Patentability dated Jul. 5, 2012, 8 pages.
International Application No. PCT/US2010/061319, International Search Report and Written Opinion dated Sep. 21, 2011, 14 pages.
International Application No. PCT/US2012/035479, International Preliminary Report on Patentability dated Nov. 7, 2013, 24 pages.
International Application No. PCT/US2012/035479, International Search Report and Written Opinion dated Jan. 10, 2012, 20 pages.
International Application No. PCT/US2013/028699, International Preliminary Report on Patentability dated Sep. 12, 2014, 8 pages.
International Application No. PCT/US2013/028699, International Search Report and Written Opinion dated Jul. 1, 2013, 7 pages.
International Application No. PCT/US2013/041354, International Search Report and Written Opinion dated Aug. 14, 2013, 16 pages.
International Application No. PCT/US2013/041906, International Preliminary Report on Patentability dated Dec. 4, 2014, 16 pages.
International Application No. PCT/US2013/041906, International Search Report and Written Opinion dated Jul. 16, 2013, 12 pages.
International Application No. PCT/US2013/050145, International Preliminary Report on Patentability dated Jan. 22, 2015, 12 pages.
International Application No. PCT/US2013/050145, International Search Report and Written Opinion dated Oct. 23, 2013, 10 pages.
International Application No. PCT/US2014/025132, International Preliminary Report on Patentability dated Sep. 24, 2015, 16 pages.
International Application No. PCT/US2014/025132, International Search Report and Written Opinion dated Jul. 30, 2014, 16 pages.
International Application No. PCT/US2015/020250, International Search Report and Written Opinion dated May 28, 2015, 12 pages.
International Application No. PCT/US2015/020250, International Preliminary Report on Patentability dated Sep. 22, 2016, 8 pages.
International Application No. PCT/US2015/054903, International Preliminary Report on Patentability dated Apr. 20, 2017, 15 pages.
International Application No. PCT/US2015/054903, International Search Report and Written Opinion dated Mar. 30, 2016, 21 pages.
Pearson et al., High-Performance Anion-Exchange Chromatography Of Oligonucleotides, Journal of Chromatography, vol. 255, Jan. 21, 1983, pp. 137-149.
Pearson et al., Improved Tools for Biological Sequence Comparison, Proc. Natl. Acad. Sci. USA, vol. 85, No. 8, Apr. 1988, pp. 2444-2448.
Perry-O'Keefe et al., Peptide Nucleic Acid Pre-gel Hybridization: An Alternative to Southern Hybridization, Proceedings of the National Academy of Sciences of the USA, vol. 93, No. 25, Dec. 10, 1996, pp. 14670-14675.
Pertl et al., Rapid Molecular Method for Prenatal Detection of Down's Syndrome, Lancet, vol. 343, No. 8907, May 14, 1994, pp. 1197-1198.
Peters et al., Noninvasive Prenatal Diagnosis of a Fetal Microdeletion Syndrome, New England Journal of Medicine, vol. 365, No. 19, Nov. 10, 2011, pp. 1847-1848.
Petersen et al., Nondisjunction in Trisomy 21: Origin and Mechanisms, Cytogenetics and Cell Genetics, vol. 91, No. 1-4, 2000, pp. 199-203.
Pinkert et al., An Albumin Enhancer Located 10kb Upstream Functions Along with its Promoter to Direct Efficient, Liver-Specific Expression in Transgenic Mice, Genes & Development, vol. 1, Mar. 4, 1987, pp. 268-277.
Poon et al., Differential DNA Methylation between Fetus ad Mother as a Strategy for Detecting Fetal DNA in Maternal Plasma, Clinical Chemistry, vol. 48, No. 1, Jan. 1, 2002, pp. 35-41.
Poon et al., Presence of Fetal RNA in Maternal Plasma, Clinical Chemistry, vol. 46, No. 11, Nov. 2000, pp. 1832-1834.
Porter et al., N7-Cyanoborane-2'-Deoxyguanosine 5'-Triphosphate is a Good Substrate for DNA Polymerase, Biochemistry, vol. 34, No. 37, Sep. 19, 1995, pp. 11963-11969.
Qu et al., Analysis of Drug-DNA Binding Data, Methods in Enzymology, vol. 321, 2000, pp. 353-369.
Queen et al., Immunoglobulin Gene Transcription is Activated by Downstream Sequence Elements, Cell, vol. 33, No. 3, Jul. 1983, pp. 741-748.
Radding, Homologous Pairing and Strand Exchange in Genetic Recombination, Annual Review of Genetics, vol. 16, 1982, pp. 405-437.
Randen et al., Prenatal Genotyping of RHD and SRY Using Maternal Blood, Vox Sanguinis, vol. 85, No. 4, Nov. 2003, pp. 300-306.
Rashtchian, Amplification of RNA, PCR Methods and Applications, vol. 4, 1994, pp. S83-S91.
Rivas et al., New Developments in the Study of Biomolecular Associations Via Sedimentation Equilibrium, Trends in Biochemical Sciences, vol. 18, No. 8, Aug. 1993, pp. 284-287.
Roach et al., Association Between the Abnormal Expression of Matrix-Degrading Enzymes by Human Osteoarthritic Chondrocytes and Demethylation of Specific CpG Sites in the Promoter Regions, Arthritis & Rheumatism, vol. 52, No. 10, Oct. 2005, pp. 3110-3124.
Robertson et al., DNA Methylation in Health and Disease, Nature Reviews Genetics, vol. 1, 2000, pp. 11-19.
Robinson et al., A Comparison of Affymetrix Gene Expression Arrays, BMC Bioinformatics, vol. 8, No. 449, Nov. 15, 2007, 16 pages.
Rojo et al., Cusativin, a New Cytidine-Specific Ribonuclease Accumulated in Seeds of Cucumis Sativus L., Planta, vol. 194, No. 3, 1994, pp. 328-338.
Rollins et al., Large-Scale Structure of Genomic Methylation Patterns, Genome Research, vol. 16, No. 2, Feb. 2006, pp. 157-163.
Romero et al., Diagnostic Molecular Biology: Principles and Applications, Mayo Foundation, Rochester, Minn., 1993, pp. 401-406.
Roschke et al., Karyotypic complexity of the NCI-60 drug-screening panel, Cancer Research, vol. 63, No. 24, Dec. 15, 2003, pp. 8634-8647.
Rosenkranz et al., Physicochemical Effects of High-Speed Mixing on Deoxyribonucleic Acid, Journal of the American Chemical Society, vol. 82, No. 12, Jun. 1960, pp. 3198-3201.
Rossolini et al., Use of Deoxyinosine-Containing Primers Vs Degenerate Primers for Polymerase Chain Reaction Based on Ambiguous Sequence Information, Molecular and Cellular Probes, vol. 8, No. 2, Apr. 1994, pp. 91-98.
Sadri et al., Rapid Analysis of DNA Methylation Using New Restriction Enzyme Sites Created by Bisulfite Modification, Nucleic Acids Research, vol. 24, No. 24, Nov. 6, 1996, pp. 5058-5059.
Saito et al., Prenatal DNA Diagnosis of a Single-Gene Disorder from Maternal Plasma, The Lancet, vol. 356, No. 9236, Sep. 30, 2000, pp. 1170.
Salgame et al., An ELISA for Detection of Apoptosis, Nucleic Acids Research, vol. 25, No. 3, 1997, pp. 680-681.
Sambrook et al., Molecular Cloning: A Laboratory Manual, Cold Spring Harbor, vol. 1, 3rd Edition, 2001, 20 pages.
Sanchez et al., Effects of Sulpiride on Prolactin and mRNA Levels of Steroid 5α-Reductase Isozymes in Adult Rat Brain, Neurochemical Research, vol. 33, No. 5, Oct. 17, 2007, pp. 820-825.
Sancho et al., "Depletion of Human Histone H1 Variants Uncovers Specific Roles in Gene Expression and Cell Growth", PLoS Genetics, vol. 4, No. 10, e1000227, Oct. 17, 2008, 17 pages.
Santoro et al., A General Purpose RNA-Cleaving DNA Enzyme, Proc. Natl. Acad. Sci. USA, vol. 94, Apr. 29, 1997, pp. 4262-4266.
Sargent et al., "Isolation of Differentially Expressed Genes", Methods in Enzymology, vol. 152, 1988, pp. 423-432.
Sayres et al., "Cell-Free Fetal Nucleic Acid Testing: A Review of the Technology and Its Applications", Obstetrical and Gynecological Survey, vol. 66, No. 7, Jul. 2011, pp. 431-442.
Schlesinger et al., Polycomb-Mediated Methylation on Lys27 of Histone H3 Pre-marks Genes for De Novo Methylation in Cancer, Nature Genetics, vol. 39, No. 2, Feb. 2007, pp. 232-236.
Schouten et al., Relative Quantification of 40 Nucleic Acid Sequences by Multiplex Ligation-dependent Probe Amplification, Nucleic Acids Research, vol. 30, No. 12, e57, Jun. 15, 2002, 13 pages.
Schriefer et al., Low Pressure DNA Shearing: A Method for Random DNA Sequence Analysis, Nucleic Acids Research, vol. 18, No. 24, Dec. 25, 1990, pp. 7455-7456.

(56) References Cited

OTHER PUBLICATIONS

Schroeder, The Human Placenta Methylome, PNAS, vol. 110, No. 15, 2013, pp. 6037-6042.
Schuler, Sequence Mapping by Electronic PCR, Genome Research, vol. 7, No. 5, May 1997, pp. 541-550.
Scott et al., Enzymatic Synthesis and 19F NMR Studies of 2-Fluoroadenine-Substituted RNA, Journal of the American Chemical Society, vol. 126, No. 38, Sep. 29, 2004, pp. 11776-11777.
Sekizawa et al., Cell-free Fetal DNA is Increased in Plasma of Women with Hyperemesis Gravidarum, Clinical Chemistry, vol. 47, No. 12, Dec. 2001, pp. 2164-2165.
Sharma et al., Mass Spectrometric Based Analysis, Characterization and Applications of Circulating Cell free DNA Isolated from Human Body Fluids, International Journal of Mass Spectrometry, vol. 304, Jul. 2011, pp. 172-183.
Sheffield et al., Identification of Novel Rhodopsin Mutations Associated with Retinitis Pigmentosa by GC-Clamped Denaturing Gradient Gel Electrophoresis, American Journal of Human Genetics, vol. 49, No. 4, Oct. 1991, pp. 699-706.
Silverman et al., Methylation Inhibitor Therapy in the Treatment of Myelodysplastic Syndrome, Nature Clinical Practice Oncology, vol. 2, Supplement 1, Dec. 1, 2005, pp. S12-S23.
Simoncsits et al., New Rapid Gel Sequencing Method for RNA, Nature, vol. 269, No. 5631, Oct. 27, 1977, pp. 833-836.
Singer et al., Optimization of in Situ Hybridization Using Isotopic and Non-Isotopic Detection Methods, BioTechniques, vol. 4, No. 3, 1986, pp. 230-250.
Sjolander et al., Integrated Fluid Handling System for Biomolecular Interaction Analysis, Analytical Chemistry, vol. 63, No. 20, Oct. 1991, pp. 2338-2345.
Slater et al., Rapid, High Throughput Prenatal Detection of Aneuploidy using a Novel Quantitative Method (MLPA), Journal Medical Genetics, vol. 40, No. 12, Dec. 2003, pp. 907-912.
Smith et al., Identification of common molecular subsequences, Journal of Molecular Biology, vol. 147, No. 1, Mar. 25, 1981, pp. 195-197.
Smith et al., Single-Step Purification of Polypeptides Expressed in *Escherichia coli* as Fusions with Glutathione S-Transferase, Genetics, vol. 67, No. 1, Jul. 15, 1988, pp. 31-40.
Snijders et al., Assembly of Microarrays for Genome-Wide Measurement of DNA Copy Number, Nature Genetics, vol. 29, No. 3, Nov. 2001, pp. 263-264.
Snijders et al., First-Trimester Ultrasound Screening for Chromosomal Defects, Ultrasound in Obstetrics & Gynecology, vol. 7, No. 3, Mar. 1996, pp. 216-226.
Snijders et al., UK Multicentre Project on Assessment of Risk of Trisomy 21 by Maternal Age and Fetal Nuchal-translucency Thickness at 10-14 Weeks of Gestation, The Lancet, vol. 352, No. 9125, Aug. 1, 1998, pp. 343-346.
Soni et al., Progress toward Ultrafast DNA Sequencing Using Solid-State Nanopores, Clinical Chemistry, vol. 53, No. 11, Nov. 2007, pp. 1996-2001.
Sousa et al., A Mutant T7 RNA Polymerase as a DNA Polymerase, The Embo Journal, vol. 14, No. 18, Sep. 15, 1995, pp. 4609-4621.
Spetzler et al., Enriching for Rare Subpopulations of Circulating Microvesicles by the Depletion of Endothelial-and Leukocyte-Derived Microvesicles, CARIS Life Sciences, Carisome Posters, Papers, Abstracts and Presentations, American Academy of Cancer Research (AACR2011)., 2011, 1 Page.
Srinivasan et al., Noninvasive Detection of Fetal Subchromosome Abnormalities Via Deep Sequencing of Maternal Plasma, The American Journal of Human Genetics, vol. 92, Feb. 7, 2013, pp. 167-176.
Stanssens et al., High-Throughput MALDI-TOF Discovery of Genomic Sequence Polymorphisms, Genome Research, vol. 14, No. 1, Jan. 2004, pp. 126-133.
Staunton et al., Chemosensitivity Prediction by Transcriptional Profiling, PNAS, vol. 98, No. 19, Sep. 11, 2001, pp. 10787-10792.
Strachan, The Human Genome, BIOS Scientific Publishers, 1992, 7 pages.
Strathdee et al., Primary Ovarian Carcinomas Display Multiple Methylator Phenotypes Involving Known Tumor Suppressor Genes, American Journal of Pathology, vol. 158, No. 3, 2001, pp. 1121-1127.
Strauss, Using DNA Fragments as Probes, Current Protocols in Molecular Biology, John Wiley & Sons, N.Y., 1993, pp. 6.3.1-6.3.6.
Strohmeier, A New High-Performance Capillary Electrophoresis Instrument, Hewlett-Packard Journal, Jun. 1995, pp. 10-19.
Szabo et al., Surface Plasmon Resonance and its Use in Biomolecular Interaction Analysis (BIA), Current Opinion in Structural Biology, vol. 5, No. 5, Oct. 1995, pp. 699-705.
Tabor et al., Non-Invasive Fetal Genome Sequencing: Opportunities and Challenges, American Journal of Medical Genetics Part A, vol. 158A, No. 10, 2012, pp. 2382-2384.
Takai et al., Comprehensive analysis of CpG islands in human chromosomes 21 and 22, PNAS, vol. 99, No. 6, Mar. 19, 2002, pp. 3740-3745.
Tang et al., Improvement in the Apparent Mass Resolution of Oligonucleotides by Using 12C/14N-Enriched Samples, Analytical Chemistry, vol. 74, No. 1, Jan. 1, 2002, pp. 226-331.
Terme et al., Histone H1 Variants Are Differentially Expressed and Incorporated into Chromatin during Differentiation and Reprogramming to Pluripotency, The Journal of Biological Chemistry, vol. 286, No. 41, Oct. 14, 2011, pp. 35347-35357.
The Cancer Test, Cell Free DNA, Health Screen Inc., 2007, Available on internet at: http://www.thecancertest.com/science-of-cell-free-dna/, Retrieved on Mar. 20, 2011, 6 pages.
The World Health Organization Histological Typing Of Lung Tumours: Second Edition, American Journal Clinical Pathology, vol. 77, 1982, pp. 123-136.
Thorstenson et al., An Automated Hydrodynamic Process for Controlled, Unbiased DNA Shearing, Genome Research, vol. 8, 1998, pp. 848-855.
Tolbert et al., Preparation of Specifically Deuterated and 13C-Labeled RNA for NMR Studies Using Enzymatic Synthesis, Journal of the American Chemical Society, vol. 119, No. 50, Dec. 17, 1997, pp. 12100-12108.
Tolbert et al., Preparation of Specifically Deuterated RNA for NMR Studies Using a Combination of Chemical and Enzymatic Synthesis, Journal of the American Chemical Society, vol. 118, No. 34, Aug. 28, 1996, pp. 7929-7940.
Tong et al., Noninvasive Prenatal Detection of Fetal Trisomy 18 by Epigenetic Allelic Ratio Analysis in Maternal Plasma: Theoretical and Empirical Considerations, Clinical Chemistry, vol. 52, No. 12, Oct. 13, 2006, pp. 2194-2202.
Tooke et al., CpG Methylation in Clinical Studies: Utility, Methods, and Quality Assurance, IVD Technology, vol. 41, Nov.-Dec. 2004, 7 pages.
Tost et al., Analysis and Accurate Quantification of CpG Methylation by MALDI Mass Spectrometry, Nucleic Acids Research, vol. 31, No. 9, e50, May 1, 2003, 10 pages.
Toyota et al., Identification of Differentially Methylated Sequences in Colorectal Cancer by Methylated CpG Island Amplification, Cancer Research, vol. 59, May 15, 1999, pp. 2307-2312.
Toyota et al., Methylation Profiling in Acute Myeloid Leukemia, Blood, vol. 97, No. 9, May 1, 2001, pp. 2823-2829.
Tsaliki et al., MeDIP Real-Time qPCR of Maternal Peripheral Blood Reliably Identifies Trisomy 21, Prenatal Diagnosis, vol. 32, 2012, pp. 996-1001.
Tsui et al., Systematic Identification of Placental Epigenetic Signatures for the Noninvasive Prenatal Detection of Edwards Syndrome, PLoS One, vol. 5, No. 11, e15069, Nov. 2010, 12 pages.
Tungwiwat et al., Non-invasive Fetal Sex Determination using a Conventional Nested PCR Analysis of fetal DNA in Maternal Plasma, Clinica Chimica Acta, vol. 334, No. 1-2, Aug. 2003, pp. 173-177.
Tynan et al., Fractional DNA Quantification by Massively Parallel Shotgun Sequencing-Implications for Fetal Fraction Measurement in Maternal Plasma, Sequenom CMM, ASHG Poster, 2011, 1 page.
Uhlmann et al., Evaluation of a Potential Epigenetic Biomarker by Quantitative Methyl-single Nucleotide Polymorphism Analysis, Electrophoresis, vol. 23, Issue 24, Dec. 2002, pp. 4072-4079.

(56) References Cited

OTHER PUBLICATIONS

Valk et al., Prognostically Useful Gene-Expression Profiles in Acute Myeloid Leukemia, The New England Journal of Medicine, vol. 350, No. 16, Apr. 15, 2004, pp. 1617-1628.

Valk-Lingbeek et al., Stem Cells and Cancer: The Polycomb Connection, Cell, vol. 118, Aug. 20, 2004, pp. 409-418.

Van Der Schoot et al., Real-Time PCR of Bi-Allelic Insertion/Deletion Polymorphisms Can Serve as a Reliable Positive Control for Cell-Free Fetal DNA in Non-Invasive Prenatal genotyping, Blood, vol. 102, Abstract 315, 2003, p. 93a.

Veltman et al., High-Throughput Analysis of Subtelomeric Chromosome Rearrangements by Use of Array-Based Comparative Genomic Hybridization, American Journal of Human Genetics, Epub Apr. 9, 2002, vol. 70, No. 5, May 2002, pp. 1269-1276.

Venter et al., The Sequence of the Human Genome, Science, vol. 291, Feb. 16, 2001, pp. 1304-1351.

Verbeck et al., A Fundamental Introduction to Ion Mobility Mass Spectrometry Applied to the Analysis of Biomolecules, Journal of Biomolecular Techniques, vol. 13, No. 2, Jun. 2002, pp. 56-61.

Verma et al., Rapid and Simple Prenatal DNA Diagnosis of Down's Syndrome, Lancet, vol. 352, No. 9121, Jul. 4, 1998, pp. 9-12.

Vincent et al., Helicase-Dependent Isothermal DNA Amplification, EMBO reports, vol. 5, No. 8, Jul. 9, 2004, pp. 795-800.

Vire et al., The Polycomb Group Protein EZH2 Directly Controls DNA Methylation, Nature, Epub Dec. 14, 2005, vol. 439, No. 7078, Feb. 16, 2006, pp. 871-874.

Vogelstein et al., Digital PCR, Proc. Natl. Acad. Sci. USA, vol. 96, Aug. 3, 1999, pp. 9236-9241.

Voelkerding et al., Next-Generation Sequencing: From Basic Research to Diagnostics, Clinical Chemistry, vol. 55, No. 4, Jan. 29, 2009, pp. 641-658.

Vu et al., Symmetric and Asymmetric DNA Methylation in the Human IGF2-H19 Imprinted Region, Genomics, vol. 64, No. 2, Mar. 1, 2000, pp. 132-143.

Wada et al., Codon Usage Tabulated from the GenBank Genetic Sequence Data, Nucleic Acids Research, vol. 20, Supplement, May 11, 1992, pp. 2111-2118.

Wald et al., Combining Ultrasound and Biochemistry in First-Trimester Screening for Down's Syndrome, Prenatal Diagnosis, vol. 17, No. 9, Sep. 1997, pp. 821-829.

Wang et al., Comparative Analysis and Integrative Classification of NCI60 Cell Lines and Primary Tumors Using Gene Expression Profiling Data, BMC Genomics, vol. 7, No. 166, Jul. 3, 2006, 11 pages.

Wapner et al., First-Trimester Screening for Trisomies 21 and 18, The New England Journal of Medicine, vol. 349, No. 15, Oct. 9, 2003, pp. 1405-1413.

Weber et al., Mitogenic Signaling of Ras is Regulated by Differential Interaction with Raf Isozymes, Oncogene, vol. 19, No. 2, Jan. 13, 2000, pp. 169-176.

Weisenberger et al., CPG Island Methylator Phenotype Underlies Sporadic Microsatellite Instability and is Tightly Associated with BRAF Mutation in Colorectal Cancer, Nature Genetics, vol. 38, No. 7, Jul. 2006, pp. 787-793.

Weiss et al., Histone H1 Variant-Specific Lysine Methylation by G9a/KMT1C and Glp1/KMT1D, Epigenetics & Chromatin, vol. 3, No. 7, Mar. 24, 2010, pp. 1-13.

White et al., Detecting Single Base Substitutions as Heteroduplex Polymorphisms, Genomics, vol. 12, No. 2, Feb. 1992, pp. 301-306.

Widschwendter et al., Epigenetic Stem Cell Signature in Cancer, Nature Genetics, vol. 39, No. 2, Feb. 2007, pp. 157-158.

Wilkinson, In Situ Hybridization: A Practical Approach, (Wilkinson ed.), IRL Press, Oxford University Press, Oxford (1998).

Winoto et al., A Novel, Inducible and T Cell-Specific Enhancer Located at the 3' End of the T Cell Receptor Alpha Locus, The EMBO Journal, vol. 8, No. 3, Mar. 1989, pp. 729-733.

Xiong et al., COBRA: A Sensitive and Quantitative DNA Methylation Assay, Nucleic Acids Research, vol. 25, No. 12, Jun. 15, 1997, pp. 2532-2534.

Yamada et al., A Comprehensive Analysis of Allelic Methylation Status of CpG Islands on Human Chromosome 21q, Genome Research, vol. 14, Issue 2, Feb. 2004, pp. 247-266.

Yamada et al., Suppressive Effect of Epigallocatechin Gallate (EGCg) on DNA Methylation in Mice: Detection by Methylation Sensitive Restriction Endonuclease Digestion and PCR, Journal of Food, Agriculture & Environment, vol. 3, No. 2, 2005, pp. 73-76.

Yan et al., A Novel Diagnostic Strategy for Trisomy 21 Using Short Tandem Repeats, Electrophoresis, vol. 27, No. 2, Feb. 2006, pp. 416-422.

Zahra et al., Plasma Microparticles are Not Elevated in Fresh Plasma from Patients with Gynaecological Malignancy—An Observational Study, Gynecologic Oncology, vol. 123, No. 1, Oct. 2011, pp. 152-156.

Zervos et al., Mxi1, a Protein that Specifically Interacts with Max to Bind Myc-Max Recognition Sites, Cell, vol. 72, Jan. 29, 1993, pp. 223-232.

Zhang, Histone H1 Depletion Impairs Embryonic Stem Cell Differentiation, PLoS Genetics, vol. 8, Issue 5, e1002691, May 2012, pp. 1-14.

Zhao et al., Detection of Fetal Subchromosomal Abnormalities by Sequencing Circulating Cell-Free DNA from Maternal Plasma, Clinical Chemistry, vol. 61, No. 4, Feb. 20, 2015, pp. 608-616.

Zhao et al., Quantification and Application of the Placental Epigenetic Signature of the RASSF1A Gene in Maternal Plasma, Prenatal Diagnosis, vol. 30, No. 8, Aug. 2010, pp. 778-782.

Zheng et al., Nonhematopoietically Derived DNA is Shorter than Hematopoietically Derived DNA in Plasma: A Transplantation Model, Clinical Chemistry, vol. 58, No. 2, Nov. 3, 2011, 16 pages.

Zhong et al., Elevation of Both Maternal and Fetal Extracellular Circulating Deoxyribonucleic Acid Concentrations in the Plasma of Pregnant Women with Preeclampsia, American Journal of Obstetrics & Gynecology, vol. 184, Issue 3, Feb. 2001, pp. 414-419.

Zhong et al., Fetal DNA in Maternal Plasma is Elevated in Pregnancies with Aneuploid Fetuses, Prenatal Diagnosis, vol. 20, No. 10, Oct. 2000, pp. 795-798.

Zimmermann et al., Novel Real-Time Quantitative PCR Test for Trisomy 21, Clinical Chemistry, vol. 48, No. 2, Feb. 2002, pp. 362-363.

Zimmermann et al., Serum Parameters and Nuchal Translucency in First Trimester Screening for Fetal Chromosomal Abnormalities, British Journal of Obstetrics and Gynaecology, vol. 103, No. 10, Oct. 1996, pp. 1009-1014.

Zuker, Mfold Web Server for Nucleic Acid Folding and Hybridization Prediction, Nucleic Acids Research, vol. 31, No. 13, Jul. 1, 2003, pp. 3406-3415.

U.S. Appl. No. 15/517,107, "Non-Final Office Action", dated Jan. 21, 2020, 9 pages.

Flicek et al., "Sense from Sequence Reads: Methods for Alignment and Assembly", Nature Methods Supplement, vol. 6, No. 11s, Nov. 2009, pp. S6-S12.

"*Homo sapiens* Chromosome 13, GRCh37 Primary Reference Assembly", GenBank Accession No. CM000675.1, Available Online at, https://www.ncbi.nlm.nih.gov/nuccore/CM000675.1, Jun. 29, 2009, 2 pages.

"*Homo sapiens* Genomic DNA, Chromosome 21q22.2, DSCR Region, Clone D47-S479, Segment 12/16, Complete Sequence", GenBank Accession No. AP000160.1, Available Online at, https://www.ncbi.nlm.nih.gov/nuccore/AP000160.1/, Jan. 8, 2000, 22 pages.

"Human DNA Sequence from Clone RP11-417C20 on Chromosome 13, Complete Sequence", GenBank Accession No. AL138704.12, Available Online at, https://www.ncbi.nlm.nih.gov/nuccore/AL138704.12/, Dec. 13, 2012, 35 pages.

U.S. Appl. No. 14/772,544, "Final Office Action", dated Dec. 11, 2019, 20 pages.

U.S. Appl. No. 15/443,051, "Non Final Office Action", dated Oct. 2, 2019, 14 pages.

EP15753247.4, "Office Action", dated Oct. 14, 2019, 4 pages.

EP15753247.4, "Office Action", dated Aug. 19, 2019, 5 pages.

Schwartzentruber, "Driver Mutations in Histone H3.3 and Chromatin Remodelling Genes in Paediatric Glioblastoma", Nature, vol. 482, Feb. 9, 2012, pp. :226-:231.

(56) References Cited

OTHER PUBLICATIONS

U.S. Appl. No. 14/772,544, Non-Final Office Action, dated Dec. 23, 2020, 10 pages.
U.S. Appl. No. 15/443,051, Notice of Allowance, dated Apr. 20, 2020, 10 pages.
U.S. Appl. No. 15/517,107, Final Office Action, dated May 26, 2020, 8 pages.
U.S. Appl. No. 15/517,107, Notice of Allowance, dated Sep. 8, 2020, 8 pages.
EP 15714069.0, Notice of Decision to Grant, dated Apr. 9, 2020, 2 pages.
EP 15753247.4, Notice of Decision to Grant, dated Jul. 2, 2020, 2 pages.
EP 15785002.5, Notice of Decision to Grant, dated Apr. 9, 2020, 2 pages.
EP 18174047.3, Notice of Decision to Grant, dated Mar. 26, 2020, 2 pages.
EP 20170556.3, Extended European Search Report, dated Nov. 4, 2020, 9 pages.
EP 20172801.1, Extended European Search Report, dated Sep. 22, 2020, 9 pages.
EP 20172959.7, Extended European Search Report, dated Sep. 29, 2020, 9 pages.
EP 20187578.8, Extended European Search Report, dated Nov. 11, 2020, 13 pages.
Hsu, L. et al., "Denoising Array-Based Comparative Genomic Hybridization Data Using Wavelets", Biostatistics 6(2):211-226 (2005).
Mouliere, F. et al., "Multi-marker Analysis of Circulating Cell-free DNA Toward Personalized Medicine for Colorectal Cancer", Molecular Oncology 8(5):927-941 (2014).
Willenbrock, H. and Fridlyand, J., "A Comparison Study: Applying Segmentation To Array CGH Data for Downstream Analyses", Bioinformatics 21(22):4084-4091 (2005).
Yoon, S. et al., "Sensitive and Accurate Detection of Copy Number Variants using Read Depth of Coverage", Genome Research 19(9):1586-1592 (2009).
Yu, S. et al., "Size-Based Molecular Diagnostics Using Plasma DNA for Noninvasive Prenatal Testing", PNAS 111(23):8583-8588 (2014).
Haar, A. , "On the Theory of Orthogonal Function Systems", Mathematische Annalen, 69(3):1-37 (2009).
Hupe, P. et al., "Analysis of Array CGH Data: From Signal Ratio to Gain and Loss of DNA Regions", Bioinformatics, 20(18):3413-3422 (2004).
Nason, G., "Wavelet Methods in Statistics with R", Springer, New York ISBN: 978-0-387-75960-9, Jan. 2008, 1 page.
Nguyen, N. et al., "Denoising of Array-Based DNA Copy Number Data Using The Dual-Tree Complex Wavelet Transform", Institute of Electrical and Electronics Engineers 7th International Symposium on BioInformatics and BioEngineering, Oct. 14-17, 2007, pp. 137-144.
Olshen, A. et al., "Circular Binary Segmentation for the Analysis of Array-Based DNA Copy Number Data", Biostatistics 5(4):557-572 (2004).
Venkatraman, E. and Olshen, A., "A Faster Circular Binary Segmentation Algorithm for the Analysis of Array CGH Data", Bioinformatics, 23(6):657-663 (2007).
Wang, Y. and Wang, S., "A Novel Stationary Wavelet Denoising Algorithm for Array-Based DNA Copy Number Data", Intl. J. Bioinformatics Research and Applications, 3(2):206-222 (2007).
U.S. Appl. No. 14/772,544, Notice of Allowance, dated Apr. 1, 2021, 11 pages.
EP Application No. 14721601.4, Office Action, 5 pages, Feb. 23, 2017.
EP Application No. 14721601.4, Summons to Attend Oral Proceedings, 8 pages, Sep. 12, 2018.
EP Application No. 19174694.0, Extended European Search Report, 11 pages, dated Nov. 25, 2019.
EP Application No. 19174694.0, Office Action, 5 pages, dated Oct. 12, 2020.
Gottesman, Minimizing Proteolysis in *Escherichia Coli*:Genetic Solutions, Gene Expression Technology: Methods in Enzymology, vol. 185, pp. 119-129, 1990.
U.S. Appl. No. 14/772,544, "Advisory Action", dated Jun. 10, 2020, 7 pages.
U.S. Appl. No. 16/884,528, "Non-Final Office Action", dated Jul. 12, 2021, 15 pages.
Hybridization with Radioactive Probes, Current Protocols in Molecular Biology, John Wiley & Sons, Inc., 1989, pp. 6.3.1-6.3.6.
Products and Contract Services, Caliper Life Sciences, Lab Chip GX 2010, Available on internet at http://www.caliperl.com/products/labchip-gx.htm, Mar. 15, 2011, pp. 1-3.
U.S. Appl. No. 14/735,477, Advisory Action dated May 15, 2018, 4 pages.
U.S. Appl. No. 14/735,477, Final Office Action dated Dec. 22, 2017, 10 pages.
U.S. Appl. No. 14/735,477, Final Office Action dated Mar. 21, 2019, 11 pages.
U.S. Appl. No. 14/735,477, Non-Final Office Action dated May 15, 2017, 8 pages.
U.S. Appl. No. 14/735,477, Notice of Allowance dated Mar. 30, 2020, 8 pages.
U.S. Appl. No. 15/261,457, Final Office Action dated Apr. 17, 2020, 12 pages.
U.S. Appl. No. 15/261,457, Final Office Action dated Jul. 15, 2019, 15 pages.
U.S. Appl. No. 15/261,457, Non-Final Office Action dated Apr. 23, 2021, 15 pages.
U.S. Appl. No. 15/261,457, Non-Final Office Action dated Oct. 23, 2018, 15 pages.
U.S. Appl. No. 15/261,457, Notice of Allowance dated Jan. 18, 2022, 11 pages.
U.S. Appl. No. 15/428,659, Final Office Action mailed on Sep. 20, 2019, 5 pages.
U.S. Appl. No. 15/428,659, Non-Final Office Action dated Jan. 11, 2019, 9 pages.
U.S. Appl. No. 15/428,659, Notice of Allowance dated Dec. 18, 2019, 5 pages.
U.S. Appl. No. 16/884,528, Notice of Allowance dated Dec. 24, 2021, 10 pages.
Adams et al., Automated DNA Sequencing and Analysis, Academic Press, May 19, 1994, 11 pages.
Australian Application No. 2009293232, First Examination Report dated Mar. 11, 2014, 3 pages.
Australian Application No. 2009293232, Notice of Acceptance dated Apr. 30, 2015, 2 pages.
Australian Application No. 2010295968, First Examination Report dated Jul. 17, 2014, 4 pages.
Australian Application No. 2010295968, Notice of Acceptance dated Aug. 10, 2015, 3 pages.
Australian Application No. 2012249531, First Examination Report dated Jun. 28, 2016, 3 pages.
Australian Application No. 2013290102, First Examination Report dated Apr. 19, 2018, 3 pages.
Australian Application No. 2013290102, Notice of Acceptance dated Nov. 6, 2018, 3 pages.
Australian Application No. 2015252141, First Examination Report dated Oct. 28, 2016, 4 pages.
Australian Application No. 2015252141, Second Examination Report dated Oct. 3, 2017, 3 pages.
Australian Application No. 2017251674, First Examination Report dated Sep. 14, 2018, 6 pages.
Australian Application No. 2017251674, Notice of Acceptance dated Jul. 17, 2019, 3 pages.
Australian Application No. 2019200556, First Examination Report dated Jun. 30, 2020, 3 pages.
Australian Application No. 2019200556, Notice of Acceptance dated Jan. 20, 2021, 3 pages.
Australian Application No. 2019257485, First Examination Report dated Mar. 15, 2021, 3 pages.

(56) References Cited

OTHER PUBLICATIONS

Australian Application No. 2019257485, Notice of Acceptance dated Feb. 16, 2022, 3 pages.
Brockman et al., Quality Scores and SNP Detection in Sequencing-By-Synthesis Systems, Genome Research, vol. 18, No. 5, May 2008, pp. 763-770.
Canadian Application No. 2,737,200, Notice of Allowance dated Aug. 6, 2019, 1 page.
Canadian Application No. 2,737,200, Office Action dated Dec. 11, 2017, 3 pages.
Canadian Application No. 2,737,200, Office Action dated Dec. 22, 2015, 4 pages.
Canadian Application No. 2,737,200, Office Action dated Jan. 27, 2017, 4 pages.
Canadian Application No. 2,737,200, Office Action dated Nov. 22, 2016, 4 pages.
Canadian Application No. 2,774,342, Notice of Allowance dated May 23, 2018, 1 page.
Canadian Application No. 2,774,342, Office Action dated Mar. 28, 2017, 3 pages.
Canadian Application No. 2,834,218, Notice of Allowance dated Sep. 8, 2020, 1 page.
Canadian Application No. 2,834,218, Office Action dated Jun. 5, 2019, 3 pages.
Canadian Application No. 2,834,218, Office Action dated Apr. 23, 2018, 4 pages.
Canadian Application No. 2,878,979, Notice of Allowance dated Mar. 22, 2021, 1 page.
Canadian Application No. 2,878,979, Office Action dated Feb. 24, 2020, 3 pages.
Canadian Application No. 2,878,979, Office Action dated Feb. 7, 2019, 4 pages.
Canadian Application No. 3,024,967, Notice of Allowance dated Feb. 9, 2021, 1 page.
Canadian Application No. 3,024,967, Office Action dated Nov. 25, 2019, 4 pages.
Canadian Application No. 3,073,079, Office Action dated Feb. 16, 2022, 4 pages.
Canadian Application No. 3,073,079, Office Action dated Feb. 18, 2021, 4 pages.
Chomczynski et al., Short Technical Reports. Modification of the TRI Reagent Procedure for Isolation of RNA from Polysaccharide- and Proteoglycan-Rich Sources, Biotechniques, vol. 19, No. 6, Dec. 1995, pp. 942-945.
Dominguez et al., Wild-Type Blocking Polymerase Chain Reaction for Detection of Single Nucleotide Minority Mutations from Clinical Specimens, Oncogene, Nature Publishing Group, vol. 24, No. 45, Oct. 13, 2005, pp. 6830-6834.
Eckstein, Oligonucleotides and Analogues: A Practical Approach, IRL Press, Oxford, 1991, 11 pages.
European Application No. 09815148.3, Notice of Decision to Grant dated Jul. 14, 2016, 3 pages.
European Application No. 09815148.3, Office Action dated Nov. 13, 2014, 4 pages.
European Application No. 09815148.3, Office Action dated May 14, 2014, 5 pages.
European Application No. 09815148.3, Office Action dated Jan. 3, 2013, 7 pages.
European Application No. 10817598.5, Notice of Decision to Grant dated Jun. 29, 2017, 3 pages.
European Application No. 10817598.5, Office Action dated Jan. 29, 2014, 5 pages.
European Application No. 12718553.6, Notice of Decision to Grant dated Dec. 21, 2017, 2 pages.
European Application No. 12718553.6, Office Action dated Jun. 3, 2016, 5 pages.
European Application No. 13739590.1, Notice of Decision to Grant dated Aug. 8, 2019, 1 page.
European Application No. 13739590.1, Office Action dated Aug. 1, 2017, 4 pages.
European Application No. 13739590.1, Office Action dated Feb. 1, 2016, 5 pages.
European Application No. 13739590.1, Office Action dated Jun. 18, 2018, 5 pages.
European Application No. 13739590.1, Office Action dated Nov. 26, 2018, 5 pages.
European Application No. 16173137.7, Notice of Decision to Grant dated Jul. 2, 2020, 3 pages.
European Application No. 16173137.7, Office Action dated Jun. 26, 2019, 5 pages.
European Application No. 16173137.7, Office Action dated Oct. 1, 2018, 6 pages.
European Application No. 17182863.5, Extended European Search Report dated Feb. 26, 2018, 9 pages.
European Application No. 17182863.5, Notice of Decision to Grant dated Feb. 13, 2020, 1 page.
European Application No. 17182863.5, Office Action dated Jul. 19, 2019, 4 pages.
European Application No. 18151693.1, Extended European Search Report dated Jun. 27, 2018, 10 pages.
European Application No. 18151693.1, Notice of Decision to Grant dated Jan. 21, 2021, 2 pages.
European Application No. 18151693.1, Office Action dated Feb. 7, 2020, 5 pages.
European Application No. 20155147.0, Extended European Search Report dated Sep. 11, 2020, 7 pages.
European Application No. 20155147.0, Office Action dated Oct. 5, 2021, 6 pages.
European Application No. 20187954.1, Extended European Search Report dated Dec. 1, 2020, 8 pages.
Indian Application No. 3139/DELNP/2012, First Examination Report dated Oct. 25, 2017, 8 pages.
Japanese Application No. 2011-527069, Notice of Decision to Grant dated Mar. 4, 2015, 6 pages.
Japanese Application No. 2011-527069, Office Action dated Mar. 7, 2014, 14 pages.
Japanese Application No. 2012-529756, Notice of Decision to Grant dated Dec. 24, 2015, 5 pages.
Japanese Application No. 2012-529756, Office Action dated Jul. 14, 2014, 14 pages.
Japanese Application No. 2012-529756, Office Action dated Jun. 2, 2015, 17 pages.
Japanese Application No. 2014-180865, Notice of Decision to Grant dated Apr. 1, 2016, 6 pages.
Japanese Application No. 2014-180865, Office Action dated Oct. 9, 2015, 7 pages.
Japanese Application No. 2015-005024, Office Action dated Jan. 25, 2016, 5 pages.
Japanese Application No. 2015-076001, Office Action dated Feb. 10, 2016, 6 pages.
Japanese Application No. 2015-076001, Office Action dated Oct. 2, 2017, 7 pages.
Japanese Application No. 2015-076001, Office Action dated Nov. 11, 2016, 9 pages.
Japanese Application No. 2015-195591, Notice of Decision to Grant dated Oct. 26, 2016, 6 pages.
Japanese Application No. 2015-195591, Office Action dated Jul. 15, 2016, 6 pages.
Japanese Application No. 2015-521823, Office Action dated Apr. 19, 2018, 10 pages.
Japanese Application No. 2015-521823, Office Action dated Jun. 28, 2017, 15 pages.
Japanese Application No. 2016-199141, Office Action dated May 28, 2018, 18 pages.
Japanese Application No. 2016-199141, Office Action dated Jun. 16, 2017, 4 pages.
Japanese Application No. 2017-241844, Office Action dated Oct. 19, 2018, 4 pages.
Japanese Application No. 2018-017348, Office Action dated Feb. 6, 2019, 15 pages.
Japanese Application No. 2018-017349, Office Action dated Dec. 26, 2018, 4 pages.

(56) References Cited

OTHER PUBLICATIONS

Nygren et al., Quantification of Fetal DNA by Use of Methylation-Based DNA Discrimination: Supplemental Fig. 1, Clinical Chemistry, vol. 6, No. 10, Aug. 20, 2010, 1 page.
International Application No. PCT/US2008/54470, International Search Report and Written Opinion dated Aug. 18, 2008, 9 pages.
International Application No. PCT/US2012/043388, Written Opinion daed Apr. 5, 2013, 6 pages.
Sambrook et al., Molecular Biology: A Laboratory Approach, Cold Spring Harbor, N.Y, 1989, 18 pages.
Tang et al., Chip-based Genotyping by Mass Spectrometry, Proceedings of the National Academy of Sciences, vol. 96, No. 18, Aug. 1999, pp. 10016-10020.
Ackerveken et al. A Novel Proteomics Approach to Epigenetic Profiling of Circulating Nucleosomes, Scientific Reports, vol. 11, No. 7256, 2021, 12 pages.
Wilkinson, In Situ Hybridization: A Practical Approach, Annals Human Genetics, vol. 63, No. 4, Aug. 13, 2009, 10 pages.

\* cited by examiner

METHODS AND PROCESSES FOR NON-INVASIVE ASSESSMENT OF GENETIC VARIATIONS

RELATED PATENT APPLICATIONS

This patent application claims the benefit of U.S. provisional patent application No. 61/952,135 filed on Mar. 13, 2014, entitled METHODS AND PROCESSES FOR NON-INVASIVE ASSESSMENT OF GENETIC VARIATIONS, naming Taylor Jensen et al. as inventors. The entire content of the foregoing provisional patent application is incorporated herein by reference for all purposes, including all text, tables and drawings.

SEQUENCE LISTING

The instant patent application contains a Sequence Listing which has been submitted electronically in ASCII format and is hereby incorporated by reference in its entirety. Said ASCII copy, created on Feb. 28, 2014, is named SEQ-6075-PV_SL.txt and is 171,779 bytes in size.

FIELD

Technology provided herein relates in part to methods, processes, systems and apparatuses for non-invasive assessment of genetic variations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turners Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations or variances can lead to diagnosis of, or determining predisposition to, a particular medical condition. Identifying a genetic variance can result in facilitating a medical decision and/or employing a helpful medical procedure. Identification of one or more genetic variations or variances sometimes involves the analysis of cell-free DNA.

Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive diagnostics (e.g., prenatal diagnostics).

The presence of fetal nucleic acid in maternal plasma allows for non-invasive prenatal diagnosis through the analysis of a maternal blood sample. For example, quantitative abnormalities of fetal DNA in maternal plasma can be associated with a number of pregnancy-associated disorders, including preeclampsia, preterm labor, antepartum hemorrhage, invasive placentation, fetal Down syndrome, and other fetal chromosomal aneuploidies. Hence, fetal nucleic acid analysis in maternal plasma can be a useful mechanism for the monitoring of fetomaternal well-being.

SUMMARY

Provided in certain aspects is a method for detecting one, two, three or four copies of a fetal chromosome, or portion thereof, in a sample, comprising (a) determining amounts of three or more target polynucleotides in each of chromosome 13, chromosome 18 and chromosome 21 in circulating cell-free nucleic acid from a sample from a human pregnant female bearing a fetus, where the three or more target polynucleotides in chromosome 13 are in chromosome 13 polynucleotides comprising chromosome 13 polynucleotides of SEQ ID NOs: 209, 211 and 214, or complement thereof, the three or more target polynucleotides in chromosome 18 are in chromosome 18 polynucleotides comprising chromosome 18 polynucleotides of SEQ ID NOs: 232, 222 and 231, or complement thereof, and the three or more target polynucleotides in chromosome 21 are in chromosome 21 polynucleotides comprising chromosome 21 polynucleotides of SEQ ID NOs: 256, 253 and 252, or complement thereof, and (b) quantifying, from the amounts, one, two, three or four copies of one or more of chromosome 13, chromosome 18, chromosome 21, or portion thereof, in the fetus. In certain aspects the method comprises prior to (a), contacting nucleic acid from the sample with a cleavage agent under cleavage conditions, thereby generating cleaved nucleic acid and non-cleaved nucleic acid. In some aspects the cleavage agent is a methylation sensitive restriction enzyme. In certain aspects the restriction enzyme preferentially cleaves nucleic acid comprising one or more non-methylated recognition sequences and the nucleic acid in (a) from which the amounts of the three or more target polynucleotides are determined is substantially the non-cleaved nucleic acid. In certain embodiments the amounts of the three or more target polynucleotides are determined by a process comprising mass spectrometry. In certain embodiments the amounts of the three or more target polynucleotides are determined by a process comprising sequencing.

Also provided herein, in certain aspects, is a method for detecting one, two, three or four copies of a fetal chromosome or portion thereof in a sample, comprising (a) determining amounts of target polynucleotides in each of chromosome 13, chromosome 18 and chromosome 21 in circulating cell-free nucleic acid from a sample from a human pregnant female bearing a fetus, where the target polynucleotides are in chromosome 13 polynucleotides of SEQ ID NOs: 193-198, 200-204, 206, 208-210, 212-215, or complement thereof, chromosome 18 polynucleotides of SEQ ID NOs: 216-218, 220-230, 232, or complement thereof, and chromosome 21 polynucleotides of SEQ ID NOs: 234, 236, 238-240, 242-246, 248-253, 255, 256, or complement thereof, and (b) quantifying, from the amounts, one, two, three or four copies of one or more of chromosome 13, chromosome 18, chromosome 21, or portion thereof, in the fetus. In certain embodiments, the method comprising determining in (a) the amounts of target polynucleotides in chromosome 13 polynucleotides of SEQ ID NOs: 199, 205, 207, 211 or complement thereof, chromosome 18 polynucleotides of SEQ ID NOs: 219, 231, or complement thereof, and chromosome 21 polynucleotides of SEQ ID NOs: 233, 235, 237, 241, 247, 254 or complement thereof.

Also provided herein, in certain aspects, is a method of amplifying one or more target polynucleotides in a sample comprising (a) contacting a sample comprising circulating cell-free nucleic acid from a human pregnant female bearing a fetus with a collection of primers under amplification conditions, where the primers specifically hybridize to nucleotide sequences located within three or more target polynucleotides in each of chromosome 13, chromosome 18 and chromosome 21 under specific hybridization conditions, where the three or more target polynucleotides in chromosome 13 are in chromosome 13 polynucleotides comprising chromosome 13 polynucleotides of SEQ ID NOs: 209, 211 and 214, or complement thereof, the three or more target polynucleotides in chromosome 18 are in chromosome 18 polynucleotides comprising chromosome 18 polynucleotides of SEQ ID NOs: 232, 222 and 231, or complement thereof and the three or more target polynucleotides in chromosome 21 are in chromosome 21 polynucleotides comprising chromosome 21 polynucleotides of SEQ ID NOs: 256, 253 and 252, or complement thereof, thereby providing target-specific amplicons.

Also provided herein, in certain aspects, is a method of amplifying one or more target polynucleotides in a sample comprising (a) contacting a sample comprising circulating cell-free nucleic acid from a human pregnant female bearing a fetus with a collection of primers under amplification conditions, where the primer pairs specifically hybridize to nucleotide sequences located within three or more target polynucleotides in each of chromosome 13, chromosome 18 and chromosome 21 under specific hybridization conditions, where the target polynucleotides are in chromosome 13 polynucleotides of SEQ ID NOs: 193-198, 200-204, 206, 208-210, 212-215, or complement thereof, chromosome 18 polynucleotides of SEQ ID NOs: 216-218, 220-230, 232, or complement thereof, and chromosome 21 polynucleotides of SEQ ID NOs: 234, 236, 238-240, 242-246, 248-253, 255, 256, or complement thereof, thereby providing target-specific amplicons.

Provided also in certain aspects is a method for detecting one, two, three or four copies of a fetal chromosome, or portion thereof, in a sample, comprising (a) determining amounts of three or more target polynucleotides chromosome 13, chromosome 18 or chromosome 21 in circulating cell-free nucleic acid from a sample from a human pregnant female bearing a fetus, where the three or more target polynucleotides in chromosome 13 are in chromosome 13 polynucleotides comprising chromosome 13 polynucleotides of SEQ ID NOs: 209, 211 and 214, or complement thereof, the three or more target polynucleotides in chromosome 18 are in chromosome 18 polynucleotides comprising chromosome 18 polynucleotides of SEQ ID NOs: 232, 222 and 231, or complement thereof, or the three or more target polynucleotides in chromosome 21 are in chromosome 21 polynucleotides comprising chromosome 21 polynucleotides of SEQ ID NOs: 256, 253 and 252, or complement thereof, and (b) quantifying, from the amounts, one, two, three or four copies of chromosome 13, chromosome 18 or chromosome 21, or portion thereof, in the fetus.

Also provided herein, in certain aspects, is a method for detecting one, two, three or four copies of a fetal chromosome or portion thereof in a sample, comprising (a) determining amounts of target polynucleotides in chromosome 13, chromosome 18 or chromosome 21 in circulating cell-free nucleic acid from a sample from a human pregnant female bearing a fetus, where the target polynucleotides are in chromosome 13 polynucleotides of SEQ ID NOs: 193-198, 200-204, 206, 208-210, 212-215, or complement thereof, chromosome 18 polynucleotides of SEQ ID NOs: 216-218, 220-230, 232, or complement thereof, or chromosome 21 polynucleotides of SEQ ID NOs: 234, 236, 238-240, 242-246, 248-253, 255, 256, or complement thereof, and (b) quantifying, from the amounts, one, two, three or four copies of chromosome 13, chromosome 18 or chromosome 21, or portion thereof, in the fetus. In certain embodiments, the method comprising determining in (a) the amounts of target polynucleotides in chromosome 13 polynucleotides of SEQ ID NOs: 199, 205, 207, 211 or complement thereof, chromosome 18 polynucleotides of SEQ ID NOs: 219, 231, or complement thereof, or chromosome 21 polynucleotides of SEQ ID NOs: 233, 235, 237, 241, 247, 254 or complement thereof.

Provided also herein, in certain aspects, is a method of amplifying one or more target polynucleotides in a sample comprising (a) contacting a sample comprising circulating cell-free nucleic acid from a human pregnant female bearing a fetus with a collection of primers under amplification conditions, where the primers specifically hybridize to nucleotide sequences located within target polynucleotides in chromosome 13, chromosome 18 or chromosome 21 under specific hybridization conditions, where the three or more target polynucleotides in chromosome 13 are in chromosome 13 polynucleotides comprising chromosome 13 polynucleotides of SEQ ID NOs: 209, 211 and 214, or complement thereof, the three or more target polynucleotides in chromosome 18 are in chromosome 18 polynucleotides comprising chromosome 18 polynucleotides of SEQ ID NOs: 232, 222 and 231, or complement thereof, or the three or more target polynucleotides in chromosome 21 are in chromosome 21 polynucleotides comprising chromosome 21 polynucleotides of SEQ ID NOs: 256, 253 and 252, or complement thereof, thereby providing target-specific amplicons.

Also provided herein, in certain aspects, is a method of amplifying one or more target polynucleotides in a sample comprising (a) contacting a sample comprising circulating cell-free nucleic acid from a human pregnant female bearing a fetus with a collection of primers under amplification conditions, where the primer pairs specifically hybridize to nucleotide sequences located within three or more target polynucleotides in chromosome 13, chromosome 18 or chromosome 21 under specific hybridization conditions, where the target polynucleotides are in chromosome 13 polynucleotides of SEQ ID NOs: 193-198, 200-204, 206, 208-210, 212-215, or complement thereof, chromosome 18 polynucleotides of SEQ ID NOs: 216-218, 220-230, 232, or complement thereof, or chromosome 21 polynucleotides of SEQ ID NOs: 234, 236, 238-240, 242-246, 248-253, 255, 256, or complement thereof, thereby providing target-specific amplicons. In certain embodiment, the target polynucleotides are in chromosome 13 polynucleotides of SEQ ID NOs: 199, 205, 207, 211 or complement thereof, chromosome 18 polynucleotides of SEQ ID NOs: 219, 231, or complement thereof and chromosome 21 polynucleotides of SEQ ID NOs: 233, 235, 237, 241, 247, 254 or complement thereof.

Also provided herein, in certain aspects, is a kit for detecting one, two, three or four copies of a fetal chromosome, or portion thereof, in circulating cell-free nucleic acid from a sample from a human pregnant female bearing a fetus, comprising a collection of oligonucleotide primer pairs where each primer pair is configured for amplifying three or more target polynucleotides in each of chromosome 13, chromosome 18 and chromosome 21, where the three or more target polynucleotides in chromosome 13 are in chromosome 13 polynucleotides comprising chromosome 13 polynucleotides of SEQ ID NOs: 209, 211 and 214, or complement thereof, the three or more target polynucleotides in chromosome 18 are in chromosome 18 polynucleotides comprising chromosome 18 polynucleotides of SEQ ID NOs: 232, 222 and 231, or complement thereof and the three or more target polynucleotides in chromosome 21 are in chromosome 21 polynucleotides comprising chromosome 21 polynucleotides of SEQ ID NOs: 256, 253 and 252, or complement thereof.

Provided also herein, in certain aspects, is a kit for detecting one, two, three or four copies of a fetal chromosome, or portion thereof, in circulating cell-free nucleic acid from a sample from a human pregnant female bearing a fetus, comprising a collection of oligonucleotide primer pairs where each primer pair is configured for amplifying three or more target polynucleotides in chromosome 13, chromosome 18 or chromosome 21, where the three or more target polynucleotides in chromosome 13 are in chromosome 13 polynucleotides comprising chromosome 13 polynucleotides of SEQ ID NOs: 209, 211 and 214, or complement thereof, the three or more target polynucleotides in chromosome 18 are in chromosome 18 polynucleotides comprising chromosome 18 polynucleotides of SEQ ID NOs: 232, 222 and 231, or complement thereof, or the three or more target polynucleotides in chromosome 21 are in chromosome 21 polynucleotides comprising chromosome 21 polynucleotides of SEQ ID NOs: 256, 253 and 252, or complement thereof.

Also provided herein is a kit for detecting one, two, three or four copies of a fetal chromosome, or portion thereof, in circulating cell-free nucleic acid from a sample from a human pregnant female bearing a fetus, comprising a collection of oligonucleotide primer pairs where each primer pair is configured for amplifying three or more target polynucleotides in each of chromosome 13, chromosome 18 and chromosome 21, where the target polynucleotides are in chromosome 13 polynucleotides of SEQ ID NOs: 193-198, 200-204, 206, 208-210, 212-215, or complement thereof, chromosome 18 polynucleotides of SEQ ID NOs: 216-218, 220-230, 232, or complement thereof, and chromosome 21 polynucleotides of SEQ ID NOs: 234, 236, 238-240, 242-246, 248-253, 255, 256, or complement thereof. In certain embodiment, the target polynucleotides are in
chromosome 13 polynucleotides of SEQ ID NOs: 199, 205, 207, 211 or complement thereof,
chromosome 18 polynucleotides of SEQ ID NOs: 219, 231, or complement thereof and
chromosome 21 polynucleotides of SEQ ID NOs: 233, 235, 237, 241, 247, 254 or complement thereof.

Provided also herein is a kit for detecting one, two, three or four copies of a fetal chromosome, or portion thereof, in circulating cell-free nucleic acid from a sample from a human pregnant female bearing a fetus, comprising a collection of oligonucleotide primer pairs where each primer pair is configured for amplifying three or more target polynucleotides in chromosome 13, chromosome 18 or chromosome 21, where the target polynucleotides are in chromosome 13 polynucleotides of SEQ ID NOs: 193-198, 200-204, 206, 208-210, 212-215, or complement thereof, chromosome 18 polynucleotides of SEQ ID NOs: 216-218, 220-230, 232, or complement thereof, or chromosome 21 polynucleotides of SEQ ID NOs: 234, 236, 238-240, 242-246, 248-253, 255, 256, or complement thereof. In some aspects of the kit the target polynucleotides are in
chromosome 13 polynucleotides of SEQ ID NOs: 199, 205, 207, 211 or complement thereof,
chromosome 18 polynucleotides of SEQ ID NOs: 219, 231, or complement thereof and
chromosome 21 polynucleotides of SEQ ID NOs: 233, 235, 237, 241, 247, 254 or complement thereof.

In certain aspects a kit comprises one or more methylation sensitive restriction enzymes. In some aspects a kit comprises one or more competitor oligonucleotides and/or one or more extension primers presented in Table 1.

Certain aspects of the technology are described further in the following description, examples, drawings and claims.

BRIEF DESCRIPTION OF THE DRAWINGS

The drawings illustrate aspects of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

Figure 1A:
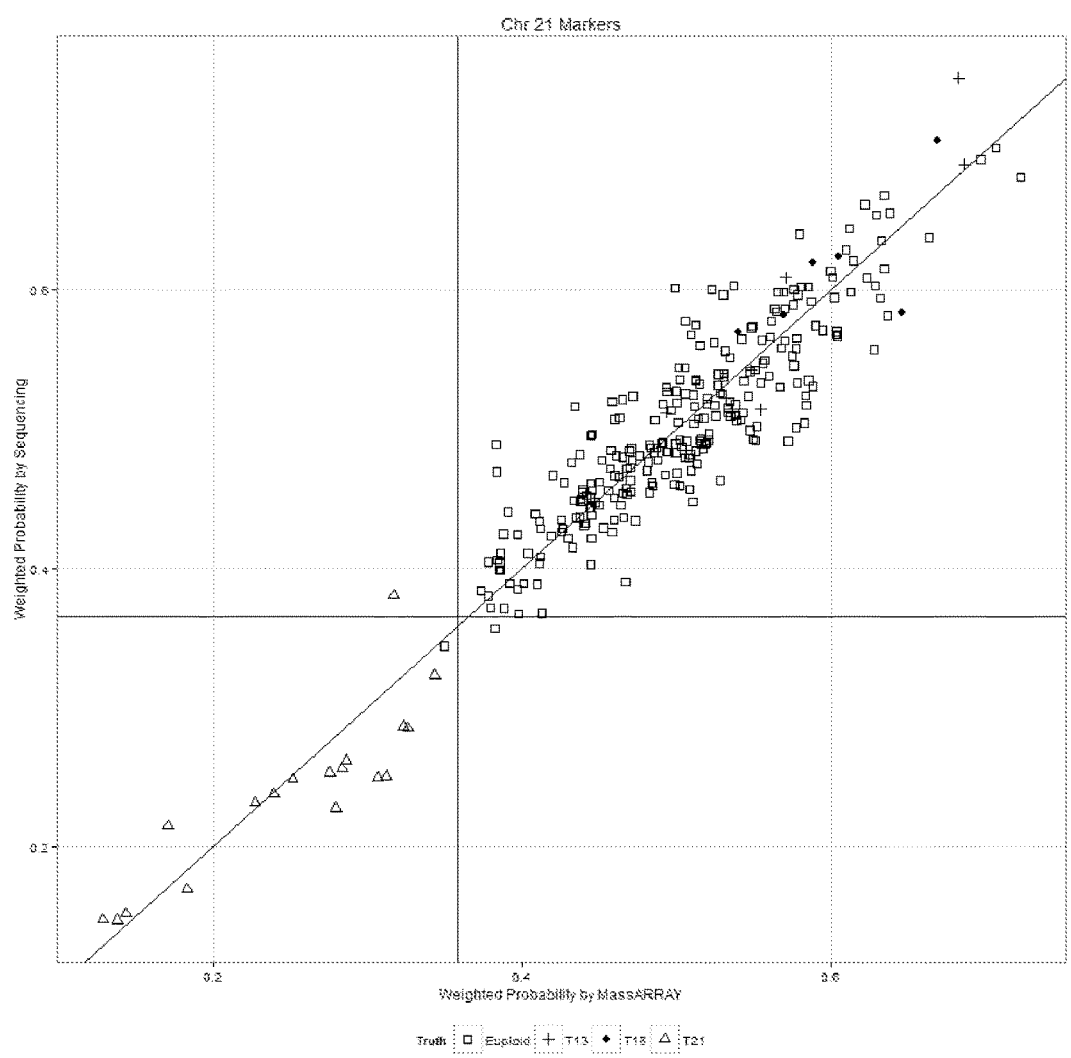
FIG. 1 shows weighted probability from Sequencing (y-axis) vs MassARRAY (x-axis) for chromosome 21 (FIG. 1A), chromosome 13 (FIG. 1B) and chromosome 18 (FIG. 1C). Euploids are indicated by a square, trisomy 13 (T13) is indicated by a cross, trisomy 18 (T18) is indicated by a filled-in circle, and trisomy 21 (T21) is indicated by a triangle. For each marker classification, markers indicating the presence of three copies of a chromosome are shown within the lower left quadrant.

Cell free nucleic acid sometimes comprises a mixture of nucleic acids from different sources (e.g., fetal versus maternal tissue) and nucleic acid from different sources are sometimes differentially methylated. Such differential methylation of certain subpopulations of cell free nucleic acid can be useful for analyzing fetal nucleic acid. Provided also are non-invasive methods, processes and apparatuses useful for identifying a genetic variation in a fetus. Also provided herein, in some embodiments are methods, systems, kits and machines for detecting and/or quantifying one, two, three or four copies of a fetal chromosome, or portion thereof, in a test sample, where the test sample comprises circulating cell free nucleic acid obtained from a pregnant female. In some embodiments methods herein comprise detecting and/or quantifying one, two, three or four copies of chromosome 13, 18 and/or 21, or a portion thereof in a fetus.

In some embodiments, determining a copy number of a chromosome or portion thereof in a fetus comprises detecting and/or quantifying specific target polynucleotides in polynucleotides of chromosomes 13, 18 and/or 21 shown in Tables 1A and 1B. Polynucleotides in Tables 1A and 1B were empirically chosen according to, in part, differential methylation between fetus and mother. In some embodiments methylation sensitive restriction endonucleases are used to digest portions of specific polynucleotides in chromosomes 13, 18 and 21 that are present in circulating cell free nucleic acid. In some embodiments, undigested fragments remain after digestion that comprise fetal nucleic acid and these fragments can be amplified using specific primer pairs that flank or are within methylation sensitive restriction sites. In certain embodiments presented herein are methods and systems for analyzing and quantifying polynucleotide specific amplicons, for example by use of nucleic acid sequencing and/or mass spectrometry, to determine the presence of one, two, three or four copies of fetal chromosomes.

In some embodiments, identifying a genetic variation by a method described herein can lead to a diagnosis of, or determining a predisposition to, a particular medical condition. Identifying a genetic variance can result in facilitating a medical decision and/or employing a helpful medical procedure.

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, sample origins, subject origins, and the like), or combinations thereof.

Nucleic acid or a nucleic acid mixture utilized in methods and apparatuses described herein often is isolated from a sample obtained from a subject (e.g., a test subject). A test subject can be any living or non-living organism, including but not limited to a human (e.g., including a human embryo, fetus, or unborn human child), a non-human animal, a plant, a bacterium, a fungus or a protist. Non-limiting examples of a non-human animal include a mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, rodent (e.g., mouse, rat, and the like), fish, dolphin, whale and shark. A test subject may be a male or female (e.g., woman). In some embodiments a test subject is a pregnant human female.

Nucleic acid may be isolated from any type of suitable test subject, biological specimen or sample (e.g., a test sample). A sample or test sample can be any specimen that is isolated or obtained from a test subject. Non-limiting examples of specimens include fluid or tissue from a subject, including, without limitation, umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo), celocentesis sample, fetal nucleated cells or fetal cellular remnants, washings of female reproductive tract, urine, feces, sputum, saliva, nasal mucous, prostate fluid, lavage, semen, lymphatic fluid, bile, tears, sweat, breast milk, breast fluid, embryonic cells and fetal cells (e.g. placental cells). In some embodiments, a biological sample is a cervical swab from a subject. In some embodiments, a biological sample may be blood and sometimes plasma or serum. As used herein, the term "blood" encompasses whole blood or any fractions of blood, such as serum and plasma as conventionally defined, for example. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise blood cells (e.g., white blood cells, e.g., leukocytes, T-cells, B-cells, platelets, and the like). In certain instances, buffy coats comprise maternal and/or fetal cells and maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols that hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments fetal cells or cancer cells may be included in a sample.

A sample often is heterogeneous, by which is meant that more than one type of nucleic acid species is present in the sample. For example, heterogeneous nucleic acid can include, but is not limited to, (i) fetal derived and maternal derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell.

For prenatal applications of a technology described herein, a fluid or tissue sample (e.g., a test sample) may be collected from a female (e.g., a pregnant female) at a gestational age suitable for testing, or from a female who is being tested for possible pregnancy. A suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation). In some embodiments, a fluid or tissue sample is collected from a pregnant female during or just after (e.g., 0 to 72 hours after) giving birth (e.g., vaginal or non-vaginal birth (e.g., surgical delivery)).

Nucleic Acid Isolation and Processing

Nucleic acid may be derived from one or more sources (e.g., cells, serum, plasma, buffy coat, lymphatic fluid, skin, soil, and the like) by methods known in the art. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

The terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A polynucleotide can be a nucleic acid and/or a nucleic acid fragment. A nucleic acid may be, or may be from, a plasmid, phage, autonomously replicating sequence (ARS), centromere, artificial chromosome, chromosome (chr), or other nucleic acid able to replicate or be replicated in vitro or in a host cell, a cell, a cell nucleus or cytoplasm of a cell in certain embodiments. A nucleic acid in some embodiments can be from a single chromosome or fragment thereof (e.g., a nucleic acid sample may be from one chromosome of a sample obtained from a diploid organism). Nucleic acids sometimes comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term "extracellular nucleic acid" as used herein can refer to nucleic acid isolated from a source having substantially no cells and also is referred to as "cell-free" nucleic acid and/or "cell-free circulating" nucleic acid. Extracellular nucleic acid can be present in and obtained from blood (e.g., from the blood of a pregnant female). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less). In some embodiments, the majority of fetal nucleic acid in nucleic acid is of a length of about 250 base pairs or less (e.g., about 80, 85, 90, 91, 92, 93, 94, 95, 96, 97, 98, 99 or 100% of fetal nucleic acid is of a length of about 250 base pairs or less). In some embodiments, the majority of fetal nucleic acid in nucleic acid is of a length of about 200 base pairs or less (e.g., about 80, 85, 90, 91, 92, 93, 94, 95, 96, 97, 98, 99 or 100% of fetal nucleic acid is of a length of about 200 base pairs or less). In some embodiments, the majority of fetal nucleic acid in nucleic acid is of a length of about 150 base pairs or less (e.g., about 80, 85, 90, 91, 92, 93, 94, 95, 96, 97, 98, 99 or 100% of fetal nucleic acid is of a length of about 150 base pairs or less). In some embodiments, the majority of fetal nucleic acid in nucleic acid is of a length of about 100 base pairs or less (e.g., about 80, 85, 90, 91, 92, 93, 94, 95, 96, 97, 98, 99 or 100% of fetal nucleic acid is of a length of about 100 base pairs or less). In some embodiments, the majority of fetal nucleic acid in nucleic acid is of a length of about 50 base pairs or less (e.g., about 80, 85, 90, 91, 92, 93, 94, 95, 96, 97, 98, 99 or 100% of fetal nucleic acid is of a length of about 50 base pairs or less). In some embodiments, the majority of fetal nucleic acid in nucleic acid is of a length of about 25 base pairs or less (e.g., about 80, 85, 90, 91, 92, 93, 94, 95, 96, 97, 98, 99 or 100% of fetal nucleic acid is of a length of about 25 base pairs or less). The term "fetal nucleic acid" as referred to herein means any nucleic acid (e.g., polynucleotide) derived from a tissue, cell or fluid originating from a human embryo, fetus, or unborn human child. Non-limiting examples of fetal tissue include umbilical cord, portions of the placenta, fetal organs, fetal skin, fetal hair, fetal blood (e.g., fetal plasma, fetal blood cells), fetal lymphatic fluid, amniotic fluid, the like or combinations thereof).

A nucleic acid sample obtained from blood, serum, plasma or urine often comprises circulating cell free (ccf) DNA (e.g., circulating cell free nucleic acids). Circulating cell free DNA from a pregnant female often comprise fetal nucleic acid and maternal nucleic acid. In some embodiments ccf DNA isolated from a test subject comprises a nucleic acid derived from one or more tumors and nucleic acid derived from normal healthy (e.g., non-cancerous) tissues or cells. Circulating cell free DNA often comprises nucleic acid fragments ranging from about 1000 nucleotides in length or less. In some embodiments the mean, average, median, mode or absolute size of ccf fragments is about 700 nucleotides (nt) or less, 600 nt or less, 500 nt or less, 400 nt or less, 350 nt or less, 300 nt or less, 250 nt or less, 200 nt or less, 190 nt or less, 180 nt or less, 170 nt or less, 160 nt or less, 150 nt or less, 140 nt or less, 130 nt or less, 120 nt or less, 110 nt or less or 100 nt or less. In some embodiments the mean, average, median, mode or absolute size of ccf fragments is associated with a methylation status. For example, in some embodiments ccf fragments of about 250 nt or less, 225 nt or less, 200 nt or less, 190 nt or less, 180 nt or less, 170 nt or less, 160 nt or less, 150 nt or less, 140 nt or less, 130 nt or less, 120 nt or less, 110 nt or less or 100 nt or less in length are derived from a locus that is hypermethylated. In some embodiments ccf fragments of about 150 nt or more, 160 nt or more, 170 nt or more, 180 nt or more, 190 nt or more, 200 nt or more, 250 nt or more, or 300 nt or more are derived from a locus that is hypermethylated.

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components.

The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, nucleosomes comprising small fragments of fetal nucleic acid can be purified from a mixture of larger nucleosome complexes comprising larger fragments of maternal nucleic acid.

Nucleic acid also may be exposed to a process that modifies certain nucleotides in the nucleic acid before providing nucleic acid for a method described herein. A process that selectively modifies nucleic acid based upon the methylation status of nucleotides therein can be applied to nucleic acid, for example. In addition, conditions such as high temperature, ultraviolet radiation, x-radiation, can induce changes in the sequence of a nucleic acid molecule. Nucleic acid may be provided in any form useful for conducting a sequence analysis or manufacture process described herein, such as solid or liquid form, for example. In certain embodiments, nucleic acid may be provided in a liquid form optionally comprising one or more other components, including without limitation one or more buffers or salts.

Nucleic acid may be single or double stranded. Single stranded DNA, for example, can be generated by denaturing double stranded DNA by heating or by treatment with alkali, for example. Nucleic acid sometimes is in a D-loop structure, formed by strand invasion of a duplex DNA molecule by an oligonucleotide or a DNA-like molecule such as peptide nucleic acid (PNA). D loop formation can be facilitated by addition of *E. coli* RecA protein and/or by alteration of salt concentration, for example, using methods known in the art.

The term "polynucleotide" as used herein refers to all or a portion of a nucleic acid. The term "polynucleotide" as used herein can refer to a portion or all of a genome, chromosome, gene or locus. A polynucleotide is sometimes a nucleic acid fragment (e.g., a fragment of nucleic acid produced from shearing or an enzymatic reaction, a ccf nucleic acid fragment, an amplicon, an extension product, or the like). A polynucleotide can be single or double stranded.

Methylation-Sensitive Cleavage

As used herein, "cleavage" refers to a procedure or conditions in which a nucleic acid molecule, such as a nucleic acid template gene molecule or amplified product thereof, may be severed into two or more smaller nucleic acid molecules. Cleavage of a nucleic acid often takes place when a nucleic acid comprising a specific restriction enzyme recognition sequence in contacted, under cleavage conditions, with a restriction enzyme that cuts at that specific restriction enzyme recognition sequence. Nucleic acid molecules resulting from a cleavage (of a nucleic acid, polynucleotide (e.g., target polynucleotide), or amplified product thereof are referred to herein as "cleaved" (e.g., "cleavage products" or "cleaved products" or grammatical variants thereof). In some embodiments a polynucleotide (e.g., target polynucleotide) is contacted with a restriction enzyme under cleavage conditions and the polynucleotide is not cleaved. Polynucleotides that are not cleaved by a restriction enzyme are referred to herein as uncleaved (e.g., uncleaved products, uncleaved nucleic acid, uncleaved polynucleotides). In some embodiments target polynucleotides in a mixture are partially cleaved. In certain embodiments a restriction enzyme reaction is not 100% efficient and results in some target polynucleotides that are not cleaved. For example, some (e.g., a small percentage of) target polynucleotides comprising an unmethylated HpaII restriction site are not cleaved when contacted with HpaII under conditions favorable for digestion by HpaII. In some embodiments target polynucleotides in a test sample are substantially cleaved by a cleavage agent. The term "substantially cleaved" refers to cleavage of 80% or more, 85% or more, 90% or more, 95% or more, 96%, 97%, 98%, or about 99% of target polynucleotides, where each of the target polynucleotides comprises a restriction site capable of being cleaved my a specific restriction enzyme. In certain embodiments partially cleaved or substantially cleaved target polynucleotides are analyzed. For example, in some embodiments one, two, three or four copies of a fetal chromosome, or portion thereof, are detected and/or quantified where the target polynucleotides are partially or substantially cleaved by a methylation sensitive cleavage agent. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel).

Nucleic acid may be specifically cleaved by contacting the nucleic acid with one or more enzymatic cleavage agents (e.g., nucleases, restriction enzymes). The term "specific cleavage agent" as used herein refers to an agent, sometimes a chemical or an enzyme that can cleave a nucleic acid at one or more specific sites. Specific cleavage agents often cleave specifically according to a particular nucleotide sequence at a particular site.

In some embodiments, a test sample comprising nucleic acid (e.g., a test sample comprising maternal nucleic acids, fetal nucleic acids or a mixture thereof, (e.g., ccf DNA)) is digested with one or more methylation sensitive cleavage agents. Any suitable sample nucleic acid can be contacted with or digested with a methylation sensitive cleavage agent. Non-limiting examples of sample nucleic acid that can be contacted with or digested with a methylation sensitive cleavage agent include nucleic acid (e.g., polynucleotides, or portions thereof) isolated from the blood, serum, plasma or urine of a test subject (e.g., a pregnant female, a cancer patient), nucleic acid enriched for fetal nucleic acid, maternal nucleic acid, or a sample enriched for unmethylated nucleic acid, methylated nucleic acid, the like or combinations thereof. In some embodiments sample nucleic acid is contacted with one or more methylation sensitive cleavage agents under suitable conditions (e.g., using a suitable buffer, enzyme concentration, DNA concentration, pH, temperature and/or incubation duration) which often results in digested nucleic acid fragments and/or undigested nucleic acid fragments. Digested nucleic acid fragments can comprise any suitable subset of nucleic acid fragments or target polynucleotides. In some embodiments undigested nucleic acid fragments can comprise any suitable subset of nucleic acid fragments or target polynucleotides. Non-limiting examples of digested or undigested subsets of nucleic acid fragments include fetal nucleic acid, maternal nucleic acid, unmethylated nucleic acid, methylated nucleic acid, the like, fragments thereof or combinations thereof. Digested and/or undigested nucleic acid fragments are often enriched, separated and/or analyzed by a method described herein.

In some embodiments, one or more methylation sensitive cleavage agents are methylation sensitive restriction enzymes (e.g., methylation sensitive restriction endonucleases). Methylation sensitive cleavage agents and methylation sensitive restriction enzymes are agents that cleave nucleic acid depending on the methylation status of their recognition site. For example, methylation sensitive DNA restriction endonucleases are generally dependent on the methylation status of their DNA recognition site for activity. In some instances, certain methylation sensitive endonucleases cleave or digest nucleic acid only if it is not methylated at their DNA recognition sequence. Some methylation sensitive endonucleases cleave or digest nucleic acid only if it is methylated at their DNA recognition sequence. Some methylation sensitive endonucleases cleave or digest nucleic acid at their or near their recognition sequence. (i.e. digest at unmethylated or hypomethylated sites). Some methylation sensitive endonucleases cleave or digest nucleic acid 5' and/or 3' of their recognition sequence. Sometimes methylation sensitive endonucleases cleave or digest nucleic acids at random distances (e.g., 5, 10, 20, 50, 100, or 150 base pairs or more) at a site located 5' and/or 3' of their recognition sequences. In some embodiments an unmethylated DNA fragment can be cut into smaller fragments compared to a methylated DNA fragment that is not digested. In some embodiments a methylated DNA fragment can be cut into smaller fragments compared to an unmethylated DNA fragment that is not digested. For example, the average, mean, median or nominal length of certain digested nucleic acid fragments can be about 20 bases to about 200 bases (e.g., about 30, 40, 50, 60, 70, 80, 90, 100, 150 bases). In certain embodiments nucleic acids in a sample (e.g., genomic DNA or ccf DNA) are digested with an enzyme to produce digested nucleic acid fragments with an average, mean, median or nominal length of about 1000 bases or less, about 500 bases or less, about 250 bases or less, about 200 bases or less, about 150 bases or less or about 100 bases (e.g., 100 base pairs) or less. In some embodiments nucleic acids in a sample are digested to produce nucleic acid fragments with an average, mean, median or nominal length between about 25 bases and about 500 bases, between about 25 bases and about 250 bases, between about 25 bases and about 200 bases, between about 25 bases and about 150 bases, between about 40 bases and about 100 bases, or between about 40 bases and about 80 bases. In some embodiments nucleic acids in a sample are digested to produce nucleic acid fragments with an average, mean, median or nominal length between about 500 bases, about 450 bases, about 400 bases, about 350 bases, about 300 bases, about 250 bases, about 200 bases, about 190 bases, about 180 bases, about 170 bases, about 160 bases, about 150 bases, about 140 bases, about 130 bases, about 120 bases, about 110 bases or about 100 bases. The terms "cleave", "cut" and "digest" are used interchangeably herein.

In some embodiments the expected average fragment size of digested fragments for a given restriction enzyme can be estimated based, in part, on the length of the recognition sequence of the restriction enzyme. For example, without being limited to theory, in a genome with 50% GC content and no dinucleotide bias, a four-cutter (e.g., an endonuclease having a 4 base recognition sequence) can be estimated to cut at about every 256 bases, a six-cutter (e.g., an endonuclease having a 6 base recognition sequence) can be expected to cut at about every 4,096 bases, and an eight-cutter (e.g., an endonuclease having a 8 base recognition sequence) should cut at about every 65,536 bases. The expected average fragment size of digested fragments for a given enzyme reaction can be reduced (e.g., frequency of cutting can be increased) by including additional restriction endonucleases in a digestion reaction where each restriction endonuclease has a different recognitions sequence and/or specificity. Sometimes the expected average fragment size of digested fragments for a given restriction enzyme or for a given digestion can be determined empirically for a given sample or sample type (e.g., genomic DNA, ccf DNA). In some embodiments nucleic acid is digested with one or more restriction endonucleases comprising a recognition sequence of 16 bases pairs or less, 12 base pairs or less, 8 base pairs or less, 6 base pairs or less or 4 base pairs or less. In some embodiments nucleic acid is digested with one or more restriction endonucleases comprising a recognition sequence of 4 base pairs or less.

Methylation sensitive restriction enzymes can include any suitable methylation sensitive restriction enzyme described herein or known in the art. For example, a methylation sensitive restriction enzyme can include any suitable Type I, Type II, Type III, Type IV or Type V restriction endonuclease. Type I enzymes are generally complex, multi-subunit, combination restriction-and-modification enzymes that cut DNA at random sites far from their recognition sequences. Type II enzymes generally cut DNA at defined positions close to or within their recognition sequences.

Type II enzymes generally recognize DNA sequences that are symmetric, because they often bind to DNA as homodimers, but a some recognize asymmetric DNA sequences, because they bind as heterodimers. Some Type II enzymes recognize continuous sequences in which the two half-sites of the recognition sequence are adjacent, while others recognize discontinuous sequences in which the half-sites are separated. Type II enzymes generally leaves a 3'-hydroxyl on one side of each cut and a 5'-phosphate on the other. Sometimes Type II enzymes (e.g., Type IIS) cleave outside of their recognition sequence to one side. These enzymes generally recognize sequences that are continuous and asymmetric. Some Type II enzymes (e.g., Type IIG) cleave outside of their recognition sequences, recognize continuous sequences and cleave on just one side. Other Type II enzymes cleave outside of their recognition sequences, recognize discontinuous sequences and cleave on both sides releasing a small fragment containing the recognition sequence. Type III enzymes generally cleave outside of their recognition sequences and require two such sequences in opposite orientations within the same DNA molecule to accomplish cleavage. Type IV enzymes generally recognize modified, typically methylated DNA and are generally exemplified by the McrBC and Mrr systems of *E. coli*. Non-limiting examples of restriction enzymes that can be used for a method described herein include AatII, AccII, ACiI, AclI, AfeI, AgeI, AgeI-HF, Aor13HI, Aor51HI, AscI, AseI, BceAI, BmgBI, BsaAI, BsaHI, BsiEI, BspDI, BsrFI, BspT104I, BssHII, BstBI, BstUI, Cfr10I, ClaI, CpoI, EagI, Eco52I, FauI, FseI, FspI, DpnI, DpnII, HaeII, HaeIII, HapII, HfaI, HgaI, HhaI, HinP1I, HPAII, Hpy99I, HpyCH4IV, KasI, MaeII, McrBC, MluI, MspI, NaeI, NgoMIV, NotI, NotI-HF, NruI, NsbI, NtBsmAI, NtCviPII, PaeR7I, PluTI, PmlI, PmaCI, Psp1406I, PvuI, RsrII, SacII, SalI, SalI-HF, ScrFI, SfoI, SfrAI, SmaI, SnaBI, TspMI, ZraI, the like, isoschizomers thereof, or combinations thereof. Non-limiting examples of enzymes that digest nucleic acid according to a non-methylated recognition sequence include HpaII, HinP1I, HhaI, MaeII, BstUI and AciI. In some embodiments, one or more of the restriction enzymes are selected from HHAI, HinP1I and HPAII. In some embodiments, an enzyme that can be used is HpaII that cuts only the unmethylated sequence CCGG. In some embodiments, an enzyme that can be used is HhaI that cuts only the unmethylated sequence GCGC. In some embodiments, an enzyme that can be used is HinP1I that cuts only the unmethylated sequence GCGC. Such enzymes are available from New England BioLabs®, Inc. and from other suitable sources. In some embodiments combinations of two or more methyl-sensitive enzymes can be used. In some embodiments combinations of two or more methyl-sensitive enzymes that digest only unmethylated DNA also can be used. In some embodiments combinations of two or more methyl-sensitive enzymes that digest only methylated DNA also can be used. Suitable enzymes that digest only methylated DNA include, but are not limited to, DpnI, which cuts at a recognition sequence GATC, and McrBC, which belongs to the family of AAA$^+$ proteins and cuts DNA containing modified cytosines and cuts at recognition site 5' . . . Pu$^m$C(N$_{40-3000}$) Pu$^m$C . . . 3' (New England BioLabs®, Inc., Beverly, Mass.).

In some embodiments, one or more restriction enzymes are selected according to the overhangs (i.e., one or more unpaired nucleotides) that result from digestion with a restriction endonuclease. An overhang is generally one or more unpaired nucleotides at the end of a double stranded polynucleotide fragment. In some embodiment, one or more unpaired nucleotides of an overhang extend from the 3' end or 5' end of a polynucleotide strand. Such overhangs sometimes can be referred to as "sticky ends" and can be used, for example, for ligating to an oligonucleotide, adaptor or other molecule as described herein. In some embodiments overhangs are utilizes for hybridization of a primer sequence or part thereof, often for a subsequent amplification process. In some embodiments, one or more restriction enzymes are selected that produce blunt ends (e.g., no overhang). Blunt ends can also be utilized for ligating an adaptor (i.e., adapter). In some embodiment, a restriction enzyme digest produces digested fragments comprising sticky ends, blunt ends and/or a combination thereof. For example, sometimes a digested fragment includes an overhang at both ends, a blunt end at both ends, or an overhang and a blunt end. In some embodiments an overhang can be produced as a result of a polymerase extension (e.g., as a result of a PCR reaction).

In some embodiments a locus, polynucleotides, and/or target polynucleotide comprises one or more restriction endonuclease recognition sequence(s) (restriction site(s)) where each restriction site can be cleaved in an unmethylated state, by a methylation sensitive restriction endonuclease. In certain embodiments a polynucleotide comprising a restriction endonuclease recognition sequence can be cleaved by a methylation sensitive restriction endonuclease in an unmethylated state. A restriction endonuclease recognition sequence is often referred to herein as a restriction endonuclease recognition site (e.g., a restriction site). A restriction site that can be specifically cleaved, either in a methylated state or unmethylated state, by a methylation sensitive restriction endonuclease is sometimes referred to herein as a "methylation sensitive restriction site". A polynucleotide can comprise one or more methylation sensitive restriction sites that are recognized by one or more methylation sensitive restriction endonucleases. A target polynucleotide often comprises at least one methylation sensitive restriction site.

Nucleic acid in a sample or mixture can be treated with an agent that modifies a methylated nucleotide to another moiety. In some embodiments nucleic acid in a sample or mixture may be treated with an agent (e.g., a chemical agent), and the resulting modified nucleic acid may be cleaved. In some embodiments nucleic acid in a sample or mixture may be treated with an agent (e.g., a chemical agent), and the resulting modified nucleic acid may be resistant to cleavage by a cleavage agent. In some embodiments, target polynucleotides comprising methylation sites that are unmethylated can be targeted for specific cleavage by chemical methods that involve the use of nucleic acid modifying agents. Non-limiting examples of nucleic acid modifying agents include (i) alkylating agents such as methylnitrosourea that generate several alkylated bases, including N3-methyladenine and N3-methylguanine, which are recognized and cleaved by alkyl purine DNA-glycosylase; (ii) sodium bisulfite (i.e., bisulfite), which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

Oligonucleotide Ligation

Any suitable overhang or blunt end can be used to ligate an oligonucleotide or adaptor to one end or both ends of a nucleic acid fragment. In some embodiments, digestion of nucleic acid (e.g., methylation sensitive digestion of hypomethylated nucleic acid) generates digested nucleic acid fragments having blunt ends and/or overhangs (i.e., one or more unpaired nucleotides) at the 3' and/or 5' ends of the digested fragments. Such blunt ends and/or overhangs can be ligated to an oligonucleotide, adaptor or other molecule having a complementary overhang sequence (e.g., ligation sequence). For example, a digested fragment having a 5'-CG-3' overhang can be ligated (e.g., using a DNA ligase) to an oligonucleotide having a 3'-GC-5' overhang. Oligonucleotides comprising an overhang used for ligation are often double-stranded. In some embodiments, the oligonucleotide can ligate to substantially all fragments produced by a particular cleavage agent. For example, an oligonucleotide can ligate to at least 90%, 95%, 96%, 97%, 98%, 99%, 99.9% or 100% of the fragments produced by a particular cleavage agent in some embodiments. In some embodiments, different oligonucleotides are used.

In some embodiments ligation is not required for amplification and/or enrichment of nucleic acids digested by a methylation sensitive restriction enzyme. Digested nucleic acid can be amplified by one or more primer sets, often added in excess, comprising a 3' end that is complementary to overhangs produced as a result of a restriction digest or extension. In some embodiments digested nucleic acid can be amplified using target specific primer sets directed to hybridize to nucleic acid sequences (e.g., target polynucleotide sequences) of hypomethylated or hypermethylated loci. In some embodiments, hypomethylated or hypermethylated nucleic acid can be enriched prior to or after restriction digest by a suitable size selection method (e.g., size selection by PEG precipitation, size selection by column chromatograph, size selection by bridge amplification, the like or combinations thereof). In some embodiments, hypomethylated nucleic acid can be enriched prior to, during or after amplification of restriction digested products by a suitable method (e.g., size selection by PEG precipitation, size selection by column chromatograph, size selection by bridge amplification, the like or combinations thereof).

In some embodiment an overhang is not required for enrichment and/or amplification of hypermethylated nucleic acids. For example, hypomethylated nucleic acid can be enriched by precipitation using a methyl-specific binding agent (e.g., an antibody, a methyl binding protein), or by another suitable method followed by digestion of the hypomethylated nucleic acid by a restriction enzyme that produces blunt-ends or overhang ends. In either embodiment, oligonucleotides (e.g., double stranded oligonucleotides) can be ligated to the digested fragments and the ligated sequences can be captured, enriched, amplified, and/or sequenced by using nucleic acid sequences, or a portion thereof, of the newly ligated oligonucleotides.

In some embodiments, an oligonucleotide comprises an element useful for enrichment and/or analysis of the digested nucleic acid fragments. Elements useful for enrichment and/or analysis of the digested nucleic acid fragments may include, for example, binding agents, capture agents (e.g., binding pairs), affinity ligands, antibodies, antigens, primer hybridization sequences (e.g., a sequence configured for a primer to specifically anneal), a suitable predetermined sequence that can be used for enrichment and/or capture (e.g., a sequence that can hybridize to a complementary nucleic acid comprising a binding agent, e.g., biotin), adaptor sequences, identifier sequences, detectable labels and the like, some of which are described in further detail below. For example, an oligonucleotide may be biotinylated such that it can be captured onto a streptavidin-coated bead. In some embodiments, an oligonucleotide comprises an element useful for a targeted enrichment and/or analysis of the digested nucleic acid fragments. For example, certain nucleotide sequences in a sample may be targeted for enrichment and/or analysis (e.g., using oligonucleotides comprising sequence-specific amplification primers). In some embodiments, an oligonucleotide comprises an element useful for global (i.e., non-targeted) enrichment and/or analysis of the digested nucleic acid fragments. For example, certain oligonucleotides may comprise universal amplification hybridization sequences useful for global (e.g., non-target sequence dependent) enrichment and/or analysis of digested nucleotide sequence fragments.

Oligonucleotides can be designed and synthesized using a suitable process, and may be of any length suitable for ligating to certain nucleic acid fragments (e.g., digested nucleic acid fragments) and performing enrichment and/or analysis processes described herein. Oligonucleotides may be designed based upon a nucleotide sequence of interest (e.g., target fragment sequence, target polynucleotides, reference fragment sequence) or may be non-sequence specific (e.g., for a global enrichment process described herein) and/or may be sample-specific (e.g., may comprise a sample-specific identifier as described below). An oligonucleotide, in some embodiments, may be about 10 to about 300 nucleotides, about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. An oligonucleotide may be composed of naturally occurring and/or non-naturally occurring nucleotides (e.g., labeled nucleotides), or a mixture thereof. Oligonucleotides suitable for use with embodiments described herein, may be synthesized and labeled using known techniques. Oligonucleotides may be chemically synthesized according to the solid phase phosphoramidite triester method first described by Beaucage and Caruthers (1981) Tetrahedron Letts. 22:1859-1862, using an automated synthesizer, and/or as described in Needham-VanDevanter et al. (1984) Nucleic Acids Res. 12:6159-6168. Purification of oligonucleotides can be effected by native acrylamide gel electrophoresis or by anion-exchange high-performance liquid chromatography (HPLC), for example, as described in Pearson and Regnier (1983) J. Chrom. 255:137-149.

Primers

A primer is often a strand of nucleic acid (e.g., an oligonucleotide, an oligonucleotide primer) that serves as a starting point for nucleic acid synthesis. The terms "primer" and "oligonucleotide primer" are used interchangeably herein. A primer is often used for nucleic acid sequencing, amplification, fill-in reactions and extension reactions. A portion of a primer is often complementary to, and can hybridize to, a portion of a nucleic acid template (e.g., a target polynucleotide). A portion of a primer that is complimentary to a portion of a target sequence which the primer pair is configured to amplify is sometimes referred to herein as a hybridization sequence. In some embodiments, an oligonucleotide primer comprises a hybridization sequence (e.g., a sequence complementary to a portion of a target sequence or template nucleic acid). All or a portion of a primer hybridization sequence can be complementary to a portion of a target polynucleotide or template nucleic acid. In some embodiments a primer, or portion thereof is complementary to an adaptor that was previously ligated to a target polynucleotide or template nucleic acid. In some embodiments a primer, or portion thereof is complementary to an overhang generated by a restriction enzyme cleavage reaction. In some embodiments, a primer is useful for amplification (unidirectional amplification, bi-directional amplification) of certain nucleic acid fragments (e.g., digested nucleic acid fragments). In some embodiments, oligonucleotides comprise hybridization sequences that are specific for certain genomic target sequences (e.g., target polynucleotides). An oligonucleotide primer, primer pair or nucleic acid that is specific for a target polynucleotide often hybridized specifically to the target polynucleotide or a portion thereof under suitable hybridization conditions. In some embodiments, oligonucleotides comprise primer hybridization sequences that are not specific for certain genomic target sequences (e.g., universal primer hybridization sequences configured to anneal to a universal adaptor or linker that is ligated or attached to one or more target polynucleotides). Universal primer hybridization sequences may be useful for global (i.e., non-targeted) amplification of certain nucleic acid fragments (e.g., digested nucleic acid fragments). The term "primer" as used herein refers to a nucleic acid that includes a nucleotide sequence capable of hybridizing or annealing to a target polynucleotide, at or near (e.g., adjacent to) a specific region of interest or universal primer site (e.g., a ligated adaptor, an overhang). Primers can allow for specific determination of a target polynucleotide nucleotide sequence or detection of the target polynucleotide (e.g., presence or absence of a sequence or copy number of a sequence), or feature thereof, for example. A primer may be naturally occurring or synthetic. The term "specific" or "specificity", as used herein, refers to the binding or hybridization of one molecule to another molecule, such as a primer for a target polynucleotide or universal primer for a universal primer hybridization sequence. That is, "specific" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "primer", "oligo", or "oligonucleotide" may be used interchangeably throughout the document, when referring to primers.

A primer or primer pair can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof.

Primers suitable for use with embodiments described herein, may be synthesized and labeled using known techniques. Primers may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of primers can be effected by native acrylamide gel electrophoresis or by anion-exchange high-performance liquid chromatography (HPLC), for example, as described in Pearson and Regnier, J. Chrom., 255:137-149, 1983.

A primer pair refers to a pair of two oligonucleotide primers, oriented in opposite directions and configured for amplifying (e.g., by PCR) a nucleic acid template (e.g., a specific target polynucleotide). A nucleic acid template (e.g., target polynucleotide) can be single and/or double stranded. A primer pair or a collection of primer pairs can be designed by a suitable method that often optimizes or matches various features of each primer of a primer pair. In some embodiments where a collection of primer pairs is used in an amplification reaction, various features of each primer pair in a collection are optimized. Algorithms and methods for designing and optimizing primer pairs, as well as collections of primer pairs for an amplification (e.g., an amplification reaction) are well known. Any suitable method of designing and optimizing primer pairs or collections of primer pairs can be used to design primer pairs or collections of primer pairs for amplification of target polynucleotides. Non-limiting examples of features of oligonucleotide primers that are often used for design and optimization of primer pairs include primer length, GC content and Tm. Primers of a primer pair often comprise a similar Tm. In some embodiments a primer pair is optimized for amplification of a specific target polynucleotide.

All or a portion of a primer nucleic acid sequence (e.g., where a primer comprises naturally occurring, synthetic or modified nucleotides, and/or an identifier) may be substantially complementary to a target polynucleotide, or to an adaptor or linker of a target polynucleotide, in some embodiments. As referred to herein, "substantially complementary" with respect to sequences, refers to nucleotide sequences that will hybridize with each other. The stringency of the hybridization conditions can be altered to tolerate varying amounts of sequence mismatch. Included are target and primer hybridization sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Primers that are substantially complementary to a target polynucleotide sequence or portion thereof (e.g., linker or adaptor thereof) are also substantially identical to the complement of a target polynucleotide sequence or portion thereof. That is, sometimes primers are substantially identical to the anti-sense strand of a target polynucleotide. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Primer hybridization sequences and lengths thereof may affect hybridization of a primer to a target polynucleotide sequence, or portion thereof. Depending on the degree of mismatch between the primer and target polynucleotide, low, medium or high stringency conditions may be used to effect primer/target annealing. As used herein, the term "stringent conditions" refers to conditions for hybridization and washing. Methods for hybridization reaction temperature condition optimization are known to those of skill in the art, and may be found in Current Protocols in Molecular Biology, John Wiley & Sons, N.Y., 6.3.1-6.3.6 (1989) or in chapter 11 of Sambrook et al., MOLECULAR CLONING: A LABORATORY MANUAL, second edition, Cold Spring Harbor Laboratory Press, New York (1990), both of which are incorporated by reference herein. Aqueous and non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target polynucleotide sequence that is complementary to the primer.

A primer, in certain embodiments, may contain a modification such as one or more inosines, abasic sites, locked nucleic acids, minor groove binders, duplex stabilizers (e.g., acridine, spermidine), Tm modifiers or any modifier that changes the binding properties of the primers. A primer, in certain embodiments, may contain a detectable molecule or entity (e.g., a fluorophore, radioisotope, colorimetric agent, particle, enzyme and the like).

A primer also may refer to a polynucleotide sequence that hybridizes to a subsequence of a target polynucleotide or another primer and facilitates the detection of a primer, a target polynucleotide or both, as with molecular beacons, for example. The term "molecular beacon" as used herein refers to detectable molecule, where the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size.

A primer often comprises one or more non-native elements. A non-native element can be any feature of an oligonucleotide primer that is made by the hand of a person. A non-native element associated with an oligonucleotide is often not associated with an oligonucleotide (e.g., DNA or RNA) in nature (e.g., not found in nature). In some embodiments, a non-native element comprises an identifier. Non-limiting examples of an identifier include sequence tags, labels (e.g., a radiolabel (e.g., an isotope), a metallic label, a fluorescent label, a fluorophore, a chemiluminescent label, an electrochemiluminescent label (e.g., Origen™), a phosphorescent label, a light scattering molecule, a quencher (e.g., a fluorophore quencher), a fluorescence resonance energy transfer (FRET) pair (e.g., donor and acceptor), a dye, a protein (e.g., an enzyme (e.g., alkaline phosphatase and horseradish peroxidase), an antibody (e.g., a suitable binding agent) or part thereof, a linker, a member of a binding pair), an enzyme substrate (e.g., any moiety capable of participating in an enzyme reaction), a small molecule (e.g., biotin, avidin), a mass tag, quantum dots, nanoparticles, the like or combinations thereof), an amino acid, protein, carbohydrate, fatty acid, lipid, a modified nucleotide (e.g., a non-native nucleotide, e.g., a nucleotide comprising an additional element (e.g., an element of the periodic table of elements), molecule, or a secondary group not found associated with a nucleotide of a DNA or RNA oligonucleotide found in nature), the like, or a combination thereof. For embodiments in which the identifier is a detectable label, the identifier often is a molecule that emits a detectable signal having an intensity different than the intensity of a signal emitted by a naturally occurring nucleotide base under the same conditions (e.g., at the same emission wavelength for a fluorophore). In some embodiments a non-native element comprises or consists of a heterologous nucleotide sequence. A heterologous nucleotide sequence can be any suitable sequence of nucleotides not from the same type of organism (e.g., not from the same species or strain) from which a polynucleotide in the primer is from. A heterologous nucleotide sequence sometimes is synthetic and sometime originates from a type of organism (e.g., a non-human organism or non-mammalian organism) different than the organism from which a sample is derived from. A primer sometimes is a chimeric molecule comprising a hybridization sequence and a heterologous polynucleotide (e.g., heterologous to the hybridization sequence) made by the hand of a person or by a machine and not found in nature. A non-native element can be attached or associated with a primer by any suitable method. In some embodiments a non-native element is attached to a primer by a covalent bond. In some embodiments a non-native element is associated or bound to a primer by a non-covalent bond.

Adaptors

In some embodiments, an oligonucleotide comprises an adaptor sequence and/or complement thereof. Adaptor sequences often are useful for certain sequencing methods such as, for example, a sequencing-by-synthesis process described herein. Adaptors sometimes are referred to as sequencing adaptors or adaptor oligonucleotides. Adaptor sequences typically include one or more sites useful for attachment to a solid support (e.g., flow cell). In some embodiments, adaptors comprise one or more binding and/or capture agents. Adaptors also may include sequencing primer hybridization sites (e.g., sequences complementary to primers used in a sequencing reaction) and identifiers (e.g., indices) as described below. Adaptor sequences can be located at the 5' and/or 3' end of a nucleic acid and sometimes can be located within a larger nucleic acid sequence. Adaptors can be any length and any sequence, and may be selected based on standard methods in the art for adaptor design.

One or more adaptor sequences may be incorporated into a nucleic acid (e.g. oligonucleotide) by any method suitable for incorporating adaptor sequences into a nucleic acid. For example, PCR primers used for generating PCR amplicons (i.e., amplification products) may comprise adaptor sequences or complements thereof. Thus, PCR amplicons that comprise one or more adaptor sequences can be generated during an amplification process. In some instances, one or more adaptor sequences can be ligated to a nucleic acid by any ligation method suitable for attaching adaptor sequences to a nucleic acid. In some embodiments an adaptor, or portion thereof, is ligated to one or both ends of a nucleic acid fragment. Sometimes one or more adaptors are ligated to one or more unpaired nucleotides at the 5' and 3' end of a digested nucleic acid fragment. In some embodiments the sequence of an adaptor ligated to one end of a nucleic acid fragment is different that the sequence of an adaptor ligated at the other end of a nucleic acid fragment. In some embodiments a portion of an adaptor is complementary to a sticky end that remains after digestion of a nucleic acid by a restriction endonuclease. Adaptors used for ligation are often initially double stranded. Sometimes after ligation an unligated strand of an adaptor is removed, discarded or displaced leaving a single strand of the adaptor ligated to its target. Ligation processes may include, for example, blunt-end ligations, ligations that exploit 3' adenine (A) overhangs generated by Taq polymerase during an amplification process and ligate adaptors having 3' thymine (T) overhangs, and other "sticky-end" ligations. Ligation processes can be optimized such that adaptor sequences hybridize to each end of a nucleic acid and not to each other.

The term "modified variant" as used herein refers to a nucleic acid (e.g., a digested nucleic acid fragment) comprising any suitable modification or combination of modifications. Non-limiting examples of suitable modifications of nucleic acids include chemically modified residues, enzymatically modified residues, cleaved fragments of a nucleic acid, a nucleic acid comprising one or more ligated adaptors or linkers, a nucleic acid comprising an identifier, binding agent or capture agent, amplicons or extension products of a nucleic acid or a modified variant thereof, amplicons or extension products comprising a portion of a nucleic acid, amplicons or extension products comprising additional nucleotides and/or modified sequences (e.g., additions, deletions, and/or mutations), the like or combinations thereof.

Identifiers

In some embodiments, a nucleic acid (e.g., an oligonucleotide), protein or binding agent comprises an identifier. An identifier can be any feature that can identify a particular origin or aspect of a nucleic acid fragment (e.g., digested nucleic acid fragment), protein and/or binding agent. An identifier may be referred to herein as a tag, label, index, barcode, identification tag, sequence tag, index primer, and the like. An identifier can be a suitable detectable label or sequence tag incorporated into or attached to a nucleic acid (e.g., a polynucleotide) that allows detection, identification and/or quantitation of nucleic acids and/or nucleic acid targets that comprise the identifier. In some embodiments an identifier allows detection, identification and/or quantitation of nucleic acids and/or nucleic acid targets that are associated with an identifier. For example, in some embodiments a first nucleic acid (e.g., a target) is associated with a second nucleic acid comprising an identifier, the first nucleic acid can hybridized to the second nucleic acid and the first nucleic can be identified, quantitated or characterized according to the identifier on the second nucleic acid. An identifier (e.g., a sample identifier) can identify the sample from which a particular fragment originated. For example, an identifier (e.g., a sample aliquot identifier) can identify the sample aliquot from which a particular fragment originated. In another example, an identifier (e.g., chromosome identifier) can identify the chromosome from which a particular fragment originated. A nucleic acid comprising an identifier is sometimes referred to herein as "labeled" (e.g., for a nucleic acid comprising a suitable label) or "tagged" (e.g., for a nucleic acid comprising a sequence tag). In some embodiments an identifier is distinguishable from another identifier. A "distinguishable identifier" as used herein means that a signal from one identifier can be distinguished and/or differentiated from the signal from another identifier. A "signal" as referred to herein can be a suitable detectable read-out and/or change thereof, non-limiting example of which include nucleotide sequence, mass, any detectable electromagnetic radiation (e.g., visible light (e.g., fluorescence, phosphorescence, chemiluminescence), infrared, ultraviolet, radiation (e.g., X-rays, gamma, beta or alpha), anions and ions (e.g., ionization, pH), the like or combinations thereof. In some embodiments a presence, absence or change in a signal can be detected and/or quantitated. For example, a change in wavelength or a change in the intensity (e.g., a loss or a gain) of a wavelength of electromagnetic radiation may be a detectable and/or quantifiable read-out. In some embodiments of nucleic acid sequencing, a signal may comprise the detection and/or quantitation of a collection of signals.

Non-limiting examples of detectable labels include a radiolabel (e.g., an isotope), a metallic label, a fluorescent label, a fluorophore, a chemiluminescent label, an electrochemiluminescent label (e.g., Origen™), a phosphorescent label, a light scattering molecule, a quencher (e.g., a fluorophore quencher), a fluorescence resonance energy transfer (FRET) pair (e.g., donor and acceptor), a dye, a protein (e.g., an enzyme (e.g., alkaline phosphatase and horseradish peroxidase), an antibody or part thereof, a linker, a member of a binding pair), an enzyme substrate (e.g., any moiety capable of participating in an enzyme reaction), a small molecule (e.g., biotin, avidin), a mass tag, quantum dots, nanoparticles, the like or combinations thereof.

An identifier may be a unique sequence of nucleotides (e.g., sequence-based identifiers) and/or a particular length of polynucleotide (e.g., length-based identifiers; size-based identifiers, a stuffer sequence). Identifiers for a collection of samples or plurality of chromosomes, for example, may each comprise a unique sequence of nucleotides (e.g., a sequence tag). As used herein, the term "sequence tag" or "tag" refers to any suitable sequence of nucleotides in a nucleic acid (e.g., a polynucleotide, a nucleic acid fragment). A sequence tag is sometimes a polynucleotide label. A sequence tag sometimes comprises a heterologous or artificial nucleotide sequence. A sequence tag may comprise a nucleic acid index, barcode and/or one or more nucleotide analogues. A nucleic acid sequence of a sequence tag is often known. In some embodiments a "sequence tag" is a known and/or identifiable sequence of nucleotides and/or nucleotide analogues. In some embodiments a "sequence tag" is a unique sequence. A unique sequence may be a nucleotide sequence (e.g., a "sequence tag"), or reverse complement thereof, that is not present in a sample of nucleic acids where the sequence tag is used. In some embodiments a unique sequence does not hybridize directly, under hybridization conditions, to sample nucleic acids or target polynucleotides.

In some embodiments a sequence tag is configured to hybridize to a target sequence (e.g., a sequence complementary to a sequence tag). In some embodiments a sequence tag is a probe. A probe is often a nucleic acid comprising one or more identifiers that is configured to hybridize to a specific sequence of a target polynucleotide. In some embodiments a sequence tag is a primer or portion thereof. In some embodiments a primer comprises a sequence tag. A primer is often a polynucleotide configured to bind in a sequence-specific manner to a target polynucleotide where the primer is configured for extension by a polymerase while using a portion of the target as a template. In some embodiments a target polynucleotide comprises a sequence tag.

A sequence tag sometimes is incorporated into a target polynucleotide species using a method known in the art. In some embodiments, a sequence tag is incorporated into a target polynucleotide species as part of library preparation. In some embodiments, a sequence tag is native to sample nucleic acid, is predetermined and/or pre-exists within a target polynucleotide. In some embodiments target specific oligonucleotides are designed to hybridize near or adjacent to a predetermined and/or pre-existing sequence tag. For example, a predetermined sequence tag may be a suitable four nucleotide sequence (e.g., ATGC) where the location of the sequence tag within a target polynucleotide (e.g., a chromosome) is known. In certain embodiments one or more target specific oligonucleotides are designed to hybridize to one or more locations on a target polynucleotide (e.g., a chromosome) adjacent to a predetermined and/or pre-existing sequence tag (e.g., ATGC). In such embodiments, the sequence tag (e.g., ATGC) is detected and/or quantitated by using the target specific oligonucleotides as a primer and by sequencing the next four nucleotides (e.g., ATGC). In certain embodiments, complementary nucleotides (e.g., or nucleotide analogues, labeled nucleotides) are added by a suitable polymerase. In some embodiments, sequence tags may be detected directly or indirectly by a mass spectrometry method (e.g., using MALDI-TOF). In embodiments where a 3 nucleotide sequence tag is used, 9 potential target polynucleotides may be detected by a suitable DNA sequencing method. Likewise, for example, a 4 nucleotide sequence tag may permit detection of 16 targets, a 5 nucleotide sequence tag may permit detection of 25 targets and so on.

A sequence tag identifier (e.g., sequence-based identifiers, length-based identifiers) may be of any length suitable to distinguish certain nucleic acid fragments from other nucleic acid fragments. In some embodiments, identifiers may be from about one to about 100 nucleotides in length. A sequence tag may comprise 1 or more, 2 or more, 3 or more, 4 or more, 5 or more, 6 or more, 7 or more, 8 or more, 9 or more, 10 or more, 20 or more, 30 or more or 50 or more contiguous nucleotides. In some embodiments a sequence tag comprises about 1 to about 50, about 2 to about 30, about 2 to about 20 or about 2 to about 10 contiguous nucleotides. For example, sequence tag identifiers independently may be about 1, 2, 3, 4, 5, 6, 7, 8, 9, 10, 11, 12, 13, 14, 15, 20, 30, 40, 50, 60, 70, 80, 90 or 100 nucleotides (e.g., contiguous nucleotides) in length. In some embodiments, an identifier contains a sequence of six nucleotides. In some instances, an identifier is part of an adaptor sequence for a sequencing process, such as, for example, a sequencing-by-synthesis process described in further detail herein. In some instances, an identifier may be a repeated sequence of a single nucleotide (e.g., poly-A, poly-T, poly-G, poly-C). Such sequence tag identifiers may be detected and distinguished from each other by any suitable method, for example, by using a suitable sequencing method, mass spectrometry, a nanopore technology, the like or combinations thereof.

An identifier may be directly attached (e.g., by a covalent bond, e.g., by a phosphodiester linkage) or indirectly attached and/or associated with a nucleic acid. Indirect attachment may comprise use of one or more binding pairs (e.g., antibody/antigen, biotin/avidin, the like). Indirect attachment may comprise hybridization (e.g., sequence-specific, non-covalent, base-pairing interactions).

An identifier may be covalently bound or non-covalently bound to a nucleic acid. An identifier may be permanently or reversibly attached. In some embodiments an identifier is incorporated into or attached to a nucleic acid during a sequencing method (e.g., by a polymerase). In some embodiments, an identifier is located within or adjacent to an adaptor sequence. In some embodiments, an identifier is located within a portion of one or more primer hybridization sequences. A identifier may permit the detection, identification, quantitation and/or tracing of (i) polynucleotides to which the identifier is attached or incorporated (e.g., a labeled or tagged oligonucleotide, a labeled or tagged primer or extension product thereof), (ii) a polynucleotide to which a labeled or tagged polynucleotide hybridizes, and/or (iii) a polynucleotide to which a labeled or tagged polynucleotide is ligated to.

Any suitable type and/or number of identifiers can be used (e.g., for multiplexing). In some embodiments 1 or more, 2 or more, 3 or more, 4 or more, 5 or more, 6 or more, 7 or more, 8 or more, 9 or more, 10 or more, 20 or more, 30 or more or 50 or more different (e.g., distinguishable) identifiers are utilized in a method described herein (e.g., a nucleic acid detection, quantitation and/or sequencing method). In some embodiments, one, two, three or more identifiers are associated with a nucleic acid or a subset of nucleic acids.

In some embodiments identifiers (e.g., sequence tags, labels) are chromosome-specific, locus specific, or gene specific. In some embodiments a locus-specific identifier is used to analyze (e.g., identify, quantitate, or the like) a suitable locus (e.g., hypomethylated region, hypomethylated nucleotides, SNPs, the like or a combination thereof) or a collection of loci that are the same or different. For example, a locus-specific sequence tag sometimes is a sequence of nucleic acids that is configured to selectively identify one specific target locus. In some embodiments a locus-specific identifier is configured to selectively identify two or more specific target loci.

In some embodiments, an analysis comprises analyzing (e.g., detecting, counting, sequencing, quantitating, processing counts, the like or combinations thereof) one or more identifiers. In some embodiments, a detection process includes detecting an identifier and sometimes not detecting other features (e.g., sequences) of a nucleic acid. In some embodiments, a counting process includes counting each identifier. In some embodiments, an identifier is the only feature of a nucleic acid that is detected, analyzed and/or counted.

Binding/Capture Agents

In some embodiments a method described herein involves the use of a binding agent and/or a capture agent (e.g., a binding pair). The term "binding agent" as used herein refers to any molecule (e.g., nucleic acid, protein, carbohydrate, lipid, the like or combination thereof) that specifically binds another molecule (e.g., a target molecule (e.g., an antigen), a binding partner). An binding agent "specifically binds" to a corresponding binding partner where the binding agent often has less than about 30%, 20%, 10%, 5% or 1% cross-reactivity with another agent. A binding agent and it's corresponding binding partner are often referred to collectively herein as a binding pair. In some embodiments a capture agent comprises a binding agent. In some embodiments a capture agent comprises a binding agent immobilized on a solid support or a binding agent configured to bind a solid support. In some embodiments a capture agent comprises a member of a binding pair immobilized on a solid support or a member of a binding pair configured to bind a solid support. In some embodiments a binding agent binds to a capture agent. In certain embodiments a binding agent is covalently linked to a capture agent or a member of a binding pair. For example, a binding agent may comprise an antibody covalently linked to biotin and a capture agent can comprise avidin immobilized on a solid support where the binding agent is configured to bind to the solid support. Non-limiting examples of binding pairs include, without limitation: avidin/biotin; an antibody/antigen; antibody/epitope; antibody/hapten; operator/repressor; nuclease/nucleotide; lectin/polysaccharide; steroid/steroid-binding protein; ligand/receptor; enzyme/substrate; Ig/protein A; Fc/protein A; Ig/protein G; Fc/protein G; Histidine polymers (e.g., a His tag) and heavy metals; a polynucleotide and its corresponding complement; the like or combinations thereof.

A binding agent and/or corresponding partners can be directly or indirectly coupled to a substrate or solid support. In some embodiments, a substrate or solid support is used to separate certain nucleic acid fragments (e.g., species of nucleic acid fragments, digested nucleic acid fragments) in a sample. Some methods involve binding partners where one partner is associated with an oligonucleotide and the other partner is associated with a solid support. In some instances, a single binding agent can be employed for the enrichment of certain nucleic acid fragments (e.g., digested nucleic acid fragments). In some instances, a combination of different binding agents may be employed for the enrichment of certain nucleic acid fragments (e.g., digested nucleic acid fragments). For example, at least 2, 3, 4, 5, 6, 7, 8, 9, 10, 11, 12, 13, 14, 15, 16, 17, 18, 19, 20, 25, 50, 75 or 100 different binding agents may be used for the enrichment of certain nucleic acid fragments (e.g., digested nucleic acid fragments).

Methods of separation are known in the art. Any suitable method of separation can be used. Non-limiting examples of separation methods include adsorption, centrifugation, chromatography (e.g., affinity chromatography, flow cytometry, various fluid separation methods (e.g., chip based separation), molecular size exclusion, the like or combinations thereof), crystallization, decantation, drying, electrophoresis, flotation, flocculation, filtration, dialysis, magnetic separation, precipitation (e.g., nucleic acid precipitation, immuno-precipitation, solid phase or solid support precipitation, or the like), sedimentation, gravity separation, sieving, the like or combinations thereof. A sample is often subjected to a separation process resulting in one or more separation products. In some embodiments two or more nucleic acid species (e.g., nucleic acid species fragments) are separated by an enrichment process. Non-limiting examples of a separation product comprises an isolated product, a purified or partially purified product, a fractionated product (e.g., an elution fraction, a flow though fraction), an immobilized product, an enriched product, the like or a combination thereof.

In some embodiments, a binding/capture agent is an antibody or a portion thereof, naturally occurring or synthetic (e.g., genetically engineered). Antibodies can be immunoglobulin molecules or immunologically active portions (e.g., binding fragments) of immunoglobulin molecules (e.g., molecules that contain an antigen binding site that specifically binds an antigen). Antibodies, portions thereof (e.g., binding portions), mutants or chimeras thereof can be expressed and/or isolated from any suitable biological organism or source. Non-limiting examples of binding/capture agents include monoclonal antibodies, polyclonal antibodies, Fabs, Fab', single chain antibodies, synthetic antibodies, DNA, RNA, aptamers (DNA/RNA), peptoids, zDNA, peptide nucleic acids (PNAs), locked nucleic acids (LNAs), lectins, synthetic or naturally occurring chemical compounds (including but not limited to drugs, labeling reagents), dendrimers, peptides, polypeptides, biotin, streptavidin, or combinations thereof. A variety of antibodies and antibody fragments can be generated for use as a specific binding agent. Antibodies sometimes are IgG, IgM, IgA, IgE, or an isotype thereof (e.g., IgG1, IgG2a, IgG2b or IgG3), sometimes are polyclonal or monoclonal, and sometimes are chimeric, humanized or bispecific versions of such antibodies. In some embodiments a binding/capture agent used herein is an antibody, or fragment thereof that specifically binds 5-methylcytosine. Polyclonal antibodies, monoclonal antibodies, fragments thereof, and variants thereof that bind specific antigens are commercially available, and methods for generating such antibodies are known.

A binding agent also can be a polypeptide or peptide. A polypeptide may include a sequence of amino acids, amino acid analogs, or peptidomimetics, typically linked by peptide bonds. The polypeptides may be naturally occurring, processed forms of naturally occurring polypeptides (such as by enzymatic digestion), chemically synthesized, or recombinant expressed. The polypeptides for use in a method herein may be chemically synthesized using standard techniques. Polypeptides may comprise D-amino acids (which are resistant to L-amino acid-specific proteases), a combination of D- and L-amino acids, beta amino acids, or various other designer or non-naturally occurring amino acids (e.g., beta-methyl amino acids, C alpha-methyl amino acids, N alpha-methyl amino acids, and the like) to convey special properties. Synthetic amino acids may include ornithine for lysine, and norleucine for leucine or isoleucine. In some instances, polypeptides can have peptidomimetic bonds, such as ester bonds, to prepare polypeptides with novel properties. Polypeptides also may include peptoids (N-substituted glycines), in which the side chains are appended to nitrogen atoms along the molecule's backbone, rather than to the alpha-carbons, as in amino acids.

In some embodiments a binding agent is a methyl-specific binding agent. In some embodiments a methyl-specific binding agent selectively and/or specifically (e.g., with high affinity) binds a methylated nucleotide (e.g., 5-methyl cytosine). In some embodiments a methyl-specific binding agent selectively and/or specifically binds a methylation site or locus that is unmethylated (e.g., unmethylated cytosine, unmethylated CpG). In some embodiments a methyl-specific binding agent is an antibody or portion thereof (e.g., a binding fragment thereof). In some embodiments a methyl-specific binding agent comprises a portion of an antibody (e.g., an Fc portion of an immunoglobulin). A methyl-specific binding agent can be an antibody that specifically binds a methylation site or locus that is methylated. A methyl-specific binding agent can be an antibody that specifically binds a hypermethylated locus. Non-limiting examples of antibodies that specifically bind methylated nucleic acid, hypermethylated nucleic acid and/or hypermethylated loci include anti-5-methylcytosine antibody, clone 33D3; anti-5-hydroxymethylcytosine (5hmC) antibody, clone HMC-MA01; anti-5-hydroxymethylcytosine antibody, clone AB3/63.3; anti-5-hydroxymethylcytosine (5hmC) antibody, clone HMC 31, the like or a combination thereof. In certain embodiments, a methyl-specific binding agent can be an antibody that specifically binds a methylation site that is not methylated (e.g., an unmethylated CpG). Often, a methyl-specific binding agent that specifically binds a methylation site that is unmethylated does not substantially bind to a methylation site that is methylated. In some embodiments a methyl-specific binding agent is not an antibody or binding fragment thereof. In some embodiments a methyl-specific binding agent comprises a methyl-specific binding protein (e.g., a methyl-binding domain protein) or a portion thereof. Any suitable methyl-specific binding protein, or portion thereof, can be used for a method described herein. Non-limiting examples of methyl-specific binding proteins include methyl CpG Binding Protein 2 (Rett Syndrome) (MECP2), Methyl-CpG-binding domain protein 1 (MBD1), Methyl-CpG-binding domain protein 2 (MBD2), Methyl-CpG-binding domain protein 4 (MBD4) and Methyl-CpG-binding domain proteins 5-12. Methyl-CpG-binding domain proteins that specifically bind methylated CpG can be isolated, purified or cloned and expressed from a suitable plant, animal, insect, yeast or prokaryote.

Solid Support

In some embodiments, a binding/capture agent can be linked directly or indirectly to a solid support (e.g., a substrate). In some embodiments, nucleic acid fragments are associated with a solid support, such as the solid supports described below, by one or more binding agents, such as the binding agents described herein. A solid support or substrate can be any physically separable solid to which a nucleic acid, protein, carbohydrate or binding agent can be directly or indirectly attached.

A solid support can be any shape (e.g., flat, concave, convex, a groove, a channel, a cylinder, a tube, a sphere (e.g., a bead)) or size, and can exist as a separate entity or as an integral part of an apparatus or machine (e.g., a collection of beads (e.g., beads in a column), membrane, microwell, matrix, cuvette, plate, vessel, plate, centrifuge tube, slide, chip, wafer, flow cell, the like, or combinations thereof. In some embodiments a solid support comprises a suitable surface, for example as provided by a suitable substrate (e.g., a microarray substrate, a chip). In some embodiments a solid support is a flow cell configured for use in a DNA sequencer. In some embodiments a solid support is configured for a massively parallel sequencing (MPS) method or configured for use in a massively parallel sequencing (MPS) apparatus, machine or device.

A solid support can comprise a suitable material, non-limiting examples of which include glass, borosilicate glass, silica, quartz, fused quartz, mica, silicon (Si), carbon (e.g., diamond) modified silicon, a suitable metal (e.g., gold, titanium, silver, brass, aluminum and the like), steel (e.g., a steel alloy), ceramic, germanium, graphite, plastic, dextran, semiconductor fabrics, high refractive index dielectrics, crystals, a suitable polymer such as (poly)tetrafluoroethylene, (poly)vinylidenedifluoride, polymethacrylate (PMA), polymethyl methacrylate (PMMA), polydimethylsiloxane (PDMS), polystyrene, polycarbonate, polyacrylamide, nylon, latex, cellulose (e.g., activated cellulose), the like or combinations thereof. In some embodiments a solid support comprises particles such as beads (e.g., paramagnetic beads, magnetic beads, microbeads, nanobeads), microparticles, and nanoparticles. Solid supports also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, coated beads or particles, other suitable chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidene difluoride (PVDF), and the like), polysaccharides, nylon or nitrocellulose, resins, silica or silica-based materials including silicon, silica gel, and modified silicon, Sephadex®, Sepharose®, agarose, carbon, metals (e.g., steel, gold, silver, aluminum, silicon and copper), inorganic glasses, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, other fibrous or stranded polymers, the like or combinations thereof. In some embodiments a solid support is a collection of particles. In some instances, the solid support or substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, the solid phase can be a collection of particles. In certain embodiments, the particles can comprise silica, and the silica may comprise silica dioxide. In some embodiments the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of $Fe^{2+}$ and $Fe^{3+}$).

In some embodiments a solid support is configured to immobilize a nucleic acid, protein, carbohydrate, a nucleic acid library, a reagent, binding agent, analyte, the like, combination thereof or portion thereof. In some embodiments a solid support comprises a plurality of molecules (e.g., proteins, nucleic acids, functional groups, binding agents, one or members of a binding pair, reactive chemical moieties, the like or combinations thereof). In certain embodiments a solid support comprises a plurality of oligonucleotides (e.g., primers) configured to capture a nucleic acid library or part thereof. In certain embodiments oligonucleotides are attached to a solid support at their 5' ends or at their 3'ends. In some embodiments attachment of an oligonucleotide to a solid support is reversible (e.g., by cleavage with a nuclease or restriction endonuclease). In some embodiments, a plurality of primers are attached or immobilized to a support at their 5' ends. In some embodiments, the 5' end of one or more primers immobilized on a support comprise a single stranded region of about 5 nucleotides to about 30 nucleotides.

In some embodiments a solid support comprises discrete locations (e.g., addresses, mapped locations) where target polynucleotide species are disposed. For example, in some embodiments a solid support may comprises target-specific oligonucleotides immobilized at discrete locations where the target-specific oligonucleotides are configured to capture and/or amplify specific target sequences (e.g., target polynucleotides). In some embodiments target polynucleotides may be amplified at discrete locations on a solid support and the location of the specific amplicons is known (e.g., mapped, e.g., identifiable with a suitable imaging device). In some embodiments amplifying target polynucleotides on a solid support generates cluster of amplified target polynucleotide species at discrete locations on the solid phase.

In some embodiments a nucleic acid library, or portion thereof is immobilized to a suitable solid support. The term "immobilized" as used herein means direct or indirect attachment to a solid support. In some embodiments the term "capture" as used herein refers to immobilization of a nucleic acid, protein, carbohydrate, analyte or reagent. Immobilization can be covalent or non-covalent. Immobilization can be permanent or reversible. In some embodiments immobilization comprises hybridization of complementary nucleic acid sequences. In some embodiments a plurality of oligonucleotides is complementary to one or more universal sequences or sequence tags integrated into a library of nucleic acids. In some embodiments a plurality of nucleic acids comprises specific nucleic acid sequences configured to hybridize, immobilize and/or capture nucleic acids comprising one or more specific loci (e.g., a hyper or hypo methylated locus). In some embodiments nucleic acids are immobilized by use of one or more binding agents (e.g., a binding protein or antibody) that bind specifically to a nucleic acid sequence, protein, carbohydrate, reagent, analyte or portion thereof. For example, a binding agent can specifically bind to and/or immobilize (e.g., capture) polynucleotides comprising specific nucleic acid sequences. In some embodiments a binding agent can specifically bind to and/or immobilize (e.g., capture) polynucleotides comprising specific nucleic acid sequences (e.g., CpG) with a specific methylation status (e.g., a methylated, unmethylated or partially methylated sequence).

Methylated Nucleotides and Polynucleotides

A methylated nucleotide or a methylated nucleotide base refers to the presence of a methyl moiety (e.g., a methyl group) on a nucleotide base, where the methyl moiety is not normally present in the nucleotide base. For example, cytosine can comprise a methyl moiety at position 5 of its pyrimidine ring and can be referred to herein as methylated or as methyl cytosine. Cytosine, in the absence of a 5-methyl group is not a methylated nucleotide and can be referred to herein as unmethylated. In another example, thymine contains a methyl moiety at position 5 of its pyrimidine ring, however, for purposes herein, thymine is not considered a methylated nucleotide. A "methylation site" as used herein refers to a location of a nucleotide (e.g., a cytosine) within a nucleic acid where the nucleotide is methylated or has the possibility of being methylated. For example the nucleic acid sequence CpG is a methylation site where the cytosine may or may not be methylated. Cytosine methylation may also occur at the methylation sites CHG and/or CHH (e.g., where H=A, T or C). Where the particular methylated or unmethylated nucleotide is not specified, "methylation status" (e.g., unmethylated, methylated, hypomethylated, hypermethylated) often refers to cytosine methylation.

In some embodiments a polynucleotide in a chromosome (e.g., a locus, a target polynucleotide) comprises one or more methylation sites. A polynucleotide (e.g., locus) of a chromosome often refers to a defined segment of a chromosome. In some embodiments a polynucleotide of a chromosome is defined by two flanking markers (e.g., chromosome locators or positions) or by distinct flanking nucleic acid sequences. In some embodiments a polynucleotide of a chromosome comprises a defined nucleic acid sequence (e.g., a SEQ ID Number). A polynucleotide of a chromosome can be any suitable length that is less than the total length of the chromosome. In some embodiments a polynucleotide of a chromosome comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 CpG methylation sites.

The term "methylation status," are used herein refers to the state of methylation (e.g., methylated, unmethylated, percent methylated, or the like) of one or more methylation sites on a polynucleotide (e.g., a nucleic acid, a target polynucleotide), a nucleic acid species or subset, or a genetic locus (e.g., a defined region on a chromosome). A methylation status can refer to a frequency of methylation, relative methylation, differential methylation, absolute methylation, a ratio or percentage of methylation, the like or a combination thereof. A genetic locus comprising one or more methylation sites is sometimes referred to herein as a methylation locus or loci. The term "methylation status" often refers to the amount or relative amount of methylated or unmethylated methylation sites on a polynucleotide, a nucleic acid species or subset, or locus. A "methylation status" sometimes refers to a relative state of methylation for a polynucleotide (e.g., a locus) between two nucleic acid subsets or samples (e.g., fetal nucleic acid compared to maternal nucleic acid). For example, a polynucleotide can be relatively more methylated in fetal than in maternal nucleic acid. The term "amount" as used herein can refer to a mean, average, median, mode or absolute amount (e.g., quantity, number, count, total, aggregate, sum, quota, group, size, mass, weight, volume, bulk, lot, quantum, moles, concentration, percentage, or the like).

A methylation status of a methylation site can be referred to as unmethylated or methylated, for example. Methylation status can be determined by any suitable method. A methylation site comprising a methylated nucleotide is referred to herein as methylated. A methylation site comprising an unmethylated nucleotide is referred to herein as unmethylated. Methylation status of a methylation site is often provided as a percent or ratio. In some embodiments a methylation status of a methylation site in a sample is a ratio of the quantity of the methylation sites that are methylated to either the amount of methylation sites that are unmethylated, or to the total number of sites. In some embodiments a methylation status of a methylation site in a sample is expressed as a percentage derived from the amount of methylation sites that are methylated to the total amount of methylation sites present in a sample or population of nucleic acid. For example, for a given sample, the methylation status for a methylation site can be 0.7 (e.g., 70%) indicating that 70% of polynucleotides containing the methylation site are methylated at the methylation site.

The methylation status of a polynucleotide can be referred to as unmethylated, methylated, hypomethylated (e.g., less methylated), hypermethylated (e.g., more methylated), or differentially methylated, for example. A polynucleotide comprising one or more methylated nucleotides can be referred to herein as methylated. For example methylated polynucleotides often comprise one or more methylated nucleotides. A polynucleotide that does not contain any methylated nucleotides is referred to herein as unmethylated. The methylation status of a polynucleotide can be determined by any suitable method. In some embodiments the methylation status of a polynucleotide is determined as an average, mean or median of the methylation status of all methylation sites within the polynucleotide for a given sample or population of nucleic acid. For example, the mean methylation status of a polynucleotide containing three methylation sites is 0.4 (40%) where the methylation status is 0.3 (30%) for the first site, 0.4 (40%) for the second site, and 0.45 (45%) for the third site.

In some embodiments a methylation site, polynucleotide (e.g., target polynucleotide) or locus (e.g., region) is differentially methylated between two or more samples (e.g., sources) or subsets of nucleic acids. A differentially methylated site or locus (e.g., a differentially methylated region (e.g., DMR)), sometimes refers to a difference in the methylation status of a methylation site, region or locus between two or more samples or subsets of nucleic acids (e.g., fetal derived ccf DNA verse maternal derived ccf DNA). In some embodiments a methylation status of a locus is determined as an average, mean or median of the methylation status of a locus obtained from multiple test subjects (e.g., multiple samples) derived from the same source (e.g., enriched fetal nucleic acid). For example a methylation status for a methylation locus can be determined as an average, mean or median of the methylation status of a locus of a first sample, second sample and third sample where all three samples were derived from a different test subject and all three samples were derived from the same source (e.g., enriched fetal nucleic acid). In the foregoing example the presence or absence of a differentially methylated locus can be determined by comparing the methylation status of the first methylation locus derived from multiple samples of a first source (e.g., multiple samples of enriched fetal nucleic acid) to the methylation status of the same methylation locus derived from multiple samples of a second source (e.g., maternal nucleic acid).

In some embodiments methylation sites or loci are determined as differentially methylated or not differentially methylated by a suitable statistical method.

Detecting and Quantifying Chromosomes, Polynucleotides, and Portions Thereof

The presence or absence of one or more fetal chromosomes (e.g., a number of copies of fetal chromosomes) can be detected by methods presented herein. Fetal chromosomes can be detected and/or quantified non-invasively by analyzing a test sample from a test subject using methods described herein. In certain embodiments some or all fetal chromosomes of a fetus are detected and/or quantified. In some embodiments the number of copies of one or more chromosomes, or copies of portions of one or more chromosomes in a fetus are determined and/or quantified. In some embodiments, one, two, three or four copies of a fetal chromosome, or portion thereof, are detected and/or quantified from a test sample (e.g., from ccf nucleic acid in a test sample). The term "quantify" or "quantifying" as used herein refers to a process comprising determining the amount of a certain chromosome, polynucleotide, target polynucleotide, amplicon, competitor oligonucleotide, extension product, read, primer, or any suitable nucleic acid or identifier.

A method of detecting and/or quantifying the amount of copies of a fetal chromosome often comprises determining the amount of one or more target polynucleotides. Target polynucleotides are polynucleotides (e.g., nucleic acids) that are located within a portion of a chromosome (e.g., a polynucleotide of a chromosome, e.g., a loci of a chromosome). In some embodiments a target polynucleotide is located within a selected portion (e.g., a selected polynucleotide, DMR, selected loci) of a chromosome. Target polynucleotides can be in any suitable polynucleotide (e.g., polynucleotide portion of a chromosome, e.g., a locus) in a chromosome. The meaning of a target polynucleotides being "in" a particular polynucleotide in a chromosome is that a target polynucleotide is generally a subsequence of a particular polynucleotide in a chromosome. Target polynucleotides can be selected from any suitable portion of a polynucleotide in a chromosome (e.g., a DMR listed in Table 1A and Table 1B). Target polynucleotides can be selected by a suitable method, software or algorithm. In some embodiments target polynucleotides are suitable regions in a polynucleotide that can be amplified by a selected primer pair. In some embodiments target polynucleotides are selected using available software, that, when provided with a specified polynucleotide sequence in a chromosome, generate primer pairs that are configured to amplify a plurality of suitable target polynucleotides located in the specified polynucleotide sequence.

One or more target polynucleotides can be in a polynucleotide in chromosome. Two or more target polynucleotides in a polynucleotide of a chromosome may overlap, may be adjacent (e.g., end to end), or may be separated by one or more nucleotides bases. Target polynucleotides can be single stranded or double stranded. Either strand of a nucleic acid (e.g. polynucleotide in a chromosome) can be targeted for detecting the amount of a polynucleotide. One strand sometimes is targeted for a subset of regions and the other strand sometimes is targeted for the remaining regions in an assay, and sometimes one strand is targeted for all regions in an assay. In some embodiment, a target polynucleotide sequence is known. In some embodiments, a target polynucleotide sequence, or portion thereof, is unknown. Non-limiting examples of target polynucleotides and/or amplicon sequences generated for quantification of target polynucleotides are provided in Table 1A and Table 1B according to the start (Amp Start) and stop (Amp Stop) positions for primers within the human chromosomes indicated in Table 1A for each assay. In some embodiments target polynucleotides are in polynucleotides in chromosomes 13, 18 and 21.

Detecting the number of copies of a fetal chromosome, or portions thereof, in some embodiments, comprises determining the amount of one or more target polynucleotides in a polynucleotide (e.g. DMR, e.g., a DMR listed in Table 1A) in a chromosome. In some embodiments the amount of 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 32 or more, 34 or more, 36 or more, 38 or more, 40 or more, 42 or more, 44 or more, 46 or more, 48 or more, or 50 or more target polynucleotides within a particular chromosome are determined. In certain embodiments the amount of 1 to 50, 1 to 40, 1 to 30, 1 to 20, 1 to 15, 1 to 10, or 1 to 5 target polynucleotides are determined. In some embodiments, the amount of 20, 19, 18, 17, 16, 15, 14, 13, 12, 11, 10, 9, 8, 7, 6, 5, 4, 3, or 2 target polynucleotides are determined in a particular chromosome. In some embodiments the amount of one or more target polynucleotides in 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 32 or more, 34 or more, 36 or more, 38 or more, 40 or more, 42 or more, 44 or more, 46 or more, 48 or more, or 50 or more chromosome polynucleotides within a particular chromosome are determined. In certain embodiments the amount of one or more target polynucleotides in 1 to 50, 1 to 40, 1 to 30, 1 to 20, 1 to 15, 1 to 10, or 1 to 5 chromosome polynucleotides in a particular chromosome are determined. In some embodiments, the amount of one or more target polynucleotides in 20, 19, 18, 17, 16, 15, 14, 13, 12, 11, 10, 9, 8, 7, 6, 5, 4, 3, or 2 chromosome polynucleotides are determined in a particular chromosome. The amount of one target polynucleotide per chromosome polynucleotide often is determined, and for certain chromosome polynucleotides, two or more target polynucleotides per chromosome polynucleotide sometimes is determined (e.g., 2, 3, 4, 5, 6, 7, 8, 9 or 10 target polynucleotides in a chromosome polynucleotide). Certain non-limiting examples of chromosome polynucleotides within chromosomes 13, 18 and 21 are described in Table 1A (DMR column) and Table 1B (DMR start and DMR end columns).

A chromosome polynucleotide in a chromosome often represents a selected portion of a chromosome, which sometimes is a differentially methylated region (DMR) described herein. The meaning of a chromosome polynucleotide being "in" a particular chromosome is that a chromosome polynucleotide generally is a subsequence within a particular chromosome. Chromosome polynucleotides presented herein (e.g., Table 1A and 1B) often are predetermined according to one or more features, non-limiting examples of which include methylation status in fetal and maternal nucleic acid (e.g., differentially methylated loci), length, number, frequency and/or spacing of one or more methylation sensitive restriction endonuclease sites, number, frequency and/or spacing of methylation sites, presence or absence of polymorphisms, number and/or density of genes and/or certain empirical data (e.g., ability to reproducibly generate amplicons). Selected chromosome polynucleotides (e.g., DMRs) in chromosomes 13, 18 and 21 are provided in Table 1A. A target polynucleotide generally is a subsequence of a chromosome polynucleotide, which often includes or is flanked by specific amplification primers that can specifically hybridize to a chromosome polynucleotide or complement thereof, or to a sequence that flanks a chromosome polynucleotide or complement thereof. A chromosome polynucleotide in a chromosome and/or a target polynucleotide can be single stranded or double stranded. A chromosome polynucleotide in a chromosome and/or a target polynucleotide can be the sense and/or anti-sense strand of a chromosome. A chromosome polynucleotide in a chromosome and/or a target polynucleotide can be a reverse complement of a sequence provided by Table 1A or Table 1B.

Detecting the number of copies of one or more fetal chromosomes, or portions thereof, in some embodiments, comprises determining the amount of one or more target polynucleotides in a polynucleotide in chromosome 13. Detecting the number of copies of one or more fetal chromosomes, or portions thereof, in some embodiments, comprises determining the amount of one or more target polynucleotides in a polynucleotide in chromosome 13 where the polynucleotides in chromosome 13 are chosen from SEQ ID NOs: 193-215 or a complement thereof. In some embodiments, the polynucleotides in chromosome 13 consist of SEQ ID NOs: 193-215 or a complement thereof. In some embodiments, the polynucleotides in chromosome 13 are selected from SEQ ID NOs: 193-198, 200-204, 206, 208-210, 212-215 or a complement thereof.

Detecting the number of copies of one or more fetal chromosomes, or portions thereof, in some embodiments, comprises determining the amount of one or more target polynucleotides in a polynucleotide in chromosome 18. Detecting the number of copies of one or more fetal chromosomes, or portions thereof, in some embodiments, comprises determining the amount of one or more target polynucleotides in a polynucleotide in chromosome 18 where the polynucleotides in chromosome 18 are chosen from SEQ ID NOs: 216-232 or a complement thereof. In some embodiments, the polynucleotides in chromosome 18 consist of SEQ ID NOs: 216-232 or a complement thereof. In some embodiments, the polynucleotides in chromosome 18 are selected from SEQ ID NOs: 216-218, 220-230, 232 or a complement thereof.

Detecting the number of copies of one or more fetal chromosomes, or portions thereof, in some embodiments, comprises determining the amount of one or more target polynucleotides in a polynucleotide in chromosome 21. Detecting the number of copies of one or more fetal chromosomes, or portions thereof, in some embodiments, comprises determining the amount of one or more target polynucleotides in a polynucleotide in chromosome 21 where the polynucleotides in chromosome 21 are chosen from SEQ ID NOs: 233-256 or a complement thereof. In some embodiments, the polynucleotides in chromosome 21 consist of SEQ ID NOs: 233-256 or a complement thereof. In some embodiments, the polynucleotides in chromosome 21 are selected from SEQ ID NOs: 234, 236, 238-240, 242-246, 248-253, 255, 256 or a complement thereof.

Target polynucleotides are often detected and/or quantitated by a process comprising nucleic acid amplification. Target polynucleotides can be amplified by contacting target polynucleotides with one or more primers or primer pairs under amplification conditions. Any suitable primer pair can be used to amplify a target polynucleotide. Examples of primers are provided in Table 1 for amplifying specific target polynucleotides. A primer in Table 1 can be substituted with an oligonucleotide comprising a nucleotide sequence that is substantially identical to the primer in Table 1. A substantially identical primer can be used effectively for a method or kit provided herein. Substantially identical nucleotide sequences generally comprise about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity. Primers used for methods and kits here can also comprise sequence tags, sequence identifiers, universal hybridization sequences, one or more identifiers or binding agents, or mismatched nucleotide bases that generally are not configured to hybridize to a target polynucleotide.

In some embodiments target polynucleotides are amplified in a reaction comprising a competitor oligonucleotide. A competitor oligonucleotide (e.g., a competitor) is a polynucleotide that comprises a nucleic acid sequence that is identical or substantially identical to a target polynucleotide. A competitor oligonucleotide often comprises at least one distinguishing feature that is different than a target polynucleotide to which the competitor is identical to, or substantially identical to. A distinguishing feature can be a suitable identifier. In some embodiments, a distinguishing feature is one or more nucleotide base substitutions within the competitor that differentiates the competitor from its corresponding target polynucleotide. In certain embodiments, a distinguishing feature is a single nucleotide base substitution. Target polynucleotides and their corresponding competitors can often be distinguished by a suitable detection method (e.g., by sequencing, mass spectrometry, fluorescence spectrometry, flow cytometry, the like or combinations thereof).

In certain embodiments target polynucleotide and competitor oligonucleotides are amplified together in the same reaction mixture. In some embodiment, target polynucleotides and competitor oligonucleotides are amplified using the same amplification conditions. A competitor and its corresponding target polynucleotide are often amplified using the same primers or primer set. In some embodiments the amount of a competitor polynucleotide is known. In certain embodiments a known amount of one or more competitors is contacted (e.g., mixed) with target polynucleotides and the amount of each competitor in the mixture (e.g., in an amplification reaction) is known. In some embodiments a known amount of one or more competitor oligonucleotides are contacted with a test sample comprising nucleic acid (e.g., ccf nucleic acid, e.g., target polynucleotides) and primers, under amplification conditions. In certain embodiments a known amount of one or more competitor oligonucleotides are contacted with primers and a test sample comprising cleaved and uncleaved target polynucleotides, under amplification conditions, where target specific and competitor specific amplicons are generated. Target specific amplicons are often generated from uncleaved target polynucleotides.

Target polynucleotides and/or competitors can be amplified using primer sets provided herein thereby providing amplicons (target specific amplicons, competitor specific amplicons). Amplicons of target polynucleotides and competitors can be detected and/or quantitated using a suitable method. In some embodiments a ratio of target specific amplicons to competitor specific amplicons is determined for a certain target polynucleotide and its corresponding competitor oligonucleotide. The amount of target polynucleotide in a mixture can often be determined according to a ratio of target specific amplicons to competitor specific amplicons when the amount of counterpart is known. For example, once a ratio value is determined, the amount of target polynucleotide in a sample can be ascertained, for example by multiplying the known amount of a competitor by the ratio value.

In some embodiments, target specific and competitor specific amplicons are further processed after an amplification reaction. Target specific and/or competitor specific amplicons can be contacted with one or more extension oligonucleotides (e.g., extension primers) under conditions in which the extension oligonucleotides anneal to the amplicons and are extended by one or more nucleotides, sometimes referred to herein as extension conditions. Any suitable extension condition can be used to perform an extension resulting in the production of extension products (e.g., polynucleotides resulting from an extension reaction). In some embodiments a sample comprising target polynucleotides is contacted with one or more target specific extension primers under extension conditions where target specific extension products are generated. Extension conditions often comprise a mixture of nucleic acid templates (e.g., amplicons), one or more extension oligonucleotides, a suitable polymerase and a suitable extension reaction mixture. Extension conditions can comprise a single extension primer species, or two or more target specific extension primers configured to hybridize to and extend from different target specific and/or competitor specific amplicons. An extension reaction (e.g., extension conditions) comprising a plurality of target specific extension primers configured to hybridize to and extend from different target specific and/or competitor specific amplicons is sometimes referred to herein as a multiplex reaction. Extension reaction mixtures can comprise a suitable buffer, suitable salts, nucleotide triphosphates and sometimes additional components, chemicals and co-factors necessary for polymerase activity. Components of an extension reaction mixture are often recommended by a manufacturer or supplier of a polymerase. In some embodiments, non-naturally occurring nucleotides or nucleotide analogs, such as analogs containing a detectable label (e.g., fluorescent or colorimetric label), may be used for example. Polymerases can be selected by a skilled reader and can include any suitable polymerase used for thermocycle amplification and/or DNA modification (e.g., Klenow fragments, T4 polymerase, T7 polymerase, Pol I, Pol II, Pol III, or any other suitable natural or recombinant polymerase, combination or portion thereof).

An extension oligonucleotide is often configured to hybridize to a portion or all of an amplicon (e.g., a target specific and/or competitor specific amplicon). An extension oligonucleotide often comprise a portion that specifically hybridizes to a target specific and/or competitor specific amplicon (e.g., a hybridization sequence). A portion of an extension oligonucleotide (e.g., a hybridization sequence) is often identical to or substantially identical to the reverse complement of a portion of a target specific and/or competitor specific amplicon. An extension oligonucleotide can sometimes hybridize to a portion of a target specific amplicon and/or to an identical or substantially identical portion of a corresponding competitor specific amplicon. In some embodiments an extension primer, or a portion thereof, can comprise additional components, nucleotides or nucleic acid sequence that does not hybridize to an amplicon (e.g., an amplicon for which the extension primer is configured to hybridize to). For example an extension primer can comprise of an identifier, label, binding agent, the like or combinations thereof. Any suitable extension primer can be used to generate an extension product from a specific amplicon. Extension primer can be designed by a skilled read and/or can be designed by a suitable software or algorithm for a give amplicon template. Examples of extension oligonucleotides that are suitable for generating extension products for target specific and competitor specific amplicons are provided in Table 1. Any extension primer in Table 1 can be substituted with a suitable oligonucleotide comprising a nucleotide sequence that is substantially identical to an extension primer in Table 1 for use in the methods or kits described herein.

Extension products of an extension reaction can be detected and/or quantitated by a suitable method. In some embodiments extension products are detected and/or quantitated by a process comprising nucleic acid sequencing. In some embodiments extension products are detected and/or quantitated by a process comprising mass spectrometry (e.g., MALDI mass spectrometry). Extension products often comprise an extended portion (e.g., a nucleic acid portion that is extended by a polymerase) that is identical or substantially identical to the reverse complement of its corresponding template (e.g., target specific amplicon or target specific competitor). Extension products generated from a target specific amplicon and its corresponding (e.g., substantially identical) target specific competitor are often different and distinguishable. A target specific amplicon and its corresponding (e.g., substantially identical) target specific competitor can often be differentiated according to a distinguishing feature that originates in the nucleic acid sequence of a competitor. For example a specific competitor may comprise a single nucleotide substitution which is replicated in a competitor specific amplicon, and which is subsequently replicated in the extension product generated from the competitor amplicon. Therefore extension products derived from a target specific amplicon and its corresponding (e.g., substantially identical) target specific competitor can be independently detected and quantitated using a method described herein.

In some embodiments the amount of one or more extension products is quantified and the amount, or relative amount, of each extension product is used to determine the amount of a target polynucleotide. In some embodiments the amount of an extension product is used to determine the amount of an amplicon from which the extension product was generated. In some embodiments a ratio of two extension products is used to determine the amount of a target polynucleotide, for example where a first extension product is derived from a target specific amplicon and a second extension product is derived from a competitor specific amplicon.

Tables 1A and 1B provide examples of nucleic acids useful for incorporation into kits and for conducting assays for methods described herein. Each assay can be identified in Table 1A and 1B by a unique reference number (IPLEX ID). Each assay may comprise one or more of: a first primer (Primer 1), a second primer (Primer 2), an extension primer (Ext. Primer), a competitor oligonucleotide (Competitor) and a chromosome polynucleotide (i.e., differentially methylated region (DMR)) located in the indicated chromosome (Chr.). Examples of chromosome polynucleotides (DMR, e.g., chromosome 13 polynucleotides, chromosome 18 polynucleotides and chromosome 21 polynucleotides) within chromosomes 13 (chr13), 18 (chr18) and 21 (chr21) are provided in Table 1A and Table 1B. The location and/or position (DMR Start/DMR End) of each chromosome polynucleotide (DMR) in the indicated human chromosome (Chr.) is provided in Table 1B. Primers (Primer 1, Primer 2) and extension primers (Ext. Primer) provided in Table 1A are configured for hybridizing to a target polynucleotide in each specified chromosome polynucleotide (DMR), and the sequence of each primer and extension polynucleotide is provided in the same assay row. In some embodiments oligonucleotides of Primer 1 and Primer 2 are an example of a primer pair configured for amplification of a target polynucleotide located in the indicated chromosome polynucleotide (DMR). The location and/or position (Amp Start/Amp End) of each example of a target polynucleotide for an assay is provided in Table 1B. Final 52 Assay indicates a set of 52 assays that can be conducted together in a multiplex format. Final 64 Assay indicates a set of 64 assays that can be conducted together in a multiplex format. Information and sequences provided in Tables 1A and 1B are according to the Genome Reference Consortium Human Build hg19/GRCh37.

TABLE 1A

| IPLEX ID | Chr. | Primer 1 | Primer 2 | Ext. Primer | Competitor | DMR |
|---|---|---|---|---|---|---|
| 49 | chr13 | SEQ ID NO: 1 | SEQ ID NO: 65 | SEQ ID NO: 129 | SEQ ID NO: 257 | SEQ ID NO: 193 |
| 53 | chr13 | SEQ ID NO: 2 | SEQ ID NO: 66 | SEQ ID NO: 130 | SEQ ID NO: 258 | SEQ ID NO: 194 |
| 101 | chr13 | SEQ ID NO: 3 | SEQ ID NO: 67 | SEQ ID NO: 131 | SEQ ID NO: 259 | SEQ ID NO: 195 |
| 103 | chr13 | SEQ ID NO: 4 | SEQ ID NO: 68 | SEQ ID NO: 132 | SEQ ID NO: 260 | SEQ ID NO: 196 |
| 78 | chr13 | SEQ ID NO: 5 | SEQ ID NO: 69 | SEQ ID NO: 133 | SEQ ID NO: 261 | SEQ ID NO: 197 |
| 137 | chr13 | SEQ ID NO: 6 | SEQ ID NO: 70 | SEQ ID NO: 134 | SEQ ID NO: 262 | SEQ ID NO: 198 |
| 180 | chr13 | SEQ ID NO: 7 | SEQ ID NO: 71 | SEQ ID NO: 135 | SEQ ID NO: 263 | SEQ ID NO: 199 |
| 54 | chr13 | SEQ ID NO: 8 | SEQ ID NO: 72 | SEQ ID NO: 136 | SEQ ID NO: 264 | SEQ ID NO: 200 |
| 95 | chr13 | SEQ ID NO: 9 | SEQ ID NO: 73 | SEQ ID NO: 137 | SEQ ID NO: 265 | SEQ ID NO: 201 |
| 200 | chr13 | SEQ ID NO: 10 | SEQ ID NO: 74 | SEQ ID NO: 138 | SEQ ID NO: 266 | SEQ ID NO: 202 |
| 123 | chr13 | SEQ ID NO: 11 | SEQ ID NO: 75 | SEQ ID NO: 139 | SEQ ID NO: 267 | SEQ ID NO: 203 |
| 6 | chr13 | SEQ ID NO: 12 | SEQ ID NO: 76 | SEQ ID NO: 140 | SEQ ID NO: 268 | SEQ ID NO: 204 |
| 70 | chr13 | SEQ ID NO: 13 | SEQ ID NO: 77 | SEQ ID NO: 141 | SEQ ID NO: 269 | SEQ ID NO: 205 |
| 9 | chr13 | SEQ ID NO: 14 | SEQ ID NO: 78 | SEQ ID NO: 142 | SEQ ID NO: 270 | SEQ ID NO: 206 |
| 63 | chr13 | SEQ ID NO: 15 | SEQ ID NO: 79 | SEQ ID NO: 143 | SEQ ID NO: 271 | SEQ ID NO: 207 |
| 65 | chr13 | SEQ ID NO: 16 | SEQ ID NO: 80 | SEQ ID NO: 144 | SEQ ID NO: 272 | SEQ ID NO: 208 |
| 13 | chr13 | SEQ ID NO: 17 | SEQ ID NO: 81 | SEQ ID NO: 145 | SEQ ID NO: 273 | SEQ ID NO: 209 |
| 129 | chr13 | SEQ ID NO: 18 | SEQ ID NO: 82 | SEQ ID NO: 146 | SEQ ID NO: 274 | SEQ ID NO: 210 |
| 138 | chr13 | SEQ ID NO: 19 | SEQ ID NO: 83 | SEQ ID NO: 147 | SEQ ID NO: 275 | SEQ ID NO: 211 |
| 61 | chr13 | SEQ ID NO: 20 | SEQ ID NO: 84 | SEQ ID NO: 148 | SEQ ID NO: 276 | SEQ ID NO: 212 |
| 104 | chr13 | SEQ ID NO: 21 | SEQ ID NO: 85 | SEQ ID NO: 149 | SEQ ID NO: 277 | SEQ ID NO: 213 |
| 17 | chr13 | SEQ ID NO: 22 | SEQ ID NO: 86 | SEQ ID NO: 150 | SEQ ID NO: 278 | SEQ ID NO: 214 |
| 146 | chr13 | SEQ ID NO: 23 | SEQ ID NO: 87 | SEQ ID NO: 151 | SEQ ID NO: 279 | SEQ ID NO: 215 |

TABLE 1A-continued

| IPLEX ID | Chr. | Primer 1 | Primer 2 | Ext. Primer | Competitor | DMR |
|---|---|---|---|---|---|---|
| 202 | chr18 | SEQ ID NO: 24 | SEQ ID NO: 88 | SEQ ID NO: 152 | SEQ ID NO: 280 | SEQ ID NO: 216 |
| 68 | chr18 | SEQ ID NO: 25 | SEQ ID NO: 89 | SEQ ID NO: 153 | SEQ ID NO: 281 | SEQ ID NO: 217 |
| 188 | chr18 | SEQ ID NO: 26 | SEQ ID NO: 90 | SEQ ID NO: 154 | SEQ ID NO: 282 | SEQ ID NO: 218 |
| 133 | chr18 | SEQ ID NO: 27 | SEQ ID NO: 91 | SEQ ID NO: 155 | SEQ ID NO: 283 | SEQ ID NO: 219 |
| 116 | chr18 | SEQ ID NO: 28 | SEQ ID NO: 92 | SEQ ID NO: 156 | SEQ ID NO: 284 | SEQ ID NO: 220 |
| 19 | chr18 | SEQ ID NO: 29 | SEQ ID NO: 93 | SEQ ID NO: 157 | SEQ ID NO: 285 | SEQ ID NO: 221 |
| 83 | chr18 | SEQ ID NO: 30 | SEQ ID NO: 94 | SEQ ID NO: 158 | SEQ ID NO: 286 | SEQ ID NO: 222 |
| 106 | chr18 | SEQ ID NO: 31 | SEQ ID NO: 95 | SEQ ID NO: 159 | SEQ ID NO: 287 | SEQ ID NO: 223 |
| 85 | chr18 | SEQ ID NO: 32 | SEQ ID NO: 96 | SEQ ID NO: 160 | SEQ ID NO: 288 | SEQ ID NO: 224 |
| 107 | chr18 | SEQ ID NO: 33 | SEQ ID NO: 97 | SEQ ID NO: 161 | SEQ ID NO: 289 | SEQ ID NO: 225 |
| 23 | chr18 | SEQ ID NO: 34 | SEQ ID NO: 98 | SEQ ID NO: 162 | SEQ ID NO: 290 | SEQ ID NO: 226 |
| 102 | chr18 | SEQ ID NO: 35 | SEQ ID NO: 99 | SEQ ID NO: 163 | SEQ ID NO: 291 | SEQ ID NO: 227 |
| 108 | chr18 | SEQ ID NO: 36 | SEQ ID NO: 100 | SEQ ID NO: 164 | SEQ ID NO: 292 | SEQ ID NO: 228 |
| 186 | chr18 | SEQ ID NO: 37 | SEQ ID NO: 101 | SEQ ID NO: 165 | SEQ ID NO: 293 | SEQ ID NO: 229 |
| 60 | chr18 | SEQ ID NO: 38 | SEQ ID NO: 102 | SEQ ID NO: 166 | SEQ ID NO: 294 | SEQ ID NO: 230 |
| 76 | chr18 | SEQ ID NO: 39 | SEQ ID NO: 103 | SEQ ID NO: 167 | SEQ ID NO: 295 | SEQ ID NO: 231 |
| 185 | chr18 | SEQ ID NO: 40 | SEQ ID NO: 104 | SEQ ID NO: 168 | SEQ ID NO: 296 | SEQ ID NO: 232 |
| 162 | chr21 | SEQ ID NO: 41 | SEQ ID NO: 105 | SEQ ID NO: 169 | SEQ ID NO: 297 | SEQ ID NO: 233 |
| 114 | chr21 | SEQ ID NO: 42 | SEQ ID NO: 106 | SEQ ID NO: 170 | SEQ ID NO: 298 | SEQ ID NO: 234 |
| 115 | chr21 | SEQ ID NO: 43 | SEQ ID NO: 107 | SEQ ID NO: 171 | SEQ ID NO: 299 | SEQ ID NO: 235 |
| 159 | chr21 | SEQ ID NO: 44 | SEQ ID NO: 108 | SEQ ID NO: 172 | SEQ ID NO: 300 | SEQ ID NO: 236 |
| 160 | chr21 | SEQ ID NO: 45 | SEQ ID NO: 109 | SEQ ID NO: 173 | SEQ ID NO: 301 | SEQ ID NO: 237 |
| 34 | chr21 | SEQ ID NO: 46 | SEQ ID NO: 110 | SEQ ID NO: 174 | SEQ ID NO: 302 | SEQ ID NO: 238 |
| 96 | chr21 | SEQ ID NO: 47 | SEQ ID NO: 111 | SEQ ID NO: 175 | SEQ ID NO: 303 | SEQ ID NO: 239 |
| 135 | chr21 | SEQ ID NO: 48 | SEQ ID NO: 112 | SEQ ID NO: 176 | SEQ ID NO: 304 | SEQ ID NO: 240 |
| 167 | chr21 | SEQ ID NO: 49 | SEQ ID NO: 113 | SEQ ID NO: 177 | SEQ ID NO: 305 | SEQ ID NO: 241 |
| 38 | chr21 | SEQ ID NO: 50 | SEQ ID NO: 114 | SEQ ID NO: 178 | SEQ ID NO: 306 | SEQ ID NO: 242 |
| 39 | chr21 | SEQ ID NO: 51 | SEQ ID NO: 115 | SEQ ID NO: 179 | SEQ ID NO: 307 | SEQ ID NO: 243 |
| 40 | chr21 | SEQ ID NO: 52 | SEQ ID NO: 116 | SEQ ID NO: 180 | SEQ ID NO: 308 | SEQ ID NO: 244 |
| 140 | chr21 | SEQ ID NO: 53 | SEQ ID NO: 117 | SEQ ID NO: 181 | SEQ ID NO: 309 | SEQ ID NO: 245 |
| 42 | chr21 | SEQ ID NO: 54 | SEQ ID NO: 118 | SEQ ID NO: 182 | SEQ ID NO: 310 | SEQ ID NO: 246 |
| 169 | chr21 | SEQ ID NO: 55 | SEQ ID NO: 119 | SEQ ID NO: 183 | SEQ ID NO: 311 | SEQ ID NO: 247 |
| 44 | chr21 | SEQ ID NO: 56 | SEQ ID NO: 120 | SEQ ID NO: 184 | SEQ ID NO: 312 | SEQ ID NO: 248 |
| 150 | chr21 | SEQ ID NO: 57 | SEQ ID NO: 121 | SEQ ID NO: 185 | SEQ ID NO: 313 | SEQ ID NO: 249 |
| 153 | chr21 | SEQ ID NO: 58 | SEQ ID NO: 122 | SEQ ID NO: 186 | SEQ ID NO: 314 | SEQ ID NO: 250 |
| 45 | chr21 | SEQ ID NO: 59 | SEQ ID NO: 123 | SEQ ID NO: 187 | SEQ ID NO: 315 | SEQ ID NO: 251 |
| 155 | chr21 | SEQ ID NO: 60 | SEQ ID NO: 124 | SEQ ID NO: 188 | SEQ ID NO: 316 | SEQ ID NO: 252 |
| 46 | chr21 | SEQ ID NO: 61 | SEQ ID NO: 125 | SEQ ID NO: 189 | SEQ ID NO: 317 | SEQ ID NO: 253 |
| 163 | chr21 | SEQ ID NO: 62 | SEQ ID NO: 126 | SEQ ID NO: 190 | SEQ ID NO: 318 | SEQ ID NO: 254 |
| 47 | chr21 | SEQ ID NO: 63 | SEQ ID NO: 127 | SEQ ID NO: 191 | SEQ ID NO: 319 | SEQ ID NO: 255 |
| 164 | chr21 | SEQ ID NO: 64 | SEQ ID NO: 128 | SEQ ID NO: 192 | SEQ ID NO: 320 | SEQ ID NO: 256 |

TABLE 1B

| IPLEX ID | DMR Start | DMR End | Final 64 Assay | Final 52 Assay | Amp Start | Amp End |
|---|---|---|---|---|---|---|
| 49 | 28498680 | 28499290 | 1 | 1 | 28498889 | 28498946 |
| 53 | 29105141 | 29105830 | 1 | 1 | 29105636 | 29105699 |
| 101 | 33002061 | 33003102 | 1 | 1 | 33002224 | 33002290 |
| 103 | 33002061 | 33003102 | 1 | 1 | 33002389 | 33002463 |
| 78 | 43148292 | 43149272 | 1 | 1 | 43149151 | 43149229 |
| 137 | 43148292 | 43149272 | 1 | 1 | 43148630 | 43148708 |
| 180 | 43148292 | 43149272 | 1 | 0 | 43148676 | 43148731 |
| 54 | 70681596 | 70682349 | 1 | 1 | 70682100 | 70682160 |
| 95 | 93879909 | 93880819 | 1 | 1 | 93880426 | 93880488 |
| 200 | 100084740 | 100085374 | 1 | 1 | 100085223 | 100085302 |
| 123 | 100310242 | 100311033 | 1 | 1 | 100310555 | 100310630 |
| 6 | 100547250 | 100547908 | 1 | 1 | 100547824 | 100547908 |
| 70 | 100621001 | 100621697 | 1 | 0 | 100621384 | 100621463 |
| 9 | 102568511 | 102568872 | 1 | 1 | 102568788 | 102568856 |
| 63 | 109148608 | 109149254 | 1 | 0 | 109148845 | 109148920 |
| 65 | 109148608 | 109149254 | 1 | 1 | 109148779 | 109148857 |
| 13 | 112707658 | 112711587 | 1 | 1 | 112711342 | 112711431 |
| 129 | 112707658 | 112711587 | 1 | 1 | 112710442 | 112710499 |
| 138 | 112707658 | 112711587 | 1 | 0 | 112708019 | 112708095 |
| 61 | 112715162 | 112716339 | 1 | 1 | 112715694 | 112715757 |
| 104 | 112723178 | 112724441 | 1 | 1 | 112723301 | 112723369 |
| 17 | 112757946 | 112761434 | 1 | 1 | 112761032 | 112761087 |
| 146 | 113807380 | 113807864 | 1 | 1 | 113807443 | 113807522 |
| 202 | 906368 | 907244 | 1 | 1 | 906982 | 907059 |
| 68 | 11148397 | 11149031 | 1 | 1 | 11148446 | 11148525 |
| 188 | 11148397 | 11149031 | 1 | 1 | 11148747 | 11148806 |
| 133 | 12911201 | 12912128 | 1 | 0 | 12911321 | 12911389 |
| 116 | 31803130 | 31804139 | 1 | 1 | 31803728 | 31803806 |

TABLE 1B-continued

| IPLEX ID | DMR Start | DMR End | Final 64 Assay | Final 52 Assay | Amp Start | Amp End |
|---|---|---|---|---|---|---|
| 19 | 32956375 | 32957367 | 1 | 1 | 32956646 | 32956720 |
| 83 | 32956375 | 32957367 | 1 | 1 | 32956995 | 32957061 |
| 106 | 32956375 | 32957367 | 1 | 1 | 32956636 | 32956692 |
| 85 | 49866574 | 49867697 | 1 | 1 | 49866584 | 49866648 |
| 107 | 55094805 | 55096737 | 1 | 1 | 55095558 | 55095635 |
| 23 | 55104995 | 55106507 | 1 | 1 | 55105645 | 55105723 |
| 102 | 55104995 | 55106507 | 1 | 1 | 55106421 | 55106496 |
| 108 | 55104995 | 55106507 | 1 | 1 | 55106166 | 55106225 |
| 186 | 56935174 | 56935836 | 1 | 1 | 56935489 | 56935547 |
| 60 | 56939161 | 56940153 | 1 | 1 | 56939560 | 56939624 |
| 76 | 77558297 | 77559328 | 1 | 0 | 77558686 | 77558763 |
| 185 | 77558297 | 77559328 | 1 | 1 | 77558896 | 77558969 |
| 162 | 26934120 | 26935234 | 1 | 0 | 26934750 | 26934802 |
| 114 | 33783761 | 33784889 | 1 | 1 | 33784200 | 33784277 |
| 115 | 33783761 | 33784889 | 1 | 0 | 33783804 | 33783858 |
| 159 | 34394948 | 34396167 | 1 | 1 | 34395865 | 34395943 |
| 160 | 34394948 | 34396167 | 1 | 0 | 34395787 | 34395850 |
| 34 | 34398447 | 34399243 | 1 | 1 | 34398926 | 34399011 |
| 96 | 34400146 | 34400987 | 1 | 1 | 34400696 | 34400774 |
| 135 | 38076764 | 38077971 | 1 | 1 | 38076975 | 38077054 |
| 167 | 38076764 | 38077971 | 1 | 0 | 38077795 | 38077862 |
| 38 | 38078319 | 38079295 | 1 | 1 | 38078976 | 38079062 |
| 39 | 38080185 | 38081984 | 1 | 1 | 38080863 | 38080946 |
| 40 | 38080185 | 38081984 | 1 | 1 | 38081302 | 38081379 |
| 140 | 38082506 | 38083353 | 1 | 1 | 38082561 | 38082637 |
| 42 | 38629495 | 38630973 | 1 | 1 | 38630219 | 38630285 |
| 169 | 38629495 | 38630973 | 1 | 0 | 38630464 | 38630538 |
| 44 | 42213549 | 42214149 | 1 | 1 | 42213616 | 42213681 |
| 150 | 45592550 | 45593181 | 1 | 1 | 45592804 | 45592877 |
| 153 | 46128038 | 46129688 | 1 | 1 | 46129385 | 46129438 |
| 45 | 46131933 | 46132602 | 1 | 1 | 46132135 | 46132224 |
| 155 | 47392741 | 47393477 | 1 | 1 | 47393381 | 47393448 |
| 46 | 47717336 | 47717995 | 1 | 1 | 47717382 | 47717456 |
| 163 | 47717336 | 47717995 | 1 | 0 | 47717792 | 47717862 |
| 47 | 48086975 | 48087706 | 1 | 1 | 48087405 | 48087476 |
| 164 | 48086975 | 48087706 | 1 | 1 | 48087579 | 48087654 |

For assays conducted using a mass spectrometry readout (e.g., MALDI MS readout), a selection of amplification primers, competitor oligonucleotides and extension oligonucleotides from Table 1A can be utilized. For assays conducted using a sequencing readout (e.g., massively parallel sequencing readout), a selection of amplification primers and competitor oligonucleotides can be utilized.

Kits

Kits often comprise one or more containers that contain one or more components described herein. A kit comprises one or more components in any number of separate containers, packets, tubes, vials, multiwell plates and the like, or components may be combined in various combinations in such containers. One or more of the following components, for example, may be included in a kit: (i) one or more amplification primers for amplifying a nucleotide sequence species of a set, (ii) one or more extension primers for discriminating between amplified nucleic acid species or nucleotide sequence species of each set, (iii) a solid support for multiplex detection of amplified nucleic acid species or nucleotide sequence species of each set (e.g., a solid support that includes matrix for matrix-assisted laser desorption ionization (MALDI) mass spectrometry; (iv) reagents for detecting amplified nucleic acid species or nucleotide sequence species of each set; (vi) a detector for detecting the amplified nucleic acid species or nucleotide sequence species of each set (e.g., mass spectrometer); (vii) reagents and/or equipment for quantifying fetal nucleic acid in extracellular nucleic acid from a pregnant female; (viii) reagents and/or equipment for enriching fetal nucleic acid from extracellular nucleic acid from a pregnant female; (ix) software and/or a machine for analyzing signals resulting from a process for detecting the amplified nucleic acid species or nucleotide sequence species of the sets; (x) information for identifying presence or absence of a chromosome abnormality (e.g., a table or file that converts signal information or amounts into outcomes), (xi) equipment for drawing blood); (xii) equipment for generating cell-free blood; (xiii) reagents for isolating nucleic acid (e.g., DNA, RNA) from plasma, serum or urine; (xiv) reagents for stabilizing serum, plasma, urine or nucleic acid for shipment and/or processing.

A kit sometimes is utilized in conjunction with a process, and can include instructions for performing one or more processes and/or a description of one or more compositions. A kit may be utilized to carry out a process (e.g., using a solid support) described herein. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions (e.g., a URL for the World-Wide Web).

In some embodiments provided herein are one or more kits configured to conduct one or more assays described herein. In some embodiments an assay is configured for generating target specific and competitor specific amplicons from a target polynucleotide in a polynucleotide in a chromosome. In certain embodiments an assay is configured for generating extension products. One or more assays (e.g., a collection of assays) are often configured to detect and/or quantify one, two, three or four copies of a fetal chromosome, or portion thereof, in a test sample. Sometimes at least 100, at least 90, at least 80, at least 70, at least 65, at least 60, at least 55, at least 50, at least 40, at least 30 or at least 20 assays are configured to detect and/or quantify one, two, three or four copies of a fetal chromosome, or portion thereof, in a test sample. In some embodiments 70, 69, 68, 67, 66, 65, 64, 63, 62, 61, 59, 58, 57, 56, 55, 54, 53, 52, 51 or 50 assays are configured to detect and/or quantify one, two, three or four copies of a fetal chromosome, or portion thereof, in a test sample.

Provided herein, in some embodiments is a kit, comprising components needed to conduct one or more methods or assays described herein. A kit can comprise one or more primers configured for amplifying target polynucleotides. In some embodiments a kit comprises a collection of oligonucleotide primer pairs where each primer pair is configured for amplifying three or more target polynucleotides in each of chromosome 13, chromosome 18 and chromosome 21. In certain embodiments a kit comprises competitor oligonucleotides. In certain embodiments a kit comprises extension primers. In some embodiments a kit comprises competitor oligonucleotides and a collection of oligonucleotide primer pairs configured for amplifying three or more target polynucleotides in each of chromosome 13, chromosome 18 and chromosome 21 and their corresponding competitor oligonucleotides, and extension primers configured for generating extension products from target specific and competitor specific amplicons. Kits provided herein can optionally comprise one or more of the following: buffers (e.g., comprising salts and components required for polymerase activity), restriction enzymes, dNTPs, polymerases, instructions, tubes, trays, the like or combinations thereof. In some embodiments a kit comprises nucleic acid controls (e.g., ccf DNA obtained from a euploid test subject). In some embodiments a kit comprises components suitable for conducting 10 or more, 20 or more, 30 or more, 40 or more, 50 or more or 60 or more assays. In some embodiments a kit comprises components suitable for conducting 1-60, 1-50, 1-40, 1-30, 1-25, 1-20, 1-15, 1-10 or 1-5 assay. In some embodiments a kit comprises components suitable for conducting about 70, 69, 68, 67, 66, 65, 64, 63, 62, 61, 59, 58, 57, 56, 55, 54, 53, 52, 51 or 50 assays. Amplification primers, extension oligonucleotides and competitor oligonucleotides suitable for performing assays for 1-64, 1-60, 1-52, 1-50, 1-40, 1-30, 1-25, 1-20, 1-15, 1-10 or 1-5 assays are provided in Table 1A.

Determining Fetal Nucleic Acid Content

In some embodiments an analysis (e.g., an analysis of nucleic acids) comprises determining an amount of fetal nucleic acid in a nucleic acid sample. An amount of fetal nucleic acid (e.g., concentration, relative amount, ratio, absolute amount, copy number, and the like) in nucleic acid (e.g., a nucleic acid sample or mixture) is determined in some embodiments. In some embodiments, the amount of fetal nucleic acid in a sample is referred to as "fetal fraction". In some embodiments, "fetal fraction" refers to the fraction of fetal nucleic acid in circulating cell-free nucleic acid in a sample (e.g., a blood sample, a serum sample, a plasma sample) obtained from a pregnant female. In some embodiments determining an amount of fetal nucleic acid comprises determining a ratio (e.g., percentage, a percent representation) of fetal nucleic acid to a total amount of nucleic acid in a sample. In some embodiments determining an amount of fetal nucleic acid comprises determining a ratio (e.g., percentage) of the amount of fetal nucleic acid to the amount of maternal nucleic acid in a sample. In some embodiments, a method in which a genetic variation is determined also can comprise determining fetal fraction. Determining fetal fraction can be performed in a suitable manner, non-limiting examples of which include methods described below.

In some embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Determination of fetal nucleic acid content (e.g., fetal fraction) sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. The amount of fetal nucleic acid from a maternal sample sometimes can be determined relative to the total amount of nucleic acid present, thereby providing the percentage of fetal nucleic acid in the sample. The copy number of fetal nucleic acid sometimes can be determined in a maternal sample. The amount of fetal nucleic acid sometimes can be determined in a sequence-specific (or locus-specific) manner and sometimes with sufficient sensitivity to allow for accurate chromosomal dosage analysis (for example, to detect the presence or absence of a fetal aneuploidy or other genetic variation).

A fetal quantifier assay (FQA) can be performed in conjunction with any method described herein. Such an assay can be performed by any method known in the art and/or described in U.S. Patent Application Publication No. 2010/0105049, such as, for example, by a method that can distinguish between maternal and fetal DNA based on differential methylation status, and quantify (i.e. determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-28); methylation specific antibodies; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching for fetal DNA). Methyl-sensitive enzymes also can be used to differentiate nucleic acid based on methylation status, which, for example, can preferentially or substantially cleave or digest at their DNA recognition sequence if the latter is non-methylated. Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No. 2007/0065823. In some embodiments, the restriction efficiency can be determined and the efficiency rate is used to further determine the amount of fetal DNA.

A fetal quantifier assay (FQA) sometimes can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. The absolute copy number of fetal nucleic acid in a maternal sample sometimes can be determined, for example, using mass spectrometry and/or a system that uses a competitive PCR approach for absolute copy number measurements. See for example, Ding and Cantor (2003) Proc.Natl.Acad.Sci. USA 100:3059-3064, and U.S. Patent Application Publication No. 2004/0081993, both of which are hereby incorporated by reference.

Fetal fraction sometimes can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. Fetal alleles can be identified, for example, by their relative minor contribution to the mixture of fetal and maternal nucleic acids in the sample when compared to the major contribution to the mixture by the maternal nucleic acids. Accordingly, the relative abundance of fetal nucleic acid in a maternal sample can be determined as a parameter of the total number of unique sequence reads mapped to a target polynucleotide sequence on a reference genome for each of the two alleles of a polymorphic site.

The amount of fetal nucleic acid in extracellular nucleic acid can be quantified and used in conjunction with a method provided herein. Thus, in certain embodiments, methods of the technology described herein comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting counts, removing samples, making a call or not making a call).

The determination step can be performed before, during, at any one point in a method described herein, or after certain (e.g., aneuploidy detection) methods described herein. For example, to achieve an aneuploidy determination method with a given sensitivity or specificity, a fetal nucleic acid quantification method may be implemented prior to, during or after aneuploidy determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for the presence or absence of aneuploidy or genetic variation, for example. In certain embodiments, determinations of, for example, the presence or absence of aneuploidy are selected (e.g., selected and communicated to a patient) only for samples having a certain threshold amount of fetal nucleic acid (e.g., about 15% or more fetal nucleic acid; about 4% or more fetal nucleic acid).

In some embodiments, the determination of fetal fraction or determining the amount of fetal nucleic acid is not required or necessary for identifying the presence or absence of a chromosome aneuploidy. In some embodiments, identifying the presence or absence of a chromosome aneuploidy does not require the sequence differentiation of fetal versus maternal DNA. This is because the summed contribution of both maternal and fetal sequences in a particular chromosome, chromosome portion or segment thereof is analyzed, in some embodiments. In some embodiments, identifying the presence or absence of a chromosome aneuploidy does not rely on a priori sequence information that would distinguish fetal DNA from maternal DNA.

Nucleic Acid Amplification

In many instances, it is desirable to amplify a target polynucleotide sequence or a subset of a polynucleotide sequence herein using any of several nucleic acid amplification procedures which are well known in the art, some of which are listed or described herein. Specifically, nucleic acid amplification is the enzymatic synthesis of nucleic acid amplicons (copies) which contain a sequence that is complementary to a nucleic acid sequence being amplified. In some embodiments amplification comprises ligating one or more adaptors to a nucleic acid target or target subset of nucleic acids (e.g., digested nucleic acid, enriched nucleic acid, separated nucleic acid). Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest. One or more nucleic acids can be amplified in solution or while immobilized on a solid phase. One or more nucleic acids can be amplified prior to and/or after immobilization on a solid support (e.g., a solid support in a flow cell). In some embodiments one or more nucleic acids can be amplified after release from a solid phase.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., PCR Protocols: A Guide to Methods and Applications, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a polynucleotide sequence (e.g., a target polynucleotide) is typically used in practicing the present technology, one of skill in the art will recognize that the amplification of a genomic sequence found in a maternal blood sample may be accomplished by a known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular genomic sequence of the technology herein, which represents a particular methylation pattern, or to quantitatively determine the amount of this particular genomic sequence in the maternal blood. For a review of branched-DNA signal amplification for direct quantitation of nucleic acid sequences in clinical samples, see Nolte, Adv. Clin. Chem. 33:201-235, 1998.

The compositions and processes of the technology herein are also particularly useful when practiced with digital PCR. Digital PCR was first developed by Kalinina and colleagues (Kalinina et al., "Nanoliter scale PCR with TaqMan detection." Nucleic Acids Research. 25; 1999-2004, (1997)) and further developed by Vogelstein and Kinzler (Digital PCR. Proc Natl Acad Sci USA. 96; 9236-41, (1999)). The application of digital PCR for use with fetal diagnostics was first described by Cantor et al. (PCT Patent Publication No. WO05023091A2) and subsequently described by Quake et al. (US Patent Publication No. US 20070202525), which are both hereby incorporated by reference. Digital PCR takes advantage of nucleic acid (DNA, cDNA or RNA) amplification on a single molecule level, and offers a highly sensitive method for quantifying low copy number nucleic acid. Fluidigm® Corporation offers systems for the digital analysis of nucleic acids.

The term "amplified" as used herein refers to subjecting a target polynucleotide in a sample to a process that linearly or exponentially generates amplicon nucleic acids having the same or substantially the same nucleotide sequence as a target polynucleotide, or segment thereof. A target polynucleotide is sometimes represented in a sample as a polynucleotide fragment. In some embodiments a nucleotide sequence, or portion thereof, of a target polynucleotide is known. The term "amplified" as used herein can refer to subjecting a target polynucleotide (e.g., in a sample comprising other nucleic acids) to a process that selectively and linearly or exponentially generates amplicon nucleic acids having the same or substantially the same nucleotide sequence as the target polynucleotide, or segment thereof. Amplicons that are generated from, and have the same or substantially the same nucleotide sequence as a target polynucleotide, are referred to herein as target specific amplicons. The term "amplified" as used herein can refer to subjecting a population of nucleic acids to a process that non-selectively and linearly or exponentially generates amplicon nucleic acids having the same or substantially the same nucleotide sequence as nucleic acids, or portions thereof, that were present in the sample prior to amplification. In some embodiments, the term "amplified" refers to a method that comprises a polymerase chain reaction (PCR). The terms "amplify", "amplification", "selective amplification", "amplification reaction", or "amplifying" refer to any in vitro process for multiplying the copies of a nucleic acid.

Any suitable amplification technique can be utilized. Amplification of polynucleotides include, but are not limited to, polymerase chain reaction (PCR); ligation amplification (or ligase chain reaction (LCR)); amplification methods based on the use of Q-beta replicase or template-dependent polymerase (see US Patent Publication Number US20050287592); helicase-dependent isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, digital PCR, combinations thereof, and the like. For example, amplification can be accomplished using digital PCR, in certain embodiments (see e.g. Kalinina et al., "Nanoliter scale PCR with TaqMan detection." Nucleic Acids Research. 25; 1999-2004, (1997); Vogelstein and Kinzler (Digital PCR. Proc Natl Acad Sci USA. 96; 9236-41, (1999); PCT Patent Publication No. WO05023091A2; US Patent Publication No. US 20070202525). Digital PCR takes advantage of nucleic acid (DNA, cDNA or RNA) amplification on a single molecule level, and offers a highly sensitive method for quantifying low copy number nucleic acid. Systems for digital amplification and analysis of nucleic acids are available (e.g., Fluidigm® Corporation). Reagents and hardware for conducting PCR are commercially available.

A generalized description of a selective amplification process is presented herein. Primers (e.g., a primer pair, a collection of primer pairs) and nucleic acid (e.g., target polynucleotides) are contacted under suitable hybridization conditions, and complementary sequences anneal to one another, for example. Primers can anneal to a nucleic acid, at or near (e.g., adjacent to, abutting, flanking, and the like) a sequence of interest (e.g., a target polynucleotide). In some embodiments, a primer pair hybridizes within about 10 to 30 nucleotides from a nucleic acid sequence of interest and, under amplification conditions can produce amplified products (e.g., amplicons). In some embodiments, primers hybridize within a nucleic acid sequence of interest (e.g., a target polynucleotide).

Any suitable amplification conditions can be used to perform an amplification resulting in the production of amplicons. In some embodiments a sample comprising target polynucleotides is contacted with one or more target specific primer pairs (e.g., a collection of primers) under amplification conditions where target specific amplicons are generated. Amplification conditions often comprise a reaction mixture containing a polymerase, at least one primer (e.g., a primer pair), at least one target polynucleotide and additional components (e.g., buffers, salts and nucleotide triphosphates) necessary for polymerase activity. Non-limiting examples of components of an amplification reaction may include, but are not limited to, e.g., primers (e.g., individual primers, primer pairs, a collection of primer pairs and the like) a polynucleotide template, polymerase, nucleotides, dNTPs and the like. In some embodiments, non-naturally occurring nucleotides or nucleotide analogs, such as analogs containing a detectable label (e.g., fluorescent or colorimetric label), may be used for example. Polymerases can be selected by a person of ordinary skill and include polymerases for thermocycle amplification (e.g., Taq DNA Polymerase; Q-Bio™ Taq DNA Polymerase (recombinant truncated form of Taq DNA Polymerase lacking 5'-3'exo activity); SurePrime™ Polymerase (chemically modified Taq DNA polymerase for "hot start" PCR); Arrow™ Taq DNA Polymerase (high sensitivity and long template amplification)) and polymerases for thermostable amplification (e.g., RNA polymerase for transcription-mediated amplification (TMA) described at World Wide Web URL "genprobe.com/pdfs/tma_whiteppr.pdf"). Other enzyme components can be added, such as reverse transcriptase for transcription mediated amplification (TMA) reactions, for example.

Amplification conditions can be dependent upon primer sequences (e.g., primer hybridization sequences), abundance of nucleic acid, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. Digital PCR is also known in the art; see, e.g., United States Patent Application Publication no. 20070202525, filed Feb. 2, 2007, which is hereby incorporated by reference). Amplification conditions often comprise a plurality of suitable temperature changes (e.g., temperature cycles) and incubation times (e.g., an incubation time for annealing, melting and extension). Amplification is typically carried out as an automated process, often in a thermocycler with a thermostable enzyme. In this process, the temperature of the reaction mixture is cycled multiple times through a denaturing step, a primer-annealing step, and an extension reaction step automatically. Some amplification protocols also include an activation step and a final extension step. Machines specifically adapted for this purpose are commercially available. A non-limiting example of a amplification protocol that may be suitable for embodiments described herein is, treating the sample at 95° C. for 5 minutes; repeating thirty-five cycles of 95° C. for 45 seconds and 68° C. for 30 seconds; and then treating the sample at 72° C. for 3 minutes. A completed amplification reaction can optionally be kept at 4° C. until further action is desired. Multiple cycles frequently are performed using a commercially available thermal cycler. Suitable isothermal amplification processes known and selected by the person of ordinary skill in the art also may be applied, in certain embodiments.

In some embodiments, an amplification product (e.g., an amplicon) may include naturally occurring nucleotides, non-naturally occurring nucleotides, nucleotide analogs and the like and combinations of the foregoing. An amplicon often has a nucleotide sequence that is identical to or substantially identical to a nucleic acid sequence herein, or complement thereof. A "substantially identical" nucleotide sequence in an amplification product will generally have a high degree of sequence identity to the nucleotide sequence species being amplified or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations sometimes are a result of infidelity of the polymerase used for extension and/or amplification, or additional nucleotide sequence(s) added to the primers used for amplification.

Nucleic acids in a sample can be enriched by an amplification method described herein. An amplification product (e.g., amplicons) can be generated before, during or after any step of a method described herein. An amplification product can be generated before, during or after a digestion or cleavage reaction. An amplification product can be generated before, during or after a modification of nucleic acids in a sample. An amplification product can be generated before, during or after an enrichment method. An amplification product can be generated before, during or after a separation or purifications step. An amplification product can be generated before, during or after a process comprising nucleic acid sequencing. In some embodiments digested nucleic acids or undigested nucleic acids are enriched by an amplification. In some embodiments enriched and/or separated nucleic acid are further enriched by an amplification. In some embodiments enriched and/or separated methylated, hypermethylated and/or hypomethylated nucleic acid are further enriched by an amplification.

Nucleic Acid Analysis

In some embodiments, nucleic acid fragments (e.g., digested nucleic acid fragments) may be amplified and/or subjected to an analysis and/or detection process (e.g., sequence-based analysis, mass spectrometry). In some embodiments, nucleic acid fragments are (e.g., digested nucleic acid fragments) subjected to a detection process (e.g., sequencing) without amplification.

Nucleic acid fragments (e.g., digested nucleic acid fragments), polynucleotides or amplicon sequences, or detectable products prepared from the foregoing, can be analyzed (e.g., detected, identified, quantitated, compared) by a suitable process. Non-limiting examples of methods of analysis include mass detection and analysis (e.g., matrix-assisted laser desorption ionization (MALDI) mass spectrometry and electrospray (ES) mass spectrometry), primer extension methods (e.g., iPLEX™; Sequenom, Inc.), direct DNA sequencing, Molecular Inversion Probe (MIP) technology from Affymetrix, restriction fragment length polymorphism (RFLP analysis), allele specific oligonucleotide (ASO) analysis, methyl-specific PCR (MSPCR), pyrosequencing analysis, acycloprime analysis, reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader assay, hybridization using at least one probe, cloning and sequencing, electrophoresis, the use of hybridization probes and quantitative real time polymerase chain reaction (QRT-PCR), digital PCR, nanopore sequencing, chips, the like and combinations thereof. In some embodiments the amount of a polynucleotide or nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like. Nucleic acid detection and/or quantification also may include, for example, solid support array based detection of fluorescently labeled nucleic acid with fluorescent labels incorporated during or after PCR, single molecule detection of fluorescently labeled molecules in solution or captured on a solid phase, or other sequencing technologies such as, for example, sequencing using ION TORRENT or MISEQ platforms or single molecule sequencing technologies using instrumentation such as, for example, PACBIO sequencers, HELICOS sequencer, or nanopore sequencing technologies.

An analysis can be a target-based analysis (e.g., targeted analysis) or a non-target-based analysis (e.g., non-targeted). A target-based analysis generally comprises analysis (e.g., sequencing, quantitation) of selected nucleic acids or a selected subset of nucleic acids (e.g., a subpopulation of nucleic acids). In some embodiments a selective nucleic acid subset comprises selected genes, selected loci (e.g., hypomethylated loci, hypermethylated loci), selected alleles (e.g., selected polymorphisms), nucleic acids derived from one or more selected chromosomes, selected fetal nucleic acids, the like or combinations thereof. In some embodiments a target-bases analysis comprises a suitable target specific amplification or sequencing method. A target-based analysis generally comprises use of one or more sequence-specific oligonucleotides (e.g., primers or capture agents) that hybridize to specific selected nucleic acid sequences that are expected and/or known to exist in a test sample (e.g., an unmanipulated sample isolated from a test subject). A non-target-based analysis generally does not comprise a sequence-specific selection process or utilizes oligonucleotides that hybridize to specific selected nucleic acid sequences that are expected and/or known to exist in a test sample. In some embodiments a non-target-based analysis utilizes adaptors and/or adaptor specific primers to amplify and/or sequence nucleic acids or a subset of nucleic acids in a test sample. For example, a non-target-based analysis sometimes comprises ligation of adaptors and/or hybridization of primers to sticky ends that results from restriction enzyme cleavage followed by a suitable capture, primer extension, amplification and/or sequencing method.

Sequencing

In some embodiments, nucleic acids (e.g., nucleic acid fragments, sample nucleic acid, cell-free nucleic acid) are sequenced. In certain embodiments, a full or substantially full sequence is obtained and sometimes a partial sequence is obtained. Sequencing, mapping and related analytical methods are known in the art (e.g., United States Patent Application Publication US2009/0029377, incorporated by reference). Certain aspects of such processes are described hereafter.

In some embodiments some or all nucleic acids in a sample are enriched and/or amplified (e.g., non-specifically, e.g., by a PCR based method) prior to or during sequencing. In certain embodiments specific nucleic acid portions or subsets in a sample are enriched and/or amplified prior to or during sequencing. In some embodiments, a portion or subset of a pre-selected pool of nucleic acids is sequenced randomly. In some embodiments, nucleic acids in a sample are not enriched and/or amplified prior to or during sequencing.

As used herein, "reads" (i.e., "a read", "a sequence read") are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads).

The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 by to about 900 bp long. In certain embodiments sequence reads are of a mean, median, average or absolute length about 1000 bp or more.

In some embodiments the nominal, average, mean or absolute length of single-end reads sometimes is about 15 contiguous nucleotides to about 50 or more contiguous nucleotides, about 15 contiguous nucleotides to about 40 or more contiguous nucleotides, and sometimes about 15 contiguous nucleotides or about 36 or more contiguous nucleotides. In certain embodiments the nominal, average, mean or absolute length of single-end reads is about 20 to about 30 bases, or about 24 to about 28 bases in length. In certain embodiments the nominal, average, mean or absolute length of single-end reads is about 1, 2, 3, 4, 5, 6, 7, 8, 9, 10, 11, 12, 13, 14, 15, 16, 17, 18, 19, 21, 22, 23, 24, 25, 26, 27, 28 or about 29 bases or more in length.

In certain embodiments, the nominal, average, mean or absolute length of the paired-end reads sometimes is about 10 contiguous nucleotides to about 25 contiguous nucleotides or more (e.g., about 10, 11, 12, 13, 14, 15, 16, 17, 18, 19, 20, 21, 22, 23, 24 or 25 nucleotides in length or more), about 15 contiguous nucleotides to about 20 contiguous nucleotides or more, and sometimes is about 17 contiguous nucleotides or about 18 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a copy number variation (e.g., a maternal and/or fetal copy number variation), genetic variation or an aneuploidy, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, a representative fraction of a genome is sequenced and is sometimes referred to as "coverage" or "fold coverage". For example, a 1-fold coverage indicates that roughly 100% of the nucleotide sequences of the genome are represented by reads. In some embodiments "fold coverage" is a relative term referring to a prior sequencing run as a reference. For example, a second sequencing run may have 2-fold less coverage than a first sequencing run. In some embodiments a genome is sequenced with redundancy, where a given region of the genome can be covered by two or more reads or overlapping reads (e.g., a "fold coverage" greater than 1, e.g., a 2-fold coverage).

In some embodiments, one nucleic acid sample from one individual is sequenced. In certain embodiments, nucleic acids from each of two or more samples are sequenced, where samples are from one individual or from different individuals. In certain embodiments, nucleic acid samples from two or more biological samples are pooled, where each biological sample is from one individual or two or more individuals, and the pool is sequenced. In the latter embodiments, a nucleic acid sample from each biological sample often is identified by one or more unique identifiers.

In some embodiments a sequencing method utilizes identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane are dependent on the number of unique identifiers utilized during library preparation and/or probe design. single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments sequencing technologies that include the use of nucleic acid imaging technologies (e.g. transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments MPS sequencing methods utilize a targeted approach, where specific chromosomes, genes or regions of interest are sequences. In certain embodiments a non-targeted approach is used where most or all nucleic acids in a sample are sequenced, amplified and/or captured randomly.

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

MPS sequencing sometimes makes use of sequencing by synthesis and certain imaging processes. A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego Calif.)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

Sequencing by synthesis, in some embodiments, comprises iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEM-FET sensor), the like or combinations thereof. Other sequencing methods that may be used to conduct methods herein include digital PCR and sequencing by hybridization.

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number.

In certain embodiments, sequencing by hybridization can be used. The method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in a method described herein. Nanopore sequencing is a single-molecule sequencing technology whereby a single nucleic acid molecule (e.g. DNA) is sequenced directly as it passes through a nanopore.

A suitable MPS method, system or technology platform for conducting methods described herein can be used to obtain nucleic acid sequencing reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, US patent publication no. US20130012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing, In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening 'bridge' oligonucleotide to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13.

Mapping Reads

Sequence reads can be mapped and the number of reads mapping to a specified nucleic acid region (e.g., a chromosome, portion or segment thereof) are referred to as counts. Any suitable mapping method (e.g., process, algorithm, program, software, module, the like or combination thereof) can be used. Certain aspects of mapping processes are described hereafter.

Mapping nucleotide sequence reads (i.e., sequence information from a fragment whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped", "a mapped sequence read" or a "mapped read". In certain embodiments, a mapped sequence read is referred to as a "hit" or "count". In some embodiments, mapped sequence reads are grouped together according to various parameters and assigned to particular portions of a genome, which are discussed in further detail below.

As used herein, the terms "aligned", "alignment", or "aligning" refer to two or more nucleic acid sequences that can be identified as a match (e.g., 100% identity) or partial match. Alignments can be done manually or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In certain embodiments a nucleic acid sequence is aligned with the reverse complement of another nucleic acid sequence.

Various computational methods can be used to map sequence reads to specific or general genomic positions. Non-limiting examples of computer algorithms that can be used to align sequences include, without limitation, BLAST, BLITZ, FASTA, BOWTIE 1, BOWTIE 2, ELAND, MAQ, PROBEMATCH, SOAP or SEQMAP, or variations thereof or combinations thereof. In some embodiments, sequence reads can be aligned with sequences in a reference genome. In some embodiments, the sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database. Search hits can then be used to map, identify, quantitate, and/or sort the identified sequences according to their appropriate genomic positions (e.g., genomic sections, genomic locations and/or positions, chromosomes, chromosome segments, chromosome locations and/or positions, pre-determined loci, polynucleotides of a chromosome, specific target polynucleotides, and the like), for example.

In some embodiments, a read may uniquely or non-uniquely map to portions in the reference genome. A read is considered to be "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at www.ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

Counting

Sequence reads that have been mapped on a selected feature or variable can be quantified to determine the number of reads that were mapped to a portion of a genome (e.g., polynucleotide of a chromosome, genomic segment and the like), in some embodiments. In certain embodiments, reads of amplicons and/or extension products are mapped, analyzed, compared and/or counted.

Quantifying or counting sequence reads can be done in any suitable manner including but not limited to manual counting methods and automated counting methods. In some embodiments, an automated counting method can be embodied in software that determines or counts the number of sequence reads mapping to a chromosome and/or one or more selected polynucleotides of a chromosome. As used herein, software refers to computer readable program instructions that, when executed by a computer, perform computer operations.

In certain embodiments, data or data sets can be organized into a matrix having two or more dimensions based on one or more features of variables. Data organized into matrices can be stratified using any suitable features or variables. A non-limiting example of data organized into a matrix includes data that is stratified by maternal age, maternal ploidy, genomic location or position, fetal fraction, the like or combinations thereof.

Mass Spectrometry

In some embodiments a mass spectrometer is used to analyze nucleic acids and/or enriched nucleic acids (e.g., enriched fetal or maternal nucleic acids). Analysis of nucleic acids by a mass spectrometer can be a target-based analysis or a non-target based analysis. In some embodiments a mass spectrometer is used quantitate nucleic acids and/or specific subsets (e.g., subpopulations) of nucleic acids. In some embodiments a mass spectrometer is used to detect, measure and/or quantitate an identifier (e.g., a sequence tag, a label, a mass tag) associated with a selected subset or subpopulation of nucleic acids or associated with a specific target polynucleotide. In some embodiments detection, identification and/or quantitation of a target polynucleotide (e.g., a specific polynucleotide, a target comprising a tag) is determined by mass spectrometry (e.g., by a target-based analysis). In certain embodiments, a sequence of an oligonucleotide or polynucleotide is determined by a mass spectrometer. Mass spectrometry methods typically are used to determine the mass of a molecule, such as a nucleic acid fragment, sequence tag or an identifier. In some embodiments, the length and/or the sequence of a nucleic acid fragment (e.g., a sequence tag) can be extrapolated from the mass of a fragment, tag or a fragment comprising a tag. In some embodiments, the length and/or the sequence of a first nucleic acid fragment and/or a first sequence tag can be extrapolated from the mass of a second nucleic acid fragment that hybridizes to the first fragment or tag. In some embodiments, presence of a target and/or reference nucleic acid of a given length and/or sequence can be verified by comparing the mass of the detected signal with the expected mass of the target and/or a reference fragment. The relative signal strength, e.g., mass peak on a spectra, for a particular nucleic acid fragment and/or fragment length sometimes can indicate the relative population of the fragment species amongst other nucleic acids in a sample (see e.g., Jurinke et al. (2004) Mol. Biotechnol. 26, 147-164).

Mass spectrometry generally works by ionizing chemical compounds to generate charged molecules or molecule fragments and measuring their mass-to-charge ratios. A typical mass spectrometry procedure involves several steps, including (1) loading a sample onto the mass spectrometry instrument followed by vaporization, (2) ionization of the sample components by any one of a variety of methods (e.g., impacting with an electron beam), resulting in charged particles (ions), (3) separation of ions according to their mass-to-charge ratio in an analyzer by electromagnetic fields, (4) detection of ions (e.g., by a quantitative method), and (5) processing of the ion signal into mass spectra.

Mass spectrometry methods are well known in the art (see, e.g., Burlingame et al. Anal. Chem. 70:647R-716R (1998)), and include, for example, quadrupole mass spectrometry, ion trap mass spectrometry, time-of-flight mass spectrometry, gas chromatography mass spectrometry and tandem mass spectrometry can be used with the methods described herein. The basic processes associated with a mass spectrometry method are the generation of gas-phase ions derived from the sample, and the measurement of their mass. The movement of gas-phase ions can be precisely controlled using electromagnetic fields generated in the mass spectrometer. The movement of ions in these electromagnetic fields is proportional to the m/z (mass to charge ratio) of the ion and this forms the basis of measuring the m/z and therefore the mass of a sample. The movement of ions in these electromagnetic fields allows for the containment and focusing of the ions which accounts for the high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution, that is, the ability to resolve peaks between ions closely related in mass. The resolution is defined as $R=m/\text{delta } m$, where m is the ion mass and delta m is the difference in mass between two peaks in a mass spectrum. For example, a mass spectrometer with a resolution of 1000 can resolve an ion with a m/z of 100.0 from an ion with a m/z of 100.1.

Certain mass spectrometry methods can utilize various combinations of ion sources and mass analyzers which allows for flexibility in designing customized detection protocols. In some embodiments, mass spectrometers can be programmed to transmit all ions from the ion source into the mass spectrometer either sequentially or at the same time. In some embodiments, a mass spectrometer can be programmed to select ions of a particular mass for transmission into the mass spectrometer while blocking other ions.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Mass analyzers include, for example, a quadrupole mass filter, ion trap mass analyzer and time-of-flight mass analyzer.

The ion formation process is a starting point for mass spectrum analysis. Several ionization methods are available and the choice of ionization method depends on the sample used for analysis. For example, for the analysis of polypeptides a relatively gentle ionization procedure such as electrospray ionization (ESI) can be desirable. For ESI, a solution containing the sample is passed through a fine needle at high potential which creates a strong electrical field resulting in a fine spray of highly charged droplets that is directed into the mass spectrometer. Other ionization procedures include, for example, fast-atom bombardment (FAB) which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix (e.g., 2,5-dihydroxybenzoic acid, alpha-cyano-4-hydroxycinnammic acid, 3-hydroxypicolinic acid (3-HPA), di-ammoniumcitrate (DAC) and combinations thereof). Other ionization procedures known in the art include, for example, plasma and glow discharge, plasma desorption ionization, resonance ionization, and secondary ionization.

A variety of mass analyzers are available that can be paired with different ion sources. Different mass analyzers have different advantages as known in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Ion mobility mass (IM) spectrometry is a gas-phase separation method. IM separates gas-phase ions based on their collision cross-section and can be coupled with time-of-flight (TOF) mass spectrometry. IM-MS is discussed in more detail by Verbeck et al. in the *Journal of Biomolecular Techniques* (Vol 13, Issue 2, 56-61).

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole.

This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering.

A quadrupole mass analyzer, as well as the other mass analyzers described herein, can be programmed to analyze a defined m/z or mass range. Since the desired mass range of nucleic acid fragment is known, in some instances, a mass spectrometer can be programmed to transmit ions of the projected correct mass range while excluding ions of a higher or lower mass range. The ability to select a mass range can decrease the background noise in the assay and thus increase the signal-to-noise ratio. Thus, in some instances, a mass spectrometer can accomplish a separation step as well as detection and identification of certain mass-distinguishable nucleic acid fragments.

Ion trap mass spectrometry utilizes an ion trap mass analyzer. Typically, fields are applied such that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis can be accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. Control of the number of ions can be accomplished by varying the time over which ions are injected into the trap.

Time-of-flight mass spectrometry utilizes a time-of-flight mass analyzer. Typically, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

Gas chromatography mass spectrometry often can analyze a target in real-time. The gas chromatography (GC) portion of the system separates the chemical mixture into pulses of analyte and the mass spectrometer (MS) identifies and quantifies the analyte.

Tandem mass spectrometry can utilize combinations of the mass analyzers described above. Tandem mass spectrometers can use a first mass analyzer to separate ions according to their m/z in order to isolate an ion of interest for further analysis. The isolated ion of interest is then broken into fragment ions (called collisionally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however the mass analyzer is used sequentially to isolate an ion, induce fragmentation, and then perform mass analysis.

Mass spectrometers in the tandem in space category have more than one mass analyzer. For example, a tandem quadrupole mass spectrometer system can have a first quadrupole mass filter, followed by a collision cell, followed by a second quadrupole mass filter and then the detector. Another arrangement is to use a quadrupole mass filter for the first mass analyzer and a time-of-flight mass analyzer for the second mass analyzer with a collision cell separating the two mass analyzers. Other tandem systems are known in the art including reflectron-time-of-flight, tandem sector and sector-quadrupole mass spectrometry.

Mass spectrometers in the tandem in time category have one mass analyzer that performs different functions at different times. For example, an ion trap mass spectrometer can be used to trap ions of all m/z. A series of rf scan functions are applied which ejects ions of all m/z from the trap except the m/z of ions of interest. After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

Several types of tandem mass spectrometry experiments can be performed by controlling the ions that are selected in each stage of the experiment. The different types of experiments utilize different modes of operation, sometimes called "scans," of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor ion scan, the first mass analyzer is scanned to sequentially transmit the mass analyzed ions into the collision cell for fragmentation. The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans.

Any suitable mass spectrometer, mass spectrometer format, configuration or technology described herein or known can be used to perform a method described herein, non-limiting examples of which include Matrix-Assisted Laser Desorption/Ionization Time-of-Flight (MALDI-TOF) Mass Spectrometry (MS), Laser Desorption Mass Spectrometry (LDMS), Electrospray (ES) MS, Ion Cyclotron Resonance (ICR) MS, Fourier Transform MS, inductively coupled plasma-mass spectrometry (ICP-MS), accelerator mass spectrometry (AMS), thermal ionization-mass spectrometry (TIMS), spark source mass spectrometry (SSMS), as described in international patent application number PCT/US2012/038710 (i.e., International Publication No. WO 2012/159089, which is incorporated herein by reference in its entirety), the like and combinations thereof.

For quantification, controls may be used which can provide a signal in relation to the amount of the nucleic acid fragment, for example, that is present or is introduced. A control to allow conversion of relative mass signals into absolute quantities can be accomplished by addition of a known quantity of a mass tag or mass label to each sample before detection of the nucleic acid fragments. See for example, Ding and Cantor (2003) PNAS USA March 18; 100(6):3059-64. Any mass tag that does not interfere with detection of the fragments can be used for normalizing the mass signal. Such standards typically have separation properties that are different from those of any of the molecular tags in the sample, and could have the same or different mass signatures.

A separation step sometimes can be used to remove salts, enzymes, or other buffer components from the nucleic acid sample. Several methods well known in the art, such as chromatography, gel electrophoresis, or precipitation, can be used to clean up the sample. For example, size exclusion chromatography or affinity chromatography can be used to remove salt from a sample. The choice of separation method can depend on the amount of a sample. For example, when small amounts of sample are available or a miniaturized apparatus is used, a micro-affinity chromatography separation step can be used. In addition, whether a separation step is desired, and the choice of separation method, can depend on the detection method used. Salts sometimes can absorb energy from the laser in matrix-assisted laser desorption/ionization and result in lower ionization efficiency. Thus, the efficiency of matrix-assisted laser desorption/ionization and electrospray ionization sometimes can be improved by removing salts from a sample.

Data Processing

In some embodiments, data and/or results in a data set can be processed (e.g., mathematically and/or statistically manipulated) and/or displayed to facilitate providing an outcome. In certain embodiments, data sets, including larger data sets, may benefit from processing to facilitate further analysis. Processing of data sets sometimes involves removal of redundant and/or uninformative data, and/or over represented or under-represented data. Without being limited by theory, data processing and/or preprocessing may (i) remove noisy data (e.g., data with a high level of uncertainty, high standard deviation), (ii) remove uninformative data, (iii) remove redundant data, (iv) reduce the complexity of larger data sets, and/or (v) facilitate transformation of the data from one form into one or more other forms. Processing can render data more amenable to further analysis, and can generate an outcome in some embodiments.

A cutoff threshold value or range of values often is calculated by mathematically and/or statistically manipulating sequence read data (e.g., from a reference and/or subject), in some embodiments, and in certain embodiments, sequence read data manipulated to generate a threshold cutoff value or range of values is sequence read data (e.g., from a reference and/or subject). In some embodiments, a threshold cutoff value is obtained by calculating the standard deviation and/or median absolute deviation (e.g., MAD) of a raw or normalized count profile and multiplying the standard deviation for the profile by a constant representing the number of standard deviations chosen as a cutoff threshold (e.g., multiply by 3 for 3 standard deviations), whereby a value for an uncertainty is generated.

Any suitable procedure can be utilized for processing data sets described herein. Non-limiting examples of procedures suitable for use for processing data sets include filtering, normalizing, weighting, monitoring peak heights, monitoring peak areas, monitoring peak edges, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set. In some embodiments, one or more processing steps can comprise one or more filtering steps.

In some embodiments, one or more processing steps can comprise one or more normalization steps. The term "normalization" as used herein refers to division of one or more data sets by a predetermined variable. Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data.

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak elevations, determination of peak edge locations, calculation of peak area ratios, analysis of median chromosomal elevation, calculation of mean absolute deviation, sum of squared residuals, mean, standard deviation, standard error, the like or combinations thereof. A mathematical and/or statistical manipulation can be performed on all or a portion of a data set, or processed products thereof.

In some embodiments, a processing step can include the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta-analysis, simple linear regression, robust linear regression, the like or combinations of the foregoing. Non-limiting examples of data set variables or features that can be analyzed using statistical algorithms include raw counts, filtered counts, normalized counts, P-values, relative representation of nucleic acid species, the like or combinations thereof.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation, depending on the genetic status of the reference samples (e.g., positive or negative for a selected genetic variation). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation or medical condition.

In some embodiments, analysis and processing of data can include the use of one or more assumptions. Any suitable number or type of assumptions can be utilized to analyze or process a data set. Non-limiting examples of assumptions that can be used for data processing and/or analysis include maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a fetal quantifier assay (e.g., FQA), assumptions regarding twins (e.g., if 2 twins and only 1 is affected the effective fetal fraction is only 50% of the total measured fetal fraction (similarly for triplets, quadruplets and the like)), fetal cell free DNA (e.g., cfDNA) uniformly covers the entire genome, the like and combinations thereof.

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion or genomic deletion; represent the presence or absence of a variation in the physical amount of a sequence associated with medical conditions). A virtual representation sometimes is further transformed into one or more numerical values or graphical representations of the digital representation of the starting material. These procedures can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). Any suitable feature or variable can be utilized to reduce data set complexity and/or dimensionality. Non-limiting examples of features that can be chosen for use as a target feature for data processing include GC content, fetal gender prediction, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

Machines, Software and Interfaces

Apparatuses, software and interfaces may be used to conduct methods described herein. Using apparatuses, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by any suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A user may, for example, place a query to software which then may acquire a data set via internet access, and in certain embodiments, a programmable processor may be prompted to acquire a suitable data set based on given parameters. A programmable processor also may prompt a user to select one or more data set options selected by the processor based on given parameters. A programmable processor may prompt a user to select one or more data set options selected by the processor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, apparatuses, or computer programs.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, any suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by any suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus may serve as data that can be input via an input device. In certain embodiments, mapped sequence reads may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process described herein, and software can include one or more modules for performing such processes (e.g., data acquisition module, data processing module, data display module). The term "software" refers to computer readable program instructions that, when executed by a computer, perform computer operations. The term "module" refers to a self-contained functional unit that can be used in a larger software system. For example, a software module is a part of a program that performs a particular process or task.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash drives, RAM, floppy discs, the like, and other such media on which the program instructions can be recorded. In online implementation, a server and web site maintained by an organization can be configured to provide software downloads to remote users, or remote users may access a remote system maintained by an organization to remotely access software.

Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

In some embodiments, provided are computer program products, such as, for example, a computer program product comprising a computer usable medium (e.g., a non-transitory storage medium) having a computer readable program code embodied therein, the computer readable program code adapted to be executed to implement a method comprising: (a) obtaining nucleotide sequence reads from a sample comprising circulating, cell-free nucleic acid from a pregnant female, where the sample has been enriched for fetal nucleic acid, (b) mapping the nucleotide sequence reads to reference genome sections, (c) counting the number of nucleotide sequence reads mapped to each reference genome section, (d) comparing the number of counts of the nucleotide sequence reads mapped in (c), or derivative thereof, to a reference, or portion thereof, thereby making a comparison, and (e) determining the presence or absence of a fetal aneuploidy based on the comparison.

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more processors in certain embodiments. A processor can be connected to a communication bus. A computer system may include a main memory, often random access memory (RAM), and can also include a secondary memory. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A processor may implement software in a system. In some embodiments, a processor may be programmed to automatically perform a task described herein that a user could perform. Accordingly, a processor, or algorithm conducted by such a processor, can require little to no supervision or input from a user (e.g., software may be programmed to implement a function automatically). In some embodiments, the complexity of a process is so large that a single person or group of persons could not perform the process in a timeframe short enough for providing an outcome determinative of the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

Genetic Variations and Medical Conditions

Some genetic variations are associated with medical conditions. Genetic variations often include a gain, a loss, and/or alteration (e.g., duplication, deletion, substitution, reorganization, fusion, insertion, mutation, reorganization, substitution or aberrant methylation) of genetic information (e.g., chromosomes, portions of chromosomes, polymorphic regions, translocated regions, altered nucleotide sequence, the like or combinations of the foregoing) that result in a change (e.g., a detectable change) in a genome or genetic information of a test subject with respect to a reference subject that is substantially free of a genetic variation. The presence or absence of a genetic variation can be determined by analyzing and/or manipulating nucleic acids. In some embodiments, the presence or absence of a genetic variation can be determined by analyzing and/or manipulating amplicons, polymerase extension products, and/or sequence reads as described herein.

The presence or absence of a genetic variance can be determined using a method or apparatus described herein. In certain embodiments, the presence or absence of one or more genetic variations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation is a chromosome abnormality (e.g., aneuploidy), partial chromosome abnormality or mosaicism, each of which is described in greater detail herein. Non-limiting examples of genetic variations include one or more deletions (e.g., micro-deletions), duplications (e.g., micro-duplications), insertions, mutations, polymorphisms (e.g., single-nucleotide polymorphisms (SNPs)), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 1,000 kilobases (kb) in length (e.g., about 10 bp, 50 bp, 100 bp, 500 bp, 1 kb, 5 kb, 10 kb, 50 kb, 100 kb, 500 kb, or 1000 kb in length).

A genetic variation is sometime a deletion. In some embodiments, a deletion is a mutation (e.g., a genetic aberration) in which a part of a chromosome or a sequence of DNA is missing.

A deletion is often the loss of genetic material. Any number of nucleotides can be deleted. A deletion can comprise the deletion of one or more entire chromosomes, a segment of a chromosome, an allele, a gene, an intron, an exon, any non-coding region, any coding region, a segment thereof or combination thereof. A deletion can comprise a microdeletion. A deletion can comprise the deletion of a single base.

A genetic variation is sometimes a genetic duplication. In some embodiments, a duplication is a mutation (e.g., a genetic aberration) in which a part of a chromosome or a sequence of DNA is copied and inserted back into the genome. In some embodiments, a genetic duplication (i.e. duplication) is any duplication of a region of DNA. In some embodiments a duplication is a nucleic acid sequence that is repeated, often in tandem, within a genome or chromosome. In some embodiments a duplication can comprise a copy of one or more entire chromosomes, a segment of a chromosome, an allele, a gene, an intron, an exon, any non-coding region, any coding region, segment thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation is sometimes an insertion. An insertion is sometimes the addition of one or more nucleotide base pairs into a nucleic acid sequence. An insertion is sometimes a microinsertion. In some embodiments, an insertion comprises the addition of a segment of a chromosome into a genome, chromosome, or segment thereof. In some embodiments, an insertion comprises the addition of an allele, a gene, an intron, an exon, any non-coding region, any coding region, segment thereof or combination thereof into a genome or segment thereof. In some embodiments, an insertion comprises the addition (i.e., insertion) of nucleic acid of unknown origin into a genome, chromosome, or segment thereof. In some embodiments, an insertion comprises the addition (i.e. insertion) of a single base.

As used herein a "copy number variation" generally is a class or type of genetic variation or chromosomal aberration. A copy number variation can be a deletion (e.g. microdeletion), duplication (e.g., a micro-duplication) or insertion (e.g., a micro-insertion). Often, the prefix "micro" as used herein sometimes is a segment of nucleic acid less than 5 Mb in length. A copy number variation can include one or more deletions (e.g. micro-deletion), duplications and/or insertions (e.g., a micro-duplication, micro-insertion) of a segment of a chromosome. In some embodiments, a duplication comprises an insertion. In some embodiments, an insertion is a duplication. In some embodiments, an insertion is not a duplication.

In some embodiments a copy number variation is a fetal copy number variation. Often, a fetal copy number variation is a copy number variation in the genome of a fetus. In some embodiments a copy number variation is a maternal copy number variation. In some embodiments, a maternal and/or fetal copy number variation is a copy number variation within the genome of a pregnant female (e.g., a female subject bearing a fetus), a female subject that gave birth or a female capable of bearing a fetus. A copy number variation can be a heterozygous copy number variation where the variation (e.g., a duplication or deletion) is present on one allele of a genome. A copy number variation can be a homozygous copy number variation where the variation is present on both alleles of a genome. In some embodiments a copy number variation is a heterozygous or homozygous fetal copy number variation. In some embodiments a copy number variation is a heterozygous or homozygous maternal and/or fetal copy number variation. A copy number variation sometimes is present in a maternal genome and a fetal genome, a maternal genome and not a fetal genome, or a fetal genome and not a maternal genome.

"Ploidy" refers to the number of chromosomes present in a fetus or mother. In some embodiments, "Ploidy" is the same as "chromosome ploidy". In humans, for example, autosomal chromosomes are often present in pairs. For example, in the absence of a genetic variation, most humans have two of each autosomal chromosome (e.g., chromosomes 1-22). The presence of the normal complement of 2 autosomal chromosomes in a human is often referred to as euploid.

Outcomes

A determination of the presence or absence of a genetic variation (e.g., fetal aneuploidy) can be generated for a sample (e.g., for an enriched nucleic acid), thereby providing an outcome (e.g., thereby providing an outcome determinative of the presence or absence of a genetic variation (e.g., fetal aneuploidy)) by a suitable method or by a method described here.

Methods described herein sometimes determine presence or absence of a fetal aneuploidy (e.g., full chromosome aneuploidy (e.g., monosomy, trisomy, partial chromosome aneuploidy or segmental chromosomal aberration (e.g., mosaicism, deletion and/or insertion)) for a test sample from a pregnant female bearing a fetus. Sometimes methods described herein detect euploidy or lack of euploidy (non-euploidy) for a sample from a pregnant female bearing a fetus. Methods described herein sometimes detect trisomy for one or more chromosomes (e.g., chromosome 13, chromosome 18, chromosome 21 or combination thereof) or segment thereof.

A suitable reference (e.g., reference sample, reference polynucleotides, control) can be used to compare amounts of polynucleotides of a chromosome, amplicons of target polynucleotides, extension products and/or sequence reads (e.g., counts) for determining the presence or absence of a genetic variation (e.g., one, two, three or four copies of a fetal chromosome) in a test subject. In some embodiments, a fetal fraction determination can be factored with methods described herein to determine the presence or absence of a genetic variation. A suitable process for quantifying fetal fraction can be utilized, non-limiting examples of which include a mass spectrometric process, sequencing process or combination thereof.

Laboratory personnel (e.g., a laboratory manager) can analyze data (e.g., qualitative or quantitative results of an analysis) underlying a determination of the presence or absence of a genetic variation (e.g., determination of euploid or non-euploid for a test sample). For calls pertaining to presence or absence of a genetic variation that are close or questionable, laboratory personnel can re-order the same test, and/or order a different test (e.g., karyotyping and/or amniocentesis in the case of fetal aneuploidy determinations), that makes use of the same or different sample nucleic acid from a test subject.

A genetic variation sometimes is associated with medical condition. An outcome determinative of a genetic variation is sometimes an outcome determinative of the presence or absence of a condition (e.g., a medical condition), disease, syndrome or abnormality, or includes, detection of a condition, disease, syndrome or abnormality (e.g., non-limiting examples listed in Table 2). In some cases a diagnosis comprises assessment of an outcome. An outcome determinative of the presence or absence of a condition (e.g., a medical condition), disease, syndrome or abnormality by methods described herein can sometimes be independently verified by further testing (e.g., by karyotyping and/or amniocentesis).

Analysis and processing of data can provide one or more outcomes. In some embodiments an analysis (e.g., an analysis of nucleic acids) comprises determining an outcome. The term "outcome" as used herein refers to a result of data processing that facilitates determining whether a subject was, or is at risk of having, a genetic variation. An outcome often comprises one or more numerical values generated using a processing method described herein in the context of one or more considerations of probability. A consideration of probability includes but is not limited to: measure of variability, confidence level, sensitivity, specificity, standard deviation, coefficient of variation (CV) and/or confidence level, Z-scores, Chi values, Phi values, ploidy values, fitted fetal fraction, area ratios, median elevation, the like or combinations thereof. A consideration of probability can also facilitate determining whether a subject is at risk of having, or has, a genetic variation, and an outcome determinative of a presence or absence of a genetic disorder often includes such a consideration. An outcome or call can also be determined according to a statistical difference. A statistical difference is often determined by comparing two or more data values or sets of data. A statistical difference (e.g., a significant difference) can be determined by a suitable statistical method. Non-limiting examples of suitable statistical tests or methods that can compare two or more data values or data sets and/or determine a statistical difference include a t-test (e.g., a mean, median, or absolute t-statistic), a student's t-test, a Z-test, an F-test, Chi-squared test, Wilcox test, ANOVA, MANOVA, MANCOVA, logistic regression, maximum likelihood, p-values, the like, combinations thereof or variations thereof. Determining the presence of a statistical difference can also facilitate determining whether a subject is at risk of having, or has, a genetic variation, and/or an outcome determinative of a presence or absence of a genetic disorder.

An outcome often is a phenotype with an associated level of confidence (e.g., fetus is positive for trisomy 21 with a confidence level of 99%, test subject is negative for a cancer associated with a genetic variation at a confidence level of 95%). Different methods of generating outcome values sometimes can produce different types of results. Generally, there are four types of possible scores or calls that can be made based on outcome values generated using methods described herein: true positive, false positive, true negative and false negative. The terms "score", "scores", "call" and "calls" as used herein refer to calculating the probability that a particular genetic variation is present or absent in a subject/sample. The value of a score may be used to determine, for example, a variation, difference, or ratio of mapped sequence reads that may correspond to a genetic variation. For example, calculating a positive score for a selected genetic variation from a data set, with respect to a reference genome can lead to an identification of the presence or absence of a genetic variation, which genetic variation sometimes is associated with a medical condition (e.g., cancer, preeclampsia, trisomy, monosomy, and the like). In some embodiments, an outcome comprises a profile. In those embodiments in which an outcome comprises a profile, any suitable profile or combination of profiles can be used for an outcome. Non-limiting examples of profiles that can be used for an outcome include z-score profiles, p-value profiles, chi value profiles, phi value profiles, the like, and combinations thereof.

An outcome generated for determining the presence or absence of a genetic variation sometimes includes a null result (e.g., a data point between two clusters, a numerical value with a standard deviation that encompasses values for both the presence and absence of a genetic variation, a data set with a profile plot that is not similar to profile plots for subjects having or free from the genetic variation being investigated). In some embodiments, an outcome indicative of a null result still is a determinative result, and the determination can include the need for additional information and/or a repeat of the data generation and/or analysis for determining the presence or absence of a genetic variation.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a genetic variation can be expressed in any suitable form, which form comprises without limitation, a probability (e.g., odds ratio, p-value), likelihood, value in or out of a cluster, value over or under a threshold value, value with a measure of variance or confidence, or risk factor, associated with the presence or absence of a genetic variation for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value (e.g., greater than 1, less than 1), and an uncertainty or confidence level associated with the value. An outcome also can describe any assumptions used in data processing. In certain embodiments, an outcome comprises a value that falls within or outside a predetermined range of values and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. The term "true positive" as used herein refers to a subject correctly diagnosed as having a genetic variation. The term "false positive" as used herein refers to a subject wrongly identified as having a genetic variation. The term "true negative" as used herein refers to a subject correctly identified as not having a genetic variation. The term "false negative" as used herein refers to a subject wrongly identified as not having a genetic variation. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative. The term "sensitivity" as used herein refers to the number of true positives divided by the number of true positives plus the number of false negatives, where sensitivity (sens) may be within the range of 0≤sens≤1. Ideally, the number of false negatives equal zero or close to zero, so that no subject is wrongly identified as not having at least one genetic variation when they indeed have at least one genetic variation. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of 0≤spec≤1. Ideally, the number of false positives equal zero or close to zero, so that no subject is wrongly identified as having at least one genetic variation when they do not have the genetic variation being assessed.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein.

A method that has sensitivity and specificity equaling one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

After one or more outcomes have been generated, an outcome often is used to provide a determination of the presence or absence of a genetic variation and/or associated medical condition. An outcome typically is provided to a health care professional (e.g., laboratory technician or manager; physician or assistant). In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in any suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing.

In some embodiments, presence or absence of a genetic variation (e.g., chromosome aneuploidy) is determined for a fetus. In such embodiments, presence or absence of a fetal genetic variation (e.g., fetal chromosome aneuploidy) is determined. In some embodiments an analysis (e.g., an analysis of nucleic acids) comprises determining the presence or absence of one or more genetic variations (e.g., in a fetus). In some embodiments an analysis comprises determining the presence or absence of one or more chromosome aneuploidies (e.g., a fetal aneuploidy). In some embodiments a fetal aneuploidy is a trisomy. In some embodiments a fetal trisomy is a trisomy of chromosome 13, 18, and/or 21.

In certain embodiments, presence or absence of a genetic variation (e.g., chromosome aneuploidy) is determined for a test sample. In such embodiments, presence or absence of a genetic variation in test sample nucleic acid (e.g., chromosome aneuploidy) is determined. In some embodiments, a variation detected or not detected resides in sample nucleic acid from one source but not in sample nucleic acid from another source. Non-limiting examples of sources include placental nucleic acid, fetal nucleic acid, maternal nucleic acid, cancer cell nucleic acid, non-cancer cell nucleic acid, the like and combinations thereof. In non-limiting examples, a particular genetic variation detected or not detected (i) resides in placental nucleic acid but not in fetal nucleic acid and not in maternal nucleic acid; (ii) resides in fetal nucleic acid but not maternal nucleic acid; or (iii) resides in maternal nucleic acid but not fetal nucleic acid.

Use of Outcomes

A health care professional, or other qualified individual, receiving a report comprising one or more outcomes determinative of the presence or absence of a genetic variation can use the displayed data in the report to make a call regarding the status of the test subject or patient. The healthcare professional can make a recommendation based on the provided outcome, in some embodiments. A health care professional or qualified individual can provide a test subject or patient with a call or score with regards to the presence or absence of the genetic variation based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient. The term "receiving a report" as used herein refers to obtaining, by any communication means, a written and/or graphical representation comprising an outcome, which upon review allows a healthcare professional or other qualified individual to make a determination as to the presence or absence of a genetic variation in a test subject or patient. The report may be generated by a computer or by human data entry, and can be communicated using electronic means (e.g., over the internet, via computer, via fax, from one network location to another location at the same or different physical sites), or by any other method of sending or receiving data (e.g., mail service, courier service and the like). In some embodiments the outcome is transmitted to a health care professional in a suitable medium, including, without limitation, in verbal, document, or file form. The file may be, for example, but not limited to, an auditory file, a computer readable file, a paper file, a laboratory file or a medical record file.

The term "providing an outcome" and grammatical equivalents thereof, as used herein also can refer to any method for obtaining such information, including, without limitation, obtaining the information from a laboratory file. A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

A healthcare professional or qualified individual, can provide any suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing. In some embodiments the recommendation is dependent on the outcome based classification provided (e.g., Down's syndrome, Turner syndrome, medical conditions associated with genetic variations in T13, medical conditions associated with genetic variations in T18).

Software can be used to perform one or more steps in the process described herein, including but not limited to; counting, data processing, generating an outcome, and/or providing one or more recommendations based on generated outcomes.

Fetal Gender

In some embodiments, the prediction of a fetal gender or gender related disorder (e.g., sex chromosome aneuploidy) can be determined by a method or apparatus described herein. In some embodiments, a method in which fetal gender is determined can also comprise determining fetal fraction and/or presence or absence of a fetal genetic variation (e.g., fetal chromosome aneuploidy). Determining presence or absence of a fetal genetic variation can be performed in a suitable manner, non-limiting examples of which include karyotype analysis, amniocentesis, circulating cell-free nucleic acid analysis, cell-free fetal DNA analysis, nucleotide sequence analysis, sequence read quantification, targeted approaches, amplification-based approaches, mass spectrometry-based approaches, differential methylation-based approaches, differential digestion-based approaches, polymorphism-based approaches, hybridization-based approaches (e.g., using probes), and the like.

Gender determination generally is based on a sex chromosome. In humans, there are two sex chromosomes, the X and Y chromosomes. The Y chromosome contains a gene, SRY, which triggers embryonic development as a male. The Y chromosomes of humans and other mammals also contain other genes needed for normal sperm production. Individuals with XX are female and XY are male and non-limiting variations, often referred to as sex chromosome aneuploidies, include X0, XYY, XXX and XXY. In some instances, males have two X chromosomes and one Y chromosome (XXY; Klinefelter's Syndrome), or one X chromosome and two Y chromosomes (XYY syndrome; Jacobs Syndrome), and some females have three X chromosomes (XXX; Triple X Syndrome) or a single X chromosome instead of two (X0; Turner Syndrome). In some instances, only a portion of cells in an individual are affected by a sex chromosome aneuploidy which may be referred to as a mosaicism (e.g., Turner mosaicism). Other cases include those where SRY is damaged (leading to an XY female), or copied to the X (leading to an XX male).

In certain cases, it can be beneficial to determine the gender of a fetus in utero. For example, a patient (e.g., pregnant female) with a family history of one or more sex-linked disorders may wish to determine the gender of the fetus she is carrying to help assess the risk of the fetus inheriting such a disorder. Sex-linked disorders include, without limitation, X-linked and Y-linked disorders. X-linked disorders include X-linked recessive and X-linked dominant disorders. Examples of X-linked recessive disorders include, without limitation, immune disorders (e.g., chronic granulomatous disease (CYBB), Wiskott-Aldrich syndrome, X-linked severe combined immunodeficiency, X-linked agammaglobulinemia, hyper-IgM syndrome type 1, IPEX, X-linked lymphoproliferative disease, Properdin deficiency), hematologic disorders (e.g., Hemophilia A, Hemophilia B, X-linked sideroblastic anemia), endocrine disorders (e.g., androgen insensitivity syndrome/Kennedy disease, KAL1 Kallmann syndrome, X-linked adrenal hypoplasia congenital), metabolic disorders (e.g., ornithine transcarbamylase deficiency, oculocerebrorenal syndrome, adrenoleukodystrophy, glucose-6-phosphate dehydrogenase deficiency, pyruvate dehydrogenase deficiency, Danon disease/glycogen storage disease Type IIb, Fabry's disease, Hunter syndrome, Lesch-Nyhan syndrome, Menkes disease/occipital horn syndrome), nervous system disorders (e.g., Coffin-Lowry syndrome, MASA syndrome, X-linked alpha thalassemia mental retardation syndrome, Siderius X-linked mental retardation syndrome, color blindness, ocular albinism, Norrie disease, choroideremia, Charcot-Marie-Tooth disease (CMTX2-3), Pelizaeus-Merzbacher disease, SMAX2), skin and related tissue disorders (e.g., dyskeratosis congenital, hypohidrotic ectodermal dysplasia (EDA), X-linked ichthyosis, X-linked endothelial corneal dystrophy), neuromuscular disorders (e.g., Becker's muscular dystrophy/Duchenne, centronuclear myopathy (MTM1), Conradi-Hünermann syndrome, Emery-Dreifuss muscular dystrophy 1), urologic disorders (e.g., Alport syndrome, Dent's disease, X-linked nephrogenic diabetes insipidus), bone/tooth disorders (e.g., AMELX Amelogenesis imperfecta), and other disorders (e.g., Barth syndrome, McLeod syndrome, Smith-Fineman-Myers syndrome, Simpson-Golabi-Behmel syndrome, Mohr-Tranebjærg syndrome, Naso-digitoacoustic syndrome). Examples of X-linked dominant disorders include, without limitation, X-linked hypophosphatemia, Focal dermal hypoplasia, Fragile X syndrome, Aicardi syndrome, Incontinentia pigmenti, Rett syndrome, CHILD syndrome, Lujan-Fryns syndrome, and Orofaciodigital syndrome 1. Examples of Y-linked disorders include, without limitation, male infertility, retinits pigmentosa, and azoospermia.

Chromosome Abnormalities

In some embodiments, the presence or absence of a fetal chromosome abnormality can be determined by using a method or apparatus described herein. Chromosome abnormalities include, without limitation, a gain or loss of an entire chromosome or a region of a chromosome comprising one or more genes. Chromosome abnormalities include monosomies, trisomies, polysomies, loss of heterozygosity, deletions and/or duplications of one or more nucleotide sequences (e.g., one or more genes), including deletions and duplications caused by unbalanced translocations. The terms "aneuploidy" and "aneuploid" as used herein refer to an abnormal number of chromosomes in cells of an organism. As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a segment of a chromosome.

The term "monosomy" as used herein refers to lack of one chromosome of the normal complement. Partial monosomy can occur in unbalanced translocations or deletions, in which only a segment of the chromosome is present in a single copy. Monosomy of sex chromosomes (45, X) causes Turner syndrome, for example.

The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "euploid", in some embodiments, refers a normal complement of chromosomes.

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47, XYY in Jacobs Syndrome).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing nondisjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the segment that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

Tables 2A and 2B present a non-limiting list of disease associations (e.g., medical conditions, chromosome conditions, syndromes, genetic variations and/or abnormalities) that can be potentially identified by methods, systems, machines and apparatus described herein. Table 2B is from the DECIPHER database as of Oct. 6, 2011 (e.g., version 5.1, based on positions mapped to GRCh37; available at uniform resource locator (URL) dechipher.sanger.ac.uk).

TABLE 2A

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphproliferative disease |
| 1 | 1p (somatic) monosomy trisomy | neuroblastoma |
| 2 | monosomy trisomy 2q | growth retardation, developmental and mental delay, and minor physical abnormalities |

TABLE 2A-continued

| Chromosome | Abnormality | Disease Association |
|---|---|---|
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobson Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | 16q13.3 deletion monosomy trisomy (somatic) | Rubenstein-Taybi papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy | |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

TABLE 2B

| Syndrome | Chromosome | Start | End | Interval (Mb) | Grade |
|---|---|---|---|---|---|
| 12q14 microdeletion syndrome | 12 | 65,071,919 | 68,645,525 | 3.57 | |
| 15q13.3 microdeletion syndrome | 15 | 30,769,995 | 32,701,482 | 1.93 | |
| 15q24 recurrent microdeletion syndrome | 15 | 74,377,174 | 76,162,277 | 1.79 | |
| 15q26 overgrowth syndrome | 15 | 99,357,970 | 102,521,392 | 3.16 | |
| 16p11.2 microduplication syndrome | 16 | 29,501,198 | 30,202,572 | 0.70 | |
| 16p11.2-p12.2 microdeletion syndrome | 16 | 21,613,956 | 29,042,192 | 7.43 | |
| 16p13.11 recurrent microdeletion (neurocognitive disorder susceptibility locus) | 16 | 15,504,454 | 16,284,248 | 0.78 | |
| 16p13.11 recurrent microduplication (neurocognitive disorder susceptibility locus) | 16 | 15,504,454 | 16,284,248 | 0.78 | |
| 17q21.3 recurrent microdeletion syndrome | 17 | 43,632,466 | 44,210,205 | 0.58 | 1 |
| 1p36 microdeletion syndrome | 1 | 10,001 | 5,408,761 | 5.40 | 1 |
| 1q21.1 recurrent microdeletion (susceptibility locus for neurodevelopmental disorders) | 1 | 146,512,930 | 147,737,500 | 1.22 | 3 |

TABLE 2B-continued

| Syndrome | Chromosome | Start | End | Interval (Mb) | Grade |
|---|---|---|---|---|---|
| 1q21.1 recurrent microduplication (possible susceptibility locus for neurodevelopmental disorders) | 1 | 146,512,930 | 147,737,500 | 1.22 | 3 |
| 1q21.1 susceptibility locus for Thrombocytopenia-Absent Radius (TAR) syndrome | 1 | 145,401,253 | 145,928,123 | 0.53 | 3 |
| 22q11 deletion syndrome (Velocardiofacial/DiGeorge syndrome) | 22 | 18,546,349 | 22,336,469 | 3.79 | 1 |
| 22q11 duplication syndrome | 22 | 18,546,349 | 22,336,469 | 3.79 | 3 |
| 22q11.2 distal deletion syndrome | 22 | 22,115,848 | 23,696,229 | 1.58 | |
| 22q13 deletion syndrome (Phelan-Mcdermid syndrome) | 22 | 51,045,516 | 51,187,844 | 0.14 | 1 |
| 2p15-16.1 microdeletion syndrome | 2 | 57,741,796 | 61,738,334 | 4.00 | |
| 2q33.1 deletion syndrome | 2 | 196,925,089 | 205,206,940 | 8.28 | 1 |
| 2q37 monosomy | 2 | 239,954,693 | 243,102,476 | 3.15 | 1 |
| 3q29 microdeletion syndrome | 3 | 195,672,229 | 197,497,869 | 1.83 | |
| 3q29 microduplication syndrome | 3 | 195,672,229 | 197,497,869 | 1.83 | |
| 7q11.23 duplication syndrome | 7 | 72,332,743 | 74,616,901 | 2.28 | |
| 8p23.1 deletion syndrome | 8 | 8,119,295 | 11,765,719 | 3.65 | |
| 9q subtelomeric deletion syndrome | 9 | 140,403,363 | 141,153,431 | 0.75 | 1 |
| Adult-onset autosomal dominant leukodystrophy (ADLD) | 5 | 126,063,045 | 126,204,952 | 0.14 | |
| Angelman syndrome (Type 1) | 15 | 22,876,632 | 28,557,186 | 5.68 | 1 |
| Angelman syndrome (Type 2) | 15 | 23,758,390 | 28,557,186 | 4.80 | 1 |
| ATR-16 syndrome | 16 | 60,001 | 834,372 | 0.77 | 1 |
| AZFa | Y | 14,352,761 | 15,154,862 | 0.80 | |
| AZFb | Y | 20,118,045 | 26,065,197 | 5.95 | |
| AZFb + AZFc | Y | 19,964,826 | 27,793,830 | 7.83 | |
| AZFc | Y | 24,977,425 | 28,033,929 | 3.06 | |
| Cat-Eye Syndrome (Type I) | 22 | 1 | 16,971,860 | 16.97 | |
| Charcot-Marie-Tooth syndrome type 1A (CMT1A) | 17 | 13,968,607 | 15,434,038 | 1.47 | 1 |
| Cri du Chat Syndrome (5p deletion) | 5 | 10,001 | 11,723,854 | 11.71 | 1 |
| Early-onset Alzheimer disease with cerebral amyloid angiopathy | 21 | 27,037,956 | 27,548,479 | 0.51 | |
| Familial Adenomatous Polyposis | 5 | 112,101,596 | 112,221,377 | 0.12 | |
| Hereditary Liability to Pressure Palsies (HNPP) | 17 | 13,968,607 | 15,434,038 | 1.47 | 1 |
| Leri-Weill dyschondrostosis (LWD)-SHOX deletion | X | 751,878 | 867,875 | 0.12 | |
| Leri-Weill dyschondrostosis (LWD)-SHOX deletion | X | 460,558 | 753,877 | 0.29 | |
| Miller-Dieker syndrome (MDS) | 17 | 1 | 2,545,429 | 2.55 | 1 |
| NF1-microdeletion syndrome | 17 | 29,162,822 | 30,218,667 | 1.06 | 1 |
| Pelizaeus-Merzbacher disease | X | 102,642,051 | 103,131,767 | 0.49 | |

TABLE 2B-continued

| Syndrome | Chromosome | Start | End | Interval (Mb) | Grade |
|---|---|---|---|---|---|
| Potocki-Lupski syndrome (17p11.2 duplication syndrome) | 17 | 16,706,021 | 20,482,061 | 3.78 | |
| Potocki-Shaffer syndrome | 11 | 43,985,277 | 46,064,560 | 2.08 | 1 |
| Prader-Willi syndrome (Type 1) | 15 | 22,876,632 | 28,557,186 | 5.68 | 1 |
| Prader-Willi Syndrome (Type 2) | 15 | 23,758,390 | 28,557,186 | 4.80 | 1 |
| RCAD (renal cysts and diabetes) | 17 | 34,907,366 | 36,076,803 | 1.17 | |
| Rubinstein-Taybi Syndrome | 16 | 3,781,464 | 3,861,246 | 0.08 | 1 |
| Smith-Magenis Syndrome | 17 | 16,706,021 | 20,482,061 | 3.78 | 1 |
| Sotos syndrome | 5 | 175,130,402 | 177,456,545 | 2.33 | 1 |
| Split hand/foot malformation 1 (SHFM1) | 7 | 95,533,860 | 96,779,486 | 1.25 | |
| Steroid sulphatase deficiency (STS) | X | 6,441,957 | 8,167,697 | 1.73 | |
| WAGR 11p13 deletion syndrome | 11 | 31,803,509 | 32,510,988 | 0.71 | |
| Williams-Beuren Syndrome (WBS) | 7 | 72,332,743 | 74,616,901 | 2.28 | 1 |
| Wolf-Hirschhorn Syndrome | 4 | 10,001 | 2,073,670 | 2.06 | 1 |
| Xq28 (MECP2) duplication | X | 152,749,900 | 153,390,999 | 0.64 | |

Grade 1 conditions often have one or more of the following characteristics; pathogenic anomaly; strong agreement amongst geneticists; highly penetrant; may still have variable phenotype but some common features; all cases in the literature have a clinical phenotype; no cases of healthy individuals with the anomaly; not reported on DVG databases or found in healthy population; functional data confirming single gene or multi-gene dosage effect; confirmed or strong candidate genes; clinical management implications defined; known cancer risk with implication for surveillance; multiple sources of information (OMIM, GeneReviews, Orphanet, Unique, Wikipedia); and/or available for diagnostic use (reproductive counseling).

Grade 2 conditions often have one or more of the following characteristics; likely pathogenic anomaly; highly penetrant; variable phenotype with no consistent features other than DD; small number of cases/reports in the literature; all reported cases have a clinical phenotype; no functional data or confirmed pathogenic genes; multiple sources of information (OMIM, Genereviews, Orphanet, Unique, Wikipedia); and/or may be used for diagnostic purposes and reproductive counseling.

Grade 3 conditions often have one or more of the following characteristics; susceptibility locus; healthy individuals or unaffected parents of a proband described; present in control populations; non penetrant; phenotype mild and not specific; features less consistent; no functional data or confirmed pathogenic genes; more limited sources of data; possibility of second diagnosis remains a possibility for cases deviating from the majority or if novel clinical finding present; and/or caution when using for diagnostic purposes and guarded advice for reproductive counseling.

EXAMPLES

The examples set forth below illustrate certain embodiments and do not limit the technology.

Example 1: Assays to Determine the Presence or Absence of a Chromosome Aneuploidy in Chromosomes 13, 18 and/or 21

Assay Design

PCR primers and MALDI-TOF MS TyperPLEX extension primers were designed using Assay Design Suite1.0, online tool hosted at www.MYSequenom.com (Design Suite 1.0 [online], [retrieved on 2014 Mar. 4], retrieved from the World Wide Web internet URL mysequenom.com).

All DNA sequences were retrieved from UCSC genome browser (http://genome.ucsc.edu/). DNA sequences with more than one restriction enzyme recognition site for the methylation sensitive restriction enzymes HhaI and HpaII were loaded to Assay Design Suite 1.0. The target regions (i.e., portions of DMRs which spanned at least one restriction site) were loaded into the Assay Design Suite. The parameters of design were as follows: amplicon length was 60-100 bp, optimum (amplicon length) was 80 bp, mass range was 4300-9000 Da, overall amplicons design confidence score cutoff was 0.3, extension primer false primer potential was 0.2, hairpin/dimer extension potential was 0.2, overall confidence score cutoff was 0.2, minimum multiplex level was 5, and multiplex confidence score cutoff was 0.4. All additional parameters were set as default values. All designed assays were unique to chromosome 13 (chr13), chromosome 18 (chr18) and chromosome 21 (chr21), had at least one methylation sensitive restriction enzyme site, and did not contain any known SNPs within PCR primers, extension primers, or restriction enzyme sites.

A competitor oligonucleotide was designed for each assay. Each competitor oligonucleotide matched the sequence of the target sequence of each assay in all positions with the exception a single nucleotide base mismatch, sometimes referred to as an artificial SNP. To ensure successful annealing of PCR primers to the competitor oligonucleotide, all competitor oligonucleotides were expanded to include genomic sequences 8-10 base pairs (bp) upstream and downstream of each amplicon.

Assay Selection

For a region to be considered validated and thus move forward to inclusion in the initial evaluation of a methylation based assay, the data must show less than 3% methylation in non-pregnant plasma (as determined by the ratio of copy number of digested non-pregnant ccf DNA/undigested non-pregnant ccf DNA) and a Pearson correlation coefficient of greater than 0.8 when using a model system consisting of an increasing ratio of placenta to peripheral blood mononuclear cells. Differentially methylated regions (DMRs) described in Tables 1A and 1B were selected, and 64 assays were designed to quantify target polynucleotides in these DMRs. A subset of 52 assays also was tested. Assays designated in Tables 1A and 1B were designed with suitable amplification primers and competitor oligonucleotides (e.g., for MALDI MS and MPS assays) and suitable extension oligonucleotides (e.g., for MADLI MS assays).

Methylation Assay

Circulating cell free (ccf) DNA was extracted from 4 mL of plasma using the QIAamp circulating nucleic acid kit (Qiagen) and eluted in 55 µL buffer EB (Qiagen). A majority portion of the eluted ccf DNA (40 µL) from each extracted sample was used for the methylation based assay; 10 µL were reserved for use for an assay to determine fetal fraction and input copy number quantification (SeqFQA).

DNA samples were treated with 20 units (U) ExoI (NEB), 20 U HhaI (NEB), 50 U HpaII (NEB), 1×PCR buffer (Sequenom), and 2 mM $MgCl_2$ in a 66 microliter (µL) reaction volume and incubated at 41° C. for 60 minutes. After digestion, enzymes were inactivated by heating at 98° C. for 10 minutes.

After enzyme digestion, DNA was amplified by the addition of 22 µL PCR mixture, the final PCR reaction containing 2 mM of $MgCl_2$, 0.5 millimolar (mM) dNTPs, 60 micromolar (µM) forward PCR primer, 180 µM reverse PCR primer, 5 U of Fast Start polymerase (Roche), and competitor oligonucleotides at a known concentration. The PCR was initiated by a 5 minute incubation at 98° C., followed by 45 cycles (30 seconds (sec.) at 95° C., 30 sec. at 64° C., and 30 sec. at 72° C.), and 72° C. for 3 minutes. After PCR, 1 milliAnson unit (mAU) of protease (Qiagen) was added into the PCR reaction and incubated at 55° C. for 30 minutes to degrade peptides present in DNA extracted from plasma.

A portion (20 µL) of purified PCR product from each sample was split into 4 parallel reactions of 5 µL each. Subsequently, 2 µL of a phosphatase reaction cocktail containing 0.5 U shrimp alkaline phosphatase (SAP), 5 U RNaseIf (NEB) and 0.85×SAP buffer (Sequenom) was added. After inactivation of SAP and RNaseIf at 85° C. for 5 minutes, an extension primer cocktail was added. The extension cocktail consisted of a mixture of extension primers, 0.2×iPLEX buffer (Sequenom), 0.2× TypePLEX Termination Mix (Sequenom), and 0.04 U TypePLEX enzyme (Sequenom). The extension program was: 94° C. for 30 sec., 40 cycles (94° C. for 5 sec. followed by 5 repetitions of 52° C. for 5 sec. and 80° C. for 5 sec.), and 72° C. for 3 minutes. After desalting the mixture by adding 6 milligrams (mg) Clean Resin (Sequenom), 12 nanoliters (nL) from each reaction was transferred to SpectronCHIP II-G384 and mass spectra recorded using a MassARRAY MALDI-TOF mass spectrometer. Spectra were acquired by using Sequenom SpectroAcquire software. The software parameters were set to acquire 20 shots from each of 9 raster positions, using best 5 shots for signal calculation.

Assay Requirements and Data Modeling

In addition to the experimental validation of differentiation methylation, a power analysis was performed to approximate the number of assays that would be needed to differentiate a euploid and aneuploid sample. For this power analysis, each population was modeled as a normal distribution. For an assay with 1000 input genomic copies, a fetal fraction of 4%, an observed average of maternal and placenta methylation levels, and an observed technical variance, it was estimated that a minimum of 7 assays per chromosome can differentiate euploid and trisomy samples (e.g., with a sensitivity equal to about 99%) when the analysis is conducted using mass spectrometry. When an assay analysis is conducted using DNA sequencing, it was estimated that a minimum of 4 assays per chromosome (e.g., analysis of at least 4 target polynucleotides per chromosome) can differentiate euploid and trisomy samples (e.g., with a sensitivity equal to about 99%). While the level of methylation for each of the loci evaluated in this assay are unlikely to vary greatly moving forward, assay optimization resulting in reduced technical variance could reduce the number of required assays further.

Sequencing-Based Fetal Quantifier Assay (SeqFQA)

SeqFQA Loci PCR with competitor oligo addition for copy number determination. The SeqFQA loci PCR was modified to incorporate a synthetic competitor oligonucleotide that is included at a known copy number and can be concurrently amplified with SeqFQA target SNPs. Methods and applications of SeqFQA are described in international patent application number PCT/US2013/050145, the entire content of which is incorporated herein by reference. The competitor oligonucleotide is a known genomic DNA sequence with a single base change difference from the genomic DNA reference—an artificial SNP not present in any population. Combined with knowledge of total competitor copy number included in the reaction, the ratio of sequencing reads from competitor oligonucleotide to the number of wild type genomic locus reads can be used to determine the genomic DNA copy number in the starting material (e.g., ccf nucleic acid).

Competitor and primer sequences. The synthetic competitor oligo was designed as a double stranded plasmid containing amplicon sequences corresponding to a portion of Albumin, RNaseP and ApoE gene loci. The plasmid (pIDTSmart-Kan) was obtained from IDT and has a MluI restriction site at each end of the gene insert region. A HindIII restriction site (AAGCTT) was added between each of the 3 individual competitor sequences flanked by the 5' linker, ATA. Table lists individual competitor sequences, their position in the gene region of the dsDNA plasmid and primer sequences designed to amplify the competitor and their genomic DNA counterpart. The assay process included two steps: Loci PCR and Universal PCR. The Loci PCR step is a multiplex PCR reaction which targets and amplifies target regions within the genome or from competitor oligonucleotides. The Universal PCR step was used to add sample specific index barcode sequences and enable the hybridization of the amplified products to a fixed surface, including, but not limited to, a massively parallel sequencing flowcell (Illumina). Loci PCR primer sequences were designed to contain tags to allow sequencing adapters to be incorporated via a Universal PCR using Assay Designer v4.0. The nucleotide sequence of the forward primer tag (e.g., Tag 1, SEQ ID NO: 324) and the reverse primer tag (e.g., Tag 2, SEQ ID NO: 325) are provided in Table 3. Competitor sequences were used as input for Assay Designer but constricted so that the forward primer had to hybridize within 35 bp of the artificial SNP site in the competitor oligonucleotide so that the site can be identified with a 36 bp sequencing read. Primer sequences meeting acceptability criteria for amplification were only for RNaseP and ApoE.

manufacturer's protocol. Copy number of competitor oligo was determined by Digital PCR using PCR primers for competitor sequences. Competitor oligos and corresponding genomic sequences were amplified by Loci PCR primers in the same reaction that SeqFQA target SNPs were amplified.

Loci PCR was performed in a 96-well plate format. SeqFQA and competitor Loci PCR primers were ordered from IDT and re-suspended to 100 µM in TE (IDT, pH 8.0). RNaseP and APOE loci PCR primers were combined in a mix containing both forward and reverse primers at a

TABLE 3

Total copy competitor sequences.

| Sequence Name | Sequence ID No. | Sequence |
|---|---|---|
| Albumin competitor oligonucleotide | SEQ ID NO: 321 | GCGTAGCAACCTGTTACATATTAAAGTTTTATTATACTAC ATTTTTCTACATCCTTTGTTTTAGGGTGTTGATTGCCTTTG CTCAGTATCTTCAGCC |
| RNaseP competitor oligonucleotide | SEQ ID NO: 322 | GTGTGGTCAGCTCTTCCCTTCATCACATACTTGGAGAAC AAAGGACACCGTTATCCATGCTTTTT<u>CAACACATTACATG TGGGAGGTAGG</u> |
| ApoE competitor | SEQ ID NO: 323 | GATTGACAGTTTCTCCTTCCCCAGACTGGCCAATCACAG GCAGGAAGATGAAGGTTTTGTGGGCTGC<u>GTTGCTGGTC ACATTCCTGGC</u> |
| Linker | | ATA |
| TAG 1 (e.g., forward primer tag) | SEQ ID NO: 324 | TCTTTCCCTACACGACGCTCTTCCGATCT |
| TAG 2 (e.g., reverse primer tag) | SEQ ID NO: 325 | GTGACTGGAGTTCAGACGTGTGCTCTTCCGATCT |
| HindIII site | | AAGCTT |
| dsPlasmid gene insert region | SEQ ID NO: 326 | 5'GCGTAGCAACCTGTTACATATTAAAGTTTTATTATACTA CATTTTTCTACATCCTTTGTTTTAGGGTGTTGATTGCCTTT GCTCAGTATCTTCAGCCATAAAGCTTGTGTGGTCAGCTC TTCCCTTCATCACATACTTGGAGAACAAAGGACACCGTT ATCCATGCTTTTTCAACACATTACATGTGGGAGGTAGGA TAAAGCTTGATTGACAGTTTCTCCTTCCCCAGACTGGCC AATCACAGGCAGGAAGATGAAGGTTTTGTGGGCTGCGTT GCTGGTCACATTCCTGGCATAAAGCTT-3' |
| Albumin Loci PCR forward primer sequence | SEQ ID NO: 327 | TCTTTCCCTACACGACGCTCTTCCGATCTACT<u>ACATTTTT CTACATCC</u> |
| Albumin Loci PCR reverse primer sequence | SEQ ID NO: 328 | GTGACTGGAGTTCAGACGTGTGCTCTTCCGATCTGATAC TGAGCAAAGGCAATC |
| RNaseP Loci PCR forward primer sequence | SEQ ID NO: 329 | TCTTTCCCTACACGACGCTCTTCCGATCT<u>CTCCCACATG TAATGTGTTG</u> |
| RNaseP Loci PCR reverse primer sequence | SEQ ID NO: 330 | GTGACTGGAGTTCAGACGTGTGCTCTTCCGATCTCATAC TTGGAGAACAAAGGAC |
| ApoE Loci PCR forward primer sequence | SEQ ID NO: 331 | TCTTTCCCTACACGACGCTCTTCCGATCT<u>CCAGGAATGT GACCAGCAAC</u> |
| ApoE Loci PCR reverse primer sequence | SEQ ID NO: 332 | GTGACTGGAGTTCAGACGTGTGCTCTTCCGATCTCAATC ACAGGCAGGAAGATG |

Loci PCR plus competitor. Double stranded DNA plasmid containing competitor sequences for RNaseP and APOE302 was digested with MsuI and HindIII (NEB) according to concentration of 10 µM. Digested competitor oligo was diluted to 1500 copies/µl. See Table 4 and Table 5 for PCR cocktail and thermal cycling conditions.

TABLE 4

SeqFQA loci PCR master mix including competitor primers.

| Reagent | Concentration in 30 μl reaction | Volume reagent for n = 1 (μl) |
|---|---|---|
| Water, HPLC grade | N/A | 6.72 |
| 10× PCR Buffer (20 mM MgCL2, Roche) | 1× (2 mM MgCl2) | 3 |
| 25 mM MgCl2 (Roche) | 2.5 mM | 3 |
| dNTPs (25 mM, Roche) | 500 μM | 0.6 |
| PCR primer mix-Forward (7 μM each) | 0.3 μM | 1.29 |
| PCR primer mix-Reverse (7 μM each) | 0.3 μM | 1.29 |
| FastStart PCR Enzyme (5 U/μl, Roche) | 0.2 U/μl | 1.2 |
| DNA | Varies | 10 |
| RNase P, ApoE forward and reverse primer mix (10 μM each) | 0.3 μM | 0.9 |
| Digested competitor oligo (1500 copies/μl) | 3000 copies | 2 |
| Total | — | 30 |

TABLE 5

Thermal cycling conditions for SeqFQA Loci PCR containing competitor.

| | | |
|---|---|---|
| 95° C. | 5 min | |
| 95° C. | 15 sec | |
| 60° C. | 30 sec | 35× |
| 72° C. | 1 min | |
| 72° C. | 3 min | |
| 4° C. | hold | |

Primer Limiting Methods for Universal PCR.

To eliminate the need for Universal PCR product quantitation on LabChip GX, primer limited Universal PCR was used. This involves using a low concentration of forward and reverse Universal PCR primers and driving the Universal PCR to completion such that all universally amplified products will reach the maximum concentration allowed by the limited primers. There are two approaches utilized—limiting both forward and reverse Universal PCR primers or alternatively limiting the forward Universal PCR primer only. Forward and reverse PCR primers are shown in Table 6.

TABLE 6

SeqFQA Universal PCR primer sequences

| Primer ID | SEQ ID NO. | Sequence |
|---|---|---|
| Univ-For_Mv2 | SEQ ID NO: 333 | AATGATACGGCGACCACCGAGATCTACACTCTTTCCCTACACG ACGCTC |
| Univ-Rev_Mv2 | SEQ ID NO: 334 | CAAGCAGAAGACGGCATACGAGAT-barcode-GTGACTGGAGTTCAGACGTG |

For Universal PCR with limited forward primer only, PCR cocktail recipe conditions are given in Table 7. Cycling conditions are given in Table 8. Bead clean-up is performed after Universal PCR as described hereafter. Following bead clean-up, Universal PCR library concentration is assumed to be 3 nM and should be diluted to 2 nM after libraries are pooled for multiplexing.

TABLE 7

PCR cocktail for SeqFQA Universal forward primer limited PCR

| Reagent | Concentration in 30 μl reaction | Volume reagent for n = 1 (μl) |
|---|---|---|
| Water, HPLC grade | N/A | 12.96 |
| 10× PCR Buffer (20 mM MgCL2, Roche) | 1× (2 mM MgCl2) | 3 |
| 25 mM MgCl2 (Roche) | 2.5 mM | 3 |
| dNTPs (25 mM, Roche) | 200 μM | 0.24 |
| Universal For primer (200 nM) | 10 nM | 1.5 |
| Universal Rev primer (1 μM) | 100 nM | 3 |
| FastStart PCR Enzyme (5 U/μl, Roche) | 0.05 U/μl | 0.3 |
| Loci PCR template (1 in 400 dilution) | 1 in 2000 | 6 |
| Total | — | 30 |

TABLE 8

Cycling conditions for SeqFQA Universal forward primer limited PCR.

| | | |
|---|---|---|
| 95° C. | 5 min | |
| 95° C. | 15 sec | |
| 60° C. | 30 sec | 5× |
| 72° C. | 1 min | |
| 72° C. | 3 min | |
| 4° C. | hold | |

Bead Cleanup Method

To remove un-incorporated PCR primers from the Universal PCR, a clean-up step is performed using Agencourt AMPure XP beads (Beckman Coulter). Bead clean-up is performed on Zephyr Liquid Handler (Caliper) or manually using a 96-well magnetic bead separator. Protocol is as follows:
1. Add 1.8× beads and mix 10× by pipetting
2. Incubate for 5 minutes at RT to bind DNA to beads and mix 10× by pipetting
3. Transfer to 96 well magnet plate and incubate for 5 minutes
4. Aspirate supernatant
5. Wash beads with 200 μl 80% Ethanol
6. Incubate 2 minutes then aspirate supernatant
7. Repeat wash step
8. Incubate at 37° C. for 10 minutes to dry bead pellet
9. Add 40 μl elution buffer to beads and mix 10× by pipetting
10. Incubate for 5 minutes at RT to release DNA from beads and mix 10× by pipetting
11. Transfer to 96 well magnet plate and incubate for 5 minutes
12. Transfer supernatant to new 96 well plate SeqFQA Analysis.

Assignment of Informative Alleles and Fetal Fraction Determination

Reads were aligned to the human genome (hg19) with up to 3 mismatches in each read to allow for sequencing error and variant alleles at target SNP position. The frequency of each SNP allele was determined by counting the number of reads having the allele of interest and dividing it by the total number of reads for each SNP locus (i.e., (# reads allele 1)/(# reads allele 1+# reads allele 2)). Based on the frequency value generated from this data, the sequenced genotypes were assigned as Type 0 non-informative genotypes, Type 1 informative genotypes or Type 2 informative genotypes. A Type 0 non-informative genotype is a fetal genotype that cannot be distinguished from the maternal genotype because the fetus has the same genotype as the mother (e.g., mother is "Aa" and fetus is "Aa"). A Type I informative genotype is the situation where the mother is homozygous (AA) and the fetus is heterozygous (Aa). This genotype is informative because allele "a" is from the father. The frequency of a Type 1 informative allele can be indicative of the percentage fetal DNA in the mixture. A Type 2 informative genotype is the situation where the mother is heterozygous (Aa) and the fetus is homozygous (AA). The genotype is informative because the frequency of the maternal allele "a" will deviate from the expected Mendelian frequency of 0.5 when there is fetal DNA contributing additional "A" alleles. This deviation in value from 0.5 can be used to compute the fetal fraction.

Allele frequencies for each of the SNPs was calculated for each sample based on the number of reads containing each allele, as described above. Variation of expected allele frequency could be due to the presence of fetal DNA with a different paternal allele or could be due to mis-incorporated sequences by the Illumina Sequencer (e.g., background noise). In some cases, the amount of background noise associated with each particular SNP amplicon was determined to establish a dynamic cutoff value for each SNP. Maternal DNA (i.e. buffy coat) samples were sequenced and the deviations from the expected Mendelian ratios of 1 for homozygotes and 0.5 for heterozygotes were observed. From these values a median-adjusted deviation (MAD score) was identified for each SNP assay. In some cases, a genotype was identified as being a Type I informative genotype when the paternal allele frequency measured was greater than 3× MAD score. In some cases, multiple Type 1 informative genotypes were identified and an average allele frequency was determined. Fetal fraction was calculated by multiplying the average Type 1 informative allele frequency by 2. For example, an average informative allele frequency of 4.15% indicated a fetal fraction of 8.3%. Fetal Fraction also can be calculated from Type 2 informative genotypes by determining maternal allele "a" frequencies deviating from 0.5 bp greater than 3×MAD, for example. Fetal fraction can be identified by multiplying this deviation by 2.

SNPs with extremely low or high allele frequencies are likely to be non-informative ones. They contribute as noise to the informative SNPs. Therefore, we first remove SNPs with extremely low or high MAFs (MAF<=0.01 or MAF>=0.49), and then we use a k-means clustering algorithm to cluster the remaining SNPs into two groups. In the end, we use all the SNPs in the lower mean cluster to estimate the true fetal fraction. In essence, we are replacing the rather cumbersome EM algorithm with a simplified version. This gives us robustness and our algorithm is always guaranteed to converge. This approach can also be extended to incorporate sequencing quality scores, where alleles with low sequencing quality score can be down-weighted in the clustering step (weighted k-means clustering).

Calculation of Total Input Genomic Equivalents (Copies)
1. Calculate ratio of reference allele reads divided by competitor oligonucleotide allele reads (e.g., Table 9). For POP_ALRNAP302 ("RNaseP") reference allele=G, Competitor allele=A.
For APO_ALRNAP302 ("ApoE") reference allele=C, Competitor allele=T.

TABLE 9

| Assay | A | C | G | T | reference allele reads/ competitor allele reads |
|---|---|---|---|---|---|
| POP_ALRNAP302 | 397 | 0 | 1246 | 0 | 3.139 |
| APO_ALRNAP302 | 0 | 2522 | 1 | 584 | 4.318 |
| POP_ALRNAP302 | 404 | 0 | 1153 | 0 | 2.854 |
| APO_ALRNAP302 | 0 | 2601 | 1 | 725 | 3.588 |

2. Calculate the number of genomic equivalents (copies) by multiplying the number of competitor oligonucleotide input copies per reaction by the ratio of reference allele/competitor oligonucleotide allele (e.g., Table 10).

TABLE 10

| Assay | Competitor copies | reference allele/ competitor allele | Total genomic copies per SeqFQA reaction |
|---|---|---|---|
| POP_ALRNAP302 | 500 | 3.139 | 1569.27 |
| APO_ALRNAP302 | 500 | 4.318 | 2159.25 |
| POP_ALRNAP302 | 500 | 2.854 | 1426.98 |
| APO_ALRNAP302 | 500 | 3.588 | 1793.79 |

3. Convert "Total genomic copies per SeqFQA reaction to "copies per ml" assuming the use of 10 μl of ccf DNA from a 55 μl total elution volume and a total of 4 mL of input plasma. Therefore, 13.75 μl extracted ccf DNA is equivalent to 1 ml plasma. Multiply "Total genomic copies per SeqFQA reaction" by 13.75/10 to get "copies per ml" (e.g., Table 11):

TABLE 11

| Assay | Total genomic copies per SeqFQA reaction | Copies per ml |
|---|---|---|
| POP_ALRNAP302 | 1569.27 | 2157.75 |
| APO_ALRNAP302 | 2159.25 | 2968.96 |
| POP_ALRNAP302 | 1426.98 | 1962.10 |
| APO_ALRNAP302 | 1793.79 | 2466.47 |

Based on the fetal fraction obtained by the SNP frequencies and the total input copy determined using competitor oligonucleotides, the number of input fetal copies was calculated for each sample by multiplying the fetal fraction by the number of total input copies.

Library Preparation for Massively Parallel Sequencing Adaptation of the Assay

PCR products produced as described above for MassARRAY may also be modified for massively parallel sequencing using a number of commercial kits including, but not limited to, the TruSeq library preparation kit (Illumina, San Diego, Calif.). This process used of a portion (1 μg) of PCR products diluted into 40 μL volume with EB buffer, and combined with 30 µL of End repair (ERP) mix, incubated at 30° C. for 30 mins. After the end repair reaction, DNA was column purified (Qiagen) and eluted into 35 µL EB buffer (Qiagen). A portion (15 µL) of cleaned, end repaired product then combined with 12.5 µL of A-tailing mix and 2.5 µL suspension buffer and subsequently incubated at 37° C. for 30 mins. After A-tailing, 2.5 µL ligation mix and 1 µL adapter oligonucleotide were added into A-tailing reaction and incubated at 30° C. for 10 mins. Finally, the adapter ligated products were purified using AMPure XP beads (Beckman) according to manufacturer's protocol with a ratio of 1.1×, and eluted into 20 µL EB buffer. A minority portion of the ligated product (1 µL) was then amplified in a PCR reaction (50 µL total volume; 25 µL PCR mater mix, 5 µL PCR primer cocktail, and 19 µL water). PCR conditions were as follows: 5-min incubation at 98° C., followed by 4 cycles (10 s at 98° C., 30 s at 65° C., and 30 s at 72° C.), and 72° C. for 5 mins. Upon completion of the PCR reaction, products were purified using AMPure XP beads (Beckman) and quality and quantity checked using the Caliper GX. Libraries were normalized to 1.6 nM using EB buffer (Qiagen), multiplexed together, denatured with 0.1 N sodium hydroxide, and diluted to a final concentration of 10 pM per lane. Sequencing (64 cycles followed by 7 cycles for sample barcode identification) was performed on HiSeq2000 sequencing instruments (Illumina).

MassARRAY-Based Data Analysis.

For each assay for each sample, data were analyzed using allele ratios. Allele ratios (AR) from MassARRAY data were calculated by dividing the area of the peak which represents the native analyte (product from input ccf DNA sample) by the area of the peak which represents the synthetic competitor oligonucleotide. This ratio provides a relative quantification (allele ratio) utilized for subsequent analytical methods.

Data Normalization

Data normalization described hereafter was applied given the data set in this example was relatively small. The same type of normalization may not be required for larger data sets.

The median allele ratios (AR) for each marker were transformed in the following ways: natural log (logAR), fetal copy normalization prior to natural log (scaledlogAR), and LOESS model predicted log allele ratio (predictedAR). ScaledlogAR was determined by dividing the logAR by fetal copy number and taking the log of the quotient.

The relationship of logAR to fetal copy and scaledlogAR to fetal copy for chromosome 13 (e.g., assay chr13_49) were plotted for comparison (data not shown). PredictedAR utilized an LOESS model to determine the relationship of a sample's logAR and estimated fetal copy for euploid. Specifically, predictedAR is calculated for each sample and each marker by subtracting the predicted logAR given fetal copy and adding the median logAR across euploid samples to the observed logAR. For some analyses, missing AR were inputted using the median of the specified chromosome for a given sample. Certain residual differences between the LOESS model and the observed logAR for some samples can be seen.

In addition, logAR was further normalized by standard normal transformation using the plate median and mad (standardized logAR). This is to remove the plate differences that were observed.

That is, let
i=1:3 be the plate number,
j=1:288 be the sample number
k denote the assay marker The standardized allele ratios are then $$z_j^{(k)} = \frac{\log(AR_{ij}^{(k)}) - \text{median}\{\log(AR_{ij}^{(k)}) \mid \forall\, j \in \text{plate } i\}}{\text{mad}\{\log(AR_{ij}^{(k)}) \mid \forall\, j \in \text{plate } i\}}. \quad \text{(Equation A)}$$

The following assay marker IDs were removed due to missing values: chr13_95, chr18_83, chr21_13, and chr21_164 leaving 16 assay markers on chromosome 21, 13 assay markers on chromosome 18, and 18 markers on chromosome 13.

Intermarker correlations were then corrected by using a robust covariance matrix trained on a subset of euploids (decorrelated logAR). The transformation is such that $$\tilde{Z} = (\tilde{z}_{ijl}^{(k)}) \times S^{-1/2} = \begin{pmatrix} z_1^{(1)} & \cdots & z_1^{(47)} \\ \vdots & \ddots & \vdots \\ z_{288}^{(1)} & \cdots & z_{288}^{(47)} \end{pmatrix} \times S^{-1/2} \quad \text{(Equation B)}$$

where $S=\text{cov}((z_j^{(k)})\mid j$ is in euploid subset) is a 47×47 matrix from a subset of 233 euploids.

Classification Model

Several methods were implemented for sample classification using the above data normalization.

I. Trimmed mean Z
II. Sample specific interchromosome normalized logAR ratios
III. Linear Discriminant Analyses
   a. logAR
   b. scaledlogAR
   c. predictedAR
   d. standardized logAR
   e. decorrelated logAR
IV. Generalized Linear Model (GEE), Generalized Estimating Equations (GEEGLM)
   a. logAR
   b. scaledlogAR
   c. predictedAR
V. Weighted Average Probability of Euploid
   a. scaledlogAR The trimmed mean (trimming of 0.05) of Z-scores were generated for each sample by calculating the median and mad of the total population of euploid samples for logAR, scaledlogAR, and predictedAR for each assay. Sample specific interchromosome normalized logAR ratios were calculated by normalizing the logAR for chromosome 21 with non-chromosome 21 logAR. This was repeated for chromosome 13 and 18 and the median values across each chromosome for a given sample was used as a test statistic.

The trisomy status was coded as dummy variables for use in the linear discriminant analyses. These dummy variables were the response variable with logAR, scaledlogAR, predictedAR, standardized logAR, and decorrelated logAR as the discriminators. The LDA was performed using no, "leave-one-out", 10-fold, and inter-plate cross validation. In addition to LDA, we employed a general linear model (GLM) and generalized estimating equations (GEE). The former assumes markers are independent and the later assumes marker dependence with an explicit use of the covariance across markers into the error term.

For weighted average probability of euploid method, the probability of being a euploid is calculated for each sample, across all markers for each chromosome, as 1 minus the cumulative probability from the empirical distribution from a subset of euploids for each marker. Weights are calculated based upon the overlap in the distributions between euploid and trisomy cases and are constant for all samples. The weighted average probability is calculated and some threshold is enforced for classification.

Classification Results

Trimmed mean Z scores were determined for each sample using scaledlogAR for chromosomes 13, 18, and 21. Sample specific interchromosome normalized scaledlogAR ratios for chromosomes 13, 18, and 21 were also determined. Table 12 illustrates the results from a modified 3-fold cross validated linear discriminant analyses on scaledlogAR values. The cross validation was performed using two of the three plates as the training set and the remaining plate as the test set. GEEGLM and GLM classification results for chromosome 13, 18 and 21 were generated using scaledlogAR for modified 3-fold cross validation and without cross-validation. The results can be plotted and visualized with the modified 3-fold cross validation on the x-axis and with no cross-validation on the y-axis.

Results for the LDA model from the MassARRAY and Sequencing are tabulated in Table 13 using the de-correlated, plate normalized log allele ratio values. The markers used for each target chromosome were chosen based upon the optimal subset of markers as determine by the overlap of the densities between euploids and trisomy cases. Stratified cross-validation was utilized so that approximately the same number of trisomy cases were in each fold. Five-fold cross-validation was performed for chr 21 markers and three-fold cross-validation was performed for chr 13 and chr 18 markers.

Figure 1B:
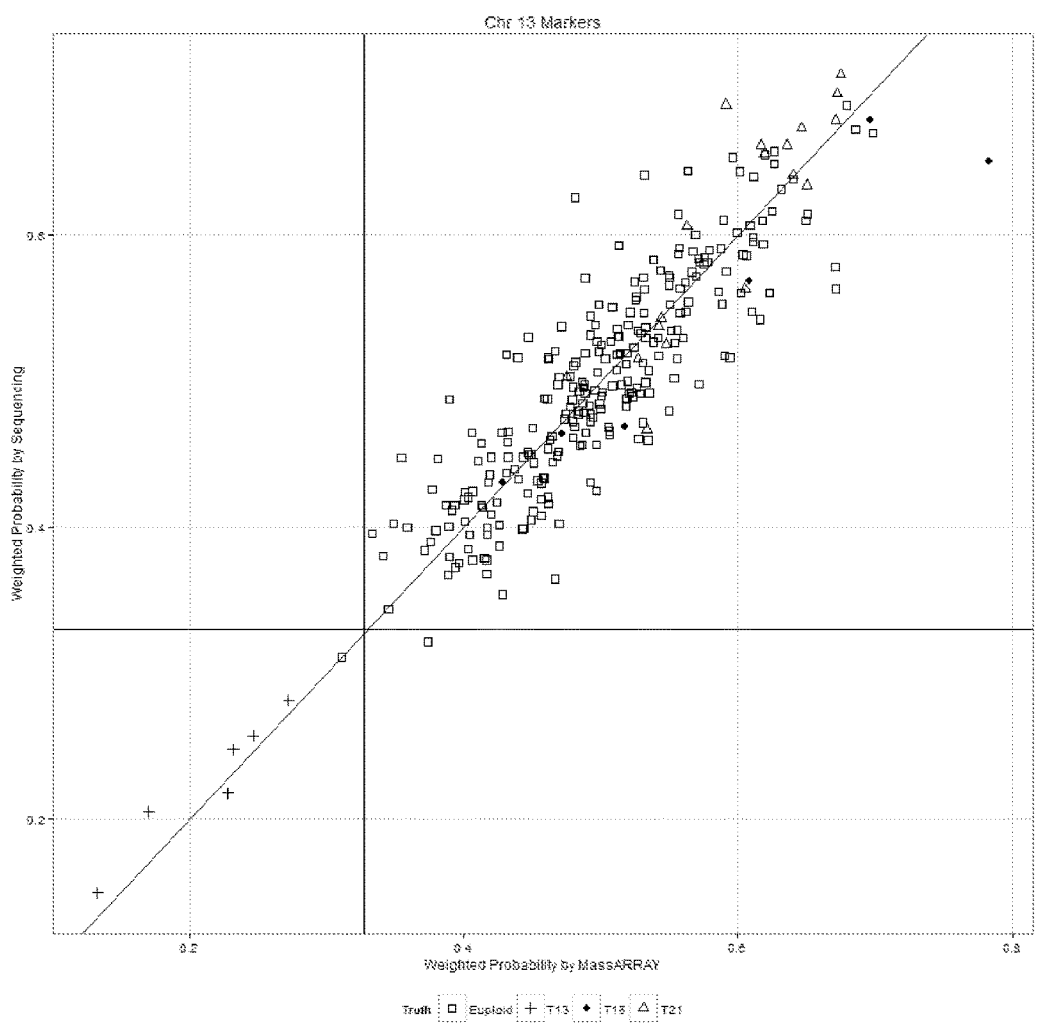
Figure 1C:
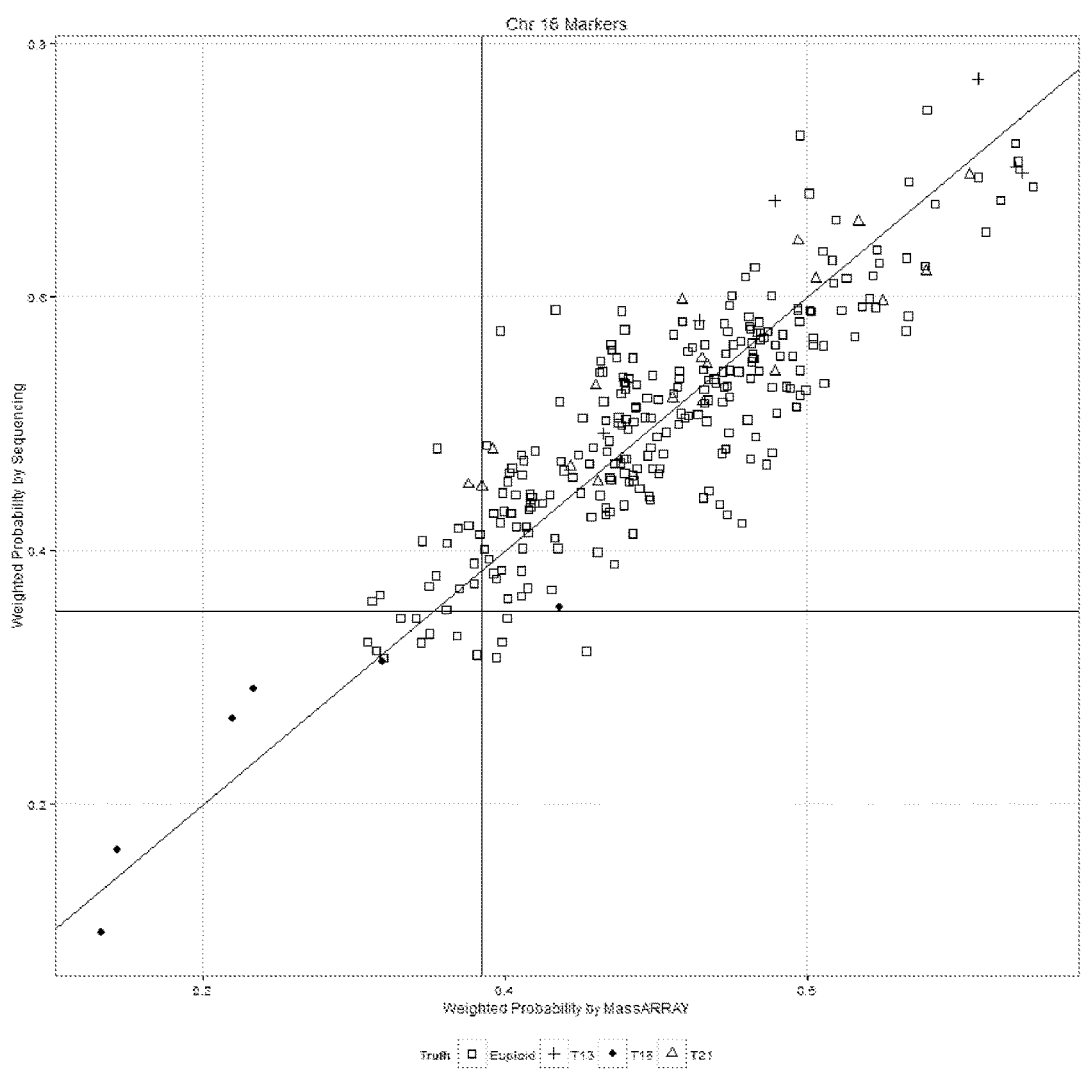

The weighted probability classification used a threshold that is half of the distance between the 5$^{th}$ percentile of the trisomies and the 95$^{th}$ percentile of the euploids. This returned results tabulated in Table 14. Results from the Sequencing and the MassARRAY are plotted against each other in FIG. 1.

TABLE 12

Linear Discriminant analyses results and classification using scaledlogAR with modified 3-fold cross validation.
LDA Fetal Copy Norm A.R. CV = 3SetFold

| | | TRUTH | | | |
|---|---|---|---|---|---|
| | | Euploid | T21 | T18 | T13 | Total |
| Predicted | Euploid | 254 | 3 | 4 | 1 | 262 |
| | T21 | 3 | 15 | 0 | 0 | 18 |
| | T18 | 0 | 0 | 2 | 0 | 2 |
| | T13 | 1 | 0 | 0 | 5 | 6 |
| | Total | 258 | 18 | 6 | 6 | 288 |

TABLE 13

Linear Discriminant Analysis Results and Classification Using De-correlated Data

| | | True Positive | Sensitivity | 95% Exact CI | True Negative | Specificity | 95% Exact CI |
|---|---|---|---|---|---|---|---|
| Mass-ARRAY | Chr 21 Markers | 14 | 0.7778 | (0.5236, 0.9359) | 268 | 0.9926 | (0.9735, 0.9991) |
| | Chr 13 Markers | 6 | 1 | (0.5407, 1) | 281 | 0.9965 | (0.9804, 0.9999) |
| | Chr 18 Markers | 4 | 0.6667 | (0.2228, 0.9567) | 281 | 0.9965 | (0.9804, 0.9999) |

TABLE 13-continued

Linear Discriminant Analysis Results and Classification Using De-correlated Data

| | | True Positive | Sensitivity | 95% Exact CI | True Negative | Specificity | 95% Exact CI |
|---|---|---|---|---|---|---|---|
| Sequencing | Chr 21 Markers | 15 | 0.8333 | (0.5858, 0.9642) | 267 | 0.9889 | (0.9679, 0.9977) |
| | Chr 13 Markers | 5 | 0.8333 | (0.3588, 0.9958) | 282 | 1 | (0.9870, 1) |
| | Chr 18 Markers | 4 | 0.6667 | (0.2228, 0.9567) | 280 | 0.9929 | (0.9746, 0.9991) |

TABLE 14

Weighted Probability Results and Classification Using Plate Normalized, Decorrelated, Scaled Data

| | | True Positive | Sensitivity | 95% Exact CI | True Negative | Specificity | 95% Exact CI |
|---|---|---|---|---|---|---|---|
| Mass-ARRAY | Chr 21 Markers | 18 | 1 | (0.8147, 1) | 269 | 0.9963 | (0.9795, 1) |
| | Chr 13 Markers | 6 | 1 | (0.5707, 1) | 281 | 0.9965 | (0.9804, 0.9999) |
| | Chr 18 Markers | 5 | 0.8333 | (0.3588, 0.9958) | 258 | 0.9149 | (0.876, 0.9447) |
| Sequencing | Chr 21 Markers | 17 | 0.9444 | (0.7271, 0.9986) | 268 | 0.9926 | (0.9735, 0.9991) |
| | Chr 13 Markers | 6 | 1 | (0.5407, 1) | 280 | 0.9929 | (0.9746, 0.9991) |
| | Chr 18 Markers | 5 | 0.8333 | (0.3588, 0.9958) | 269 | 0.9539 | (0.9225, 0.9752) |

Sequencing Data Analysis.

Resultant .bcl output files were converted to .fastq format and aligned to the human reference genome (hg19) using Bowtie. Sequencing reads overlapping the target variant site introduced by the synthetic competitor oligonucleotide were then evaluated and the variant ratio (sequencing input coverage/competitor oligonucleotide coverage) was calculated for each site within each sample. Ratios were normalized using the number of fetal copies as calculated by the SeqFQA reaction. Subsequently, z-scores were calculated for each assay for each sample used for classification and a chromosome specific 10% trimmed mean for each of the three target chromosomes (chromosomes 13, 18, and 21) calculated. The tested sample set is comprised of a set of 96 total samples including 86 plasma samples from females known to be carrying a euploid fetus, 6 females carrying a trisomy 21 fetus, two females carrying a trisomy 13 fetus, and two females carrying a trisomy 18 fetus. For this experiment, we utilized the trimmed mean chromosome values, logistic regression, and leave one out (95-fold) cross validation. A number of alternative methods could similarly be used and thus this method should not be concluded to the be best or only classification method. Using the aforementioned method and Weka software, all samples were classified correctly (below).

From WEKA version 3.6.10

Run information

Scheme:weka.classifiers.functions.Logistic-R 1.0E-8-M-1

Relation: R_data_frame

Instances: 96

Attributes: 4
   all.data2.Truth
   trim.z.13
   trim.z.18
   trim.z.21
Test mode:95-fold cross-validation
===Classifier model (full training set)===
Logistic Regression with ridge parameter of 1.0E-8

TABLE 15

Coefficients for Trisomy 21

|           | Euploid  | Trisomy 13 | Trisomy 18 |
|-----------|----------|------------|------------|
| trim.z.13 | 9.4779   | 49.2319    | −20.705    |
| trim.z.18 | 26.7595  | −4.4065    | 66.3903    |
| trim.z.21 | −38.5428 | −38.9295   | −50.3282   |
| Intercept | 35.3207  | −16.7623   | −21.312    |

TABLE 16

Odds Ratios for Trisomy 21

|           | Euploid              | T13                    | T18                   |
|-----------|----------------------|------------------------|-----------------------|
| trim.z.13 | 13068.0281           | 2.405174483066747E21   | 0                     |
| trim.z.18 | 4.183251979304027E11 | 0.0122                 | 6.806603992573679E28  |
| trim.z.21 | 0                    | 0                      | 0                     |

Time taken to build model: 0.01 seconds
Stratified Cross-Validation—Summary

| Correctly Classified Instances   | 96     | 100%    |
|----------------------------------|--------|---------|
| Incorrectly Classified Instances | 0      | 0%      |
| Kappa statistic                  | 1      |         |
| Mean absolute error              | 0.0004 |         |
| Root mean squared error          | 0.0037 |         |
| Relative absolute error          | 0.3297%|         |
| Root relative squared error      | 1.6435%|         |
| Total Number of Instances        | 96     |         |

TABLE 17

Detailed Accuracy By Class

|               | TP Rate | FP Rate | Precision | Recall | F-Measure | ROC Area | Class      |
|---------------|---------|---------|-----------|--------|-----------|----------|------------|
|               | 1       | 0       | 1         | 1      | 1         | 1        | Euploid    |
|               | 1       | 0       | 1         | 1      | 1         | 1        | Trisomy 13 |
|               | 1       | 0       | 1         | 1      | 1         | 1        | Trisomy 18 |
|               | 1       | 0       | 1         | 1      | 1         | 1        | Trisomy 21 |
| Weighted Avg. | 1       | 0       | 1         | 1      | 1         | 1        |            |

TABLE 18

Confusion Matrix

| Classification | a  | b | c | d |
|----------------|----|---|---|---|
| a = Euploid    | 86 | 0 | 0 | 0 |
| b = T13        | 0  | 2 | 0 | 0 |
| c = T18        | 0  | 0 | 2 | 0 |
| d = T21        | 0  | 0 | 0 | 6 |

Example 2: Examples of Embodiments

Listed hereafter are non-limiting examples of certain embodiments of the technology.

A1. A method for detecting one, two, three or four copies of a fetal chromosome, or portion thereof, in a sample, comprising:
(a) determining amounts of two or more target polynucleotides in each of chromosome 13, chromosome 18 and chromosome 21 in circulating cell-free nucleic acid from a sample from a human pregnant female bearing a fetus, wherein:
the two or more target polynucleotides in chromosome 13 are in chromosome 13 polynucleotides comprising chromosome 13 polynucleotides of SEQ ID NOs: 209 and 214, or complement thereof;
the two or more target polynucleotides in chromosome 18 are in chromosome 18 polynucleotides comprising chromosome 18 polynucleotides of SEQ ID NOs: 232 and 222, or complement thereof; and
the two or more target polynucleotides in chromosome 21 are in chromosome 21 polynucleotides comprising chromosome 21 polynucleotides of SEQ ID NOs: 256 and 253, or complement thereof; and
(b) quantifying, from the amounts, one, two, three or four copies of one or more of chromosome 13, chromosome 18, chromosome 21, or portion thereof, in the fetus.

A1.1. The method of embodiment A1, comprising determining the amount of one or more target polynucleotides in one or more of chromosome 13 polynucleotide SEQ ID NO: 211, chromosome 18 polynucleotide SEQ ID NO: 231 and chromosome 21 polynucleotide SEQ ID NO: 252.

A2. The method of embodiment A1 or A1.1, comprising, prior to (a), contacting nucleic acid from the sample with a cleavage agent under cleavage conditions, thereby generating cleaved nucleic acid and non-cleaved nucleic acid.

A3. The method of embodiment A2, wherein the cleavage agent is a restriction enzyme.

A4. The method of embodiment A3, wherein the restriction enzyme is a methylation sensitive restriction enzyme.

A5. The method of embodiment A4, wherein the restriction enzyme preferentially cleaves nucleic acid comprising one or more non-methylated recognition sequences.

A6. The method of any one of embodiments A2 to A5, wherein the nucleic acid in (a) from which the amounts of the two or more target polynucleotides are determined is substantially the non-cleaved nucleic acid.

A7. The method of any one of embodiments A1 to A6, wherein the amounts of the two or more target polynucleotides are determined by a process comprising mass spectrometry.

A7.1. The method of embodiment A7, wherein the mass spectrometry is matrix-assisted laser desorption ionization (MALDI) mass spectrometry.

A7.2. The method of any one of embodiments A1 to A6, wherein the amounts of the two or more target polynucleotides are determined by a process comprising sequencing.

A8. The method of any one of embodiments A1 to A7.2, wherein the amounts in (a) are determined in a single multiplex reaction.

A9. The method of any one of embodiments A1 to A8, wherein the detecting in (a) comprises contacting the nucleic acid with competitor oligonucleotide.

A10. The method of embodiment A9, wherein the competitor oligonucleotides each comprise a polynucleotide chosen from SEQ ID NOs 273, 275, 278, 296, 286, 295, 320, 317, 316 or complement thereof.

A11. The method of any one of embodiments A1 to A10, wherein the detecting in (a) comprises contacting the nucleic acid with primers under amplification conditions, thereby generating amplicons.

A12. The method of embodiment A11, wherein the primers comprise polynucleotides of SEQ ID NOs: 17, 81, 19, 83, 22, 86 or complement thereof, for amplifying target polynucleotides within chromosome 13.

A13. The method of embodiment A11 or A12, wherein the primers comprise polynucleotides of SEQ ID NOs: 40, 104, 30, 94, 39, 103 or complement thereof, for amplifying target polynucleotides within chromosome 18.

A14. The method of any one of embodiments A11 to A13, wherein the primers comprise polynucleotides of SEQ ID NOs: 64, 128, 61, 125, 60, 124 or complement thereof, for amplifying target polynucleotides within chromosome 21.

A15. The method of any one of embodiments A11 to A14, wherein the detecting in (a) comprises contacting the amplicons with extension oligonucleotides under conditions in which the extension oligonucleotides anneal to the amplicons and are extended by one or more nucleotides.

A16. The method of embodiment A15, wherein each of the extension oligonucleotides comprises a polynucleotide chosen from SEQ ID NOs: 145, 147, 150, 168, 158, 167, 192, 189, 188 or complement thereof.

A17. The method of any one of embodiments A1 to A16, wherein (a) comprises detecting the amount of four or more target polynucleotides in chromosome 13, and one or more of the target polynucleotides are in a chromosome 13 polynucleotide chosen from SEQ ID NOs: 198, 207, 206, 208, 200, 194, 210, 215, 212, 213, 204, 197, 201, 203, 193, 205, 199, 196, 195, 202 or complement thereof.

A18. The method of embodiment A17, wherein the detecting in (a) comprises contacting the nucleic acid with one or more competitor oligonucleotides comprising a polynucleotide chosen from SEQ ID NOs: 262, 271, 270, 272, 264, 258, 274, 279, 276, 277, 268, 261, 265, 267, 257, 269, 263, 260, 259, 266 or complement thereof.

A19. The method of embodiment A17 or A18, wherein the detecting in (a) comprises contacting the nucleic acid with primers under amplification conditions, thereby generating amplicons, wherein the primers comprise polynucleotides of SEQ ID NOs: 6, 70, 15, 79, 14, 78, 16, 80, 8, 72, 2, 66, 18, 82, 23, 87, 20, 84, 21, 85, 12, 76, 5, 69, 9, 73, 11, 75, 1, 65, 13, 77, 7, 71, 4, 68, 3, 67, 10, 74 or complement thereof.

A20. The method of embodiment A19, wherein the detecting in (a) comprises contacting the amplicons with extension oligonucleotides under conditions in which the extension oligonucleotides anneal to the amplicons and are extended by one or more nucleotides, wherein each of the extension oligonucleotides comprises a polynucleotide chosen from SEQ ID NOs: 134, 143, 142, 144, 136, 130, 146, 151, 148, 149, 140, 133, 137, 139, 129, 141, 135, 132, 131, 138 or complement thereof.

A21. The method of embodiment A17, wherein (a) comprises detecting the amount of five or more target polynucleotides in chromosome 13, and two of the target polynucleotides are in a chromosome 13 polynucleotide of SEQ ID NOs: 198, 207 or complement thereof.

A22. The method of embodiment A17, wherein (a) comprises detecting the amount of ten or more target polynucleotides in chromosome 13, and seven of the target polynucleotides are in a chromosome 13 polynucleotide of SEQ ID NOs: 198, 207, 206, 208, 200, 194, 210, or complement thereof.

A23. The method of embodiment A17, wherein (a) comprises detecting the amount of fifteen or more target polynucleotides in chromosome 13, and twelve of the target polynucleotides are in a chromosome 13 polynucleotide of SEQ ID NOs: 198, 207, 206, 208, 200, 194, 210, 215, 212, 213, 204, 197 or complement thereof.

A24. The method of any one of embodiments A1 to A23, wherein (a) comprises detecting the amount of four or more target polynucleotides in chromosome 18, and one or more of the target polynucleotides are in a chromosome 18 polynucleotide chosen from SEQ ID NOs: 229, 220, 219, 226, 221, 217, 218, 230, 228, 225, 216, 223, 227, 224 or complement thereof.

A25. The method of embodiment A24, wherein the detecting in (a) comprises contacting the nucleic acid with one or more competitor oligonucleotides comprising a polynucleotide chosen from SEQ ID NOs: 293, 284, 283, 290, 285, 281, 282, 294, 292, 289, 280, 287, 291, 288 or complement thereof.

A26. The method of embodiment A24 or A25, wherein the detecting in (a) comprises contacting the nucleic acid with primers under amplification conditions, thereby generating amplicons, wherein the primers comprise polynucleotides of SEQ ID NOs: 37, 101, 28, 92, 27, 91, 34, 98, 29, 93, 25, 89, 26, 90, 38, 102, 36, 100, 33, 97, 24, 88, 31, 95, 35, 99, 32, 96 or complement thereof.

A27. The method of embodiment A26, wherein the detecting in (a) comprises contacting the amplicons with extension oligonucleotides under conditions in which the extension oligonucleotides anneal to the amplicons and are extended by one or more nucleotides, wherein each of the extension oligonucleotides comprises a polynucleotide chosen from SEQ ID NOs: 165, 156, 155, 162, 157, 153, 154, 166, 164, 161, 152, 159, 163, 160 or complement thereof.

A28. The method of embodiment A24, wherein (a) comprises detecting the amount of five or more target polynucleotides in chromosome 18, and two of the target polynucleotides are in a chromosome 18 polynucleotide of SEQ ID NOs: 229, 220 or complement thereof.

A29. The method of embodiment A24, wherein (a) comprises detecting the amount of ten or more target polynucleotides in chromosome 18, and seven of the target polynucleotides are in a chromosome 18 polynucleotide of SEQ ID NOs: 229, 220, 219, 226, 221, 217, 218 or complement thereof.

A30. The method of embodiment A24, wherein (a) comprises detecting the amount of fifteen or more target polynucleotides in chromosome 18, and twelve of the target polynucleotides are in a chromosome 18 polynucleotide of SEQ ID NOs: 229, 220, 219, 226, 221, 217, 218, 230, 228, 225, 216, 223 or complement thereof.

A31. The method of any one of embodiments A1 to A30, wherein (a) comprises detecting the amount of four or more target polynucleotides in chromosome 21, and one or more of the target polynucleotides are in a chromosome 21 polynucleotide chosen from SEQ ID NOs: 244, 255, 254, 234, 240, 241, 245, 236, 239, 248, 233, 250, 251, 242, 249, 238, 243, 235, 246, 247, 237 or complement thereof.

A32. The method of embodiment A31, wherein the detecting in (a) comprises contacting the nucleic acid one or more competitor oligonucleotides comprising a polynucleotide chosen from SEQ ID NOs: 308, 319, 318, 298, 304, 305, 309, 300, 303, 312, 297, 314, 315, 306, 313, 302, 307, 299, 310, 311, 301 or complement thereof.

A33. The method of embodiment A31 or A32, wherein the detecting in (a) comprises contacting the nucleic acid with primers under amplification conditions, thereby generating amplicons, wherein the primers comprise polynucleotides of SEQ ID NOs: 52, 116, 63, 127, 62, 126, 42, 106, 48, 112, 49, 113, 53, 117, 44, 108, 47, 111, 56, 120, 41, 105, 58, 122, 59, 123, 50, 114, 57, 121, 46, 110, 51, 115, 43, 107, 54, 118, 55, 119, 45, 109 or complement thereof.

A34. The method of embodiment A33, wherein the detecting in (a) comprises contacting the amplicons with extension oligonucleotides under conditions in which the extension oligonucleotides anneal to the amplicons and are extended by one or more nucleotides, wherein each of the extension oligonucleotides comprises a polynucleotide chosen from SEQ ID NOs: 180, 191, 190, 170, 176, 177, 181, 172, 175, 184, 169, 186, 187, 178, 185, 174, 179, 171, 182, 183, 173 or complement thereof.

A35. The method of embodiment A31, wherein (a) comprises detecting the amount of five or more target polynucleotides in chromosome 21, and two of the target polynucleotides are in a chromosome 21 polynucleotide of SEQ ID NOs: 244, 255 or complement thereof.

A36. The method of embodiment A31, wherein (a) comprises detecting the amount of ten or more target polynucleotides in chromosome 21, and seven of the target polynucleotides are in a chromosome 21 polynucleotide of SEQ ID NOs: 244, 255, 254, 234, 240, 241, 245 or complement thereof.

A37. The method of embodiment A31, wherein (a) comprises detecting the amount of fifteen or more target polynucleotides in chromosome 21, and twelve of the target polynucleotides are in a chromosome 21 polynucleotide of SEQ ID NOs: 244, 255, 254, 234, 240, 241, 245, 236, 239, 248, 233, 250 or complement thereof.

B1. A method for detecting one, two, three or four copies of a fetal chromosome or portion thereof in a sample, comprising:
(a) determining amounts of target polynucleotides in each of chromosome 13, chromosome 18 and chromosome 21 in circulating cell-free nucleic acid from a sample from a human pregnant female bearing a fetus, wherein the target polynucleotides are in:
chromosome 13 polynucleotides of SEQ ID NOs: 193-198, 200-204, 206, 208-210, 212-215, or complement thereof;
chromosome 18 polynucleotides of SEQ ID NOs: 216-218, 220-230, 232, or complement thereof; and
chromosome 21 polynucleotides of SEQ ID NOs: 234, 236, 238-240, 242-246, 248-253, 255, 256, or complement thereof;
(b) quantifying, from the amounts, one, two, three or four copies of one or more of chromosome 13, chromosome 18, chromosome 21, or portion thereof, in the fetus.

B2. The method of embodiment B1, comprising determining in (a) the amounts of target polynucleotides in:
chromosome 13 polynucleotides of SEQ ID NOs: 199, 205, 207, 211 or complement thereof;
chromosome 18 polynucleotides of SEQ ID NOs: 219, 231, or complement thereof; and
chromosome 21 polynucleotides of SEQ ID NOs: 233, 235, 237, 241, 247, 254 or complement thereof.

B3. The method of embodiment B1 or B2, comprising, prior to (a), contacting nucleic acid from the sample with a cleavage agent under cleavage conditions, thereby generating cleaved nucleic acid and non-cleaved nucleic acid.

B4. The method of embodiment B3, wherein the cleavage agent is a restriction enzyme.

B5. The method of embodiment B4, wherein the restriction enzyme is a methylation sensitive restriction enzyme.

B6. The method of embodiment B5, wherein the restriction enzyme preferentially cleaves nucleic acid comprising one or more non-methylated recognition sequences.

B7. The method of any one of embodiments B3 to B6, wherein the nucleic acid in (a) from which the amounts of the target polynucleotides are determined is substantially the non-cleaved nucleic acid.

B8. The method of any one of embodiments B1 to B7, wherein the amounts of the target polynucleotides are determined by a process comprising mass spectrometry.

B8.1. The method of embodiment B8, wherein the mass spectrometry is matrix-assisted laser desorption ionization (MALDI) mass spectrometry.

B8.2. The method of any one of embodiments B1 to B7, wherein the amounts of the target polynucleotides are determined by a process comprising sequencing.

B9. The method of any one of embodiments B1 to B8.2, wherein the amounts in (a) are determined in a single multiplex reaction.

B10. The method of any one of embodiments B1 to B9, wherein the detecting in (a) comprises contacting the nucleic acid with competitor oligonucleotides.

B11. The method of embodiment B10, wherein the competitor oligonucleotides each comprise a polynucleotide chosen from SEQ ID NOs 257, 258, 259, 260, 261, 262, 264, 265, 266, 267, 268, 270, 272, 273, 274, 276, 277, 278, 279, 280, 281, 282, 284, 285, 286, 287, 288, 289, 290, 291, 292, 293, 294, 296, 298, 300, 302, 303, 304, 306, 307, 308, 309, 310, 312, 313, 314, 315, 316, 317, 319, 320, or complement thereof.

B12. The method of embodiment B11, wherein the competitor oligonucleotides each comprise a polynucleotide chosen from SEQ ID NOs 263, 269, 271, 275, 283, 295, 297, 299, 301, 305, 311, 318, or complement thereof.

B13. The method of any one of embodiments B1 to B12, wherein the detecting in (a) comprises contacting the nucleic acid with primers under amplification conditions, thereby generating amplicons.

B14. The method of embodiment B13, wherein the primers comprise polynucleotides of SEQ ID NOs: 1, 65, 2, 66, 3, 67, 4, 68, 5, 69, 6, 70, 8, 72, 9, 73, 10, 74, 11, 75, 12, 76, 14, 78, 16, 80, 17, 81, 18, 82, 20, 84, 21, 85, 22, 86, 23, 87, 24, 88, 25, 89, 26, 90, 28, 92, 29, 93, 30, 94, 31, 95, 32, 96, 33, 97, 34, 98, 35, 99, 36, 100, 37, 101, 38, 102, 40, 104, 42, 106, 44, 108, 46, 110, 47, 111, 48, 112, 50, 114, 51, 115, 52, 116, 53, 117, 54, 118, 56, 120, 57, 121, 58, 122, 59, 123, 60, 124, 61, 125, 63, 127, 64, 128, or complement thereof.

B15. The method of embodiment B14, wherein the primers comprise polynucleotides of SEQ ID NOs: 7, 71, 13, 77, 15, 79, 19, 83, 27, 91, 39, 103, 41, 105, 43, 107, 45, 109, 49, 113, 55, 119, 62, 126 or complement thereof.

B16. The method of any one of embodiments B13 to B15, wherein the detecting in (a) comprises contacting the amplicons with extension oligonucleotides under conditions in which the extension oligonucleotides anneal to the amplicons and are extended by one or more nucleotides.

B17. The method of embodiment B16, wherein each of the extension oligonucleotides comprises a polynucleotide chosen from SEQ ID NOs: 257, 258, 259, 260, 261, 262, 264, 265, 266, 267, 268, 270, 272, 273, 274, 276, 277, 278, 279, 280, 281, 282, 284, 285, 286, 287, 288, 289, 290, 291, 292, 293, 294, 296, 298, 300, 302, 303, 304, 306, 307, 308, 309, 310, 312, 313, 314, 315, 316, 317, 319, 320, or complement thereof.

B18. The method of embodiment B16, wherein each of the extension oligonucleotides comprises a polynucleotide chosen from SEQ ID NOs: 263, 269, 271, 275, 283, 295, 297, 299, 301, 305, 311, 318, or complement thereof.

C1. A kit for detecting one, two, three or four copies of a fetal chromosome, or portion thereof, in circulating cell-free nucleic acid from a sample from a human pregnant female bearing a fetus, comprising:
a collection of oligonucleotide primer pairs wherein each primer pair is configured for amplifying two or more target polynucleotides in each of chromosome 13, chromosome 18 and chromosome 21, wherein:
the two or more target polynucleotides in chromosome 13 are in chromosome 13 polynucleotides comprising chromosome 13 polynucleotides of SEQ ID NOs: 209 and 214, or complement thereof;
the two or more target polynucleotides in chromosome 18 are in chromosome 18 polynucleotides comprising chromosome 18 polynucleotides of SEQ ID NOs: 232 and 222, or complement thereof; and
the two or more target polynucleotides in chromosome 21 are in chromosome 21 polynucleotides comprising chromosome 21 polynucleotides of SEQ ID NOs: 256 and 253, or complement thereof.

C1.1. The kit of embodiment C1, comprising oligonucleotide primer pairs configured for amplifying one or more target polynucleotides in one or more of chromosome 13 polynucleotide SEQ ID NO: 211, chromosome 18 polynucleotide SEQ ID NO: 231 and chromosome 21 polynucleotide SEQ ID NO: 252.

C2. The kit of embodiment C1 or C1.1, comprising a cleavage agent.

C3. The kit of embodiment C2, wherein the cleavage agent is a restriction enzyme.

C4. The kit of embodiment C3, wherein the restriction enzyme is a methylation sensitive restriction enzyme.

C5. The kit of embodiment C4, wherein the restriction enzyme preferentially cleaves nucleic acid comprising one or more non-methylated recognition sequences.

C6. The kit of any one of embodiments C1 to C5, comprising 9 or more competitor oligonucleotides.

C7. The kit of embodiment C6, wherein each competitor oligonucleotide comprises a polynucleotide chosen from SEQ ID NOs 273, 275, 278, 296, 286, 295, 320, 317, 316 or complement thereof.

C8. The kit of any one of embodiments C1 to C7, wherein the primer pairs comprise polynucleotides of SEQ ID NOs: 17, 81, 19, 83, 22, 86 or complement thereof, and are configured for amplifying target polynucleotides within chromosome 13.

C9. The kit of any one of embodiments C1 to C8, wherein the primer pairs comprise polynucleotides of SEQ ID NOs: 40, 104, 30, 94, 39, 103 or complement thereof, and are configured for amplifying target polynucleotides within chromosome 18.

C10. The kit of any one of embodiments C1 to C9, wherein the primer pairs comprise polynucleotides of SEQ ID NOs: 64, 128, 61, 125, 60, 124 or complement thereof, and are configured for amplifying target polynucleotides within chromosome 21.

C11. The kit of any one of embodiments C1 to C10, comprising 9 or more extension oligonucleotides.

C12. The kit of embodiment C11, wherein each of the extension oligonucleotides comprises a polynucleotide chosen from SEQ ID NOs: 145, 147, 150, 168, 158, 167, 192, 189, 188 or complement thereof.

C13. The kit of any one of embodiments C1 to C12, wherein:
the two or more target polynucleotides in chromosome 13 are in a chromosome 13 polynucleotide chosen from SEQ ID NOs: 198, 207, 206, 208, 200, 194, 210, 215, 212, 213, 204, 197, 201, 203, 193, 205, 199, 196, 195, 202 or complement thereof.

C14. The kit of any one of embodiments C6 to C13, wherein the competitor oligonucleotides comprise polynucleotides chosen from SEQ ID NOs: 262, 271, 270, 272, 264, 258, 274, 279, 276, 277, 268, 261, 265, 267, 257, 269, 263, 260, 259, 266 or complement thereof.

C15. The kit of any one of embodiments C1 to C14, wherein the primer pairs comprise polynucleotides chosen from SEQ ID NOs: 6, 70, 15, 79, 14, 78, 16, 80, 8, 72, 2, 66, 18, 82, 23, 87, 20, 84, 21, 85, 12, 76, 5, 69, 9, 73, 11, 75, 1, 65, 13, 77, 7, 71, 4, 68, 3, 67, 10, 74 or complement thereof, and are configured for amplifying target polynucleotides within chromosome 13.

C16. The kit of any one of embodiments C11 to C15, wherein each of the extension oligonucleotides comprises a polynucleotide chosen from SEQ ID NOs: 134, 143, 142, 144, 136, 130, 146, 151, 148, 149, 140, 133, 137, 139, 129, 141, 135, 132, 131, 138 or complement thereof.

C17. The kit of any one of embodiments C1 to C16, wherein two of the two or more target polynucleotides in chromosome 13 are in a chromosome 13 polynucleotide chosen from SEQ ID NOs: 198, 207 or complement thereof.

C18. The kit of any one of embodiments C1 to C17, wherein seven of the two or more target polynucleotides in chromosome 13 are in a chromosome 13 polynucleotide chosen from SEQ ID NOs: 198, 207, 206, 208, 200, 194, 210, or complement thereof.

C19. The kit of any one of embodiments C1 to C18, wherein twelve of the two or more target polynucleotides in chromosome 13 are in a chromosome 13 polynucleotide chosen from SEQ ID NOs: 198, 207, 206, 208, 200, 194, 210, 215, 212, 213, 204, 197 or complement thereof.

C20. The kit of any one of embodiments C1 to C19, wherein:
the two or more target polynucleotides in chromosome 18 are in a chromosome 18 polynucleotide chosen from SEQ ID NOs: 229, 220, 219, 226, 221, 217, 218, 230, 228, 225, 216, 223, 227, 224 or complement thereof.

C21. The kit of any one of embodiments C6 to C20, wherein the competitor oligonucleotides comprise polynucleotides chosen from SEQ ID NOs: 293, 284, 283, 290, 285, 281, 282, 294, 292, 289, 280, 287, 291, 288 or complement thereof.

C22. The kit of any one of embodiments C1 to C21, wherein the primer pairs comprise polynucleotides chosen from SEQ ID NOs: 37, 101, 28, 92, 27, 91, 34, 98, 29, 93, 25, 89, 26, 90, 38, 102, 36, 100, 33, 97, 24, 88, 31, 95, 35, 99, 32, 96 or complement thereof, and are configured for amplifying target polynucleotides within chromosome 18.

C23. The kit of any one of embodiments C11 to C22, wherein each of the extension oligonucleotides comprises a polynucleotide chosen from SEQ ID NOs: 165, 156, 155, 162, 157, 153, 154, 166, 164, 161, 152, 159, 163, 160 or complement thereof.

C24. The kit of any one of embodiments C1 to C23, wherein two of the two or more target polynucleotides in chromosome 18 are in a chromosome 18 polynucleotide chosen from SEQ ID NOs: 229, 220 or complement thereof.

C25. The kit of any one of embodiments C1 to C24, wherein seven of the two or more target polynucleotides in chromosome 18 are in a chromosome 18 polynucleotide chosen from SEQ ID NOs: 229, 220, 219, 226, 221, 217, 218 or complement thereof.

C26. The kit of any one of embodiments C1 to C24, wherein twelve of the two or more target polynucleotides in chromosome 18 are in a chromosome 18 polynucleotide chosen from SEQ ID NOs: 229, 220, 219, 226, 221, 217, 218, 230, 228, 225, 216, 223 or complement thereof.

C27. The kit of any one of embodiments C1 to C26, wherein:
the two or more target polynucleotides in chromosome 21 are in a chromosome 21 polynucleotide chosen from SEQ ID NOs: 244, 255, 254, 234, 240, 241, 245, 236, 239, 248, 233, 250, 251, 242, 249, 238, 243, 235, 246, 247, 237 or complement thereof.

C28. The kit of any one of embodiments C6 to C27, wherein the competitor oligonucleotides comprise polynucleotides chosen from SEQ ID NOs: 308, 319, 318, 298, 304, 305, 309, 300, 303, 312, 297, 314, 315, 306, 313, 302, 307, 299, 310, 311, 301 or complement thereof.

C29. The kit of any one of embodiments C1 to C28, wherein the primer pairs comprise polynucleotides chosen from SEQ ID NOs: 52, 116, 63, 127, 62, 126, 42, 106, 48, 112, 49, 113, 53, 117, 44, 108, 47, 111, 56, 120, 41, 105, 58, 122, 59, 123, 50, 114, 57, 121, 46, 110, 51, 115, 43, 107, 54, 118, 55, 119, 45, 109 or complement thereof, and are configured for amplifying target polynucleotides within chromosome 21.

C30. The kit of any one of embodiments C11 to C15, wherein each of the extension oligonucleotides comprises a polynucleotide chosen from SEQ ID NOs: 180, 191, 190, 170, 176, 177, 181, 172, 175, 184, 169, 186, 187, 178, 185, 174, 179, 171, 182, 183, 173 or complement thereof.

C31. The kit of any one of embodiments C1 to C16, wherein two of the two or more target polynucleotides in chromosome 21 are in a chromosome 21 polynucleotide chosen from SEQ ID NOs: 244, 255 or complement thereof.

C32. The kit of any one of embodiments C1 to C17, wherein seven of the two or more target polynucleotides in chromosome 21 are in a chromosome 21 polynucleotide chosen from SEQ ID NOs: 244, 255, 254, 234, 240, 241, 245 or complement thereof.

C33. The kit of any one of embodiments C1 to C18, wherein twelve of the two or more target polynucleotides in chromosome 21 are in a chromosome 21 polynucleotide chosen from SEQ ID NOs: 244, 255, 254, 234, 240, 241, 245, 236, 239, 248, 233, 250 or complement thereof.

D1. A kit for detecting one, two, three or four copies of a fetal chromosome, or portion thereof, in circulating cell-free nucleic acid from a sample from a human pregnant female bearing a fetus, comprising:
a collection of oligonucleotide primer pairs wherein each primer pair is configured for amplifying target polynucleotides in each of chromosome 13, chromosome 18 and chromosome 21, wherein the target polynucleotides are in:
chromosome 13 polynucleotides of SEQ ID NOs: 193-198, 200-204, 206, 208-210, 212-215, or complement thereof;
chromosome 18 polynucleotides of SEQ ID NOs: 216-218, 220-230, 232, or complement thereof; and
chromosome 21 polynucleotides of SEQ ID NOs: 234, 236, 238-240, 242-246, 248-253, 255, 256, or complement thereof.

D2. The kit of embodiment D1, wherein the target polynucleotides are in:
chromosome 13 polynucleotides of SEQ ID NOs: 199, 205, 207, 211 or complement thereof;
chromosome 18 polynucleotides of SEQ ID NOs: 219, 231, or complement thereof; and
chromosome 21 polynucleotides of SEQ ID NOs: 233, 235, 237, 241, 247, 254 or complement thereof.

D3. The kit of embodiment D1 or D2, comprising a cleavage agent.

D4. The kit of embodiment D3, wherein the cleavage agent is a restriction enzyme.

D5. The kit of embodiment D4, wherein the restriction enzyme is a methylation sensitive restriction enzyme.

D6. The kit of embodiment D5, wherein the restriction enzyme preferentially cleaves nucleic acid comprising one or more non-methylated recognition sequences.

D7. The kit of any one of embodiments D1 to D6, comprising one or more competitor oligonucleotides.

D8. The kit of embodiment D7, wherein the competitor oligonucleotides each comprise a polynucleotide chosen from SEQ ID NOs 257, 258, 259, 260, 261, 262, 264, 265, 266, 267, 268, 270, 272, 273, 274, 276, 277, 278, 279, 280, 281, 282, 284, 285, 286, 287, 288, 289, 290, 291, 292, 293, 294, 296, 298, 300, 302, 303, 304, 306, 307, 308, 309, 310, 312, 313, 314, 315, 316, 317, 319, 320, or complement thereof.

D9. The kit of embodiment D7 or D8, wherein the competitor oligonucleotides each comprise a polynucleotide chosen from SEQ ID NOs 263, 269, 271, 275, 283, 295, 297, 299, 301, 305, 311, 318, or complement thereof.

D10. The kit of any one of embodiments D1 to D9, wherein the primer pairs comprise polynucleotides of SEQ ID NOs: 1, 65, 2, 66, 3, 67, 4, 68, 5, 69, 6, 70, 8, 72, 9, 73, 10, 74, 11, 75, 12, 76, 14, 78, 16, 80, 17, 81, 18, 82, 20, 84, 21, 85, 22, 86, 23, 87, 24, 88, 25, 89, 26, 90, 28, 92, 29, 93, 30, 94, 31, 95, 32, 96, 33, 97, 34, 98, 35, 99, 36, 100, 37, 101, 38, 102, 40, 104, 42, 106, 44, 108, 46, 110, 47, 111, 48, 112, 50, 114, 51, 115, 52, 116, 53, 117, 54, 118, 56, 120, 57, 121, 58, 122, 59, 123, 60, 124, 61, 125, 63, 127, 64, 128, or complement thereof.

D11. The kit of any one of embodiments D1 to D10, wherein the primer pairs comprise polynucleotides of SEQ ID NOs: 7, 71, 13, 77, 15, 79, 19, 83, 27, 91, 39, 103, 41, 105, 43, 107, 45, 109, 49, 113, 55, 119, 62, 126 or complement thereof.

D12. The kit of any one of embodiments D1 to D11, comprising one or more extension oligonucleotides, wherein each extension oligonucleotide is configured to anneal to an amplicon product generated from one or more of the primer pairs.

D13. The kit of embodiment D12, wherein each of the extension oligonucleotides comprises a polynucleotide chosen from SEQ ID NOs: 257, 258, 259, 260, 261, 262, 264, 265, 266, 267, 268, 270, 272, 273, 274, 276, 277, 278, 279, 280, 281, 282, 284, 285, 286, 287, 288, 289, 290, 291, 292, 293, 294, 296, 298, 300, 302, 303, 304, 306, 307, 308, 309, 310, 312, 313, 314, 315, 316, 317, 319, 320, or complement thereof.

D14. The kit of embodiment D12 or D13, wherein each of the extension oligonucleotides comprises a polynucleotide chosen from SEQ ID NOs: 263, 269, 271, 275, 283, 295, 297, 299, 301, 305, 311, 318, or complement thereof.

E1. A method of amplifying one or more target polynucleotides in a sample comprising:
(a) contacting a sample comprising circulating cell-free nucleic acid from a human pregnant female bearing a fetus with a collection of primers under amplification conditions, wherein the primers are specific for nucleic acid sequences located within two or more target polynucleotides in each of chromosome 13, chromosome 18 and chromosome 21, wherein:
the two or more target polynucleotides in chromosome 13 are in chromosome 13 polynucleotides comprising chromosome 13 polynucleotides of SEQ ID NOs: 209 and 214, or complement thereof;
the two or more target polynucleotides in chromosome 18 are in chromosome 18 polynucleotides comprising chromosome 18 polynucleotides of SEQ ID NOs: 232 and 222, or complement thereof; and
the two or more target polynucleotides in chromosome 21 are in chromosome 21 polynucleotides comprising chromosome 21 polynucleotides of SEQ ID NOs: 256 and 253, or complement thereof; thereby providing target-specific amplicons.

E1.1. The method of embodiment E1, wherein the primers are specific for nucleic acid sequences located in one or more target polynucleotides in one or more of chromosome 13 polynucleotide SEQ ID NO: 211, chromosome 18 polynucleotide SEQ ID NO: 231 and chromosome 21 polynucleotide SEQ ID NO: 252.

E1.2. The method of embodiment E1 or E1.1, comprising (b) analyzing the target specific amplicons.

E2. The method of any one of embodiments E1 to E1.2, comprising, prior to (a), contacting nucleic acid from the sample with a cleavage agent under cleavage conditions, thereby generating cleaved nucleic acid and non-cleaved nucleic acid.

E3. The method of embodiment E2, wherein the cleavage agent is a restriction enzyme.

E4. The method of embodiment E3, wherein the restriction enzyme is a methylation sensitive restriction enzyme.

E5. The method of embodiment E4, wherein the restriction enzyme preferentially cleaves nucleic acid comprising one or more non-methylated recognition sequences.

E5.1. The method of any one of embodiments E2 to E5, wherein the target specific amplicons are generated substantially from the non-cleaved nucleic acid.

E5.2. The method of any one of embodiments E1.1 to E5.1, wherein the analyzing in (b) comprises determining amounts of one or more target specific amplicons.

E5.3. The method of any one of embodiments E1.1 to E5.1, wherein the analyzing in (b) comprises determining amounts of the two or more target polynucleotides in each of chromosome 13, chromosome 18 and chromosome 21.

E.5.4. The method of E5.3, wherein the analyzing in (b) comprises quantifying one, two, three or four copies of one or more of chromosome 13, chromosome 18, chromosome 21, or portion thereof, in the fetus according to the amounts of the two or more target polynucleotides in each of chromosome 13, chromosome 18 and chromosome 21.

E6. The method of any one of embodiments E5.3 to E5, wherein the nucleic acid in (a) from which the amounts of the two or more target polynucleotides are determined is substantially the non-cleaved nucleic acid.

E7. The method of any one of embodiments E5.3 to E6, wherein the amounts of the two or more target polynucleotides are determined by a process comprising mass spectrometry.

E7.1. The method of embodiment E7, wherein the mass spectrometry is matrix-assisted laser desorption ionization (MALDI) mass spectrometry.

E7.2. The method of any one of embodiments E5.3 to E6, wherein the amounts of the two or more target polynucleotides are determined by a process comprising sequencing.

E8. The method of any one of embodiments E5.3 to E7.2, wherein the amounts of the two or more target polynucleotides are determined in a single multiplex reaction.

E9. The method of any one of embodiments E1 to E8, comprising contacting the nucleic acid in (a) with one or more competitor oligonucleotides under the amplification conditions.

E9.1. The method of any one of embodiments E1 to E9, comprising contacting the primers with the one or more competitor oligonucleotides under the amplification conditions.

E10. The method of E9 or E9.1, wherein the primers are configured to anneal to a portion of the competitor oligonucleotides thereby providing competitor specific amplicons.

E10.1. The method of any one of embodiments E9 to E10, wherein the amplification conditions comprise a known amount of the one or more competitor oligonucleotides.

E10.2. The method of any one of embodiments E9 to E10.1, wherein each of the one or more competitor oligonucleotides comprise a nucleic acid sequence that is substantially identical to a target polynucleotide.

E10.3. The method of embodiment E10.2, wherein each of the one or more competitor oligonucleotides comprises a feature that distinguishes the competitor oligonucleotide from the target polynucleotide to which it is substantially identical.

E10.4. The method of embodiment E10.3, wherein the feature comprises one or more nucleotide bases that differs between the nucleic acid sequence of the competitor oligonucleotide and the nucleic acid sequence of the target polynucleotide to which it is substantially identical to.

E10.5. The method of embodiment E10.4, wherein the feature comprises one to ten nucleotide bases that differ.

E11. The method of any one of embodiments E9 to E10.5, wherein the competitor oligonucleotides each comprise a polynucleotide chosen from SEQ ID NOs 273, 275, 278, 296, 286, 295, 320, 317, 316 or complement thereof.

E12. The method of any one of embodiments E1 to E11, wherein the primers comprise polynucleotides of SEQ ID NOs: 17, 81, 19, 83, 22, 86 or complement thereof, for amplifying target polynucleotides within chromosome 13.

E13. The method of embodiment E11 or E12, wherein the primers comprise polynucleotides of SEQ ID NOs: 40, 104, 30, 94, 39, 103 or complement thereof, for amplifying target polynucleotides within chromosome 18.

E14. The method of any one of embodiments E11 to E13, wherein the primers comprise polynucleotides of SEQ ID NOs: 64, 128, 61, 125, 60, 124 or complement thereof, for amplifying target polynucleotides within chromosome 21.

E15. The method of any one of embodiments E1.1 to E14, wherein the analyzing in (b) comprises contacting the target specific amplicons with extension oligonucleotides under conditions in which the extension oligonucleotides anneal to the target specific amplicons and are extended by one or more nucleotides.

E15.1. The method of any one of embodiments E11 to E14, wherein the analyzing in (b) comprises contacting the competitor specific amplicons with extension oligonucleotides under conditions in which the extension oligonucleotides anneal to the competitor specific amplicons and the competitor specific amplicons are extended by one or more nucleotides.

E16. The method of embodiment E15, wherein each of the extension oligonucleotides comprises a polynucleotide chosen from SEQ ID NOs: 145, 147, 150, 168, 158, 167, 192, 189, 188 or complement thereof.

E17. The method of any one of embodiments E1.1 to E16, wherein the analyzing in (b) comprises determining the amount of four or more target polynucleotides in chromosome 13, and one or more of the target polynucleotides are in a chromosome 13 polynucleotide comprising chromosome 13 polynucleotides of SEQ ID NOs: 198, 207, 206, 208, 200, 194, 210, 215, 212, 213, 204, 197, 201, 203, 193, 205, 199, 196, 195, 202 or complement thereof.

E18. The method of embodiment E17, wherein the one or more competitor oligonucleotides each comprise a polynucleotide chosen from SEQ ID NOs: 262, 271, 270, 272, 264, 258, 274, 279, 276, 277, 268, 261, 265, 267, 257, 269, 263, 260, 259, 266 or complement thereof.

E19. The method of embodiment E17 or E18, wherein the primers each comprise a polynucleotide chosen from SEQ ID NOs: 6, 70, 15, 79, 14, 78, 16, 80, 8, 72, 2, 66, 18, 82, 23, 87, 20, 84, 21, 85, 12, 76, 5, 69, 9, 73, 11, 75, 1, 65, 13, 77, 7, 71, 4, 68, 3, 67, 10, 74 or complement thereof.

E20. The method of any one of embodiments E17, E18 or E19, wherein the extension oligonucleotides comprise a polynucleotide chosen from SEQ ID NOs: 134, 143, 142, 144, 136, 130, 146, 151, 148, 149, 140, 133, 137, 139, 129, 141, 135, 132, 131, 138 or complement thereof.

E21. The method of any one of embodiments E1.1 to E20, wherein the analysis in (b) comprises determining the amount of five or more target polynucleotides in chromosome 13, and two of the target polynucleotides are in a chromosome 13 polynucleotide of SEQ ID NOs: 198, 207 or complement thereof.

E22. The method of any one of embodiments E1.1 to E21, wherein the analysis in (b) comprises determining the amount of ten or more target polynucleotides in chromosome 13, and seven of the target polynucleotides are in a chromosome 13 polynucleotide of SEQ ID NOs: 198, 207, 206, 208, 200, 194, 210, or complement thereof.

E23. The method of any one of embodiments E1.1 to E22, wherein the analysis in (b) comprises determining the amount of fifteen or more target polynucleotides in chromosome 13, and twelve of the target polynucleotides are in a chromosome 13 polynucleotide of SEQ ID NOs: 198, 207, 206, 208, 200, 194, 210, 215, 212, 213, 204, 197 or complement thereof.

E24. The method of any one of embodiments E1.1 to E23, wherein the analysis in (b) comprises determining the amount of four or more target polynucleotides in chromosome 18, and one or more of the target polynucleotides are in a chromosome 18 polynucleotide chosen from SEQ ID NOs: 229, 220, 219, 226, 221, 217, 218, 230, 228, 225, 216, 223, 227, 224 or complement thereof.

E25. The method of embodiment E24, wherein the one or more competitor oligonucleotides comprise a polynucleotide chosen from SEQ ID NOs: 293, 284, 283, 290, 285, 281, 282, 294, 292, 289, 280, 287, 291, 288 or complement thereof.

E26. The method of embodiment E24 or E25, wherein the primers comprise polynucleotides of SEQ ID NOs: 37, 101, 28, 92, 91, 27, 34, 98, 29, 93, 25, 89, 26, 90, 38, 102, 36, 100, 33, 97, 24, 88, 31, 95, 35, 99, 32, 96 or complement thereof.

E27. The method of embodiment E24, E25 or E26, wherein each of the extension oligonucleotides comprises a polynucleotide chosen from SEQ ID NOs: 165, 156, 155, 162, 157, 153, 154, 166, 164, 161, 152, 159, 163, 160 or complement thereof.

E28. The method of any one of embodiments E24 to E27, wherein the analysis in (b) comprises detecting the amount of five or more target polynucleotides in chromosome 18, and two of the target polynucleotides comprise a chromosome 18 polynucleotide of SEQ ID NOs: 229, 220 or complement thereof.

E29. The method of any one of embodiments E24 to E28, wherein the analysis in (b) comprises determining the amount of ten or more target polynucleotides in chromosome 18, and seven of the target polynucleotides comprise a chromosome 18 polynucleotide of SEQ ID NOs: 229, 220, 219, 226, 221, 217, 218 or complement thereof.

E30. The method of any one of embodiments E24 to E229, wherein the analysis in (b) comprises determining the amount of fifteen or more target polynucleotides in chromosome 18, and twelve of the target polynucleotides are in a chromosome 18 polynucleotide of SEQ ID NOs: 229, 220, 219, 226, 221, 217, 218, 230, 228, 225, 216, 223 or complement thereof.

E31. The method of any one of embodiments E1.1 to E30, wherein the analysis in (b) comprises determining the amount of four or more target polynucleotides in chromosome 21, and one or more of the target polynucleotides are in a chromosome 21 polynucleotide chosen from SEQ ID NOs: 244, 255, 254, 234, 240, 241, 245, 236, 239, 248, 233, 250, 251, 242, 249, 238, 243, 235, 246, 247, 237 or complement thereof.

E32. The method of embodiment E31, wherein the one or more competitor oligonucleotides comprise a polynucleotide chosen from SEQ ID NOs: 308, 319, 318, 298, 304, 305, 309, 300, 303, 312, 297, 314, 315, 306, 313, 302, 307, 299, 310, 311, 301 or complement thereof.

E33. The method of embodiment E31 or E32, wherein the primers comprise polynucleotides of SEQ ID NOs: 52, 116, 63, 127, 62, 126, 42, 106, 48, 112, 49, 113, 53, 117, 44, 108, 47, 111, 56, 120, 41, 105, 58, 122, 59, 123, 50, 114, 57, 121, 46, 110, 51, 115, 43, 107, 54, 118, 55, 119, 45, 109 or complement thereof.

E34. The method of embodiment E31, E32, or E33, wherein each of the extension oligonucleotides comprises a polynucleotide chosen from SEQ ID NOs: 180, 191, 190, 170, 176, 177, 181, 172, 175, 184, 169, 186, 187, 178, 185, 174, 179, 171, 182, 183, 173 or complement thereof.

E35. The method of any one of embodiments E31 to E34, wherein the analysis in (b) comprises determining the amount of five or more target polynucleotides in chromosome 21, and two of the target polynucleotides are in a chromosome 21 polynucleotide of SEQ ID NOs: 244, 255 or complement thereof.

E36. The method of any one of embodiments E31 to E35, wherein the analysis in (b) comprises determining the amount of ten or more target polynucleotides in chromosome 21, and seven of the target polynucleotides are in a chromosome 21 polynucleotide of SEQ ID NOs: 244, 255, 254, 234, 240, 241, 245 or complement thereof.

E37. The method of any one of embodiments E31 to E36, wherein the analysis in (b) comprises determining the amount of fifteen or more target polynucleotides in chromosome 21, and twelve of the target polynucleotides are in a chromosome 21 polynucleotide of SEQ ID NOs: 244, 255, 254, 234, 240, 241, 245, 236, 239, 248, 233, 250 or complement thereof.

E38. The method of any one of embodiments E1 to E37, wherein the primers are primer pairs.

E39. The method of embodiment E38, wherein each primer pair is specific for one or more target polynucleotides.

E40. The method of embodiment E38, wherein each of the primer pairs is configured for amplifying the target polynucleotide for which the primer pair is specific, wherein each of the primers of the primer pair hybridize to a portion of the target polynucleotide for which the primer pair is specific.

E41. The method of any one of embodiments E38 to E40, wherein each of which primer pairs is configured to specifically amplify at least one competitor oligonucleotide and the target polynucleotide to which it is substantially identical to.

E42. The method of any one of embodiments E10 to E41, comprising determining the amount of competitor specific amplicons.

E43. The method of any one of embodiments of E10 to E42, wherein the analyzing in (b) comprises determining a ratio of target specific amplicons to competitor specific amplicons for each of the target polynucleotides in the sample.

E44. The method of any one of embodiments E1 to E43, comprising determining an amount of fetal nucleic acid in the sample.

E45. The method of any one of embodiments E1 to E44, wherein the primers comprise one or more tags.

E46. The method of embodiment E45, wherein the one or more tags comprises a nucleic acid sequence configured for hybridization of the one or more tags to one or more universal primers.

E47. The method of embodiment E45 or E46, wherein the one or more tags are configured for hybridization of the target specific amplicons and the competitor specific amplicons to a solid phase.

E48. The method of any one of embodiments E43 to E47, comprising normalizing each of which ratios to the amount of fetal nucleic acid in the sample.

E49. The method of any one of embodiments E4 to E48, wherein the methylation sensitive restriction endonuclease is selected from AatII, AccII, ACiI, AclI, AfeI, AgeI, AgeI-HF, Aor13HI, Aor51HI, AscI, AseI, BceAI, BmgBI, BsaAI, BsaHI, BsiEI, BspDI, BsrFI, BspT104I, BssHII, BstBI, BstUI, Cfr10I, ClaI, CpoI, EagI, Eco52I, FauI, FseI, FspI, DpnI, DpnII, HaeII, HapII, HfaI, HgaI, HhaI, HinP1I, HPAII, Hpy99I, HpyCH4IV, KasI, MaeII, McrBC, MluI, MspI, NaeI, NgoMIV, NotI, NotI-HF, NruI, NsbI, NtBsmAI, NtCviPII, PaeR7I, PluTI, PmlI, PmaCI, Psp1406I, PvuI, RsrII, SacII, SalI, SalI-HF, ScrFI, SfoI, SfrAI, SmaI, SnaBI, TspMI, ZraI and isoschizomers thereof.

E50. The method of any one of embodiments E4 to E49, wherein the methylation sensitive restriction endonuclease is selected from HpaII, HinP1I, HhaI, MaeII, BstUI and AciI.

E51. The method of any one of embodiments E4 to E50, wherein the methylation sensitive restriction endonuclease is selected from HHAI, HinP1I and HPAII.

F1. A method of amplifying one or more target polynucleotides in a sample comprising:
(a) contacting a sample comprising circulating cell-free nucleic acid from a human pregnant female bearing a fetus with a collection of primers under amplification conditions, wherein each primer is specific for nucleic acid sequences located within target polynucleotides in each of chromosome 13, chromosome 18 and chromosome 21, wherein the target polynucleotides are in:
chromosome 13 polynucleotides of SEQ ID NOs: 193-198, 200-204, 206, 208-210, 212-215, or complement thereof;
chromosome 18 polynucleotides of SEQ ID NOs: 216-218, 220-230, 232, or complement thereof; and
chromosome 21 polynucleotides of SEQ ID NOs: 234, 236, 238-240, 242-246, 248-253, 255, 256, or complement thereof; thereby providing target-specific amplicons.

F1.1. The method of embodiment F1, comprising (b) analyzing the target-specific amplicons.

F2. The method of embodiment F1 or F1.1, wherein the target polynucleotides are in:
chromosome 13 polynucleotides of SEQ ID NOs: 199, 205, 207, 211 or complement thereof;
chromosome 18 polynucleotides of SEQ ID NOs: 219, 231, or complement thereof; and
chromosome 21 polynucleotides of SEQ ID NOs: 233, 235, 237, 241, 247, 254 or complement thereof.

F3. The method of embodiment F1, F1.1 or F2, comprising, prior to (a), contacting nucleic acid from the sample with a cleavage agent under cleavage conditions, thereby generating cleaved nucleic acid and non-cleaved nucleic acid.

F4. The method of embodiment F3, wherein the cleavage agent is a restriction enzyme.

F5. The method of embodiment F4, wherein the restriction enzyme is a methylation sensitive restriction enzyme.

F6. The method of embodiment F5, wherein the restriction enzyme preferentially cleaves nucleic acid comprising one or more non-methylated recognition sequences.

F6.1. The method of any one of embodiments F1.1 to F6, wherein the analyzing in (b) comprises determining amounts of one or more target specific amplicons.

F6.2. The method of any one of embodiments F1.1 to F6.1, wherein the analyzing in (b) comprises determining amounts of the target polynucleotides in each of chromosome 13, chromosome 18 and chromosome 21.

F.6.3. The method of F6.2, wherein the analyzing in (b) comprises quantifying one, two, three or four copies of one or more of chromosome 13, chromosome 18, chromosome 21, or portion thereof, in the fetus according to the amounts of the target polynucleotides in each of chromosome 13, chromosome 18 and chromosome 21.

F7. The method of any one of embodiments F6.2 or F6.3, wherein the nucleic acid in (a) from which the amounts of the target polynucleotides are determined is substantially the non-cleaved nucleic acid.

F8. The method of any one of embodiments F6.2 to F7, wherein the amounts of the target polynucleotides are determined by a process comprising mass spectrometry.

F8.1. The method of embodiment F8, wherein the mass spectrometry is matrix-assisted laser desorption ionization (MALDI) mass spectrometry.

F8.2. The method of any one of embodiments F6.2 to F7, wherein the amounts of the target polynucleotides are determined by a process comprising sequencing.

F9. The method of any one of embodiments F6.2 to F8.2, the amounts of the target polynucleotides are determined in a single multiplex reaction.

F10. The method of any one of embodiments F1 to F9, comprising contacting the nucleic acid in (a) with one or more competitor oligonucleotides under the amplification conditions.

F10.1. The method of any one of embodiments F1 to F10, comprising contacting the primers with the one or more competitor oligonucleotides under the amplification conditions.

F11. The method of F10 or F10.1, wherein the primers are configured to anneal to a portion of the competitor oligonucleotides thereby providing competitor specific amplicons.

F11.1. The method of any one of embodiments F10 to F11, wherein the amplification conditions comprise a known amount of the one or more competitor oligonucleotides.

F11.2. The method of any one of embodiments F10 to F11.1, wherein each of the one or more competitor oligonucleotides comprise a nucleic acid sequence that is substantially identical to a target polynucleotide.

F11.3. The method of embodiment F11.2, wherein each of the one or more competitor oligonucleotides comprises a feature that distinguishes the competitor oligonucleotide from the target polynucleotide to which it is substantially identical to.

F11.4. The method of embodiment F11.3, wherein the feature comprises one or more nucleotide bases that differs between the nucleic acid sequence of the competitor oligonucleotide and the nucleic acid sequence of the target polynucleotide to which it is substantially identical to.

F11.5. The method of embodiment F11.4, wherein the feature comprises one to ten nucleotide bases that differ.

F12. The method of any one of embodiments F10 to F11.5, wherein the competitor oligonucleotides each comprise a polynucleotide chosen from SEQ ID NOs 257, 258, 259, 260, 261, 262, 264, 265, 266, 267, 268, 270, 272, 273, 274, 276, 277, 278, 279, 280, 281, 282, 284, 285, 286, 287, 288, 289, 290, 291, 292, 293, 294, 296, 298, 300, 302, 303, 304, 306, 307, 308, 309, 310, 312, 313, 314, 315, 316, 317, 319, 320, or complement thereof.

F13. The method of embodiment F12, wherein the competitor oligonucleotides each comprise a polynucleotide chosen from SEQ ID NOs 263, 269, 271, 275, 283, 295, 297, 299, 301, 305, 311, 318, or complement thereof.

F14. The method of embodiment F13, wherein the primers comprise polynucleotides of SEQ ID NOs: 1, 65, 2, 66, 3, 67, 4, 68, 5, 69, 6, 70, 8, 72, 9, 73, 10, 74, 11, 75, 12, 76, 14, 78, 16, 80, 17, 81, 18, 82, 20, 84, 21, 85, 22, 86, 23, 87, 24, 88, 25, 89, 26, 90, 28, 92, 29, 93, 30, 94, 31, 95, 32, 96, 33, 97, 34, 98, 35, 99, 36, 100, 37, 101, 38, 102, 40, 104, 42, 106, 44, 108, 46, 110, 47, 111, 48, 112, 50, 114, 51, 115, 52, 116, 53, 117, 54, 118, 56, 120, 57, 121, 58, 122, 59, 123, 60, 124, 61, 125, 63, 127, 64, 128, or complement thereof.

F15. The method of embodiment F14, wherein the primers comprise polynucleotides of SEQ ID NOs: 7, 71, 13, 77, 15, 79, 19, 83, 27, 91, 39, 103, 41, 105, 43, 107, 45, 109, 49, 113, 55, 119, 62, 126 or complement thereof.

F16. The method of any one of embodiments F1.1 to F15, wherein the analyzing in (b) comprises contacting the target specific amplicons with extension oligonucleotides under conditions in which the extension oligonucleotides anneal to the target specific amplicons and are extended by one or more nucleotides.

F16.1. The method of any one of embodiments F10 to F16, wherein the analyzing in (b) comprises contacting the competitor specific amplicons with extension oligonucleotides under conditions in which the extension oligonucleotides anneal to the competitor specific amplicons and the competitor specific amplicons are extended by one or more nucleotides.

F17. The method of embodiment F16 or F16.1, wherein each of the extension oligonucleotides comprises a polynucleotide chosen from SEQ ID NOs: 257, 258, 259, 260, 261, 262, 264, 265, 266, 267, 268, 270, 272, 273, 274, 276, 277, 278, 279, 280, 281, 282, 284, 285, 286, 287, 288, 289, 290, 291, 292, 293, 294, 296, 298, 300, 302, 303, 304, 306, 307, 308, 309, 310, 312, 313, 314, 315, 316, 317, 319, 320, or complement thereof.

F18. The method of embodiment F16 or F16.1, wherein each of the extension oligonucleotides comprises a polynucleotide chosen from SEQ ID NOs: 263, 269, 271, 275, 283, 295, 297, 299, 301, 305, 311, 318, or complement thereof.

F19. The method of any one of embodiments F1 to F18, wherein the primers are primer pairs.

F20. The method of embodiment F19, wherein each primer pair is specific for one or more of the target polynucleotides.

F21. The method of embodiment F20, wherein each of the primer pairs is configured for amplifying the target polynucleotide for which the primer pair is specific, wherein each of the primers of the primer pair hybridize to a portion of the target polynucleotide for which the primer pair is specific.

F27. The method of any one of embodiments F19 to F26, wherein each of which primer pairs is configured to specifically amplify at least one competitor oligonucleotide and the target polynucleotide to which it is substantially identical to.

F28. The method of any one of embodiments F11 to F27, comprising determining the amount of competitor specific amplicons.

F29. The method of any one of embodiments of F11 to F28, wherein the analyzing in (b) comprises determining a ratio of target specific amplicons to competitor specific amplicons for each of the target polynucleotides in the sample.

F30. The method of any one of embodiments F1 to F29, comprising determining an amount of fetal nucleic acid in the sample.

F31. The method of any one of embodiments F1 to F30, wherein the primers comprise one or more tags.

F32. The method of embodiment F31, wherein the one or more tags comprises a nucleic acid sequence configured for hybridization of the one or more tags to one or more universal primers.

F33. The method of embodiment F31 or F32, wherein the one or more tags are configured for hybridization of the target specific amplicons and the competitor specific amplicons to a solid phase.

F34. The method of any one of embodiments F29 to F33, comprising normalizing each of which ratios to the amount of fetal nucleic acid in the sample.

F35. The method of any one of embodiments F5 to F34, wherein the methylation sensitive restriction endonuclease is selected from AatII, AccII, ACiI, AclI, AfeI, AgeI, AgeI-HF, Aor13HI, Aor51HI, AscI, AseI, BceAI, BmgBI, BsaAI, BsaHI, BsiEI, BspDI, BsrFI, BspT104I, BssHII, BstBI, BstUI, Cfr10I, ClaI, CpoI, EagI, Eco52I, FauI, FseI, FspI, DpnI, DpnII, HaeII, HapII, HfaI, HgaI, HhaI, HinP1I, HPAII, Hpy99I, HpyCH4IV, KasI, MaeII, McrBC, MluI, MspI, NaeI, NgoMIV, NotI, NotI-HF, NruI, NsbI, NtBsmAI, NtCviPII, PaeR7I, PluTI, PmlI, PmaCI, Psp1406I, PvuI, RsrII, SacII, SalI, SalI-HF, ScrFI, SfoI, SfrAI, SmaI, SnaBI, TspMI, ZraI and isoschizomers thereof.

F36. The method of any one of embodiments F5 to F35, wherein the methylation sensitive restriction endonuclease is selected from HpaII, HinP1I, HhaI, MaeII, BstUI and AciI.

F37. The method of any one of embodiments F5 to F36, wherein the methylation sensitive restriction endonuclease is selected from HHAI, HinP1I and HPAII.

G1. A method for detecting one, two, three or four copies of a fetal chromosome, or portion thereof, in a sample, comprising:
(a) determining amounts of two or more target polynucleotides in chromosome 13, chromosome 18 or chromosome 21 in circulating cell-free nucleic acid from a sample from a human pregnant female bearing a fetus, wherein:
the two or more target polynucleotides in chromosome 13 are in chromosome 13 polynucleotides comprising chromosome 13 polynucleotides of SEQ ID NOs: 209 and 214, or complement thereof;
the two or more target polynucleotides in chromosome 18 are in chromosome 18 polynucleotides comprising chromosome 18 polynucleotides of SEQ ID NOs: 232 and 222, or complement thereof; and
the two or more target polynucleotides in chromosome 21 are in chromosome 21 polynucleotides comprising chromosome 21 polynucleotides of SEQ ID NOs: 256 and 253, or complement thereof; and
(b) quantifying, from the amounts, one, two, three or four copies of chromosome 13, chromosome 18, or chromosome 21, or portion thereof, in the fetus.

G1.1. The method of embodiment A1, comprising determining the amount of one or more target polynucleotides in one or more of chromosome 13 polynucleotide SEQ ID NO: 211, chromosome 18 polynucleotide SEQ ID NO: 231 and chromosome 21 polynucleotide SEQ ID NO: 252.

G2. The method of embodiment G1 or G1.1, comprising, prior to (a), contacting nucleic acid from the sample with a cleavage agent under cleavage conditions, thereby generating cleaved nucleic acid and non-cleaved nucleic acid.

G3. The method of embodiment G2, wherein the cleavage agent is a restriction enzyme.

G4. The method of embodiment G3, wherein the restriction enzyme is a methylation sensitive restriction enzyme.

G5. The method of embodiment G4, wherein the restriction enzyme preferentially cleaves nucleic acid comprising one or more non-methylated recognition sequences.

G6. The method of any one of embodiments G2 to G5, wherein the nucleic acid in (a) from which the amounts of the two or more target polynucleotides are determined is substantially the non-cleaved nucleic acid.

G7. The method of any one of embodiments G1 to G6, wherein the amounts of the two or more target polynucleotides are determined by a process comprising mass spectrometry.

G7.1. The method of embodiment G7, wherein the mass spectrometry is matrix-assisted laser desorption ionization (MALDI) mass spectrometry.

G7.2. The method of any one of embodiments G1 to G6, wherein the amounts of the two or more target polynucleotides are determined by a process comprising sequencing.

G8. The method of any one of embodiments G1 to G7.2, wherein the amounts in (a) are determined in a single multiplex reaction.

G9. The method of any one of embodiments G1 to G8, wherein the detecting in (a) comprises contacting the nucleic acid with competitor oligonucleotide.

G10. The method of embodiment G9, wherein the competitor oligonucleotides each comprise a polynucleotide chosen from SEQ ID NOs 273, 275, 278, 296, 286, 295, 320, 317, 316 or complement thereof.

G11. The method of any one of embodiments G1 to G10, wherein the detecting in (a) comprises contacting the nucleic acid with primers under amplification conditions, thereby generating amplicons.

G12. The method of embodiment G11, wherein the primers comprise polynucleotides of SEQ ID NOs: 17, 81, 19, 83, 22, 86 or complement thereof, for amplifying target polynucleotides within chromosome 13.

G13. The method of embodiment G11 or G12, wherein the primers comprise polynucleotides of SEQ ID NOs: 40, 104, 30, 94, 39, 103 or complement thereof, for amplifying target polynucleotides within chromosome 18.

G14. The method of any one of embodiments G11 to G13, wherein the primers comprise polynucleotides of SEQ ID NOs: 64, 128, 61, 125, 60, 124 or complement thereof, for amplifying target polynucleotides within chromosome 21.

G15. The method of any one of embodiments G11 to G14, wherein the detecting in (a) comprises contacting the amplicons with extension oligonucleotides under conditions in which the extension oligonucleotides anneal to the amplicons and are extended by one or more nucleotides.

G16. The method of embodiment G15, wherein each of the extension oligonucleotides comprises a polynucleotide chosen from SEQ ID NOs: 145, 147, 150, 168, 158, 167, 192, 189, 188 or complement thereof.

G17. The method of any one of embodiments G1 to G16, wherein (a) comprises detecting the amount of four or more target polynucleotides in chromosome 13, and one or more of the target polynucleotides are in a chromosome 13 polynucleotide chosen from SEQ ID NOs: 198, 207, 206, 208, 200, 194, 210, 215, 212, 213, 204, 197, 201, 203, 193, 205, 199, 196, 195, 202 or complement thereof.

G18. The method of embodiment G17, wherein the detecting in (a) comprises contacting the nucleic acid with one or more competitor oligonucleotides comprising a polynucleotide chosen from SEQ ID NOs: 262, 271, 270, 272, 264, 258, 274, 279, 276, 277, 268, 261, 265, 267, 257, 269, 263, 260, 259, 266 or complement thereof.

G19. The method of embodiment G17 or G18, wherein the detecting in (a) comprises contacting the nucleic acid with primers under amplification conditions, thereby generating amplicons, wherein the primers comprise polynucleotides of SEQ ID NOs: 6, 70, 15, 79, 14, 78, 16, 80, 8, 72, 2, 66, 18, 82, 23, 87, 20, 84, 21, 85, 12, 76, 5, 69, 9, 73, 11, 75, 1, 65, 13, 77, 7, 71, 4, 68, 3, 67, 10, 74 or complement thereof.

G20. The method of embodiment G19, wherein the detecting in (a) comprises contacting the amplicons with extension oligonucleotides under conditions in which the extension oligonucleotides anneal to the amplicons and are extended by one or more nucleotides, wherein each of the extension oligonucleotides comprises a polynucleotide chosen from SEQ ID NOs: 134, 143, 142, 144, 136, 130, 146, 151, 148, 149, 140, 133, 137, 139, 129, 141, 135, 132, 131, 138 or complement thereof.

G21. The method of embodiment G17, wherein (a) comprises detecting the amount of five or more target polynucleotides in chromosome 13, and two of the target polynucleotides are in a chromosome 13 polynucleotide of SEQ ID NOs: 198, 207 or complement thereof.

G22. The method of embodiment G17, wherein (a) comprises detecting the amount of ten or more target polynucleotides in chromosome 13, and seven of the target polynucleotides are in a chromosome 13 polynucleotide of SEQ ID NOs: 198, 207, 206, 208, 200, 194, 210, or complement thereof.

G23. The method of embodiment G17, wherein (a) comprises detecting the amount of fifteen or more target polynucleotides in chromosome 13, and twelve of the target polynucleotides are in a chromosome 13 polynucleotide of SEQ ID NOs: 198, 207, 206, 208, 200, 194, 210, 215, 212, 213, 204, 197 or complement thereof.

G24. The method of any one of embodiments G1 to G23, wherein (a) comprises detecting the amount of four or more target polynucleotides in chromosome 18, and one or more of the target polynucleotides are in a chromosome 18 polynucleotide chosen from SEQ ID NOs: 229, 220, 219, 226, 221, 217, 218, 230, 228, 225, 216, 223, 227, 224 or complement thereof.

G25. The method of embodiment G24, wherein the detecting in (a) comprises contacting the nucleic acid one or more competitor oligonucleotides comprising a polynucleotide chosen from SEQ ID NOs: 293, 284, 283, 290, 285, 281, 282, 294, 292, 289, 280, 287, 291, 288 or complement thereof.

G26. The method of embodiment G24 or G25, wherein the detecting in (a) comprises contacting the nucleic acid with primers under amplification conditions, thereby generating amplicons, wherein the primers comprise polynucleotides of SEQ ID NOs: 37, 101, 28, 92, 27, 91, 34, 98, 29, 93, 25, 89, 26, 90, 38, 102, 36, 100, 33, 97, 24, 88, 31, 95, 35, 99, 32, 96 or complement thereof.

G27. The method of embodiment G26, wherein the detecting in (a) comprises contacting the amplicons with extension oligonucleotides under conditions in which the extension oligonucleotides anneal to the amplicons and are extended by one or more nucleotides, wherein each of the extension oligonucleotides comprises a polynucleotide chosen from SEQ ID NOs: 165, 156, 155, 162, 157, 153, 154, 166, 164, 161, 152, 159, 163, 160 or complement thereof.

G28. The method of embodiment G24, wherein (a) comprises detecting the amount of five or more target polynucleotides in chromosome 18, and two of the target polynucleotides are in a chromosome 18 polynucleotide of SEQ ID NOs: 229, 220 or complement thereof.

G29. The method of embodiment G24, wherein (a) comprises detecting the amount of ten or more target polynucleotides in chromosome 18, and seven of the target polynucleotides are in a chromosome 18 polynucleotide of SEQ ID NOs: 229, 220, 219, 226, 221, 217, 218 or complement thereof.

G30. The method of embodiment G24, wherein (a) comprises detecting the amount of fifteen or more target polynucleotides in chromosome 18, and twelve of the target polynucleotides are in a chromosome 18 polynucleotide of SEQ ID NOs: 229, 220, 219, 226, 221, 217, 218, 230, 228, 225, 216, 223 or complement thereof.

G31. The method of any one of embodiments G1 to G30, wherein (a) comprises detecting the amount of four or more target polynucleotides in chromosome 21, and one or more of the target polynucleotides are in a chromosome 21 polynucleotide chosen from SEQ ID NOs: 244, 255, 254, 234, 240, 241, 245, 236, 239, 248, 233, 250, 251, 242, 249, 238, 243, 235, 246, 247, 237 or complement thereof.

G32. The method of embodiment G31, wherein the detecting in (a) comprises contacting the nucleic acid with one or more competitor oligonucleotides comprising a polynucleotide chosen from SEQ ID NOs: 308, 319, 318, 298, 304, 305, 309, 300, 303, 312, 297, 314, 315, 306, 313, 302, 307, 299, 310, 311, 301 or complement thereof.

G33. The method of embodiment G31 or G32, wherein the detecting in (a) comprises contacting the nucleic acid with primers under amplification conditions, thereby generating amplicons, wherein the primers comprise polynucleotides of SEQ ID NOs: 52, 116, 63, 127, 62, 126, 42, 106, 48, 112, 49, 113, 53, 117, 44, 108, 47, 111, 56, 120, 41, 105, 58, 122, 59, 123, 50, 114, 57, 121, 46, 110, 51, 115, 43, 107, 54, 118, 55, 119, 45, 109 or complement thereof.

G34. The method of embodiment G33, wherein the detecting in (a) comprises contacting the amplicons with extension oligonucleotides under conditions in which the extension oligonucleotides anneal to the amplicons and are extended by one or more nucleotides, wherein each of the extension oligonucleotides comprises a polynucleotide chosen from SEQ ID NOs: 180, 191, 190, 170, 176, 177, 181, 172, 175, 184, 169, 186, 187, 178, 185, 174, 179, 171, 182, 183, 173 or complement thereof.

G35. The method of embodiment G31, wherein (a) comprises detecting the amount of five or more target polynucleotides in chromosome 21, and two of the target polynucleotides are in a chromosome 21 polynucleotide of SEQ ID NOs: 244, 255 or complement thereof.

G36. The method of embodiment G31, wherein (a) comprises detecting the amount of ten or more target polynucleotides in chromosome 21, and seven of the target polynucleotides are in a chromosome 21 polynucleotide of SEQ ID NOs: 244, 255, 254, 234, 240, 241, 245 or complement thereof.

G37. The method of embodiment G31, wherein (a) comprises detecting the amount of fifteen or more target polynucleotides in chromosome 21, and twelve of the target polynucleotides are in a chromosome 21 polynucleotide of SEQ ID NOs: 244, 255, 254, 234, 240, 241, 245, 236, 239, 248, 233, 250 or complement thereof.

H1. A kit for detecting one, two, three or four copies of a fetal chromosome, or portion thereof, in circulating cell-free nucleic acid from a sample from a human pregnant female bearing a fetus, comprising:
  a collection of oligonucleotide primer pairs wherein each primer pair is configured for amplifying two or more target polynucleotides in chromosome 13, chromosome 18 or chromosome 21, wherein:
  the two or more target polynucleotides in chromosome 13 are in chromosome 13 polynucleotides comprising chromosome 13 polynucleotides of SEQ ID NOs: 209 and 214, or complement thereof;
  the two or more target polynucleotides in chromosome 18 are in chromosome 18 polynucleotides comprising chromosome 18 polynucleotides of SEQ ID NOs: 232 and 222, or complement thereof; and
  the two or more target polynucleotides in chromosome 21 are in chromosome 21 polynucleotides comprising chromosome 21 polynucleotides of SEQ ID NOs: 256 and 253, or complement thereof, or complement thereof.

H1.1. The kit of embodiment C1, comprising oligonucleotide primer pairs configured for amplifying one or more target polynucleotides in one or more of chromosome 13 polynucleotide SEQ ID NO: 211, chromosome 18 polynucleotide SEQ ID NO: 231 and chromosome 21 polynucleotide SEQ ID NO: 252.

H2. The kit of embodiment H1 or H1.1, comprising a cleavage agent.

H3. The kit of embodiment H2, wherein the cleavage agent is a restriction enzyme.

H4. The kit of embodiment H3, wherein the restriction enzyme is a methylation sensitive restriction enzyme.

H5. The kit of embodiment H4, wherein the restriction enzyme preferentially cleaves nucleic acid comprising one or more non-methylated recognition sequences.

H6. The kit of any one of embodiments H1 to H5, comprising 9 or more competitor oligonucleotides.

H7. The kit of embodiment H6, wherein each competitor oligonucleotide comprises a polynucleotide chosen from SEQ ID NOs 273, 275, 278, 296, 286, 295, 320, 317, 316 or complement thereof.

H8. The kit of any one of embodiments H1 to H7, wherein the primer pairs comprise polynucleotides of SEQ ID NOs: 17, 81, 19, 83, 22, 86 or complement thereof, and are configured for amplifying target polynucleotides within chromosome 13.

H9. The kit of any one of embodiments H1 to H8, wherein the primer pairs comprise polynucleotides of SEQ ID NOs: 40, 104, 30, 94, 39, 103 or complement thereof, and are configured for amplifying target polynucleotides within chromosome 18.

H10. The kit of any one of embodiments H1 to H9, wherein the primer pairs comprise polynucleotides of SEQ ID NOs: 64, 128, 61, 125, 60, 124 or complement thereof, and are configured for amplifying target polynucleotides within chromosome 21.

H11. The kit of any one of embodiments H1 to H10, comprising 9 or more extension oligonucleotides.

H12. The kit of embodiment H11, wherein each of the extension oligonucleotides comprises a polynucleotide chosen from SEQ ID NOs: 145, 147, 150, 168, 158, 167, 192, 189, 188 or complement thereof.

H13. The kit of any one of embodiments H1 to H12, wherein: the two or more target polynucleotides in chromosome 13 are in a chromosome 13 polynucleotide chosen from SEQ ID NOs: 198, 207, 206, 208, 200, 194, 210, 215, 212, 213, 204, 197, 201, 203, 193, 205, 199, 196, 195, 202 or complement thereof.

H14. The kit of any one of embodiments H6 to H13, wherein the competitor oligonucleotides comprise polynucleotides chosen from SEQ ID NOs: 262, 271, 270, 272, 264, 258, 274, 279, 276, 277, 268, 261, 265, 267, 257, 269, 263, 260, 259, 266 or complement thereof. H15. The kit of any one of embodiments H1 to H14, wherein the primer pairs comprise polynucleotides chosen from SEQ ID NOs: 6, 70, 15, 79, 14, 78, 16, 80, 8, 72, 2, 66, 18, 82, 23, 87, 20, 84, 21, 85, 12, 76, 5, 69, 9, 73, 11, 75, 1, 65, 13, 77, 7, 71, 4, 68, 3, 67, 10, 74 or complement thereof, and are configured for amplifying target polynucleotides within chromosome 13.

H16. The kit of any one of embodiments H11 to H15, wherein each of the extension oligonucleotides comprises a polynucleotide chosen from SEQ ID NOs: 134, 143, 142, 144, 136, 130, 146, 151, 148, 149, 140, 133, 137, 139, 129, 141, 135, 132, 131, 138 or complement thereof.

H17. The kit of any one of embodiments H1 to H16, wherein two of the two or more target polynucleotides in chromosome 13 are in a chromosome 13 polynucleotide chosen from SEQ ID NOs: 198, 207 or complement thereof.

H18. The kit of any one of embodiments H1 to H17, wherein seven of the two or more target polynucleotides in chromosome 13 are in a chromosome 13 polynucleotide chosen from SEQ ID NOs: 198, 207, 206, 208, 200, 194, 210, or complement thereof.

H19. The kit of any one of embodiments H1 to H18, wherein twelve of the two or more target polynucleotides in chromosome 13 are in a chromosome 13 polynucleotide chosen from SEQ ID NOs: 198, 207, 206, 208, 200, 194, 210, 215, 212, 213, 204, 197 or complement thereof.

H20. The kit of any one of embodiments H1 to H19, wherein: the two or more target polynucleotides in chromosome 18 are in a chromosome 18 polynucleotide chosen from SEQ ID NOs: 229, 220, 219, 226, 221, 217, 218, 230, 228, 225, 216, 223, 227, 224 or complement thereof.

H21. The kit of any one of embodiments H6 to H20, wherein the competitor oligonucleotides comprise polynucleotides chosen from SEQ ID NOs: 293, 284, 283, 290, 285, 281, 282, 294, 292, 289, 280, 287, 291, 288 or complement thereof.

H22. The kit of any one of embodiments H1 to H21, wherein the primer pairs comprise polynucleotides chosen from SEQ ID NOs: 37, 101, 28, 92, 27, 91, 34, 98, 29, 93, 25, 89, 26, 90, 38, 102, 36, 100, 33, 97, 24, 88, 31, 95, 35, 99, 32, 96 or complement thereof, and are configured for amplifying target polynucleotides within chromosome 18.

H23. The kit of any one of embodiments H11 to H22, wherein each of the extension oligonucleotides comprises a polynucleotide chosen from SEQ ID NOs: 165, 156, 155, 162, 157, 153, 154, 166, 164, 161, 152, 159, 163, 160 or complement thereof.

H24. The kit of any one of embodiments H1 to H23, wherein two of the two or more target polynucleotides in chromosome 18 are in a chromosome 18 polynucleotide chosen from SEQ ID NOs: 229, 220 or complement thereof.

H25. The kit of any one of embodiments H1 to H24, wherein seven of the two or more target polynucleotides in chromosome 18 are in a chromosome 18 polynucleotide chosen from SEQ ID NOs: 229, 220, 219, 226, 221, 217, 218 or complement thereof.

H26. The kit of any one of embodiments H1 to H24, wherein twelve of the two or more target polynucleotides in chromosome 18 are in a chromosome 18 polynucleotide chosen from SEQ ID NOs: 229, 220, 219, 226, 221, 217, 218, 230, 228, 225, 216, 223 or complement thereof.

H27. The kit of any one of embodiments H1 to H26, wherein: the two or more target polynucleotides in chromosome 21 are in a chromosome 21 polynucleotide chosen from SEQ ID NOs: 244, 255, 254, 234, 240, 241, 245, 236, 239, 248, 233, 250, 251, 242, 249, 238, 243, 235, 246, 247, 237 or complement thereof.

H28. The kit of any one of embodiments H6 to H27, wherein the competitor oligonucleotides comprise polynucleotides chosen from SEQ ID NOs: 308, 319, 318, 298, 304, 305, 309, 300, 303, 312, 297, 314, 315, 306, 313, 302, 307, 299, 310, 311, 301 or complement thereof.

H29. The kit of any one of embodiments H1 to H28, wherein the primer pairs comprise polynucleotides chosen from SEQ ID NOs: 52, 116, 63, 127, 62, 126, 42, 106, 48, 112, 49, 113, 53, 117, 44, 108, 47, 111, 56, 120, 41, 105, 58, 122, 59, 123, 50, 114, 57, 121, 46, 110, 51, 115, 43, 107, 54, 118, 55, 119, 45, 109 or complement thereof, and are configured for amplifying target polynucleotides within chromosome 21.

H30. The kit of any one of embodiments H11 to H15, wherein each of the extension oligonucleotides comprises a polynucleotide chosen from SEQ ID NOs: 180, 191, 190, 170, 176, 177, 181, 172, 175, 184, 169, 186, 187, 178, 185, 174, 179, 171, 182, 183, 173 or complement thereof.

H31. The kit of any one of embodiments H1 to H16, wherein two of the two or more target polynucleotides in chromosome 21 are in a chromosome 21 polynucleotide chosen from SEQ ID NOs: 244, 255 or complement thereof.

H32. The kit of any one of embodiments H1 to H17, wherein seven of the two or more target polynucleotides in chromosome 21 are in a chromosome 21 polynucleotide chosen from SEQ ID NOs: 244, 255, 254, 234, 240, 241, 245 or complement thereof.

H33. The kit of any one of embodiments H1 to H18, wherein twelve of the two or more target polynucleotides in chromosome 21 are in a chromosome 21 polynucleotide chosen from SEQ ID NOs: 244, 255, 254, 234, 240, 241, 245, 236, 239, 248, 233, 250 or complement thereof.

I1. A method of amplifying one or more target polynucleotides in a sample comprising:
  (a) contacting a sample comprising circulating cell-free nucleic acid from a human pregnant female bearing a fetus with a collection of primers under amplification conditions, wherein the primers specifically hybridize to nucleotide sequences located within two or more target polynucleotides in chromosome 13, chromosome 18 or chromosome 21, wherein:
    the two or more target polynucleotides in chromosome 13 are in chromosome 13 polynucleotides comprising chromosome 13 polynucleotides of SEQ ID NOs: 209 and 214, or complement thereof;
    the two or more target polynucleotides in chromosome 18 are in chromosome 18 polynucleotides comprising chromosome 18 polynucleotides of SEQ ID NOs: 232 and 222, or complement thereof; and
    the two or more target polynucleotides in chromosome 21 are in chromosome 21 polynucleotides comprising chromosome 21 polynucleotides of SEQ ID NOs: 256 and 253, or complement thereof; thereby providing target-specific amplicons.

I1.1. The method of embodiment I1, wherein the primers specifically hybridize to nucleotide sequences located in one or more target polynucleotides in one or more of chromosome 13 polynucleotide SEQ ID NO: 211, chromosome 18 polynucleotide SEQ ID NO: 231 and chromosome 21 polynucleotide SEQ ID NO: 252.

I1.2. The method of embodiment I1 or I1.1, comprising (b) analyzing the target specific amplicons.

I2. The method of any one of embodiments I1 to I1.2, comprising, prior to (a), contacting nucleic acid from the sample with a cleavage agent under cleavage conditions, thereby generating cleaved nucleic acid and non-cleaved nucleic acid.

I3. The method of embodiment I2, wherein the cleavage agent is a restriction enzyme.

I4. The method of embodiment I3, wherein the restriction enzyme is a methylation sensitive restriction enzyme.

I5. The method of embodiment I4, wherein the restriction enzyme preferentially cleaves nucleic acid comprising one or more non-methylated recognition sequences.

I5.1. The method of any one of embodiments I2 to I5, wherein the target specific amplicons are generated substantially from the non-cleaved nucleic acid.

I5.2. The method of any one of embodiments I1.1 to I5.1, wherein the analyzing in (b) comprises determining amounts of one or more target specific amplicons.

I5.3. The method of any one of embodiments I1.1 to I5.1, wherein the analyzing in (b) comprises determining amounts of the two or more target polynucleotides in each of chromosome 13, chromosome 18 and chromosome 21.

I.5.4. The method of I5.3, wherein the analyzing in (b) comprises quantifying one, two, three or four copies of one or more of chromosome 13, chromosome 18, chromosome 21, or portion thereof, in the fetus according to the amounts of the two or more target polynucleotides in each of chromosome 13, chromosome 18 and chromosome 21.

I6. The method of any one of embodiments I5.3 to I5, wherein the nucleic acid in (a) from which the amounts of the two or more target polynucleotides are determined is substantially the non-cleaved nucleic acid.

I7. The method of any one of embodiments I5.3 to I6, wherein the amounts of the two or more target polynucleotides are determined by a process comprising mass spectrometry.

I7.1. The method of embodiment I7, wherein the mass spectrometry is matrix-assisted laser desorption ionization (MALDI) mass spectrometry.

I7.2. The method of any one of embodiments I5.3 to I6, wherein the amounts of the two or more target polynucleotides are determined by a process comprising sequencing.

I8. The method of any one of embodiments I5.3 to I7.2, wherein the amounts of the two or more target polynucleotides are determined in a single multiplex reaction.

I9. The method of any one of embodiments I1 to I8, comprising contacting the nucleic acid in (a) with one or more competitor oligonucleotides under the amplification conditions.

I9.1. The method of any one of embodiments I1 to I9, comprising contacting the primers with the one or more competitor oligonucleotides under the amplification conditions.

I10. The method of I9 or I9.1, wherein the primers are configured to anneal to a portion of the competitor oligonucleotides thereby providing competitor specific amplicons.

I10.1. The method of any one of embodiments I9 to I10, wherein the amplification conditions comprise a known amount of the one or more competitor oligonucleotides.

I10.2. The method of any one of embodiments I9 to I10.1, wherein each of the one or more competitor oligonucleotides comprise a nucleic acid sequence that is substantially identical to a target polynucleotide.

I10.3. The method of embodiment I10.2, wherein each of the one or more competitor oligonucleotides comprises a feature that distinguishes the competitor oligonucleotide from the target polynucleotide to which it is substantially identical.

I10.4. The method of embodiment I10.3, wherein the feature comprises one or more nucleotide bases that differs between the nucleic acid sequence of the competitor oligonucleotide and the nucleic acid sequence of the target polynucleotide to which it is substantially identical to.

I10.5. The method of embodiment I10.4, wherein the feature comprises one to ten nucleotide bases that differ.

I11. The method of any one of embodiments I9 to I10.5, wherein the competitor oligonucleotides each comprise a polynucleotide chosen from SEQ ID NOs 273, 275, 278, 296, 286, 295, 320, 317, 316 or complement thereof.

I12. The method of any one of embodiments I1 to I11, wherein the primers comprise polynucleotides of SEQ ID NOs: 17, 81, 19, 83, 22, 86 or complement thereof, for amplifying target polynucleotides within chromosome 13.

I13. The method of embodiment I11 or I12, wherein the primers comprise polynucleotides of SEQ ID NOs: 40, 104, 30, 94, 39, 103 or complement thereof, for amplifying target polynucleotides within chromosome 18.

I14. The method of any one of embodiments I11 to I13, wherein the primers comprise polynucleotides of SEQ ID NOs: 64, 128, 61, 125, 60, 124 or complement thereof, for amplifying target polynucleotides within chromosome 21.

I15. The method of any one of embodiments I1.1 to I14, wherein the analyzing in (b) comprises contacting the target specific amplicons with extension oligonucleotides under conditions in which the extension oligonucleotides anneal to the target specific amplicons and are extended by one or more nucleotides.

I15.1. The method of any one of embodiments I11 to I14, wherein the analyzing in (b) comprises contacting the competitor specific amplicons with extension oligonucleotides under conditions in which the extension oligonucleotides anneal to the competitor specific amplicons and the competitor specific amplicons are extended by one or more nucleotides.

I16. The method of embodiment I15, wherein each of the extension oligonucleotides comprises a polynucleotide chosen from SEQ ID NOs: 145, 147, 150, 168, 158, 167, 192, 189, 188 or complement thereof.

I17. The method of any one of embodiments I1.1 to I16, wherein the analyzing in (b) comprises determining the amount of four or more target polynucleotides in chromosome 13, and one or more of the target polynucleotides are in a chromosome 13 polynucleotide comprising chromosome 13 polynucleotides of SEQ ID NOs: 198, 207, 206, 208, 200, 194, 210, 215, 212, 213, 204, 197, 201, 203, 193, 205, 199, 196, 195, 202 or complement thereof.

I18. The method of embodiment I17, wherein the one or more competitor oligonucleotides each comprise a polynucleotide chosen from SEQ ID NOs: 262, 271, 270, 272, 264, 258, 274, 279, 276, 277, 268, 261, 265, 267, 257, 269, 263, 260, 259, 266 or complement thereof.

I19. The method of embodiment I17 or I18, wherein the primers each comprise a polynucleotide chosen from SEQ ID NOs: 6, 70, 15, 79, 14, 78, 16, 80, 8, 72, 2, 66, 18, 82, 23, 87, 20, 84, 21, 85, 12, 76, 5, 69, 9, 73, 11, 75, 1, 65, 13, 77, 7, 71, 4, 68, 3, 67, 10, 74 or complement thereof.

I20. The method of any one of embodiments I17, I18 or I19, wherein the extension oligonucleotides comprise a polynucleotide chosen from SEQ ID NOs: 134, 143, 142, 144, 136, 130, 146, 151, 148, 149, 140, 133, 137, 139, 129, 141, 135, 132, 131, 138 or complement thereof.

I21. The method of any one of embodiments I1.1 to I20, wherein the analysis in (b) comprises determining the amount of five or more target polynucleotides in chromosome 13, and two of the target polynucleotides are in a chromosome 13 polynucleotide of SEQ ID NOs: 198, 207 or complement thereof.

I22. The method of any one of embodiments I1.1 to I21, wherein the analysis in (b) comprises determining the amount of ten or more target polynucleotides in chromosome 13, and seven of the target polynucleotides are in a chromosome 13 polynucleotide of SEQ ID NOs: 198, 207, 206, 208, 200, 194, 210, or complement thereof.

I23. The method of any one of embodiments I1.1 to I22, wherein the analysis in (b) comprises determining the amount of fifteen or more target polynucleotides in chromosome 13, and twelve of the target polynucleotides are in a chromosome 13 polynucleotide of SEQ ID NOs: 198, 207, 206, 208, 200, 194, 210, 215, 212, 213, 204, 197 or complement thereof.

I24. The method of any one of embodiments I1.1 to I23, wherein the analysis in (b) comprises determining the amount of four or more target polynucleotides in chromosome 18, and one or more of the target polynucleotides are in a chromosome 18 polynucleotide chosen from SEQ ID NOs: 229, 220, 219, 226, 221, 217, 218, 230, 228, 225, 216, 223, 227, 224 or complement thereof.

I25. The method of embodiment I24, wherein the one or more competitor oligonucleotides comprise a polynucleotide chosen from SEQ ID NOs: 293, 284, 283, 290, 285, 281, 282, 294, 292, 289, 280, 287, 291, 288 or complement thereof.

I26. The method of embodiment I24 or I25, wherein the primers comprise polynucleotides of SEQ ID NOs: 37, 101, 28, 92, 27, 91, 34, 98, 29, 93, 25, 89, 26, 90, 38, 102, 36, 100, 33, 97, 24, 88, 31, 95, 35, 99, 32, 96 or complement thereof.

I27. The method of embodiment I24, I25 or I26, wherein each of the extension oligonucleotides comprises a polynucleotide chosen from SEQ ID NOs: 165, 156, 155, 162, 157, 153, 154, 166, 164, 161, 152, 159, 163, 160 or complement thereof.

I28. The method of any one of embodiments I24 to I27, wherein the analysis in (b) comprises detecting the amount of five or more target polynucleotides in chromosome 18, and two of the target polynucleotides comprise a chromosome 18 polynucleotide of SEQ ID NOs: 229, 220 or complement thereof.

I29. The method of any one of embodiments I24 to I28, wherein the analysis in (b) comprises determining the amount of ten or more target polynucleotides in chromosome 18, and seven of the target polynucleotides comprise a chromosome 18 polynucleotide of SEQ ID NOs: 229, 220, 219, 226, 221, 217, 218 or complement thereof.

I30. The method of any one of embodiments I24 to I229, wherein the analysis in (b) comprises determining the amount of fifteen or more target polynucleotides in chromosome 18, and twelve of the target polynucleotides are in a chromosome 18 polynucleotide of SEQ ID NOs: 229, 220, 219, 226, 221, 217, 218, 230, 228, 225, 216, 223 or complement thereof.

I31. The method of any one of embodiments I1.1 to I30, wherein the analysis in (b) comprises determining the amount of four or more target polynucleotides in chromosome 21, and one or more of the target polynucleotides are in a chromosome 21 polynucleotide chosen from SEQ ID NOs: 244, 255, 254, 234, 240, 241, 245, 236, 239, 248, 233, 250, 251, 242, 249, 238, 243, 235, 246, 247, 237 or complement thereof.

I32. The method of embodiment I31, wherein the one or more competitor oligonucleotides comprise a polynucleotide chosen from SEQ ID NOs: 308, 319, 318, 298, 304, 305, 309, 300, 303, 312, 297, 314, 315, 306, 313, 302, 307, 299, 310, 311, 301 or complement thereof.

I33. The method of embodiment I31 or I32, wherein the primers comprise polynucleotides of SEQ ID NOs: 52, 116, 63, 127, 62, 126, 42, 106, 48, 112, 49, 113, 53, 117, 44, 108, 47, 111, 56, 120, 41, 105, 58, 122, 59, 123, 50, 114, 57, 121, 46, 110, 51, 115, 43, 107, 54, 118, 55, 119, 45, 109 or complement thereof.

I34. The method of embodiment I31, I32, or I33, wherein each of the extension oligonucleotides comprises a polynucleotide chosen from SEQ ID NOs: 180, 191, 190, 170, 176, 177, 181, 172, 175, 184, 169, 186, 187, 178, 185, 174, 179, 171, 182, 183, 173 or complement thereof.

I35. The method of any one of embodiments I31 to I34, wherein the analysis in (b) comprises determining the amount of five or more target polynucleotides in chromosome 21, and two of the target polynucleotides are in a chromosome 21 polynucleotide of SEQ ID NOs: 244, 255 or complement thereof.

I36. The method of any one of embodiments I31 to I35, wherein the analysis in (b) comprises determining the amount of ten or more target polynucleotides in chromosome 21, and seven of the target polynucleotides are in a chromosome 21 polynucleotide of SEQ ID NOs: 244, 255, 254, 234, 240, 241, 245 or complement thereof.

I37. The method of any one of embodiments I31 to I36, wherein the analysis in (b) comprises determining the amount of fifteen or more target polynucleotides in chromosome 21, and twelve of the target polynucleotides are in a chromosome 21 polynucleotide of SEQ ID NOs: 244, 255, 254, 234, 240, 241, 245, 236, 239, 248, 233, 250 or complement thereof.

I38. The method of any one of embodiments I1 to I37, wherein the primers are primer pairs.

I39. The method of embodiment I38, wherein each primer pair is specific for one or more target polynucleotides.

I40. The method of embodiment I38, wherein each of the primer pairs is configured for amplifying the target polynucleotide for which the primer pair is specific, wherein each of the primers of the primer pair hybridize to a portion of the target polynucleotide for which the primer pair is specific.

I41. The method of any one of embodiments I38 to I40, wherein each of which primer pairs is configured to specifically amplify at least one competitor oligonucleotide and the target polynucleotide to which it is substantially identical to.

I42. The method of any one of embodiments I10 to I41, comprising determining the amount of competitor specific amplicons.

I43. The method of any one of embodiments of I10 to I42, wherein the analyzing in (b) comprises determining a ratio of target specific amplicons to competitor specific amplicons for each of the target polynucleotides in the sample.

I44. The method of any one of embodiments I1 to I43, comprising determining an amount of fetal nucleic acid in the sample.

I45. The method of any one of embodiments I1 to I44, wherein the primers comprise one or more tags.

I46. The method of embodiment I45, wherein the one or more tags comprises a nucleic acid sequence configured for hybridization of the one or more tags to one or more universal primers.

I47. The method of embodiment I45 or I46, wherein the one or more tags are configured for hybridization of the target specific amplicons and the competitor specific amplicons to a solid phase.

I48. The method of any one of embodiments I43 to I47, comprising normalizing each of which ratios to the amount of fetal nucleic acid in the sample.

I49. The method of any one of embodiments I4 to I48, wherein the methylation sensitive restriction endonuclease is selected from AatII, AccII, ACiI, AclI, AfeI, AgeI, AgeI-HF, Aor13HI, Aor51HI, AscI, AseI, BceAI, BmgBI, BsaAI, BsaHI, BsiEI, BspDI, BsrFI, BspT104I, BssHII, BstBI, BstUI, Cfr10I, ClaI, CpoI, EagI, Eco52I, FauI, FseI, FspI, DpnI, DpnII, HaeII, HapII, HfaI, HgaI, HhaI, HinP1I, HPAII, Hpy99I, HpyCH4IV, KasI, MaeII, McrBC, MluI, MspI, NaeI, NgoMIV, NotI, NotI-HF, NruI, NsbI, NtBsmAI, NtCviPII, PaeR7I, PluTI, PmlI, PmaCI, Psp1406I, PvuI, RsrII, SacII, SalI, SalI-HF, ScrFI, SfoI, SfrAI, SmaI, SnaBI, TspMI, ZraI and isoschizomers thereof.

I50. The method of any one of embodiments I4 to I49, wherein the methylation sensitive restriction endonuclease is selected from HpaII, HinP1I, HhaI, MaeII, BstUI and AciI.

I51. The method of any one of embodiments I4 to I50, wherein the methylation sensitive restriction endonuclease is selected from HHAI, HinP1I and HPAII.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for detecting one, two, three or four copies of a fetal chromosome or portion thereof in a sample, comprising:

(a) contacting a sample comprising circulating cell-free nucleic acid from a human pregnant female bearing a fetus with a methylation sensitive restriction enzyme under cleavage conditions to selectively digest non-methylated maternal nucleic acid from target polynucleotides on each of chromosomes 13, 18 and 21;

(b) the steps of: (i) contacting the nucleic acid of step (a) with a collection of primer pairs under amplification conditions, wherein at least one of each primer pair is specific for nucleic acid sequences located within at least one of the target polynucleotides in chromosome 13, chromosome 18 and chromosome 21, and one of the four sets of primer pairs is specific for amplifying a target polynucleotide from one of chromosomes 13, 18 or 21, thereby generating amplicons from the undigested polynucleotide targets, wherein the target polynucleotides are in:

chromosome 13 polynucleotides of SEQ ID NOs: 209 and 214, or complements thereof;
chromosome 18 polynucleotides of SEQ ID NOs: 232 and 222, or complements thereof; and
chromosome 21 polynucleotides of SEQ ID NOs: 256 and 253, or complements thereof; and (ii) contacting the sample with at least one competitor oligonucleotide under the amplification conditions such that a competitor amplicon comprising the competitor oligonucleotide is generated, wherein the competitor oligonucleotide comprises a sequence substantially identical to a first target sequence but includes at least one nucleotide substitution; and (c) determining amounts of the chromosome 13, chromosome 18 and chromosome 21 amplicons in (b) by comparing a ratio of the first target amplicon to the at least one competitor amplicon; and (d) determining, based on the relative amounts of the target amplicons from step (c), whether there is aneuploidy for any one of chromosomes 13, 18, or 21, or portion thereof, in the fetus.

2. The method of claim 1, wherein the amounts of the target amplicons and the at least one competitor amplicon are determined by a process comprising mass spectrometry.

3. The method of claim 1, wherein the amounts of the target amplicons and the at least one competitor amplicon are determined by a process comprising sequencing.

4. The method of claim 1, wherein the amounts of the target amplicons and the at least one competitor amplicon are determined by quantitative PCR.

5. The method of claim 1, wherein the amplification is performed as a single multiplex reaction.

6. The method of claim 1, wherein the primer pairs comprise polynucleotides of SEQ ID NOs: 17, 81, 22, 86, 30, 94, 40, 104, 61, 125, 64, 128, or complements thereof.

7. The method of claim 1, wherein the competitor oligonucleotides comprise polynucleotides of SEQ ID NOs: 273, 278, 286, 296, 317, 320, or complements thereof.

8. The method of claim 1, wherein (b) comprises contacting the target amplicons and the at least one competitor amplicon with extension oligonucleotides under conditions in which the extension oligonucleotides anneal to the target amplicons and the at least one competitor amplicon and are extended by one or more nucleotides to generate extended amplicons.

9. The method of claim 8, wherein the extension oligonucleotides comprise polynucleotides of SEQ ID NOs: 145, 150, 158, 168, 189, 192 or complements thereof.

10. The method of claim 1, wherein the target polynucleotides further comprise:
a chromosome 13 polynucleotide of SEQ ID NOs: 193-208, 210-213, 215 or a complement thereof;
a chromosome 18 polynucleotide of SEQ ID NOs: 216-221, 223-231 or a complement thereof; and
a chromosome 21 polynucleotide of SEQ ID NOs: 233-252, 254, 255 or a complement thereof.

11. The method of claim 10, wherein the primer pairs comprise polynucleotides chosen from SEQ ID NOs: 1, 65, 2, 66, 3, 67, 4, 68, 5, 69, 6, 70, 8, 72, 9, 73, 10, 74, 11, 75, 12, 76, 14, 78, 16, 80, 18, 82, 20, 84, 21, 85, 23, 87, 24, 88, 25, 89, 26, 90, 28, 92, 29, 93, 31, 95, 32, 96, 33, 97, 34, 98, 35, 99, 36, 100, 37, 101, 38, 102, 42, 106, 44, 108, 46, 110, 47, 111, 48, 112, 50, 114, 51, 115, 52, 116, 53, 117, 54, 118, 56, 120, 57, 121, 58, 122, 59, 123, 60, 124, 63, 127, 7, 71, 13, 77, 15, 79, 19, 83, 27, 91, 39, 103, 41, 105, 43, 107, 45, 109, 49, 113, 55, 119, 62, 126 or complements thereof.

12. The method of claim 10, wherein the competitor oligonucleotides further comprise a polynucleotide chosen from SEQ ID NOs: 257, 258, 259, 260, 261, 262, 264, 265, 266, 267, 268, 270, 272, 274, 276, 277, 279, 280, 281, 282, 284, 285, 287, 288, 289, 290, 291, 292, 293, 294, 298, 300, 302, 303, 304, 306, 307, 308, 309, 310, 312, 313, 314, 315, 316, 319, 263, 269, 271, 275, 283, 295, 297, 299, 301, 305, 311, 318, or complements thereof.

13. The method of claim 10, wherein (b) comprises contacting the target amplicons and the at least one competitor amplicon with extension oligonucleotides under conditions in which the extension oligonucleotides anneal to the target amplicons and the at least one competitor amplicon and are extended by one or more nucleotides to generate extended amplicons.

14. The method of claim 13, wherein the extension oligonucleotides comprise a polynucleotide chosen from SEQ ID NOs: 129, 130, 131, 132, 133, 134, 136, 137, 138, 139, 140, 142, 144, 146, 148, 149, 151, 152, 153, 154, 156, 157, 159, 160, 161, 162, 163, 164, 165, 166, 170, 172, 174, 175, 176, 178, 179, 180, 181, 182, 184, 185, 186, 187, 188, 191, 135, 141, 143, 147, 155, 167, 169, 171, 173, 177, 183, 190 or complements thereof.

15. A method for detecting one, two, three or four copies of a fetal chromosome or portion thereof in a sample, comprising:

(a) contacting a sample comprising circulating cell-free nucleic acid from a human pregnant female bearing a fetus with a methylation sensitive restriction enzyme under cleavage conditions to selectively digest non-methylated maternal nucleic acid from target polynucleotides on each of chromosomes 13, 18 and 21;

(b) contacting the nucleic acid of step (a) with a collection of primer pairs under amplification conditions, wherein at least one of each primer pair is specific for nucleic acid sequences located within at least one of the target polynucleotides in chromosome 13, chromosome 18 and chromosome 21, and one of the four sets of primer pairs is specific for amplifying a target polynucleotide from one of chromosomes 13, 18 or 21, thereby generating amplicons from the undigested polynucleotide targets, wherein the target polynucleotides are in:

chromosome 13 polynucleotides of SEQ ID NOs: 209 and 214, or complements thereof;
chromosome 18 polynucleotides of SEQ ID NOs: 232 and 222, or complements thereof; and
chromosome 21 polynucleotides of SEQ ID NOs: 256 and 253, or complements thereof;

(c) determining amounts of the chromosome 13, chromosome 18 and chromosome 21 amplicons in (b); and (d) determining, based on the relative amounts of the target amplicons from step (c), whether there is aneuploidy for any one of chromosomes 13, 18, or 21, or portion thereof, in the fetus, wherein step (b) further comprises contacting the sample with at least one competitor oligonucleotide under the amplification conditions such that a competitor specific amplicon comprising the competitor oligonucleotide is generated, and wherein the competitor oligonucleotide comprises a sequence substantially identical to a first target sequence but includes at least one nucleotide substitution, and wherein the competitor oligonucleotides comprises at least one polynucleotide of SEQ ID NOs: 273, 278, 286, 296, 317, 320, or a complement thereof, and step (c) further comprises comparing a ratio of the first target specific amplicon to the at least one competitor specific amplicon.

* * * * *

SEQUENCE LISTING

```
<160> NUMBER OF SEQ ID NOS: 334

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 1
agcagagggc ctaggagga                                                      19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaaggacgcc tgagaaaaca                                                     20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggagggctg gctgcgaga                                                      19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtccctacct ggaaagctg                                                      19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gccacggtgc tggagggct                                                      19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcgccctgtt cttctatttc                                                     20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
``` cagggatcg cggctgaga                                            19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccaaaagctg agaatcctcg                                          20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaggctggga gggaccctcg                                          20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaacagcaga aacttccccc                                          20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggtttgtcga tagtaatcac c                                        21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12 aaaccagcc cgcgcagag                                            19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acccacagga gccatccac                                          19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atgaccccca cagaccttg                                          19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agctccattg tctcagaggc                                         20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tccccagctg ttgcctctt                                          19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagtgtgtct cgaacttgcg                                         20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggtgacatcc tcccacccg                                          19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aagaagacgg tcttctgagc                                         20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tccaggcctc taggcaatag                                               20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgtgtccccc actcacctt                                                19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaacactgcg cccattgtc                                                19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ttagggagga cctacctggc                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cactttctcc gtgcgagaag                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcactttgtt aagaagtccc                                               20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcacgctccc ggggctctt                                                    19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtggtcatta gggcagtgg                                                    19

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgcgcctctc ccgaaagcag                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctaagggata tatgagggac                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttcacctggc agggcaggcg                                                   20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtcaggtacc ctaagggata                                                   20

```
<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
accccagtaa caagtgagag                                                  20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggagagcgga caggcctcg                                                   19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agcctcgcac agctcgctt                                                   19

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caagcgttgc tgagatgaga                                                  20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctggtgggtt ttagtacccg                                                  20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atctgagcct tagccccatc                                                  20

<210> SEQ ID NO 38
```

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccagatccca gttcctcaac                                              20

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccatgcgccc cgtcctcc                                                18

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttctgcgatt tcggagtgac                                              20

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gactcagtgg tgtcgcctc                                               19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
actggctggg cgtccgaac                                               19

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggtatctaat gccatccacc                                              20

<210> SEQ ID NO 44
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cacagagctt ccgactttgc                                              20

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tccccgacct cccaagcta                                               19

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aaaaggaggg ccagagatag                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cacaagttag ttggaagccg                                              20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcgtccgaac tccccaggt                                               19

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gaggcacaaa gtgatggcag                                              20

<210> SEQ ID NO 50
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 50
aaaaaacctc gcccgcattg                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aggtttcgga ttggaaggag                                              20

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acggcgagag cacagatgg                                               19

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aggcctccgg gctcttgctt                                              20

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgaagcacca tgcagcgcc                                               19

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ttcagtgagt gccactgacc                                              20

<210> SEQ ID NO 56
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 56
cattggaagg tcagccaatc                                                 20

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aggaagtgag cagctcctg                                                  19

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tagaaagcga gagacgagag                                                 20

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtctaggcgg caggtccc                                                   18

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcctcaggag gcggtgcca                                                  19

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aggaggcgac cccagagagt                                                 20

<210> SEQ ID NO 62
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 62
ccttcaaggg ggtccctgc                                                   19

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttcagggagc gtccggtgag                                                  20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tttccttatc cgcaggtgtg                                                  20

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccccattcaa ctgccagg                                                    18

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cctatgggga aggatcaaac                                                  20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acaacagctt tggccaagac                                                  20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 68
aggtgggagt gggtgcgtca                                        20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtcattctgc ccacccattg                                        20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aaggagatgg gcgctctcag                                        20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gactcagttt ccaagtgcgg                                        20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ttgtcccacc tcgccataac                                        20

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
aaaccagcct tgaaacgcc                                         19

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gaatccccgg ccgcttctg                                              19

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gaagacttgt cacccagtcc                                             20

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggtccccacg gaggatcag                                              19

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
acctcaagcc ctgcctctg                                              19

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tcttctccaa agtgcgcatc                                             20

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgatgcgctg aggctcgac                                              19

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 80
agacaatgga gctgacactg                                              20

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
agacaccgcg cccctctc                                                18

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ttttcgcctg gaactaccac                                              20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aagaggaagt ggcccaggag                                              20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
actgcggggt cggcgggaaa                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
taaaacccaa gtctggtgtc                                              20

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
```
aaagtctgcg cagctgctc                                                  19

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tgcatctgca cccgcccgta                                                 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cctaaactta gccagttcgg                                                 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aggtgagtct ggtccgcttt                                                 20

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tggtgagggg ctacccaga                                                  19

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
acagctgagc gcagggttct                                                 20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
aggaaggaga gatccgggac                                         20

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tggtgctgaa gtgacaggg                                          19

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tgagtccgcg caccccttc                                          19

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tcttccagag gctgctttag                                         20

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aggggaccca gggaggaga                                          19

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97 ttcccoctac actcggaatg                                         20

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ctcagcggtg cgaggaaag                                          19

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tgcagacttg caccatggg                                              19

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ctgccaagtt ccttctggt                                              19

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cttccctgga gccggcgtg                                              19

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcaaggtcaa cctaccagag                                             20

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
agtgaccaca gtccggacc                                              19

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ccctgctgtg tggggagac                                              19

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
gggaatccat ccagcgcaat                                                  20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
gttttaaagt gggccacagc                                                  20

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
acccactcag aggtgggc                                                    18

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 108 agtcagggt gaaagtcgag                                                   20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
ttcttcacct ggcaggcttc                                                  20

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
tgcaccgcag taccacagc                                                   19

```
<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gtggattgac ccagatattg                                               20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cgggtatcct acgtattctg                                               20

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tgggattaaa cgagcgcgg                                                19

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ccaagcaccc ctgcctcta                                                19

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115 aaaaacccccc tacacgctac                                              20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tgccagccct ccccacgagt                                               20

<210> SEQ ID NO 117
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
agctcctgca gggtgaatg                                                 19

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ggtaccatgt gcagcgcag                                                 19

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aaggtgcctc ctgcgcaatc                                                20

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
tggcgcgcgc ctcggaggt                                                 19

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ctcttggcag ggagggct                                                  18

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ggggaacctg ctttgatttt                                                20

<210> SEQ ID NO 123
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
aaagccctcc gagggagccc a                                            21

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gctgcccagc gctggcaac                                               19

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
acatctggaa ggaaggaagc                                              20

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tgcggcaccc aagcccctc                                               19

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tacctaagtg agaggcagac                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
acgcacgggc tttccgaatt                                              20

<210> SEQ ID NO 129
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 129
gcctaggagg accccgggcg tgg                                           23

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gcctgagaaa acagaccccg gccccgtg                                      28

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
agagccccgg gttcccttt                                                19

<210> SEQ ID NO 132
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gggacgctgg gagactcaca gcccgg                                        26

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gtgctggagg gctgcgcgg                                                19

<210> SEQ ID NO 134
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cgccctgttc ttctatttca gagcgc                                        26

<210> SEQ ID NO 135
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 135
gggatcgcgg ctgagagcgc cc                                              22

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
agctgagaat cctcgatgcc cgcgcg                                          26

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ctgggaggga ccctcgccgg gg                                              22

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
cagaaacttc ccccggctgt gg                                              22

<210> SEQ ID NO 139
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tttgtcgata gtaatcacca ccttc                                           25

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gggctcgccc gcggggtctg gg                                              22

<210> SEQ ID NO 141
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 141
ccgcagccgc cctcctc                                                    17

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ccccacagac cttggcgccg c                                               21

<210> SEQ ID NO 143
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ggcggccaag tgagggacca gtctc                                           25

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cccagctgtt gcctcttgcg cgg                                             23

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ggggctgcgg agctggccgg t                                               21

<210> SEQ ID NO 146
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cctcccaccc gggggtt                                                    17

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 147
gcgtccgccc tccccgcctc gccgcgc                                                27

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ataggcccgg cgcccctcc                                                         20

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cccactcacc ttccccgg                                                          18

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gcgcccattg tcccgggcgc tc                                                     22

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
cctggctgtg ccggtctg                                                          18

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
tttctccgtg cgagaagcac cgg                                                    23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 153
ctttgttaag aagtccccca ccc                                              23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gggctcttgg ccgcccctcg ccc                                              23

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gtcattaggg cagtggaccc gg                                               22

<210> SEQ ID NO 156
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
aaagcagccg cccgccc                                                     17

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
ggatatatga gggaccccgg ggct                                             24

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
cgcccggggt ccgccgggg                                                   19

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 159
ccctaaggga tatatgaggg                                               20

<210> SEQ ID NO 160
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
accccagtaa caagtgagag cgctcc                                        26

<210> SEQ ID NO 161
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
gagagcggac aggcctcgcc ctgcgccg                                      28

<210> SEQ ID NO 162
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
agctcgcttc cggagctgcg agctc                                         25

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
agcgttgctg agatgagaaa gcgtggc                                       27

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gtacccgccg gcttcttggg c                                             21

<210> SEQ ID NO 165
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
```

```
gccttagccc catccactcc gg                                              22
```

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166

```
caacctgggc gctttacctg g                                               21
```

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167

```
cctccggccc ggggagctcc c                                               21
```

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168

```
gatttcggag tgaccggtgg                                                 20
```

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169

```
gtggtgtcgc ctcgcccggg                                                 20
```

<210> SEQ ID NO 170
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170

```
gcacagtcta gaggttc                                                    17
```

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171

```
tgccatccac ccttccggg                                              19

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
ccttccaggc tctagactcg cgcc                                        24

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
acctcccaag ctactccggc g                                           21

<210> SEQ ID NO 174
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gggccacctg tgccggg                                                17

<210> SEQ ID NO 175
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
gccggcgttc ggtatcaga                                              19

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
aactccccag gtctgcgc                                               18

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
aaagtgatgg cagcccggc                                              19
```

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
atggaacagc tggcagcgcc                                              20

<210> SEQ ID NO 179
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
aggaccgcgc tcgtggggcg cctgtg                                       26

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
cagatggcgg ctgcggagcc gggg                                         24

<210> SEQ ID NO 181
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gctcttgctt ggtttgg                                                 17

<210> SEQ ID NO 182
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gcgcccacca gccggcagcg cccacc                                       26

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ctccgccccg gcgtccggc                                               19

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ggcgcggagc tgctcccgg                                              19

<210> SEQ ID NO 185
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cctgcggaac tctggctgg cacag                                        25

<210> SEQ ID NO 186
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gagacgagag gggaatg                                                17

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ctaggcggca ggtcccgggc tct                                         23

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
cggtgccagc ccccggc                                                17

<210> SEQ ID NO 189
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
cagagagtgg ggcgcgg                                                17

```
<210> SEQ ID NO 190
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ctgcgccccc ggagagg                                                       17

<210> SEQ ID NO 191
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
gggagcgtcc ggtgagccta ag                                                 22

<210> SEQ ID NO 192
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
aggtgtgcgc ggcgctcgc                                                     19

<210> SEQ ID NO 193
<211> LENGTH: 610
<212> TYPE: DNA
<213> ORGANISM: Homo sapiens

<400> SEQUENCE: 193
gcgaggagct tctggcgctg ccgccgccgc cgccccccgg aggtgctgtg ccgcccgctg         60
cccccgttgc cgcccgagag ggccgcctgc cgcctggcct tagcgcgtcg ccacagccct        120
ccagcgtcgc gcctcggcgg ccgcaggaac cacgatgaga ggcaggagct gctcctggct        180
gaggggcttc aaccactcgc cgaggaggag cagagggcct aggaggaccc cgggcgtgga        240
ccacccgccc tggcagttga atggggcggc aattgcgggg cccaccttag accgaagggg        300
aaaacccgct ctctcaggcg catgtgccag ttggggcccc gcgggtagat gccggcaggc        360
cttccggaag aaaaagagcc attggttttt gtagtattgg ggccctcttt tagtgatact        420
ggattggcgt tgtttgtggc tgttgcgcac atccctgccc tcctacagca ctccaccttg        480
ggacctgttt agagaagccg gctcttcaaa gacaatggaa actgtaccat acacattgga        540
aggctcccta acacacacag cggggaagct gggccgagta ccttaatctg ccataaagcc        600
attcttactc                                                              610

<210> SEQ ID NO 194
<211> LENGTH: 689
<212> TYPE: DNA
<213> ORGANISM: Homo sapiens

<400> SEQUENCE: 194
acctagacaa gtcagcccat tgcccaagct tggcatgctc tgagcagaca gctagcagct         60
gcagaggtag gggtttctgg gcagtcggga gccccttctg ccaagttccc cttcccaaca        120
```

```
gatcgagagc tcggaggctt ggcacggtcg gtcccgatgg ccccagcggg agggtcacgg      180
ttgagacagc agccccatct cattgtttaa ggccggggct tcctcttttg gcggagcggg      240
agcgggagcg ggagctgagc gggaagggga cggacgccgc gggagccttc gggatgtcta      300
ttgctgccgc tccctcccct cgccgggagc ttgggtttcc cggggtgtgt gcggattctc      360
aataaaaagg gaaaagcacg atccaagtta attttccagc gccgacagga aatgctgttt      420
cctgcatcgt acaacgctgg tgccaacaag actgacacag gagcccattg tcccgcgaac      480
aatgtggcga tggggaagga cgcctgagaa acagacccc ggcccgtga gcgcgtttgt       540 ttgatccttc cccatagggt tgtgtgaggt gtgtgtctgt gtgggtgggt gtatttgtgc      600
atgtgtggtg tacgtctgtg tgtgagattg tgtgttgggg gtgtgtgtat atgtgtggtg      660
tgtgtgggag tgtgtctatg tgtgtctcc                                       689

<210> SEQ ID NO 195
<211> LENGTH: 1041
<212> TYPE: DNA
<213> ORGANISM: Homo sapiens

<400> SEQUENCE: 195
gagcccggga ggcctcgcag gaggtagagg tgtttcctaa agctgtggcg gcgaggaggt       60 gtccccgcg ggggcggccg gggcggccgc tgccgctgct gctgctgctg gggctggagg      120
ctcagcctcc caaaagattg aaggaaactg tcctccatgg gcaggagggc tggctgcgag      180
agccccgggt tccctttact gaagtcacgg tcttggccaa agctgttgtt tttgtgactc      240
tccggccatg tgatggatag aggggcgggc gctgggagcc cagcccctcc tttccacccg      300
ccggaaccgt gctgcgtggg aggggcgtc cctacctgga aagctgggga cgctgggaga      360
ctcacagccc ggaaaacaag ggtgacgcac ccactcccac ctcgaccccc gctccgcctc      420
ctggtgccct ttgccctgag cagtggaggg gaggggcccc gtctagtagg tctctgggac      480
acttccccgg cctggaagcc aggcctcctg ccacagccct ccccaacccc agccccgacc      540
tgcctagacc ctgaaagtga aatcatttta gctgatgatt aatgagctgc ccggcattgt      600
aaatggcaac agtaaaggcc attgtctccc ccgatttgtg agcaccaaca tctggctggc      660
gtcccaaggg ctaccaccac tctcccaggg cttgtatctt ttcttatttc atctttcttt      720
agcagcctgc caaaatatat attagaaagc tttgttgccg ctacataact ttaaatctct      780
ccttcctcag aaaagcacc cataaaactc agattgattt atgaacagta gcataagggc       840
taccgcccag gtacctgccc tgttgccgcc tgagaagtgg gggcttcttg gagaactctt      900
tcagatcccc ggggaaagtg gcagagtcta ccgaaaccat ttatagagaa gtatccagac      960
tgaagttctc agttccagga actagggagt accattggt tgatcaccac agtgactctc      1020
caacagttca ccctcaagag c                                              1041

<210> SEQ ID NO 196
<211> LENGTH: 1041
<212> TYPE: DNA
<213> ORGANISM: Homo sapiens

<400> SEQUENCE: 196
gagcccggga ggcctcgcag gaggtagagg tgtttcctaa agctgtggcg gcgaggaggt       60 gtccccgcg ggggcggccg gggcggccgc tgccgctgct gctgctgctg gggctggagg      120
ctcagcctcc caaaagattg aaggaaactg tcctccatgg gcaggagggc tggctgcgag      180
```

```
agccccgggt tcccttact gaagtcacgg tcttggccaa agctgttgtt tttgtgactc      240
tccggccatg tgatggatag aggggcgggc gctgggagcc cagcccctcc tttccacccg      300
ccggaaccgt gctgcgtggg aggggcgtc cctacctgga aagctgggga cgctgggaga      360
ctcacagccc ggaaaacaag ggtgacgcac ccactccac ctcgaccccc gctccgcctc      420
ctggtgccct ttgccctgag cagtggaggg aggggcccc gtctagtagg tctctgggac      480
acttccccgg cctggaagcc aggcctcctg ccacagccct cccaaccccc agccccgacc      540
tgcctagacc ctgaaagtga aatcatttta gctgatgatt aatgagctgc ccggcattgt      600
aaatggcaac agtaaaggcc attgtctccc ccgatttgtg agcaccaaca tctggctggc      660
gtcccaaggg ctaccaccac tctcccaggg cttgtatctt ttcttatttc atctttcttt      720
agcagcctgc caaaaatatt attagaaagc tttgttgccg ctacataact ttaaatctct      780
ccttcctcag aaaaagcacc cataaaactc agattgattt atgaacagta gcataagggc      840
taccgcccag gtacctgccc tgttgccgcc tgagaagtgg gggcttcttg gagaactctt      900
tcagatcccc ggggaaagtg gcagagtcta ccgaaaccat ttatagagaa gtatccagac      960
tgaagttctc agttccagga actagggagt acccattggt tgatcaccac agtgactctc     1020
caacagttca ccctcaagag c                                               1041

<210> SEQ ID NO 197
<211> LENGTH: 980
<212> TYPE: DNA
<213> ORGANISM: Homo sapiens

<400> SEQUENCE: 197
ctcgcccgcg cgccccagga cccaaagccg ggctccaagt cggcgcccca cgtcgaggct       60
ccgccgcagc ctccggagtt ggccgcagac aagaagggga gggagcggga gagggaggag      120
agctccgaag cgagagggcc gagcgccatg cgccgcgcca gcagagacta caccaagtac      180
ctgcgtggct cggaggagat gggcggcggc cccggagccc cgcacgaggg ccccctgcac      240
gccccgccgc cgcctgcgcc gcaccagccc cctgccgcct cccgctccat gttcgtggcc      300
ctcctggggc tggggctggg ccaggttgtc tgcagcgtcg ccctgttctt ctatttcaga      360
gcgcaggtga gtggccacct tcccagggga tcgcggctga gagcgcccat ctccttcccc      420
cgcacttgga aactgagtct ggcggcaggg ctgggccacc cagagcttgc atattccgga      480
agggaaagtg actccagaag ggagagagga agtgttgagt ttggggacaa cctggcgcag      540
ggctgtcggg cgcaccctgc tctctctccg cccacgcacc ccagcttctc ggtgctctgg      600
gggcggactc ccctggccgg acgatgggtt tgaatctcac cccgtccctt cgctgggaaa      660
caacactggc ctctcacctt ttctggtagt gattgcatac ttttttctccc tgtcatttct      720 cacttgaagt taagaatcaa cttctgttca cgtaggaaaa aagatgagcg ccttcacttg      780
ggcatctacc tttcccttcc cgcccaccac ccggcgggtt tcggttcctg cgcctggctg      840
ctctgcaggt gtgctgggc cacggtgctg gagggctgcg cggagcggga ggtcgcggtg      900
ctcgtgccca gtcgcccaa tgggtgggca gaatgacacg gcgcgaccag agaggcgcgg      960
gctcgggatg ggggctctgc                                                 980

<210> SEQ ID NO 198
<211> LENGTH: 980
<212> TYPE: DNA
<213> ORGANISM: Homo sapiens

<400> SEQUENCE: 198
```

```
ctcgcccgcg cgccccagga cccaaagccg ggctccaagt cggcgcccca cgtcgaggct      60
ccgccgcagc ctccggagtt ggccgcagac aagaagggga gggagcggga gagggaggag     120
agctccgaag cgagagggcc gagcgccatg cgccgcgcca gcagagacta caccaagtac     180
ctgcgtggct cggaggagat gggcggcggc cccggagccc cgcacgaggg cccccctgcac    240 gccccgccgc cgcctgcgcc gcaccagccc cctgccgcct cccgctccat gttcgtggcc     300
ctcctggggc tggggctggg ccaggttgtc tgcagcgtcg ccctgttctt ctatttcaga     360
gcgcaggtga gtggccacct tcccagggga tcgcggctga gagcgcccat ctccttcccc     420
cgcacttgga aactgagtct ggcggcaggg ctgggccacc cagagcttgc atattccgga     480
agggaaagtg actccagaag ggagagagga agtgttgagt ttggggacaa cctggcgcag     540
ggctgtcggg cgcaccctgc tctctctccg cccacgcacc ccagcttctc ggtgctctgg     600
gggcggactc ccctggccgg acgatgggtt tgaatctcac cccgtccctt cgctgggaaa     660
caacactggc ctctcacctt ttctggtagt gattgcatac tttttctccc tgtcatttct     720
cacttgaagt taagaatcaa cttctgttca cgtaggaaaa aagatgagcg ccttcacttg     780
ggcatctacc tttcccttcc cgcccaccac ccggcgggtt tcggttcctg cgcctggctg     840
ctctgcaggt gtgctggggc cacggtgctg gagggctgcg cggagcggga ggtcgcggtg     900
ctcgtgccca ggtcgcccaa tgggtgggca gaatgacacg gcgcgaccag agaggcgcgg     960
gctcgggatg ggggctctgc                                                 980

<210> SEQ ID NO 199
<211> LENGTH: 980
<212> TYPE: DNA
<213> ORGANISM: Homo sapiens

<400> SEQUENCE: 199
ctcgcccgcg cgccccagga cccaaagccg ggctccaagt cggcgcccca cgtcgaggct      60
ccgccgcagc ctccggagtt ggccgcagac aagaagggga gggagcggga gagggaggag     120
agctccgaag cgagagggcc gagcgccatg cgccgcgcca gcagagacta caccaagtac     180
ctgcgtggct cggaggagat gggcggcggc cccggagccc cgcacgaggg cccccctgcac    240 gccccgccgc cgcctgcgcc gcaccagccc cctgccgcct cccgctccat gttcgtggcc     300
ctcctggggc tggggctggg ccaggttgtc tgcagcgtcg ccctgttctt ctatttcaga     360
gcgcaggtga gtggccacct tcccagggga tcgcggctga gagcgcccat ctccttcccc     420
cgcacttgga aactgagtct ggcggcaggg ctgggccacc cagagcttgc atattccgga     480
agggaaagtg actccagaag ggagagagga agtgttgagt ttggggacaa cctggcgcag     540
ggctgtcggg cgcaccctgc tctctctccg cccacgcacc ccagcttctc ggtgctctgg     600
gggcggactc ccctggccgg acgatgggtt tgaatctcac cccgtccctt cgctgggaaa     660
caacactggc ctctcacctt ttctggtagt gattgcatac tttttctccc tgtcatttct     720
cacttgaagt taagaatcaa cttctgttca cgtaggaaaa aagatgagcg ccttcacttg     780
ggcatctacc tttcccttcc cgcccaccac ccggcgggtt tcggttcctg cgcctggctg     840
ctctgcaggt gtgctggggc cacggtgctg gagggctgcg cggagcggga ggtcgcggtg     900
ctcgtgccca ggtcgcccaa tgggtgggca gaatgacacg gcgcgaccag agaggcgcgg     960
gctcgggatg ggggctctgc                                                 980

<210> SEQ ID NO 200
```

<211> LENGTH: 753
<212> TYPE: DNA
<213> ORGANISM: Homo sapiens

<400> SEQUENCE: 200

| | | | | | |
|---|---|---|---|---|---|
| atgaagagga | agaggaggaa | ggcttcttcc | agaaagtgct | cacaccgctt | ctctcttggc | 60 |
| ttttgagcag | gcgactctgg | ctgggtcccc | agtgctcaaa | gctgccactg | ccgtcctgtt | 120 |
| gcaggcagcc | tcccccgcc | gggccgccgg | tggaaggaga | cgggtggctg | aagagtttcc | 180 |
| agcggagtcg | cagaatgtgc | ttcacatcga | agtcttttcg | cccagagcct | gacatgcttt | 240 |
| acgcacagaa | ggcaaaaggc | tggcagctca | cgcaggagta | ggctggtcag | caggtggggg | 300 |
| aggacagcgg | ggcccggggg | cggaggaaga | ggcgggatgc | gccctctgca | ccctagagc | 360 |
| cagaagacgc | taggtgggct | gcgcgctctg | ccaggcgaag | gctggagcgc | agacggcaaa | 420 |
| gccgcgcgtt | tcagccgtgg | tcgggtccgc | aggacctggg | cgtggggaca | ccaccaggca | 480 |
| ggagcagagg | caggactggg | acgccaaaag | ctgagaatcc | tcgatgcccg | cgcgagagcc | 540 |
| ccgtgttatg | gcgaggtggg | acaacccctta | ggctggagat | gcgcgaggga | gggaggtctg | 600 |
| agcgctccga | agctccggag | gcggctgcag | ctggatacac | ctcactggga | tgcgcttgtg | 660 |
| gcagagcctt | agtagggaag | gtggtggcgt | tcttgtcctt | gcagctcaga | gttcagtgtc | 720 |
| tggagagcgc | agagagaaag | agccccaagt | ctc | | | 753 |

<210> SEQ ID NO 201
<211> LENGTH: 910
<212> TYPE: DNA
<213> ORGANISM: Homo sapiens

<400> SEQUENCE: 201

| | | | | | |
|---|---|---|---|---|---|
| gctgccgcac | gtcccactgg | ccgcccggcg | tcccttcct | tcccctgtt | gctgagttgg | 60 |
| tgctcacttt | ctgccaccgc | tatgggactc | cgcgtctccg | tgttgggcgg | cggatgctcc | 120 |
| tgcggcttct | tcggcggggg | aaggtgtgcg | tctccgccgc | tcattgtgt | gcacacgcgg | 180 |
| gagcaccctg | gctcccgcct | cccgctgctc | tcgcgccctt | ctacccctta | gttgatggct | 240 |
| caggcccggc | tggccaggga | gcccgggtca | ctccggggcg | gctgcaaggc | gcagacggag | 300 |
| agccgagccg | ggcgctcact | ccgcgttctg | gttcgggcaa | acttggaaga | actgcgaccg | 360 |
| cagtttgccc | agcgccacag | tctgagtggc | gccttctcca | ctcccgccct | tgcgccggca | 420 |
| ggggcggtgg | agagacgcgg | agggctcccc | cagcccctct | ctcccctatc | cgtccttcgg | 480 |
| gcgacagagc | gcccggcgct | cgggccgggg | gcgggcaagg | ctgggaggga | ccctcgccgg | 540 |
| ggacctggcc | tctggacgcc | ggcgtttcaa | ggctggtttg | gggacttcac | gggctgcctg | 600 |
| tttcagatgt | ggggcgggct | ttcccgttag | ggttcctcag | tgcttcccca | gttgctgttg | 660 |
| gccactcagg | gcccggggac | accctgccac | ccggtctgga | gccggcctcg | tctgccagcg | 720 |
| aacagccaac | tttagcgggt | ggctcagctg | gggattcggg | tccggttcg | ggggcccgt | 780 |
| gtccccgca | tgcccggcca | ctggcattgc | tccaccaaga | gcttgagagc | gcccacccctt | 840 |
| tctctcggcg | ccagtgtgtg | tagcacttgg | tctccgacaa | cttgcgcggc | agtctgggtg | 900 |
| cttgtttcc | | | | | | 910 |

<210> SEQ ID NO 202
<211> LENGTH: 634
<212> TYPE: DNA
<213> ORGANISM: Homo sapiens

<400> SEQUENCE: 202

```
ttgttgccag tatctcaaaa tgttattcag gctcattgct atttcaaaat cccatggtca      60
gagacccatc ctcccgggta tcagaaagca tgggagccct gaccctgacg ccaccaggc      120 tgcaggcaga ggggcatggc ccacttggac ctgagggtgt gtcattcaat ccagcaaaca     180
ttcattgagc acattctctg tgctggccac caggtccaaa gatgaacaag ccgagaccc     240 cgccaggagg aactcaggga atgcgacagg cacagatgag caagacaata gtgacaacgc    300
agcatgattc atgctgagag tgccggggag ggcgggaggc caggcagggt ttctcacggg    360
aagtcacatt tgaactggct ttctcacact tgtgaaagtg cgcccaagga cgcaggactt    420
tcctgaacca gaaaatccc tgctcgcgag tgtgcacatc tccgcttaga gtgcagagga    480
gcaaacagca gaaacttccc ccggctgtgg agccgaaaca ggaaaccacc caggagccct    540
gtgcagaagc ggccggggat tcccagttcc ccaggaccca gtgggcgttt tcacaggaag    600
cctctctggg tgaagcccct gctgtacccg tccc                                634

<210> SEQ ID NO 203
<211> LENGTH: 791
<212> TYPE: DNA
<213> ORGANISM: Homo sapiens

<400> SEQUENCE: 203
ccctgccttc ggagtttcct gctattgacc tggcggggcg cgccagccct ccctgcccgc     60
tggtgccgcg gtccctctcg gctgcagcag tggggcacag ggacgtcatg gacaaaagac    120
gaggatgcca gttcgatgtg cgagcagaag gccgcctgcg tgcgctctgc agagcaaccg    180
gcccggtttc ataaggggcc gccggcaggg gactgccatg gcgccccctc ctacccttt     240 tggcaccagc agcttcatcc gcaggcccac tcggggtgaa tagtgtggga gctctcaaga    300
gaaagaattt taggtttgtc gatagtaatc accaccttca gcgctcctcc cactgctgga    360
gagaccgcgg actgggtgac aagtcttcca ggctcccaga agtttctgc tgcaaagcgc     420 agggtccgcc tcccacttcc aggagggacc aggagggaac catcgcgaaa ccccgaggct    480
gccggggact ctgactgagg cctttcctcc tgtgtccctc tccccacgc cggcctcccc      540 tccttcaac tctctgcgct ttgaaaccgc ggagttgggg tagctaggcc ctccagcccg      600
gcgacaggcc tcggccacag gcagcggggc ggggtgtgga caggaacaag gaggtggggt    660
ggggaggaag cctcgggcag agcaggttct ctgcggagtt tcggcagccg ggtttatcca    720
ttttgattaa agaaaagtaa aaaaaatccc ccaaaaccaa acaacaaaaa ccctctccca    780
acccccaacc c                                                          791

<210> SEQ ID NO 204
<211> LENGTH: 658
<212> TYPE: DNA
<213> ORGANISM: Homo sapiens

<400> SEQUENCE: 204
gctgggaaaa cagtcctgcg ggatgaagac ttcaccgcct ccgatttgaa tttgaaagta     60
actccttccg tggcatattt cgctgggcag atagaacaaa ccatgtcgtt ttccccgtc    120 tctaaaatag acatattatt atcattcaca cttttgcacc cggtcgtttt gcgggagttc    180
gggaaactga ctttcttcat tggggacatt gtaattttct gatgatgcca cgaggagaaa    240
aaaaatacgg gtttgtttta attggaagga ccttccgctt ttatgatttc ggtttacctt    300
ggaaaactga atcttctgtg ttttatttct ttcctctagt actagaaaag caatgaatta    360
```

| | |
|---|---:|
| attgcacaaa acaggttctg agacggcccg caggccccga gctcgtggac gcggccgagg | 420 |
| gtcgggtgtg acccgcggag ccgctgccag gcttcccagc tcgtcttcgc ggggaggcgg | 480 |
| gaggcaggac cagaccccag catttcagcg tgaaagtctt cgcctttctt tccgcgctgt | 540 |
| ctttcccgcg gcggagcgg cgtacctgag cgcggtcccc acggaggatc agtgactttc | 600 |
| ccagaccccg cgggcgagcc cgcgcttggg acccggcagc tctgcgcggg ctggttttt | 658 |

<210> SEQ ID NO 205
<211> LENGTH: 696
<212> TYPE: DNA
<213> ORGANISM: Homo sapiens

<400> SEQUENCE: 205

| | |
|---|---:|
| agagcctcct gggaagtttc ttcctggaaa aatcattaag gcggactgat cccgattaga | 60 |
| gagaaaaggg gctcctggga aaacgtgctc cccaccggcc atcaggcggc ccgcaggagc | 120 |
| caagccaagg ctcccgcctc gggccacccc gacgctgctg cccccgcaga gccccgagcg | 180 |
| cccccggccc gagcgtggga cccggcggct acctcctggc cgcagcagcg ccgataaatc | 240 |
| tgccaagtga ttactgaacg taaactccag ttacttaagt gtcctccgag gggtaatcgt | 300 |
| atctgtccct ataaatcccg actgcgttcg cgctcatcag cgcttccgcc cgacgcgctg | 360 |
| gtccgctcaa agggggcaca cgacccacag gagccatcca ccgcctcgcg ccgcagccgc | 420 |
| cctcctcagc gctgtgggat ccccagaggc agggcttgag gtggggtggg agggtcccca | 480 |
| cgacgccggt ggctccccac caattccacg acagggtagg cctcaccgat ggtgggaggc | 540 |
| tcgggtcctc ctacaactag aaccttctct agaaaggcag atgtcaactc cagcaccctc | 600 |
| cagggcgagt gtgatactgc gtgtgagagg gcgcgtgggg cgtgtaaatg atgtgagtgt | 660 |
| gaggacacac aggtgtcgcg ggaatggggt gcacgc | 696 |

<210> SEQ ID NO 206
<211> LENGTH: 361
<212> TYPE: DNA
<213> ORGANISM: Homo sapiens

<400> SEQUENCE: 206

| | |
|---|---:|
| agactcaggg ggaacaggtt tcccagagcc cagcctgcag ggacgcggag ggcaggagcc | 60 |
| gccggcgagg agcagccaac ttgccatctc tggcggctgc acttctcggc ggctacaggt | 120 |
| tgcccgacag cggactccag ggtccccgcg acggcaccca gagtgctcag aagggaggcc | 180 |
| ggggccgggg tgggccggga aaaccgaggg agggaaggag cctggagaag ctccgtttag | 240 |
| gcggggaggg ggcgacccgg ggcgcatctc ccgaccatga cccccacaga ccttggcgcc | 300 |
| gcaacctgcg cttcttgagg ccgaagatgc gcactttgga aagatatcc accaggttgc | 360 |
| c | 361 |

<210> SEQ ID NO 207
<211> LENGTH: 646
<212> TYPE: DNA
<213> ORGANISM: Homo sapiens

<400> SEQUENCE: 207

| | |
|---|---:|
| aaactggcca tttcgaggga cgcggaagcc ccgttgctag gggagatggg ggaagcggcg | 60 |
| tggtcaccta cacaaccgct cccaggcgcg atgggggctc tgcttcctcc tcctctgttt | 120 |
| cttgggggat ggaaaagaga gcagaacaaa gatgtagagt gaaggaggc tcccagctg | 180 |
| ttgcctcttg cgcggattct gctgacccct ctgcgcgacc ccagctgggc agtgtcagct | 240 |

```
ccattgtctc agaggccggc ggccaagtga gggaccagtc tcacccgggg ggcgtcgagc      300
ctcagcgcat cgccccgtct tccctggctg cagaaaacca ctaggccggt ggaagtgctc      360
cgtttaattg gtccctagta cgcccccgaa aggaaatgga gacgatttcc gtcaagttct      420
cttagtattt ctgtcattta cagaaaagca gtagctactc acatgtggct cagatgtctg      480
tgtgggggtt gtgagccagg gcattaaaat tgggtgttaa ccgtttgcca ctcagaagaa      540
ttattagcca ttggaggagg agcggtttct cttgctaagc ggggttaagt gaaacttggc      600
tgctctgaat tggccagagg agtaaatgag cagagggctg acctgc                    646

<210> SEQ ID NO 208
<211> LENGTH: 646
<212> TYPE: DNA
<213> ORGANISM: Homo sapiens

<400> SEQUENCE: 208
aaactggcca tttcgaggga cgcggaagcc ccgttgctag gggagatggg ggaagcggcg       60
tggtcaccta cacaaccgct cccaggcgcg atggggctc tgcttcctcc tcctctgttt      120
ctttggggat ggaaaagaga gcagaacaaa gatgtagagt gaaggagggc tcccagctg      180 ttgcctcttg cgcggattct gctgacccct ctgcgcgacc ccagctgggc agtgtcagct      240
ccattgtctc agaggccggc ggccaagtga gggaccagtc tcacccgggg ggcgtcgagc      300
ctcagcgcat cgccccgtct tccctggctg cagaaaacca ctaggccggt ggaagtgctc      360
cgtttaattg gtccctagta cgcccccgaa aggaaatgga gacgatttcc gtcaagttct      420
cttagtattt ctgtcattta cagaaaagca gtagctactc acatgtggct cagatgtctg      480
tgtgggggtt gtgagccagg gcattaaaat tgggtgttaa ccgtttgcca ctcagaagaa      540
ttattagcca ttggaggagg agcggtttct cttgctaagc ggggttaagt gaaacttggc      600
tgctctgaat tggccagagg agtaaatgag cagagggctg acctgc                    646

<210> SEQ ID NO 209
<211> LENGTH: 3929
<212> TYPE: DNA
<213> ORGANISM: Homo sapiens

<400> SEQUENCE: 209
gagttagaca tcatcaagag gtgaaaattt gggaagacat ttcaaggatg acggaagctc       60
tgagtgagtg aacagatatt cttcgtgcag aataatcccc cgtggcactg gtttgccggc      120
agagcagaat gtttgagacc tcaccccgca gccacgcgcg ggcgtaaatc gttctcagca      180
cgagaaacac aaaggccgca ggatcccgcg agccgcaggg ggttgggtc attttttga      240 tgccgccgcc cttaagagtt ccagtccttc aggcgaaagg ggcagatcag gccttcgggg      300
aggacccttg cctgggagag ggagggcagt gccccagggg ccgcctccgg tgcctaaaca      360
aagaagacgg tcttctgagc gtccgccctc cccgcctcgc cgcgcaagga ccccgcgctc      420
ctgggccact tcctcttgca aaccacgagg aaaagccagt ttccacccag acggccggct      480
gtgggcaaag ggaataaagc gccggtgccg ccacgctctg cacttggctc tgggcctggc      540
gggggtctgg cgcggccgca gacacctggg tgacctgggc cgtggttgcc ggctctgctc      600
ggacagagag tctttttatt tgtcgcctcc gccttctcac cactgaggcc gcaggacagc      660
ctcgctgccc ggggccgagt tcggtggaca agggggcagc gcccacagca agccggaaag      720
agggaggcgc gggccgcgc ttggggcctg ccgctgcacg ccagcctggg caaagagctg      780
```

```
ccaccttctg cgggcgaagc gggtcgggac gcaggacggc agcggggctg gaggcagcta    840
cgtgggtcca caccccatg ccctgcaagg ctccttggcc ctgcttctcc tctgtctcgg     900
cgggagagga gcagcctcgg ttttacagaa tttcagggtc gcgtctccag cgccccgggc    960
gaggccacta cgtttaggag cgctcgcctt cgctgcgctg tgtaccgtgt acacactggc    1020
tccgtgcgcg agacccgat gtgggttaaa actccacttc acaaccccca ttgatacggg    1080
tttgacatct gtttgccaga gtgttttgca cttagcctaa cacccgctat taagtgacaa    1140
aattgtggca gcctgtcaaa gccagctgac tggcagctgc tccgcttaca aaaaccattc    1200
aaatatttgc aggttttgaa ggtttatgca gtgttgtacc caatctttca gcgacttaac    1260
atgtaaaata taagtcaaag ttttaaatct ggattccaaa atgtttccat tttccataca    1320
aaaggaaaaa gctttcaagg agcctgctgg aatgggtcca attccaacgt gtctccgcgt    1380
ttcccgccac gaaattcctg cacaaacccg gttttttaaa gatgtcaagg accaacttcc    1440
tcttgttacc agcatcttgg aggactgaac taaattgcct taaactccaa gggaatacag    1500
tttctcaaaa gtaaattttt taaaaatccc caagtaaaga aacgtacctg cttaattttg    1560
cttttgacac ttagaccaac gtgcctttgg gggaaagcga ggctgctagg aagagtgttc    1620
ctagtcaaca tctgagctct gcggcttcc aaaacactca ctcctccact cgcacttcta    1680
aatagcttag tccgattaag aaataatttg caaatgacat agtgtttctc tagattaaga    1740
tccatcgagt gaagtcatgt gggttttttg tctccgagat tagagccaga cagacaagga    1800
tctcctgcaa actgcagctg ccgacaatgg aaaaaaaatt accctgcgtt tgtccggggg    1860
agatgtgtgc gtgggtccgc gcgccccgca ccgacactga ggctggcac gcccttactg     1920 tctttcgatt gtgctggact tgtgcgtcct tttttttttt tttatgttgg taaacatatt    1980
gccttgggtg tgagggggtc acaaatcctc tgggcaaacg tggggtcgtc attttcaaaa    2040
aagcagtgag tttgcttgtg atacatttgc agggagtctc aagggtggtg gtcttaagtc    2100
cgaagtgctg acagcctcac tcaactgtgg ggaggaggca gagagggagg gtggagacag    2160
agacccagac cccgagaaac aagtgtggct ccagcccagg agcctcacag aacacatttc    2220
ctcctccgcc ttcggctctg cgtgggctag ccccgcgcta ggagggcag gcaactaggt    2280 cctccgaggt gaggctgggg ctccgcctgc agagggagtg acagcgcgcc gcgagggtcc    2340 gcgaccagg caggggtggc cgcaccaccc cggagcgccg cacagccccg caggcctccc    2400
ctcccgcagt gcgtgcctgg aacgcggggc cgcctggccg agggacgttt acctggagag    2460
ctttgtgtcc acaacactaa tccttagaca ctgcttcgtt cagcagctgc cgtcagtcgt    2520
gagggcacta gtgtggggat gggggcgaat tcaggagccc gtcgcagagc aatatttaaa    2580
aagggggggg ggagcggag ctgctcccag gggaggcctc gcgcggcggc gcccacggcc    2640
acggtgtccc cgctgcgagc caacaaagct gaggcgctgt ccgcgggagg agagagccca    2700
gcgcggggac cggcgcgggt gggagtgggg gcgcggcgcg gaaaaccccca gggaaggacc    2760 gggtggacac gggacgggag gggggtgaca tcctcccacc cggggttag aaaaggtccg    2820 ggtggtagtt ccaggcgaaa ataggcagcc ctctgtgatg acagaattga caactatttt    2880
ttgggggggc ggggttgga cttccgagtc cctcggacg gaggcgcagg ggagcaggag    2940
gggtgccccg tccctgcagt tgcctcggcc cgaatcccgc aggccaggcc ggaacgcggg    3000
ggcgggggcg cggagggggg acccgcggcg ggaggcgaga gcgagcgaat gggagagga    3060 gcggggagca ggagggacg cagggagag gggactgggg agcggcgaga ggaggacggg    3120
agacgcggct ccacctccca gctcaaaacg gcgtcccagc tgctcgcaaa ccaactgctc    3180
```

```
gattctattc actgtcgagt aggaacaaaa aagtggctat ttattagaat acttgtttgg    3240
tattgttccg cgccacacaa aaggcgtttc attatgtgga gggatctcct ttttccagag    3300
agaaacaata acttgaaatt gtctttaaag tcttttctat caataataaa tttcattttc    3360
ttgtctctct cgcctgcagt gtgtgtgcgc gcgcgcgagg cgaggagaga ggcgcgtgtg    3420
cgagtgagtg tgctagcggg ggtgcgcgtg tgagtgtgcg cgtgtgtgtg cgtgcgcgtg    3480
gcaccggcgc ccgcggctac ggggctgcgc ctgccggagc cgggccggac cggggtccga    3540
gatctgcgtc gcgctgggca cgctggccac ccggtccgga atgagtcggg gctccgggag    3600
gtgcccgtgg gcagagcgtt aggggcgcgg ccgtgccgga cccgccctgg ggacccgctg    3660
gagctggagg aggaactaac tgtaagtgtg tctcgaactt gcgcggggc ttcagcccgc    3720 ccggggctgc ggagctggcc ggtaaaggct ctcgggagag gggcgcggtg tctccacggt    3780
gactttccgt gaaggaggat ggggtgtctc cgcagctttg gggccccagg aaagaacagg    3840
tgggtagatg tggtggccac ggctagcgga ctcgccgcgg ggcacatttg tcattttctt    3900
atctgtgcgt tcactcctcc cccatcctc                                    3929
```

<210> SEQ ID NO 210
<211> LENGTH: 3929
<212> TYPE: DNA
<213> ORGANISM: Homo sapiens

<400> SEQUENCE: 210

```
gagttagaca tcatcaagag gtgaaaattt gggaagacat ttcaaggatg acggaagctc      60
tgagtgagtg aacagatatt cttcgtgcag aataatcccc cgtggcactg gtttgccggc     120
agagcagaat gtttgagacc tcaccccgca gccacgcgcg ggcgtaaatc gttctcagca     180
cgagaaacac aaaggccgca ggatcccgcg agccgcaggg ggttggggtc attttttga     240 tgccgccgcc cttaagagtt ccagtccttc aggcgaaagg ggcagatcag gccttcgggg     300
aggacccttg cctgggagag ggagggcagt gccccagggg ccgcctccgg tgcctaaaca     360
aagaagacgg tcttctgagc gtccgcccct cccgcctcgc cgcgcaagga ccccgcgctc     420
ctgggccact tcctcttgca aaccacgagg aaaagccagt ttccacccag acggccggct     480
gtgggcaaag ggaataaagc gccggtgccg ccacgctctg cacttggctc tgggcctggc     540 ggggggtctgg cgcggccgca gacacctggg tgacctgggc cgtggttgcc ggctctgctc     600
ggacagagag tcttttttatt tgtcgcctcc gccttctcac cactgaggcc gcaggacagc     660
ctcgctgccc ggggccgagt tcggtggaca aggggggcagc gcccacagca agccggaaag     720
agggaggcgc ggggccgcgc ttggggcctg ccgctgcacg ccagcctggg caaagagctg     780
ccaccttctg cgggcgaagc gggtcgggac gcaggacggc agcggggctg gaggcagcta     840
cgtgggtcca caccccatg ccctgcaagg ctccttggcc ctgcttctcc tctgtctcgg     900
cgggagagga gcagcctcgg ttttacagaa tttcagggtc gcgtctccag cgccccgggc     960
gaggccacta cgtttaggag cgctcgcctt cgctgcgctg tgtaccgtgt acacactggc    1020
tccgtgcgcg agaccccgat gtgggttaaa actccacttc acaacccca ttgatacggg    1080 tttgacatct gtttgccaga gtgttttgca cttagcctaa cacccgctat taagtgacaa    1140
aattgtggca gcctgtcaaa gccagctgac tggcagctgc tccgcttaca aaaaccattc    1200
aaatatttgc aggttttgaa ggtttatgca gtgttgtacc caatctttca gcgacttaac    1260
atgtaaaata taagtcaaag ttttaaatct ggattccaaa atgtttccat tttccataca    1320
```

-continued

```
aaaggaaaaa gctttcaagg agcctgctgg aatgggtcca attccaacgt gtctccgcgt    1380
ttcccgccac gaaattcctg cacaaacccg gttttttaaa gatgtcaagg accaacttcc    1440
tcttgttacc agcatcttgg aggactgaac taaattgcct taaactccaa gggaatacag    1500
tttctcaaaa gtaaatttt taaaaatccc caagtaaaga aacgtacctg cttaattttg    1560
cttttgacac ttagaccaac gtgcctttgg gggaaagcga ggctgctagg aagagtgttc    1620
ctagtcaaca tctgagctct gcggcttcc aaaacactca ctcctccact cgcacttcta    1680
aatagcttag tccgattaag aaataatttg caaatgacat agtgtttctc tagattaaga    1740
tccatcgagt gaagtcatgt gggttttg tctccgagat tagagccaga cagacaagga    1800
tctcctgcaa actgcagctg ccgacaatgg aaaaaaaatt accctgcgtt tgtccggggg    1860
agatgtgtgc gtgggtccgc gcgccccgca ccgacactga gggctggcac gcccttactg    1920
tctttcgatt gtgctggact tgtgcgtcct tttttttttt tttatgttgg taaacatatt    1980
gccttgggtg tgagggggtc acaaatcctc tgggcaaacg tggggtcgtc attttcaaaa    2040
aagcagtgag tttgcttgtg atacatttgc agggagtctc aagggtggtg gtcttaagtc    2100
cgaagtgctg acagcctcac tcaactgtgg ggaggaggca gagagggagg gtggagacag    2160
agacccagac cccgagaaac aagtgtggct ccagcccagg agcctcacag aacacatttc    2220
ctcctccgcc ttcggctctg cgtgggctag ccccgcgcta gggagggcag gcaactaggt    2280
cctccgaggt gaggctgggg ctccgcctgc agagggagtg acagcgcgcc gcgagggtcc    2340
gcgacccagg caggggtggc cgcaccaccc cggagcgccg cacagccccg caggcctccc    2400
ctcccgcagt gcgtgcctgg aacgcggggc cgcctggccg agggacgttt acctggagag    2460
ctttgtgtcc acaacactaa tccttagaca ctgcttcgtt cagcagctgc cgtcagtcgt    2520
gagggcacta gtgtggggat gggggcgaat tcaggagccc gtcgcagagc aatatttaaa    2580 aaggggggg ggagccggag ctgctcccag gggaggcctc gcgcggcggc gcccacggcc    2640
acggtgtccc cgctgcgagc caacaaagct gaggcgctgt ccgcgggagg agagagccca    2700
gcgcggggac cggcgcgggt gggagtgggg gcgcggcgcg gaaaacccca gggaaggacc    2760
gggtggacac gggacgggag gggggtgaca tcctcccacc cggggttag aaaaggtccg    2820 ggtggtagtt ccaggcgaaa ataggcagcc ctctgtgatg acagaattga caactatttt    2880 ttggggggc ggggttgga cttccgagtc cctcggacg gaggcgcagg ggagcaggag    2940
gggtgccccg tccctgcagt tgcctcggcc cgaatcccgc aggccaggcc ggaacgcggg    3000 ggcggggcg cggagggg acccgcgcg gaggcgaga gcgagcgaat ggggagagga    3060
gcggggagca ggaggggacg caggggagag gggactgggg agcggcgaga ggaggacggg    3120
agacgcggct ccacctccca gctcaaaacg gcgtcccagc tgctcgcaaa ccaactgctc    3180
gattctattc actgtcgagt aggaacaaaa aagtggctat ttattagaat acttgtttgg    3240
tattgttccg cgccacacaa aaggcgtttc attatgtgga gggatctcct tttttccagag    3300 agaaacaata acttgaaatt gtcttttaaag tcttttctat caataataaa tttcatttc    3360 ttgtctctct cgcctgcagt gtgtgtgcgc gcgcgcgagg cgaggagaga ggcgcgtgtg    3420
cgagtgagtg tgctagcggg ggtgcgcgtg tgagtgtgcg cgtgtgtgtg cgtgcgcgtg    3480
gcaccggcgc ccgcggctac ggggctggcg ctgccggagc cgggccggac cggggtccga    3540
gatctgcgtc gcgctgggca cgctggccac ccggtccgga atgagtcggg gctccgggag    3600
gtgcccgtgg gcagagcgtt agggcgcgg ccgtgccgga cccgccctgg ggacccgctg    3660
gagctggagg aggaactaac tgtaagtgtg tctcgaactt gcgcggggc ttcagcccgc    3720
```

```
ccggggctgc ggagctggcc ggtaaaggct ctcgggagag gggcgcggtg tctccacggt    3780
gactttccgt gaaggaggat ggggtgtctc cgcagctttg ggccccagg aaagaacagg     3840 tgggtagatg tggtggccac ggctagcgga ctcgccgcgg ggcacatttg tcattttctt    3900
atctgtgcgt tcactcctcc cccatcctc                                     3929

<210> SEQ ID NO 211
<211> LENGTH: 3929
<212> TYPE: DNA
<213> ORGANISM: Homo sapiens

<400> SEQUENCE: 211
gagttagaca tcatcaagag gtgaaaattt gggaagacat ttcaaggatg acggaagctc      60
tgagtgagtg aacagatatt cttcgtgcag aataatcccc cgtggcactg gtttgccggc    120
agagcagaat gtttgagacc tcaccccgca gccacgcgcg ggcgtaaatc gttctcagca    180
cgagaaacac aaaggccgca ggatcccgcg agccgcaggg ggttgggtc attttttga     240 tgccgccgcc cttaagagtt ccagtccttc aggcgaaagg ggcagatcag gccttcgggg   300
aggacccttg cctgggagag ggagggcagt gccccagggg ccgcctccgg tgcctaaaca    360
aagaagacgg tcttctgagc gtccgccctc cccgcctcgc cgcgcaagga ccccgcgctc    420
ctgggccact tcctcttgca aaccacgagg aaaagccagt ttccacccag acggccggct    480
gtgggcaaag ggaataaagc gccggtgccg ccacgctctg cacttggctc tgggcctggc    540
gggggtctgg cgcggccgca gacacctggg tgacctgggc cgtggttgcc ggctctgctc    600
ggacagagag tctttttatt tgtcgcctcc gccttctcac cactgaggcc gcaggacagc    660
ctcgctgccc ggggccgagt tcggtggaca aggggcagc gcccacagca agccggaaag    720
agggaggcgc ggggccgcgc ttggggcctg ccgctgcacg ccagcctggg caaagagctg    780
ccaccttctg cgggcgaagc gggtcgggac gcaggacggc agcggggctg gaggcagcta    840
cgtgggtcca caccccatg ccctgcaagg ctccttggcc ctgcttctcc tctgtctcgg     900
cgggagagga gcagcctcgg ttttacagaa tttcagggtc gcgtctccag cgccccgggc    960
gaggccacta cgtttaggag cgctcgcctt cgctgcgctg tgtaccgtgt acacactggc    1020
tccgtgcgcg agaccccgat gtgggttaaa actccacttc acaaccccca ttgatacggg    1080
tttgacatct gtttgccaga gtgttttgca cttagcctaa cacccgctat taagtgacaa    1140
aattgtggca gcctgtcaaa gccagctgac tggcagctgc tccgcttaca aaaaccattc    1200
aaatatttgc aggttttgaa ggtttatgca gtgttgtacc caatcttttca gcgacttaac    1260 atgtaaaata taagtcaaag ttttaaatct ggattccaaa atgtttccat tttccataca    1320
aaaggaaaaa gctttcaagg agcctgctgg aatgggtcca attccaacgt gtctccgcgt    1380
ttcccgccac gaaattcctg cacaaacccg ttttttaaa gatgtcaagg accaacttcc     1440
tcttgttacc agcatcttgg aggactgaac taaattgcct taaactccaa gggaatacag    1500
tttctcaaaa gtaaattttt taaaaatccc caagtaaaga aacgtacctg cttaattttg    1560
cttttgacac ttagaccaac gtgcctttgg gggaaagcga ggctgctagg aagagtgttc    1620
ctagtcaaca tctgagctct ggcggcttcc aaaaacactca ctcctccact cgcacttcta    1680
aatagcttag tccgattaag aaataatttg caaatgacat agtgtttctc tagattaaga    1740
tccatcgagt gaagtcatgt gggttttt tctccgagat tagagccaga cagacaagga     1800
tctcctgcaa actgcagctg ccgacaatgg aaaaaaaatt accctgcgtt tgtccggggg    1860
```

| | |
|---|---|
| agatgtgtgc gtgggtccgc gcgccccgca ccgacactga gggctggcac gcccttactg | 1920 |
| tctttcgatt gtgctggact tgtgcgtcct tttttttttt tttatgttgg taaacatatt | 1980 |
| gccttgggtg tgagggggtc acaaatcctc tgggcaaacg tggggtcgtc attttcaaaa | 2040 |
| aagcagtgag tttgcttgtg atacatttgc agggagtctc aagggtggtg gtcttaagtc | 2100 |
| cgaagtgctg acagcctcac tcaactgtgg ggaggaggca gagagggagg gtggagacag | 2160 |
| agacccagac cccgagaaac aagtgtggct ccagcccagg agcctcacag aacacatttc | 2220 |
| ctcctccgcc ttcggctctg cgtgggctag ccccgcgcta ggaggggcag gcaactaggt | 2280 |
| cctccgaggt gaggctgggg ctccgcctgc agagggagtg acagcgcgcc gcagggtcc | 2340 |
| gcgacccagg caggggtggc cgcaccaccc cggagcgccg cacagccccg caggcctccc | 2400 |
| ctcccgcagt gcgtgcctgg aacgcggggc cgcctggccg agggacgttt acctggagag | 2460 |
| ctttgtgtcc acaacactaa tccttagaca ctgcttcgtt cagcagctgc cgtcagtcgt | 2520 |
| gagggcacta gtgtggggat gggggcgaat tcaggagccc gtcgcagagc aatatttaaa | 2580 |
| aaggggggg ggagccggag ctgctcccag gggaggcctc gcgcggcggc gcccacggcc | 2640 |
| acggtgtccc cgctgcgagc caacaaagct gaggcgctgt ccgcgggagg agagagccca | 2700 |
| gcgcggggac cggcgcgggt gggagtgggg gcgcggcgcg gaaaaccccca gggaaggacc | 2760 |
| gggtggacac gggacgggag gggggtgaca tcctcccacc cgggggttag aaaaggtccg | 2820 |
| ggtggtagtt ccaggcgaaa ataggcagcc ctctgtgatg acagaattga caactatttt | 2880 |
| ttggggggc gggggttgga cttccgagtc cctcgggacg gaggcgcagg ggagcaggag | 2940 |
| gggtgccccg tccctgcagt tgcctcggcc cgaatcccgc aggccaggcc ggaacgcggg | 3000 |
| ggcggggggcg cgggagggg acccgcggcg ggaggcgaga gcgagcgaat ggggagagga | 3060 |
| gcggggagca ggaggggacg caggggagag gggactgggg agcggcgaga ggaggacggg | 3120 |
| agacgcggct ccacctccca gctcaaaacg gcgtcccagc tgctcgcaaa ccaactgctc | 3180 |
| gattctattc actgtcgagt aggaacaaaa aagtggctat ttattagaat acttgtttgg | 3240 |
| tattgttccg cgccacacaa aaggcgtttc attatgtgga gggatctcct ttttccagag | 3300 |
| agaaacaata acttgaaatt gtctttaaag tcttttctat caataataaa tttcattttc | 3360 |
| ttgtctctct cgcctgcagt gtgtgtgcgc gcgcgcgagg cgaggagaga ggcgcgtgtg | 3420 |
| cgagtgagtg tgctagcggg ggtgcgcgtg tgagtgtgcg cgtgtgtgtg cgtgcgcgtg | 3480 |
| gcaccggcgc ccgcggctac ggggctggcg ctgccggagc cgggccggac cggggtccga | 3540 |
| gatctgcgtc gcgctgggca cgctggccac ccggtccgga atgagtcggg gctccgggag | 3600 |
| gtgcccgtgg gcagagcgtt aggggcgcgg ccgtgccgga cccgccctgg ggacccgctg | 3660 |
| gagctggagg aggaactaac tgtaagtgtg tctcgaactt gcgcggggc ttcagcccgc | 3720 |
| ccggggctgc ggagctggcc ggtaaaggct ctcgggagag gggcgcggtg tctccacggt | 3780 |
| gactttccgt gaaggaggat ggggtgtctc cgcagctttg gggccccagg aaagaacagg | 3840 |
| tgggtagatg tggtggccac ggctagcgga ctcgccgcgg ggcacatttg tcattttctt | 3900 |
| atctgtgcgt tcactcctcc cccatcctc | 3929 |

<210> SEQ ID NO 212
<211> LENGTH: 1177
<212> TYPE: DNA
<213> ORGANISM: Homo sapiens

<400> SEQUENCE: 212

| | |
|---|---|
| gaagacttag cttaggcgac ttctctaaag aactcaacca aatctgaaag gcacaggcat | 60 |

```
tttctcctca aaatccgagg ctcgagaacc atctcctctg gcagggtcca gtctcagctc    120
cgcctcttgc ctcctcaccc acttgggcat aacttttgcg ggtcctagaa atctgggcag    180
cagaagaggg aggggaacgc tcccagccgg cagccgctct gggcgtgcac ccgccacgcg    240
aagccagagg ttggacgacg cagccggcca ggcgcggctc ccgggggacc ccgaaaccgc    300
ctgtggctca ggccctactt ggcaagaaga gactggggag tgagaggagg ggtcactctt    360
gctctctcgc acaatagact tcccgcaggc gagtgcgaac ggccttttgc ttcctccttc    420
ttttccagga cccttagcga caggagagga agagaagcgg cccggcggtt taattgccaa    480
tttcctgatg cagccacagg gcccagcagc ggctcagcct aggccaccgg gtccaggcct    540
ctaggcaata ggcccggcgc ccctccaag caccgtttcc cgccgacccc gcagtcatca    600
ctgtgagctc gagagtatgg gcagcctgtg gtgccctgag gcgccgggcg ctcggcgcat    660
ccgccgtgcc cacagcgctg aggaccaact agggctgccc tcggccaggg gcactgtgcc    720
cgtttgagtg gcactcggac ctggcgaggg gtggaagccc aggtagagct cgcgtcttta    780
agagccaccc gacagaactg cgcgctacat ctgcgccagc tgggctgggt gggaacagcg    840
cagaaatact cccgtgccgg ggcgtacagg gcaggtaggc ccagcagaga gtcttctcgg    900
aaagtttccc acaaaagaag ggccgggcag gccgagcggc aggaaaagcc ggtgctcagc    960
ggcgaggccc gagaggtctg gcatccggcg gcctcccagc tttgctcggg tctcccgccg   1020
cctctctcca gagccgcccg tagctccgtg gggcggaggg cgcaatgccc cgctctggtt   1080 ccagccttt tcctccccctt gtctcctctt tcattcataa acctggtggc tacagacgca   1140
gcttgaatat tgacgtctct cccccaactg ctctgcc                            1177

<210> SEQ ID NO 213
<211> LENGTH: 1263
<212> TYPE: DNA
<213> ORGANISM: Homo sapiens

<400> SEQUENCE: 213
gcgacccacg agctcgcggc ccgcgcccgg ctcccgcccc gccccggcgc ggcgtggctt     60
ttgtacagac gttcccacat tcttgtcaaa aggaaaatac tggagacgaa cgccgggtga    120
cgcgtgtccc ccactcacct tccccggaga ccctggcgac cgccgggcgc tgacaccaga    180
cttgggtttt agactgaact tcggtgtttt cttgagactt tttgtacagt atttatcacc    240
tacggaggaa gcggaaagcg ttttctttgc tcgagggac aaaaaagtca aaacgaggcg    300
agaggcgaag cccactttg tataccggcc ggcgcgctca ctttcctccg cgttgcttcc    360
ggacggcgcc gaccgccgga gcccaagtga cgcggagctc gtcgcatttg ttataaatgt    420
agtaaggcag gtccaagcac ttacaagttt tttgtagttg ttaccgctct tttgggttgg    480
tttgttaatt tatacaaaga gattaccacc accaccccct ccttcagacg gcggagttat    540
attctgggtt ttgtaaaact ttatgtatct gagcatttcc atttttttttt ttgggttttg    600 tattatttct tgtaaatgca ttgtgaaaaa tttattttc ggcgttgcaa tgcggggagg    660
agaagtcaga ttatgtacat agttttctaa aaagcctttc ttctaaaaac gaaaaaagac    720
cccccaccca aaatgtttcg agtcaacaaa tttaagagac agagcccatt ttctccataa    780
atttgtaaca tgctattttt atgtgcatgt tttatgagtt caaaatgcaa tgaggaaatc    840
tgacagggaa attatctgta tgaactaaaa gtaagggaac cccggggaat gggaggacag    900 gattttcaa ggaaccttt tcaatgaaag agaaggaagt taaaacctat aggttatttt      960
```

| | |
|---|---:|
| gtagagctga gtgttaatac gggccgagaa ataaaagtat cttctgctcc ggctgtttca | 1020 |
| ctgcggacgg ctgggctgc tgcgcgttac cttgctgcaa gcggggcgcc ttccacctgg | 1080 |
| ctggggtct gcgccacagt ttggtccaga ggagggagga ggaagggaag accccagtgg | 1140 |
| tgggaccctg gaccaggcca tgatgaagg acaaagacca gggcaggtca cgggtttccc | 1200 |
| aattccccag caattaagat ttcgagcaga atttatctaa atgtgtttca aggaaacaca | 1260 |
| atc | 1263 |

<210> SEQ ID NO 214
<211> LENGTH: 3488
<212> TYPE: DNA
<213> ORGANISM: Homo sapiens

<400> SEQUENCE: 214

| | |
|---|---:|
| aggcgtgcag ccaagcctgc ttagacctcc ccaggccacg ggcccgcggc agcccagctc | 60 |
| agcacctgca ggcgggggga ccgcgcgctt ggctcgaaga ccccgccctg ggcaggggac | 120 |
| agaaaatatg aaatcagatg gggagttatg aataactgtc ctcccctccc ctctgccgtg | 180 |
| tttcctgaat ccgtacgcta tgcaggaggg gggcggggc gggggcgcgg ggaggaggag | 240 |
| ggggccgttt gccattaatc tgggaacaag cggctaacct cggtgactgg tattttcgct | 300 |
| tttcttttct cacttttctc agtgtgggga aagcagtcaa gcccgcgcgg agcgattgtg | 360 |
| aggggctctg ctggaatttg gcagcgcgga ggcttggaga gaagcccat gctggctccc | 420 |
| attcagccgg cccgttttcc tcgagctttg gaagtttcac tcagccgtgc actcaatggc | 480 |
| ttcacaaagc tgattacaag cttcagcgca ttcctgaagg agccaaaagc gacgcaggtg | 540 |
| caaacgagcc gagggagccc cttatcccgg tgacagaatg ggacaagctg ggaaaggctt | 600 |
| agaccacaca agtccaaggc tcaccaggcc gcagaaagcc tgccttggga accggggtc | 660 |
| attatccgcc ctattcagcg gggcccgggg accctggggg ccgagcgagg ccagcccggg | 720 |
| cgggagcacc gccgccagcg cgcgccgscg acagggggga accccgctgg gcgctgcggc | 780 |
| caggccgggg ctcagggcgc tgggctgtgc gtttgcacaa atctgtgttc cggcgggccg | 840 |
| gtgtcaaccc tagtggggac acgggagaaa gagcacgcca gtaggccacg cggcgcgtgg | 900 |
| gcagtgcgca acttctgtcg gcgtccaggc tgtacggcca cgtttcagcc ggtgccccca | 960 |
| ggccatggac acccagctcc agggtcgctc tgcgcccttt ctccccagcc caccttttcc | 1020 |
| attggtcccc tctcctgtcc gagtggcagc gcggccccgc agggagcgac cccgggaggg | 1080 |
| acagtgaccg cacgcgtgga gtggggacgg cggggcacag gacggtagtc taagagtgtt | 1140 |
| cgcatggccg aggacgcttt cgctgcgagt ttggggtcga ggggcagttc cctcccggag | 1200 |
| tcattaactt cgtctcctcg tgctcaggga ccagcaactt ggtgctgcgg gcgccagaaa | 1260 |
| gaaaagggta gcgcctcgcg gagcgcgcgg gggaagaggg actgcggcag cgggacgcga | 1320 |
| gggcgggagg ggcgcagcag cggggagccg gagcgcagcg gaggggagcg ctggggggcg | 1380 |
| gggagcgctc gggcagccac cctgtccccg tctggagccc cgcgctgcgt ctaggagggc | 1440 |
| gcaacacgca gtccccgcgg gggccagagc tcggagcccc ctagtgcatg ccccctctcc | 1500 |
| tcgcgccctg ccgaggcctc ggccctgcct gccgtgccct gggcctggtt gtgcccgggg | 1560 |
| gtccccgcgg gcagggcgcg gggcaggcag ggcgcgcgcg ccgacgctct tttgtctgat | 1620 |
| aactaatttg agttaatgcg atctttatgt aaagctaaca gcggataatt gtctattttc | 1680 |
| tcgccaacag tctccatcac aatcacttat ctggaaacct gcggttggat taatcgttat | 1740 |
| attcccgaga tgagcgtcgc tgcaatccgc agcgaacgcg ggtagggacc tggagacgcc | 1800 |

| | | |
|---|---|---|
| tcccgggcgc tggcggggcc ggtgtgggcc agctccgcta ccgcctgaga cgcggtgtgc | 1860 |
| ccaggtgttg gtgcccgcgg gagagggctg tggggcgcct tccccaggat ttgcttgact | 1920 |
| tgcttttcgc tcgagtgggt ggtgcgcggg tgcgggaggc ggagggagga ggaggggtga | 1980 |
| ggggaggagg gcctgtgggg ctgcggaccc ggagcagcct gggtggagcg cggcctcggg | 2040 |
| aggccctggg tgcatcgcgg cggggcctgg gggggcccag gcgccggagg agccgtcggt | 2100 |
| gccggaatgc agccgtgttt cacttgggaga aacgttgccc tcggtccctt gcctccctcc | 2160 |
| tgttgtctcg gttttctgg cttcgtcctt cgtcccaccc acccgttccc acctcaggtc | 2220 |
| cctcccccag gatcccctcc ttaaggatcc aggtctctga aaattattgg caacagttac | 2280 |
| acgcccacg attgaaatcc acaagagaag agtcccagtt ctgcaggccg ctccagggct | 2340 |
| aggggtagag atggtggcag gtggtgcgtc aactctctag ggaagaggaa cttgcattac | 2400 |
| aaagacttgt ctttctgagc tgaagtcaaa acggggcgt caagcgcgct ccgtttggcg | 2460 |
| gcggtggagg ggccgcgcgc ccgcgctgtc ccagccggag ctgccctggc tggtgattgg | 2520 |
| aggtttaacg tccggaattc aggcgcttct gcagctcaga tttgccggcc aaggggcctc | 2580 |
| agttgcaact tttcaaaatg gtgtttctgg aaaataacaa attcagactc aactggtgac | 2640 |
| agcttttggc tatagagaat gaaactgctt ccctttggcg gtggaactct taaacttcga | 2700 |
| agagtgaaag aatacaatga aataaaatgc cataagatca ctggattttt cagaaaaagg | 2760 |
| aagaccccaa attactccca aaatgaggct ttgtaaattc ttgttaaaaa tctttaaatc | 2820 |
| tcgaatttcc ccctacaaca tctgatgagt gctttaagag caaacgagca aatcccacct | 2880 |
| cgagaatcaa caaacccaag ctctggccaa ggctctcccc gcgttttctt ctcgtgacct | 2940 |
| ggggaatgtc ccgcccatc gctcacctgg ctcttgtcat ctcgctcatc ttgaagtgac | 3000 |
| ccgtggacaa tgctgctccc tgccgcagct ccgccggtca ctcaggcaga acggggtatg | 3060 |
| caaatggcct ggagaggccg aggccgaaca ctgcgcccat tgtcccgggc gctcaaagcg | 3120 |
| ccgagcagct gcgcagactt tctgggctcg gaccctcggc cgccacgcta atgtcatcat | 3180 |
| tgcaaaacat cagattttga gaactatgca gtctgaattc attagcagcc ttctcggcga | 3240 |
| aggttctttt ccccgtgaca gtttcaaag tccagacccc ctccaacgtt ggtaggggta | 3300 |
| ggaagaggag gaggggccca gggagggggg tctttcgcaa gtgggcctc ggggatccc | 3360 |
| tgctctcctt ctggtgcatt ccgcaacttt aaaagcctcc cttggggttc tgagcgcgga | 3420 |
| tgtctgactt gaatgacctg agatttggac atattcccgt tttctcccaa gagttgcttt | 3480 |
| aatgttgc | 3488 |

<210> SEQ ID NO 215
<211> LENGTH: 484
<212> TYPE: DNA
<213> ORGANISM: Homo sapiens

<400> SEQUENCE: 215

| | | |
|---|---|---|
| tcccggggtt cacggtcgca gtttgtcctt acaaaacgcc cagccgcccc gacctgtggt | 60 |
| gcttagggag gacctacctg gctgtgccgg tctgagaagg ggccagtgag gcccggtgcg | 120 |
| ggtacgggcg ggtgcagatg cagccaggag gacgggcgga agcgggggcc tgtcccacac | 180 |
| gggggcctcg gcagcaccgg catggctgga ggccagtacg gccaggtgtg gcgggaggga | 240 |
| gcgccgtctg gcttgggtcg tccatcctga caggacgctg caaggcagg agccccgcgc | 300 |
| ccgtgtcct gcgccccgc tcgaggacaa gccccagccg ccggtctccg ctgggttccg | 360 |

```
acaggccttg ctgggaggcc ttgctgggag ctggggtcg aggctcacag actgcgctga    420
ccccagcagg cacagctggg tccagggact cgggaactcg cagcctgacg cgggccggac    480
cccc                                                                484
```

<210> SEQ ID NO 216
<211> LENGTH: 876
<212> TYPE: DNA
<213> ORGANISM: Homo sapiens

<400> SEQUENCE: 216

```
gcgcctgggg cagcgaggag cgcgcgttct gcctgcgaag ctgccttctc cgagcccgc    60 ccaggaacat tagctctggg gggccgctga tcattgattt ggacggagag atgggttctg   120
ggttctgtat taggattcca gcatctgggc tcgaggcagg gcaatatcca gaaagacccc   180
agggttcggg gtaccgggc cagggctgag gcgcatcgcc gagcaaaggc tgggtgcgag   240
gcgtgcggaa tgatgcgctt gccttgcccg ggcctctcca aggatggaga aaaggcgagt   300
gaagcagcga agtacgactc caaccccgcc cagagagtgc tactagcgct ggctgcacgc   360
caagtctctc caggggtcca aagcgagagg gatttgtttt aacccatctc tacccgtcct   420
gtgtcaagaa cggaggctgt agagggcgac tgcgaagtcg ccaggcactc gctggatctc   480
ggtccccctc ctcgtgctct ggggttgaga tggggcaccg ccatcgataa cagatcagcg   540
cgaactattc gtttagtggc cttaaaacac cctggtttca ccctcagcta ttttcaagtt   600
cccgtgtgcc tggcactttc tccgtgcgag aagcaccgga gggtgcggac gcgccacagt   660
ctgagccgcc gccgaactgg ctaagtttag gggcatttat tattcatgtt cctgccagat   720
cctcgcctgc ccaaaataga aaccgaggtt ctccgtgacc tacatctgct cggagaaggg   780
ctcccctggg ctcggaggct ggggtggggg tggctgagga gttggccccc gcacgcccca   840
cgcatcctct cctttgcttt ctgggcctcc ccattc                             876
```

<210> SEQ ID NO 217
<211> LENGTH: 634
<212> TYPE: DNA
<213> ORGANISM: Homo sapiens

<400> SEQUENCE: 217

```
tctgacgccg ctggcctccc gaatcgaacc ccagagcacc agagcccttc actttgttaa    60
gaagtccccc acccaggcgc ccccctcgtc ctcctcaagt gccctcggaa agcggaccag   120
actcacctac tgccaggcag atgggcagca gcagcctgaa gatgagcccg cacaccactt   180
ctgaggccat cgcgtcggtc cggcgagtcg gagcagaggg gcgaggctcg agggtcccta   240
ggggtggtgg gacgcaaggc ccatgcccgt ctatggcctc tcgccgccgg cagctcgcag   300
ccacccgagc atcgcctcgg gcgggccgc gacgctctcc gccccgaggg cacgctcccg   360
gggctcttgg ccgcccctcg cccaccgggc tctgggtagc ccctcaccag gtcttggcg   420 gccacctagc ccggcgcccg gcccctgcg gccggcccat ttagtgtgaa tcctggatcc   480
ggcagcggcg gcggcttctt caggggtagc tgatgccggg gccttggaga ggacgctttt   540
gggagggtcc tggaggcgg gcgcggcgagc aaaggggca agaagggcgt gctgtgctcc   600
cgcctggctc ccgggcgtc gtttgggggc ggcc                                634
```

<210> SEQ ID NO 218
<211> LENGTH: 634
<212> TYPE: DNA
<213> ORGANISM: Homo sapiens

<400> SEQUENCE: 218

```
tctgacgccg ctggcctccc gaatcgaacc ccagagcacc agagcccttc actttgttaa        60
gaagtccccc acccaggcgc ccccctcgtc ctcctcaagt gccctcggaa agcggaccag       120
actcacctac tgccaggcag atgggcagca gcagcctgaa gatgagcccg cacaccactt       180
ctgaggccat cgcgtcggtc cggcgagtcg gagcagaggg gcgaggctcg agggtcccta       240
ggggtggtgg gacgcaaggc ccatgcccgt ctatggcctc tcgccgccgg cagctcgcag       300
ccacccgagc atcgcctcgg cgcgggccgc gacgctctcc gccccgaggg cacgctcccg       360
gggctcttgg ccgcccctcg cccaccgggc tctgggtagc ccctcaccag gctcttggcg       420
gccacctagc ccggcgcccg gcccctgcg gccggcccat ttagtgtgaa tcctggatcc        480
ggcagcggcg gcggcttctt caggggtagc tgatgccggg gccttggaga gggacgcttt       540
gggagggtcc tgggaggcgg cgcggcgagc aaaggggca agaagggcgt gctgtgctcc        600
cgcctggctc ccggggcgtc gtttgggggc ggcc                                   634
```

<210> SEQ ID NO 219
<211> LENGTH: 927
<212> TYPE: DNA
<213> ORGANISM: Homo sapiens

<400> SEQUENCE: 219

```
cccccgggac ttgccagcag cgagtggggc ctgactagct cttcaccacg ctccactgca        60
tcggcaaggg ctggttctgg gagaggcgca agggcatcga cctccgcacc aatcaggtgg       120
tggtcattag ggcagtggac ccggaggagg ccgaggacgc ccagcaggag aaccctgcgc       180
tcagctgtgc tacagccccg agtcaccgct gctcttgctg ctctctgtga gtttcccccg       240
gaggcccaga gcggcggcag cgcgcaagac ttgcagaact cgggcccct ggaggagacc        300
taaccgccac ggtcttgggg aggttccgga gggcctcggt tgtctgcact cccaacacca       360
agaaacccct gagacgcgaa gctgccagcg tgctgccctc agagcagggc gacgcaaagc       420
cagcggaccc cggggtggcg gggcagccca cagacacgca ggtcgactgg aacagttctt       480
ggcagcctct tctggagggc gtctgaggtc gtcagcagcg gcctacgact tcaaggcagg       540
cttctgaccc ctggggatca cgcccatcgg actagccaag gaggagcctt cgcactccga       600
cctgcaccgc atgcgcgccc agttcctgat ccccaagagc agcccgtctg agctggagga       660
ccgcggcaag cccttggagg agctggcagg cctggcccga cgaggacccc gcgtcctgac       720
actgtcaagg agctccggga gcgcaaggcg accgcgcgct ccgccaacac cttttcttcc       780
ggggttcatg ggcgctgccg gcgctggaaa tcccaggggc acggcgagga gcccagctcc       840
taggatcccg acatcgccag cgcggcagag gacgcggatc aggcctcccc gcaacccggc       900
gtccctctac agtccggccg agtccac                                           927
```

<210> SEQ ID NO 220
<211> LENGTH: 1009
<212> TYPE: DNA
<213> ORGANISM: Homo sapiens

<400> SEQUENCE: 220

```
ggtcaccgtc ttggtcttgc ctgagtcccc gtaagtcctg aggcaccagt cctggaactg        60
gcggtacatg tcgcgctcgc tctccatgtt cccgcgctc ggccgctggc cggatgctcc        120
cagcgcactt cgcacctgtt caccctaggc tcatgaaaaa tgcagccccg gccacgttgc       180
```

| | |
|---|---|
| agggatgcga ggtcccggcc gcagcgggag cctgctttgg gtgggggaag ggatgggaag | 240 |
| aggggaggag ggtccggttg ggcaccagca atcaatgccc cgtgctacca agtctggtcc | 300 |
| attcgtaatt gcaacggctg tctcggacgt ttttcctgtt cccttagcgg tcggtctctt | 360 |
| taatattttg tgaccaggac catcccaaca ccattctggc ccagaggagc tgggttttca | 420 |
| ataattaaaa tcccattcct tggtttatta aaaatcccaa tattgaattg ggtggtccc | 480 |
| tagacgcctc gccccgggc tgcgtccggg gctgggcagg tggagcgcag cgccgcctcc | 540 |
| ccgcgcgcgc cccagaagct tccccagcca ctggccccgt ggtccaggag tgagggctgc | 600 |
| gcctctcccg aaagcagccg cccgcccagc gcctttgagc cccgaagggc acacgggtcc | 660 |
| cggatctctc cttcctcctg ggtcctgctt tgaccttccc cacgacgggt gttaagggac | 720 |
| tagaaagaga aagttcttac ctgtcatgtt tttaaaccta tcaaattctg ttttacagaa | 780 |
| ttttttatca agatattttt taaaacggtt taaaatgtca tttcttcaga tgcattttga | 840 |
| ataaattcca gccctgtatg tagattctac gagttaagtc ccagaaatta gcaaagcatt | 900 |
| gatggagatt tggccatagt tctacaggat agattgtagt gccccaaaca gatatccgtt | 960 |
| ccaggggat gtgggtaacc gaaggcaggc cgctggcggc gggtatccc | 1009 |

<210> SEQ ID NO 221
<211> LENGTH: 992
<212> TYPE: DNA
<213> ORGANISM: Homo sapiens

<400> SEQUENCE: 221

| | |
|---|---|
| gggaagcagt cacagcaaag ccaggtactc tggccaaggg caaagctggg gtctgaaccc | 60 |
| aggccgtcca catttatcca tggtgctgtg tggttagagg ccataggcag caggggccct | 120 |
| tgtggtgacc cctgcgcgtt gtctcagcgc agaggaggaa gtggcggcag gcagccgcgc | 180 |
| tcccagatga agcggggcca aagagtctg gggaacaaga cctgagaggt gggaagggtt | 240 |
| gaggccaccg gtttggagcc gtcaggtacc ctaaggggata tatgagggac cccggggcta | 300 |
| aagcagcctc tggaagagag tggccgcct gtcacttcag caccaggcgc agaatctgtg | 360 |
| ctaaacctga ggtgaggta aggaaccccc gacaccgcac gacaaccaga agaacgtcc | 420 |
| ctggagggga ggcttcgatc aaagcctggg acgcagggt cttcctgcag gggacgccgc | 480 |
| tctcggctct accctgctgt ggtgggccgg ctctgggagg gctggcttcc gaccatctcc | 540 |
| cgacctcccg cgcccaccgc gccgcgccgc gcgcctccca ggctgggaac cgccggggcg | 600 |
| aagcggcagg tggcgcgggt tcacctggca gggcaggcgc ccggggtccg ccggggaagg | 660 |
| acgaggggaa ggggtgcgcg gactcagggg caggcagcgg aggggagggg cctggggatc | 720 |
| tgggacggtg taagggtgct gcacttgcgc gcgaagggag gggtggcgac gagtccgcgg | 780 |
| ccgcctctcc gcgtcccct tccaccaccc ggggaccacc gcctctgacc gcagcctggg | 840 |
| ggccctaaag aggcctcggg tctcacctcc cgacgccgtc gggagaaac cggggaactg | 900 |
| ccagctgcgc aacaacttcc ggttctggtg gcgggtcggg gcggggcccg gaacgcgggg | 960 |
| acgttgccat ggagaagagc cgctgtggcc gc | 992 |

<210> SEQ ID NO 222
<211> LENGTH: 992
<212> TYPE: DNA
<213> ORGANISM: Homo sapiens

<400> SEQUENCE: 222

| | |
|---|---|
| gggaagcagt cacagcaaag ccaggtactc tggccaaggg caaagctggg gtctgaaccc | 60 |

| | |
|---|---|
| aggccgtcca catttatcca tggtgctgtg tggttagagg ccataggcag caggggccct | 120 |
| tgtggtgacc cctgcgcgtt gtctcagcgc agaggaggaa gtggcggcag gcagccgcgc | 180 |
| tcccagatga agcggggcca gaagagtctg gggaacaaga cctgagaggt gggaagggtt | 240 |
| gaggccaccg gtttggagcc gtcaggtacc ctaagggata tatgagggac cccggggcta | 300 |
| aagcagcctc tggaagagag tggccgccct gtcacttcag caccaggcgc agaatctgtg | 360 |
| ctaaacctga ggtgagggta aggaaccccc gacaccgcac gacaaccaga agaacgtcc | 420 |
| ctggagggga ggcttcgatc aaagcctggg acgcaggggt ctttctgcag gggacgccgc | 480 |
| tctcggctct accctgctgt ggtgggccgg ctctgggagg gctggcttcc gaccatctcc | 540 |
| cgacctcccg cgcccaccgc gccgcgccgc gcgcctccca ggctgggaac cgccggggcg | 600 |
| aagcggcagg tggcgcgggt tcacctggca gggcaggcgc ccggggtccg ccggggaagg | 660 |
| acgaggggaa ggggtgcgcg gactcagggg caggcagcgg aggggagggg cctggggatc | 720 |
| tgggacggtg taagggtgct gcacttgcgc gcgaagggag gggtggcgac gagtccgcgg | 780 |
| ccgcctctcc gcgtccccct tccaccaccc ggggaccacc gcctctgacc gcagcctggg | 840 |
| ggccctaaag aggcctcggg tctcacctcc cgacgccgtc ggggagaaac cggggaactg | 900 |
| ccagctgcgc aacaacttcc ggttctggtg gcgggtcggg gcggggcccg gaacgcgggg | 960 |
| acgttgccat ggagaagagc cgctgtggcc gc | 992 |

<210> SEQ ID NO 223
<211> LENGTH: 992
<212> TYPE: DNA
<213> ORGANISM: Homo sapiens

<400> SEQUENCE: 223

| | |
|---|---|
| gggaagcagt cacagcaaag ccaggtactc tggccaaggg caaagctggg gtctgaaccc | 60 |
| aggccgtcca catttatcca tggtgctgtg tggttagagg ccataggcag caggggccct | 120 |
| tgtggtgacc cctgcgcgtt gtctcagcgc agaggaggaa gtggcggcag gcagccgcgc | 180 |
| tcccagatga agcggggcca gaagagtctg gggaacaaga cctgagaggt gggaagggtt | 240 |
| gaggccaccg gtttggagcc gtcaggtacc ctaagggata tatgagggac cccggggcta | 300 |
| aagcagcctc tggaagagag tggccgccct gtcacttcag caccaggcgc agaatctgtg | 360 |
| ctaaacctga ggtgagggta aggaaccccc gacaccgcac gacaaccaga agaacgtcc | 420 |
| ctggagggga ggcttcgatc aaagcctggg acgcaggggt ctttctgcag gggacgccgc | 480 |
| tctcggctct accctgctgt ggtgggccgg ctctgggagg gctggcttcc gaccatctcc | 540 |
| cgacctcccg cgcccaccgc gccgcgccgc gcgcctccca ggctgggaac cgccggggcg | 600 |
| aagcggcagg tggcgcgggt tcacctggca gggcaggcgc ccggggtccg ccggggaagg | 660 |
| acgaggggaa ggggtgcgcg gactcagggg caggcagcgg aggggagggg cctggggatc | 720 |
| tgggacggtg taagggtgct gcacttgcgc gcgaagggag gggtggcgac gagtccgcgg | 780 |
| ccgcctctcc gcgtccccct tccaccaccc ggggaccacc gcctctgacc gcagcctggg | 840 |
| ggccctaaag aggcctcggg tctcacctcc cgacgccgtc ggggagaaac cggggaactg | 900 |
| ccagctgcgc aacaacttcc ggttctggtg gcgggtcggg gcggggcccg gaacgcgggg | 960 |
| acgttgccat ggagaagagc cgctgtggcc gc | 992 |

<210> SEQ ID NO 224
<211> LENGTH: 1123
<212> TYPE: DNA

<213> ORGANISM: Homo sapiens

<400> SEQUENCE: 224

| | | | | | |
|---|---|---|---|---|---|
| ctggcggaca | ccccagtaac | aagtgagagc | gctccacccc | gcagtccccc | ccgcctctcc | 60 |
| tccctgggtc | ccctcggctc | tcggaagaaa | aaccaacagc | atctccagct | ctcgcgcgga | 120 |
| attgtctctt | caactttacc | caaccgacga | caaggaacca | gcctcaacct | tttaatgcac | 180 |
| agcccggcca | caggattgcc | ttccatctcc | tcttggtccc | tcctggatgt | ggtttattga | 240 |
| tgacttgcga | gccccctcaga | gagctgtctt | ccctcctctg | gctccctccg | tttccttgag | 300 |
| ttagttttct | aaggttttac | cggggctcgg | gatctcttgg | accgaatgga | acttttttgct | 360 |
| gcctgctttt | gctgctgatt | ctgtcagtgg | acaaggaaaa | aggcttcgaa | ggcagcagag | 420 |
| gcgcagggga | ggtggagaaa | gaggtggagg | aagaggacga | ggaggaggag | gaagccgaag | 480 |
| gggctcggcg | cgtgtgtgtg | catgtgtgca | tgcgtgtgtg | agtgcatgtg | tgtgagtgct | 540 |
| gccgctgccc | gcgaccccctg | gccccgaagg | tgttggctga | aatatggaga | atagtcttag | 600 |
| atgtgtttgg | gtacccaagc | tggcttttgt | actcttcgga | gcttccttgt | tcagcgcgca | 660 |
| tcttcaagta | accggtaagt | ggctcttttcc | tttcttctcg | tcgcaccccc | ttccgtaccc | 720 |
| cacttcccctt | ctcatttcat | ttggcgagta | gtagaattgg | ggtgggggat | agcaagagat | 780 |
| ttggcgcttg | cgctgccccc | atttgcgcac | cgatgataaa | agatagaaga | gtttttttct | 840 |
| tccctggggg | cggatgatgg | tggggggggtg | gtacaagggg | cgccccttcg | ctgttttaaa | 900 |
| atctgatgct | tcacgcattt | ttgcttctgc | aaatacttgg | gttggtttgg | agagccggcg | 960 |
| ggctggggca | ggtgctgggg | atatcgttga | aaggaactgg | gctgggtcct | taaagcccca | 1020 |
| gaaacctacc | aagtggggag | gattgggggca | acaggagcag | gcgaggagga | catccagggg | 1080 |
| ctttgaggaa | gtctgcgcag | aatgtagatg | gtggggctga | gtc | | 1123 |

<210> SEQ ID NO 225
<211> LENGTH: 1932
<212> TYPE: DNA
<213> ORGANISM: Homo sapiens

<400> SEQUENCE: 225

| | | | | | |
|---|---|---|---|---|---|
| agcaccagga | cttgttgctc | cggcgggaac | tcgcgcggat | ccaccggctc | ggcacatcct | 60 |
| gcctacaagt | agggcggcgt | gtgctaggag | ccggggccccg | ggccgagtcg | tccgtgccgc | 120 |
| agcggagagc | tccgaccggc | gcggccccac | catccgctga | ccttcgcccg | gtccggcctg | 180 |
| gagcccggcc | gcggcctccc | taggcctctc | taggccgggc | gccggttcag | cgaggaccgg | 240 |
| aagcgcccgc | cgtccgccct | tccgcctcca | ggccgcgggc | gccaggccgg | gggcgggctg | 300 |
| gggacgccct | gggagtgccc | cggggggccgc | cttcttcccc | gcaagccccgg | agcgggcgtc | 360 |
| gctcccgccc | ccgcctcgtc | ttcagttccc | ccgtcgcttc | cgccgccgtg | ggtagaacag | 420 |
| acccgagctg | ggagccaggc | ctgcggcccc | tcgaacacta | gccacatctg | gcccgccggg | 480 |
| cctagcacgg | agagaggccc | tggggcttgg | cggccgggggc | cggagagggt | cgcgcggcca | 540 |
| aggacacccg | agggcctggg | ctgcctcccc | gccttccccc | gcccctcccc | tcggccctgg | 600 |
| aatcaatagt | ggccgctgac | ttttcacgac | aattgcagct | gtctaattca | tcagcgaata | 660 |
| attaaatcag | aggccgccgg | gcctgcctgg | agtcggagac | gaggggtcgc | tcctctcaaa | 720 |
| tcctgtcaaa | ttggggagcc | agtgggcagc | gcggagagcg | gacaggcctc | gcctgcgcc | 780 |
| gaggctgcga | gagccgcctg | gacccggcgc | cattccgagt | gtaggggggaa | gcaagccccc | 840 |
| aggtgtgggg | agcaaaagga | aggaggaggg | cacaggcggg | ggccccgccg | aggctggact | 900 |

```
ccctcgtcag cagggccctc ctggccggtg cgtggtccgg gtgcccggcg tggggcagcg    960
gccgtggggc ccacagacac catcctcacg cagacttcgc gaatgtcgtg gaactccatc   1020
ctcgggaggc gctttgcctt tgaggaagat ggagaggagt cgggagaagc gcctagaaac   1080
cgcattgatt tagacatcaa tcctggccgg ctccctccgc ctgccgagct gcggggccgc   1140
gccgccccgt ccccgagaag cggacctagg gtacgccggg ctccgccgag cgggcaaagg   1200
gagcggcctg cgccgccacc ccgcgcccgc ggcctcgacg ccgcagccgc cacgccaaca   1260
ccgattcctc gtggccaaca ggtttctcgc agccctccga gtcggcagcg ccgcccgcgt   1320
ccctcttcca gccgggccgg cgggacgccc tcagagcttg tgctctctcg aggccgccga   1380
gcccactgag cccggccggg gcgctggttc gcgtgggccg cggggaacag gtcccgcttc   1440
tccaacgacc acgccccggg cggctgcgaa acggccacct ccgacccttg agtccgccag   1500
agtcgctctc cctttcacat ttgcaagcaa acaacatac gtaatagtga catcgaggca   1560
cttttccaaa ctaaaatgat cctaaaataa tctgaatgta ctgttacttt tgatcgtgtt   1620
accccaaaag attagctcag attcacttgg ttctttatt tctttgggag atgatactcg   1680
aggaatctga aaaatatac gatttttaaa aacgatatga ttcgcatacc tatttcaacc   1740
cctcggttgg ttttgttagt ttccaaatag aaatattgcc ttttgaaatc ggagatcata   1800
tttctcaagt ttaaaatcta gccaagtctt tttttttta atactccgtc tgaaattttt   1860
ttccatggta gctagacaat tgaaattata cacaaagatt ttttaactct cggattttca   1920
ttggaagggg ac                                                      1932

<210> SEQ ID NO 226
<211> LENGTH: 1512
<212> TYPE: DNA
<213> ORGANISM: Homo sapiens

<400> SEQUENCE: 226
gtcccagcgt ttgctgggat ttgccaggat ttgccggggc tccgggagac cctgagcact     60
cgcaggaaga ggtgctgaga aattaaaaat tcaggttagt taatgcatcc ctgccgccgg    120
ctgcaggctc cgcctttgca ttaagcgggc gctgattgtg cgcgcctggc gaccgcgggg    180
aggactggcg gccgcgggga ggggacgggt agaggcgcgg gttacattgt tctggagccg    240
gctcggctct ttgtgcctcc tctagcgcc aagctgcgag gtacagccct ctattgttct    300
aggagcacag aaacctcctg tgtgggcggc gggtgcgcga gctagaggga aagatgcagt    360
agttactgcg actggcacgc agttgcgcgc ttttgtgcgc acggaccccg cgcggtgtgc    420
gtggcgactg cgctgcccct aggagcaagc cacgggccca gaggggcaaa atgtccaggt    480
cccccgctgg gaaggacaca ctatacccta tggcaagcca gggtgggcga cttcccatgg    540
atcgggtgga gggggggtatc tttcaggatc ggcgggcggt ctaggggaac aattcgtggt    600
ggcgatgatt tgcatagcgc gggtcttggg atgcgcgcgg ttccgagcca gcctcgcaca    660
gctcgcttcc ggagctgcga gctcaggttt ccaccccga tcccccgggc tttcctcgca    720
ccgctgagcc cagcttgtgg ggtgcactcg accaacgccc gacagggctg gggaatgtga    780
caggcagcag gttcacccgg gcttgggag ggggagtttc cgctttgaca gcattttcct    840
ttgccgtctg ctggtggatt cctattccca gtcggtaatc gccccgcagt gttgatctaa    900
gaaggtaaag aaaactaggt ttccctgcaa agagcctccc ccaaatcggc ggactccgga    960
tactttgagt ggatttagaa atttatgtaa tctttctcct ttagtttatt tttcatcctc   1020
```

```
tcctacagtt ttctctgatt tgctgttggt tcggggcaag ataaagcagc cagtagagag      1080
cgataataat agcggcggga aatgaactgg agactggctg acagttctta acattttgtc      1140
atagatcccc ccgaatgtcc caggctgtct ctggtgggtt ttagtacccg ccggcttctt      1200
gggcaccggg gaccagaagg aacttggcag ctggtcttag gggtacagtt aaaggcagga      1260
tgacagctat tctcctgctc atctcagagc gctgccgccc cctcatgccg gtcgcgcaaa      1320
gaacacagct tttaaaaaac acgtgccttc tgcccatata ggtctgaaag tgatgaggaa      1380
agtaatgctt cgcctattag cgagtttcag cttttaaaat gatcccaagc gttgctgaga      1440
tgagaaagcg tggcatcccg ggggtcctca gccccacccg cgcccatggt gcaagtctgc      1500
agggacaggc cc                                                         1512

<210> SEQ ID NO 227
<211> LENGTH: 1512
<212> TYPE: DNA
<213> ORGANISM: Homo sapiens

<400> SEQUENCE: 227
gtcccagcgt ttgctgggat ttgccaggat ttgccggggc tccgggagac cctgagcact        60
cgcaggaaga ggtgctgaga aattaaaaat tcaggttagt taatgcatcc ctgccgccgg       120
ctgcaggctc cgccttttgca ttaagcgggc gctgattgtg cgcgcctggc gaccgcgggg      180
aggactggcg gcccgcggga ggggacgggt agaggcgcgg gttacattgt tctggagccg       240
gctcggctct ttgtgcctcc tctagcggcc aagctgcgag gtacagccct ctattgttct       300
aggagcacag aaacctcctg tgtgggcggc gggtgcgcga gctagaggga aagatgcagt       360
agttactgcg actggcacgc agttgcgcgc ttttgtgcgc acggaccccg cgcggtgtgc       420
gtggcgactg cgctgcccct aggagcaagc cacgggccca gaggggcaaa atgtccaggt       480
cccccgctgg gaaggacaca ctatacccta tggcaagcca gggtgggcga cttcccatgg       540
atcgggtgga gggggggtatc tttcaggatc ggcgggcggt ctaggggaac aattcgtggt       600
ggcgatgatt tgcatagcgc gggtcttggg atgcgcgcgg ttccgagcca gcctcgcaca       660
gctcgcttcc ggagctgcga gctcaggttt ccacccccga tccccgggc tttcctcgca       720 ccgctgagcc cagcttgtgg ggtgcactcg accaacgccc gacagggctg gggaatgtga       780
caggcagcag gttcacccgg gcttggggag gggagtttc cgctttgaca gcattttcct       840
ttgccgtctg ctggtggatt cctattccca gtcggtaatc gccccgcagt gttgatctaa       900
gaaggtaaag aaaactaggt ttccctgcaa agagcctccc ccaaatcggc ggactccgga       960
tactttgagt ggatttagaa atttatgtaa tctttctcct ttagtttatt tttcatcctc      1020
tcctacagtt ttctctgatt tgctgttggt tcggggcaag ataaagcagc cagtagagag      1080
cgataataat agcggcggga aatgaactgg agactggctg acagttctta acattttgtc      1140
atagatcccc ccgaatgtcc caggctgtct ctggtgggtt ttagtacccg ccggcttctt      1200
gggcaccggg gaccagaagg aacttggcag ctggtcttag gggtacagtt aaaggcagga      1260
tgacagctat tctcctgctc atctcagagc gctgccgccc cctcatgccg gtcgcgcaaa      1320
gaacacagct tttaaaaaac acgtgccttc tgcccatata ggtctgaaag tgatgaggaa      1380
agtaatgctt cgcctattag cgagtttcag cttttaaaat gatcccaagc gttgctgaga      1440
tgagaaagcg tggcatcccg ggggtcctca gccccacccg cgcccatggt gcaagtctgc      1500
agggacaggc cc                                                         1512
```

<210> SEQ ID NO 228
<211> LENGTH: 1512
<212> TYPE: DNA
<213> ORGANISM: Homo sapiens

<400> SEQUENCE: 228

| | | | | | |
|---|---|---|---|---|---|
| gtcccagcgt | ttgctgggat | ttgccaggat | ttgccggggc | tccgggagac | cctgagcact | 60 |
| cgcaggaaga | ggtgctgaga | aattaaaaat | tcaggttagt | taatgcatcc | ctgccgccgg | 120 |
| ctgcaggctc | cgcctttgca | ttaagcgggc | gctgattgtg | cgcgcctggc | gaccgcgggg | 180 |
| aggactggcg | gcccgcggga | ggggacgggt | agaggcgcgg | gttacattgt | tctggagccg | 240 |
| gctcggctct | ttgtgcctcc | tctagcgcc | aagctgcgag | gtacagccct | ctattgttct | 300 |
| aggagcacag | aaacctcctg | tgtgggcggc | gggtgcgcga | gctagaggga | aagatgcagt | 360 |
| agttactgcg | actggcacgc | agttgcgcgc | ttttgtgcgc | acggaccccg | cgcggtgtgc | 420 |
| gtggcgactg | cgctgcccct | aggagcaagc | cacgggccca | gaggggcaaa | atgtccaggt | 480 |
| cccccgctgg | gaaggacaca | ctatacccta | tggcaagcca | gggtgggcga | cttcccatgg | 540 |
| atcgggtgga | gggggtatc | tttcaggatc | ggcgggcggt | ctagggaac | aattcgtggt | 600 |
| ggcgatgatt | tgcatagcgc | gggtcttggg | atgcgcgcgg | ttccgagcca | gcctcgcaca | 660 |
| gctcgcttcc | ggagctgcga | gctcaggttt | ccaccccga | tccccgggc | tttcctcgca | 720 |
| ccgctgagcc | cagcttgtgg | ggtgcactcg | accaacgccc | gacagggctg | gggaatgtga | 780 |
| caggcagcag | gttcacccgg | gcttggggag | ggggagtttc | cgctttgaca | gcatttccct | 840 |
| ttgccgtctg | ctggtggatt | cctattccca | gtcggtaatc | gccccgcagt | gttgatctaa | 900 |
| gaaggtaaag | aaaactaggt | ttccctgcaa | agagcctccc | ccaaatcggc | ggactccgga | 960 |
| tactttgagt | ggatttagaa | atttatgtaa | tctttctcct | ttagtttatt | tttcatcctc | 1020 |
| tcctacagtt | ttctctgatt | tgctgttggt | tcggggcaag | ataaagcagc | cagtagagag | 1080 |
| cgataataat | agcggcggga | aatgaactgg | agactggctg | acagttctta | acattttgtc | 1140 |
| atagatcccc | ccgaatgtcc | caggctgtct | ctggtgggtt | ttagtacccg | ccggcttctt | 1200 |
| gggcaccggg | gaccagaagg | aacttggcag | ctggtcttag | gggtacagtt | aaaggcagga | 1260 |
| tgacagctat | tctcctgctc | atctcagagc | gctgccgccc | cctcatgccg | gtcgcgcaaa | 1320 |
| gaacacagct | tttaaaaaac | acgtgccttc | tgcccatata | ggtctgaaag | tgatgaggaa | 1380 |
| agtaatgctt | cgcctattag | cgagtttcag | cttttaaaat | gatcccaagc | gttgctgaga | 1440 |
| tgagaaagcg | tggcatcccg | ggggtcctca | gccccacccg | cgcccatggt | gcaagtctgc | 1500 |
| agggacaggc | cc | | | | | 1512 |

<210> SEQ ID NO 229
<211> LENGTH: 662
<212> TYPE: DNA
<213> ORGANISM: Homo sapiens

<400> SEQUENCE: 229

| | | | | | |
|---|---|---|---|---|---|
| aactctgggt | tggcgagtgt | ggagcgagtt | ggggaggtta | gagagtctcg | cggctccgaa | 60 |
| aaggaaaagc | atctctttgc | ctcagttctt | gtaccgctgg | tgatcaacct | tgggtgttag | 120 |
| ggactggcac | cgaaccggag | atctgcttgg | tgaactgaga | ggagtcctta | ggagagcggg | 180 |
| gacgccaggg | gccgggggac | acttcgctct | cgccctaggg | aaggtggtct | tgacgctttc | 240 |
| tattgaagtc | aaacttgaaa | atatcagctg | ccgctggact | atgggctag | cggggaact | 300 |
| gggagcgcgc | tagcatctga | gccttagccc | catccactcc | ggaccccaag | cgcgcacgcc | 360 |

```
ggctccaggg aagggcgcct ctggtctagg ccgccgaagc gttcggaatg gggacgattc     420
tctgctgcag cgaagtgtcc ctagaatttt cacaaggaaa ccctgagctt cttctcagtc     480
ctcctctttc cctgacccac cctgtccgtc aacgcaccct cctcccgtac cccaatattc     540
actcctctcc ccaagtcctg agcgtgctta aacagagtcg aaacaaaaca agcatgtctt     600
taattctcct ctcaaatagt ttgaaactac ttatacaaaa gtttctcaaa ctctattttt     660
cc                                                                    662
```

<210> SEQ ID NO 230
<211> LENGTH: 992
<212> TYPE: DNA
<213> ORGANISM: Homo sapiens

<400> SEQUENCE: 230

```
caaggaaaca gggttttcgt ttccaactcg gtattcgcag ctagtgacga gggtggcatt      60
tggggcccca atcctgtcac cctcgatcac tacctgcatt ccatttccac tcagcaaccc     120 ccaaccccctt cctggctatg tctaatgagc tgtcggcctc ttcatcttgc aagtcattcc    180
catcttctat tttgagttta aagagggaa accccaaag gggagctcgt actacaaact      240
ggaacagact gcttgaaggg cgatgcacag gaacatcga agatctgtgc ctctcccttg      300
agactctggg catgccaagt cgaggaagga cagtaataaa tgcatggaca cccgtgaatt     360
ccgagaagca ttggctgcaa tttgggcctc gggccctccc agatcccagt tcctcaacct     420
gggcgcttta cctggacccg gacctctggt aggttgacct tgccggccag ctcctcgcgg     480
ctgtacacgt ccgggtagtg ggacttctcg aacgcgcgct ccagtcatg cagctggtac     540 gtggtgaaag tcgtgcggtt ccgccgatgc ttttcttgg gctgttcctc ctctgacagt      600
ttcgcttcgc cggtggctgg cccgacgggc agccctgggc tcggccgtgc ctccccgggc    660
tccttggggc agtagggtcg aggggctggg gcgacgaggc ccgggagggt cagatgcact    720
ccccaaaaca cccttgggcc gaccccgcct cgctgtgggc actggccagc ccgcctgcgg    780
gctccgagat ggcccgggga ggtccgtggt gagggcggcg atgggtccta agctttctct   840
gaatgcaaat tggaagctcc cgccatagac ggtccccaac cccgcgccca gttgccttaa    900
taaaagttaa ggaaggggcg ctctcgtctg gccaactcct aagctcgggc gcccgaacgg    960
cctcgcacag ccagggtgc gcactcacct tc                                   992
```

<210> SEQ ID NO 231
<211> LENGTH: 1031
<212> TYPE: DNA
<213> ORGANISM: Homo sapiens

<400> SEQUENCE: 231

```
gaggcgctcg ccggtctggc cgcgccgcgc gcgtggatgg aggtctcggc cgcggatcgc      60
cccgtctatt cgcgctggtc ctgcgggagc ccgggtgagc cgaaggcgag gaaggggcgc     120
gggtctcggg aaaacccgac tctcccggcg cccgccccgg ttcggttggg ggcgcacccg     180
gctcgcgcgg agagcgggcg gggtgtgggc gaatgctcgg cgcgctgcgc ctttcccggt     240
cccccttctc cccggagatg aacgccccac tcccgctcgg acacacgcc gcaccctac      300 tctgcctcct ccgaccagcc ggggcgcggc ccgaattggg ggagagaaga cccagctccc     360
gcagccgcga attctgcaaa cccggagccc atgcgcccg tcctccggcc cggggagctc     420
ccagccttgc ccgccgagcg cagcccgggt ccggactgtg gtcactgggg acgagaaggg    480
tccctcctgc ggggctcccg ggttcggatg gacggagggg gcgtccggca ggtgaactgg    540
```

```
gcccgctccg cgtcccgaac gttcccctaa acccacaagt cccggagacc ctggggcatt    600
ctgcgatttc ggagtgaccg gtggagcccc cgcccgcgcg cctggctccc ggggtctccc    660
cacacagcag gggctgcggg gaccccctct gtcacctcct ccaaagggtc tgggagcaat    720
tcgacctgcc tggagaattc caggaagtcc tttccctgcg ggagcctcat gggtccccc    780 ttctctgcct gcagagacct ctggcttccg cgtgcgctca aagtgagcgc cgggcagatt    840
gtaaataatg gattttgacc cagctgggag atctcagagt gattaagtgg agaggctgtt    900
ccaccctcag ccctgcccag gcagctgggt gaccccgcgg gccacatgcc acaggggcac    960
ggactcagcc ctgagtggtt ttcgttctgc tgagagtcca ggaggcttcc cgagacccca   1020
agcagaaccg c                                                        1031
```

<210> SEQ ID NO 232
<211> LENGTH: 1031
<212> TYPE: DNA
<213> ORGANISM: Homo sapiens

<400> SEQUENCE: 232

```
gaggcgctcg ccggtctggc cgcgccgcgc gcgtggatgg aggtctcggc cgcggatcgc     60
cccgtctatt cgcgctggtc ctgcgggagc ccgggtgagc cgaaggcgag gaaggggcgc    120
gggtctcggg aaaacccgac tctcccggcg cccgccccgg ttcggttggg ggcgcacccg    180
gctcgcgcgg agagcgggcg gggtgtgggc gaatgctcgc cgcgctgcgc ctttccggt    240 cccccttctc cccggagatg aacgcccac tcccgctcgg acacacgcc gcacccctac    300 tctgcctcct ccgaccagcc ggggcgcggc ccgaattggg ggagagaaga cccagctccc    360
gcagccgcga attctgcaaa cccggagccc atgcgccccg tcctccggcc cggggagctc    420
ccagccttgc ccgccgagcg cagcccgggt ccggactgtg gtcactgggg acgagaaggg    480
tccctcctgc ggggctcccg ggttcggatg gacggagggg gcgtccggca ggtgaactgg    540
gcccgctccg cgtcccgaac gttcccctaa acccacaagt cccggagacc ctggggcatt    600
ctgcgatttc ggagtgaccg gtggagcccc cgcccgcgcg cctggctccc ggggtctccc    660
cacacagcag gggctgcggg gaccccctct gtcacctcct ccaaagggtc tgggagcaat    720
tcgacctgcc tggagaattc caggaagtcc tttccctgcg ggagcctcat gggtccccc    780 ttctctgcct gcagagacct ctggcttccg cgtgcgctca aagtgagcgc cgggcagatt    840
gtaaataatg gattttgacc cagctgggag atctcagagt gattaagtgg agaggctgtt    900
ccaccctcag ccctgcccag gcagctgggt gaccccgcgg gccacatgcc acaggggcac    960
ggactcagcc ctgagtggtt ttcgttctgc tgagagtcca ggaggcttcc cgagacccca   1020
agcagaaccg c                                                        1031
```

<210> SEQ ID NO 233
<211> LENGTH: 1114
<212> TYPE: DNA
<213> ORGANISM: Homo sapiens

<400> SEQUENCE: 233

```
tcatttgaag gcgtttcctt ttctttaaga acaaaggttg gagcccaagc cttgcggcgc     60
ggtgcaggaa agtacacggc gtgtgttgag agaaaaaaaa tacacacacg caatgaccca    120
cgagaaaggg aaaggggaaa acaccaacta cccgggcgct gggcttttc gacttttcct    180 ttaaaaagaa aaaagttttt caagctgtag gttccaagaa caggcaggag gggggagaag    240
```

-continued

```
gggggggggg ttgcagaaaa ggcgcctggt cggttatgag tcacaagtga gttataaaag    300
ggtcgcacgt tcgcaggcgc gggcttcctg tgcgcggccg agcccgggcc cagcgccgcc    360
tgcagcctcg ggaagggagc ggatagcgga gccccgagcc gcccgcagag caagcgcggg    420
gaaccaagga gacgctcctg gcactgcagg tacgccgact tcagtctcgc gctcccgccc    480
gcctttcctc tcttgaacgt ggcagggacg ccggggggact tcggtgcgag ggtcaccgcc    540
gggttaactg gcgaggcaag gcggggggcag cgcgcacgtg gccgtggagc ccggcctggt    600
cccgcgcgcg cctgcgggtg cccctgggg actcagtggt gtcgcctcgc ccgggaccag    660
agattgcgct ggatggattc ccgcgggcag aggcaggggg aaggaggggt gttcgaaacc    720
taatacttga gcttctttgc aaagtttcct tggatggttg gggacgtacc tgtataatgg    780
ccctggacca gcttccctgt tggagtggcc agagaagtgt gtaaaacaca ctagaggggc    840
agggtggaaa aagagactgc cttcaaaact tgtatctttt cgatttcatt ttgaaaaata    900
actacaaatc tattttaatt ttacaaagtt agactcatag cattttagat atcaatgtct    960
tcatttaaca gaagtgaaga tggagcaaac gctcaatcag cgtctgtatt tattcgctcc    1020
tgttgtgcca gggtgcgttt ttgccgagcg gttgcctttc tttactcaca aaaccccctt    1080
gatgtctgtc ctccacgttt tacgagggag agcc    1114
```

<210> SEQ ID NO 234
<211> LENGTH: 1128
<212> TYPE: DNA
<213> ORGANISM: Homo sapiens

<400> SEQUENCE: 234

```
agatcccaat tcggtgaccc agcccttgct ggagtactag gtggtatcta atgccatcca    60
cccttccggg atctttacgg cccacctctg agtgggtccc acgggggacct cagccgcatt    120 ttctttctgc aggcctccct gcacactctg gggcgttcgc agctctggag cccgcggggc    180
agtgcgtccg gccccgccct gggcctcatt atctacgttt ccgcgtcacg cccgccgcga    240
acttggcagg ccctcccgcc gggttcggga acactgtgtg cctagcgccc gccctcctcc    300
cttccgccgg ccccgcgcga tccatagggt ttgggtcgct gggcgccagg tacccgcacc    360
cggcaagcag ccacggagcc cctcgcgcac ttgtcctcga tacccttgag ttggggctac    420
gcaggccact cctaggccac tggctgggcg tccgaacgtg ggtcaccccg cgcacagtct    480
agaggttcag aaagatgctg tggcccactt taaaacaaag cccaattatt agcgctcggc    540
ggctgtttgc gccggtgcag tgtcagatcc cccagcgctg cggacaacca gcacccaaag    600
gaagccgagc tggagctaaa gatcccggct ccggagccat ctgaccggtt ttgagacctc    660
cagctcgtcg ccgtcctggc tgcgagagct tgggcacggc gccggggctc agtctccctct    720 tctgtggaat ggcgataact gtatgtgccg ggtgactgca cgtggcgcgc ggcgggtggc    780
ggggatggca gcggtgcgat cccacgcctc caggacccca ccttcctgcg gccccccgatc    840 ggccccgccc cggggggcgcc ccagctgcac gcgcggcgct ggctccaaag tgcgtcacgg    900
gcaccggccg cgctccttct gccgccaggg cgaggctggc acccggccag cgcgggcagg    960
gccacgggtg cccggctgtt tcccgggtgt ggaaggcgct caaggtgcgc ggcccggggc    1020
gcgctactgg gggcgccctc cgcggtgggc agcgcgccag ggatcggcct gggcagccgc    1080
ggggcgcgcg aaggctgcgc tttccctacg gcccccctcg cttcctcc    1128
```

<210> SEQ ID NO 235
<211> LENGTH: 1128

```
<212> TYPE: DNA
<213> ORGANISM: Homo sapiens

<400> SEQUENCE: 235
agatcccaat tcggtgaccc agcccttgct ggagtactag gtggtatcta atgccatcca      60
cccttccggg atctttacgg cccacctctg agtgggtccc acggggacct cagccgcatt     120
ttctttctgc aggcctccct gcacactctg gggcgttcgc agctctggag cccgcggggc     180
agtgcgtccg gccccgccct gggcctcatt atctacgttt ccgcgtcacg cccgccgcga     240
acttggcagg ccctcccgcc gggttcggga acactgtgtg cctagcgccc gccctcctcc     300
cttccgccgg ccccgcgcga tccataggg ttgggtcgct gggcgccagg tacccgcacc      360
cggcaagcag ccacggagcc cctcgcgcac ttgtcctcga tacccttgag ttggggctac     420
gcaggccact cctaggccac tggctgggcg tccgaacgtg ggtcaccccg cgcacagtct     480
agaggttcag aaagatgctg tggcccactt taaaacaaag cccaattatt agcgctcggc     540
ggctgtttgc gccggtgcag tgtcagatcc cccagcgctg cggacaacca gcacccaaag     600
gaagccgagc tggagctaaa gatcccggct ccggagccat ctgaccggtt ttgagacctc     660
cagctcgtcg ccgtcctggc tgcgagagct tgggcacggc gccggggctc agtctcctct     720
tctgtggaat ggcgataact gtatgtgccg ggtgactgca cgtggcgcgc ggcgggtggc     780
ggggatggca gcggtgcgat cccacgcctc caggacccca ccttcctgcg gccccccgatc    840
ggccccgccc cggggggcgcc ccagctgcac gcgcggcgct ggctccaaag tgcgtcacgg    900
gcaccggccg cgctccttct gccgccaggg cgaggctggc acccggccag cgcgggcagg    960
gccacgggtg cccggctgtt tcccgggtgt ggaaggcgct caaggtgcgc ggcccggggc   1020
gcgctactgg gggcgccctc cgcggtgggc agcgcgccag ggatcggcct gggcagccgc   1080
ggggcgcgcg aaggctgcgc tttccctacg gccccctcg cttcctcc                  1128

<210> SEQ ID NO 236
<211> LENGTH: 1219
<212> TYPE: DNA
<213> ORGANISM: Homo sapiens

<400> SEQUENCE: 236
cggttctgac cagccgtgct gaccctggac gactccatga gctgttttgt gagaaagaca      60
cgccatttgt ttgcagagtt ctgacttctg aggggtcatg tagcacatgt ttggtagcca     120
aacgctgtca ttcacgacca ggagcgatgg ctgcaatgcc ttttttcttg ctttgctttc     180
cggtgccgga agccttgcct cccgccgcca cccctggtca gctctgcgca agaacgtcgt     240
tctgtttggc agccaggccg agacgcagcc tgaatgtgag caggaactcg gagaagggaa     300
gggagagaat cagaaagaag gcccggggagg gacccgggaa gcagtgggag gtctgcgccc     360
tggagccccg cgagagcccg ccggtttggc acgggctcct cccgggccgc ccggcggtcc     420
aacaaaggcc ggccccgaca cgcacccggt cttttgtggg agagaaacac aaagaagagg     480
gaaaaacacg gaggaggcca acagcaccag gacgcggggg ccaaccagga actcccggag     540
ccggggccca ttagcctctg caaatgagca ctccattccc caggaagggg ccccagctgc     600
gcgcgctggt gggaaccgca gtgcctggga cccgcccagg tcgcccaccc cgggcgccgg     660
gcgcaggacc cggacaagtc ctggggacgc ctccaggacg caccagggca agcttgggca     720
ccgggatcta atttctagtt attcctggga cggggtgggg aggcatagga gacacaccga     780
gaggtactca gcatccgatt ggcaccaggg ccaagggagc ccaggggcga cacagacctc     840
```

| | |
|---|---|
| cccgacctcc caagctactc cggcgacggg aggatgttga gggaagcctg ccaggtgaag | 900 |
| aaggggccag cagcagcaca gagcttccga ctttgccttc caggctctag actcgcgcca | 960 |
| tgccaagacg ggcccctcga ctttcacccc tgactcccaa ctccagccac tggaccgagc | 1020 |
| gcgcaaagaa cctgagaccg cttgctctca ccgccgcaag tcggtcgcag acagacacc | 1080 |
| agtgggcagc aacaaaaaaa gaaaccgggt tccgggacac gtgccggcgg ctggactaac | 1140 |
| ctcagcggct gcaaccaagg agcgcgcacg ttgcgcctgc tggtgtttat tagctacact | 1200 |
| ggcaggcgca caactccgc | 1219 |

<210> SEQ ID NO 237
<211> LENGTH: 1219
<212> TYPE: DNA
<213> ORGANISM: Homo sapiens

<400> SEQUENCE: 237

| | |
|---|---|
| cggttctgac cagccgtgct gaccctggac gactccatga gctgttttgt gagaaagaca | 60 |
| cgccatttgt ttgcagagtt ctgacttctg aggggtcatg tagcacatgt ttggtagcca | 120 |
| aacgctgtca ttcacgacca ggagcgatgg ctgcaatgcc ttttctttg ctttgctttc | 180 |
| cggtgccggg agccttgcct cccgccgcca cccctggtca gctctgcgca agaacgtcgt | 240 |
| tctgttttggc agccaggccg agacgcagcc tgaatgtgag caggaactcg gagaagggaa | 300 |
| gggagagaat cagaaagaag gcccgggagg gacccgggaa gcagtgggag gtctgcgccc | 360 |
| tggagccccg cgagagcccg ccggtttggc acgggctcct cccgggccgc ccggcggtcc | 420 |
| aacaaaggcc ggccccgaca cgcacccggt cttttgtggg agagaaacac aaagaagagg | 480 |
| gaaaaacacg gaggaggcca acagcaccag gacgcggggg ccaaccagga actcccggag | 540 |
| ccggggccca ttagcctctg caaatgagca ctccattccc caggaagggg ccccagctgc | 600 |
| gcgcgctggt gggaaccgca gtgcctggga cccgcccagg tcgcccaccc cgggcgccgg | 660 |
| gcgcaggacc cggacaagtc ctggggacgc ctccaggacg caccagggca agcttgggca | 720 |
| ccgggatcta atttctagtt attcctggga cggggtgggg aggcatagga gacacaccga | 780 |
| gaggtactca gcatccgatt ggcaccaggg ccaaggagc caggggcga cacagacctc | 840 |
| cccgacctcc caagctactc cggcgacggg aggatgttga gggaagcctg ccaggtgaag | 900 |
| aaggggccag cagcagcaca gagcttccga ctttgccttc caggctctag actcgcgcca | 960 |
| tgccaagacg ggcccctcga ctttcacccc tgactcccaa ctccagccac tggaccgagc | 1020 |
| gcgcaaagaa cctgagaccg cttgctctca ccgccgcaag tcggtcgcag acagacacc | 1080 |
| agtgggcagc aacaaaaaaa gaaaccgggt tccgggacac gtgccggcgg ctggactaac | 1140 |
| ctcagcggct gcaaccaagg agcgcgcacg ttgcgcctgc tggtgtttat tagctacact | 1200 |
| ggcaggcgca caactccgc | 1219 |

<210> SEQ ID NO 238
<211> LENGTH: 796
<212> TYPE: DNA
<213> ORGANISM: Homo sapiens

<400> SEQUENCE: 238

| | |
|---|---|
| ggccatttct ccagagcgac tttgctcttc tgtcctcccc acactcaccg ctgcatctcc | 60 |
| ctcaccaaaa gcgagaagtc ggagcgacaa cagctctttc tgcccaagcc ccagtcagct | 120 |
| ggtgagctcc ccgtggtctc cagatgcagc acatggactc tgggcccgc gccggctctg | 180 |
| ggtgcatgtg cgtgtgcgtg tgtttgctgc gtggtgtcga tggagataag gtggatccgt | 240 |

```
ttgaggaacc aaatcattag ttctctatct agatctccat tctccccaaa gaaaggccct    300
cacttcccac tcgtttattc cagcccgggg gctcagtttt cccacaccta actgaaagcc    360
cgaagcctct agaatgccac ccgcaccccg agggtcacca acgctccctg aaataacctg    420
ttgcatgaga gcagagggga gatagagaga gcttaattat aggtacccgc gtgcagctaa    480
aaggagggcc agagatagta gcgaggggga cgaggagcca cgggccacct gtgccgggac    540
cccgcgctgt ggtactgcgg tgcaggcggg agcagctttt ctgtctctca ctgactcact    600
ctctctctct ctccctctct ctctctctca ttctctctct tttctcctcc tctcctggaa    660
gttttcgggt ccgagggaag gaggaccctg cgaaagctgc gacgactatc ttcccctggg    720
gccatggact cggacgccag cctggtgtcc agccgcccgt cgtcgccaga gcccgatgac    780
ctttttctgc cggccc                                                   796

<210> SEQ ID NO 239
<211> LENGTH: 841
<212> TYPE: DNA
<213> ORGANISM: Homo sapiens

<400> SEQUENCE: 239
actggcgccg gcgcgttctg gcgacagggg agccaggggc cgcggggaag cgaggactgg     60
cctgcgctgg gctcgggagc tctgtcgcga ggaggggcgc aggaccatgg actgggggtg    120
gggcatggtg gggattccag catctgcgaa cccaagcaat gggggcgccc acagagcagt    180
ggggagtgag gggatgttct ctccgggacc tgatcgagcg ctgtctggct ttaacctgag    240
ctggtccagt agacatcgtt ttatgaaaag gtaccgctgt gtgcattcct cactagaact    300
catccgaccc ccgaccccca cctccggaaa aagattctaa aaacttcttt ccctgagagc    360
gtggcctgac ttgcagactc ggcttgggca gcacttcggg gggggagggg gtgttatggg    420
agggggacac attggggcct tgctcctctt cctcctttct tggcgggtgg agactccgg     480 gtagccgcac tgcagaagca acagcccgac cgcgccctcc agggtcgtcc ctggcccaag    540
gccaggggcc acaagttagt tggaagccgg cgttcggtat cagaagcgct gatggtcata    600
tccaatctca atatctgggt caatccacac cctcttagaa ctgtggccgt tcctccctgt    660
ctctcgttga tttgggagaa tatggttttc taataaatct gtggatgttc cttcttcaac    720
agtatgagca agtttataga cattcagagt agaaccactt gtggattgga ataacccaaa    780
actgccgatt tcagggggcgg gtgcattgta gttattattt taaaatagaa actaccccac    840
c                                                                    841

<210> SEQ ID NO 240
<211> LENGTH: 1207
<212> TYPE: DNA
<213> ORGANISM: Homo sapiens

<400> SEQUENCE: 240
caggcgcaga ggggacaatc cgggaagtgg taaaggggac acccgggcac agggcctgtg     60
ctttcgttgc aggcgaggaa gtggagcgcg cgctgcagat tcagcgcggg gctagaggag    120
gggacctgga tccctgaacc ccggggcgga aaggagccct ccgggcggct gtgggtgccg    180
cgctcctcgg agccagcagc tgctggggcg gcgtccgaac tccccaggtc tgcgcacggc    240
aatgggggca ccgggccttc tgtctgtcct cagaatacgt aggataccccg cgggcgacaa    300 gccgggccag gctaggagcc tccttccctg cccctcccca tcggccgcgg gaggctttct    360
```

```
tggggcgtcc ccacgaccac cccttctca cccggtcccc agtttggaaa aaggcgcaag        420
aagcgggctt ttcagggacc cggggagaa cacgagggct ccgacgcggg agaaggattg        480
aagcgtgcag aggcgcccca aattgcgaca atttactggg atccttttgt ggggaaagga       540
ggcttagagg ctcaagctat aggctgtcct agagcaacta ggcgagaacc tggccccaaa       600
ctccctcctt acgccctggc acaggttccc ggcgactggt gttcccaagg gagcccctg        660 agcctaccgc ccttgcaggg ggtcgtgctg cggcttctgg gtcataaacg ccgaggtcgg       720
gggtggcgga gctgtagagg ctgcccgcgc agaaagctcc aggatcccaa tatgtgcttg       780
cgtggagcag ggagcggaag aggcagccgg tcctcaccct cctctcccgc cacgcacata      840
tccttcttga cttcgaagtg gtttgcaatc cgaaagtgag accttgagtc ctcagatggc      900
cggcaacgcg ccgaggtcac gctccccaga aacacccctc tcccctcccc taccccagct      960 cccctggg cgggtggtaa ttggggagg agaggccgca ggcagggaag gggtgggaaa        1020
gccagagagg gaggcacaaa gtgatggcag cccggcaaac actggggctt cgggctgggc     1080
cgcgctcgtt taatcccaca aaaatcccat tttggaggtg agaaatagag gttagaggtc     1140
gggcccttct ggagatcaga ccgaggagac gggcccagct ggcgtcttaa agcaaggagg     1200
gggagtc                                                                 1207

<210> SEQ ID NO 241
<211> LENGTH: 1207
<212> TYPE: DNA
<213> ORGANISM: Homo sapiens

<400> SEQUENCE: 241
caggcgcaga gggacaatc cgggaagtgg taaaggggac acccgggcac agggcctgtg        60
ctttcgttgc aggcgaggaa gtggagcgcg cgctgcagat tcagcgcggg gctagaggag       120
gggacctgga tccctgaacc ccggggcgga aagggagcct ccgggcggct gtgggtgccg       180
cgctcctcgg agccagcagc tgctgggcg gcgtccgaac tccccaggtc tgcgcacggc       240
aatgggggca ccgggccttc tgtctgtcct cagaatacgt aggataccg cgggcgacaa      300 gccgggccag gctaggagcc tcttcccctg cccctcccca tcggccgcgg gaggcttct      360 tggggcgtcc ccacgaccac cccttctca cccggtcccc agtttggaaa aaggcgcaag       420
aagcgggctt ttcagggacc cggggagaa cacgagggct ccgacgcggg agaaggattg       480
aagcgtgcag aggcgcccca aattgcgaca atttactggg atccttttgt ggggaaagga      540
ggcttagagg ctcaagctat aggctgtcct agagcaacta ggcgagaacc tggccccaaa      600
ctccctcctt acgccctggc acaggttccc ggcgactggt gttcccaagg gagcccctg       660 agcctaccgc ccttgcaggg ggtcgtgctg cggcttctgg gtcataaacg ccgaggtcgg      720
gggtggcgga gctgtagagg ctgcccgcgc agaaagctcc aggatcccaa tatgtgcttg      780
cgtggagcag ggagcggaag aggcagccgg tcctcaccct cctctcccgc cacgcacata     840
tccttcttga cttcgaagtg gtttgcaatc cgaaagtgag accttgagtc ctcagatggc     900
cggcaacgcg ccgaggtcac gctccccaga aacacccctc tcccctcccc taccccagct     960 cccctggg cgggtggtaa ttggggagg agaggccgca ggcagggaag gggtgggaaa       1020
gccagagagg gaggcacaaa gtgatggcag cccggcaaac actggggctt cgggctgggc    1080
cgcgctcgtt taatcccaca aaaatcccat tttggaggtg agaaatagag gttagaggtc    1140
gggcccttct ggagatcaga ccgaggagac gggcccagct ggcgtcttaa agcaaggagg    1200
gggagtc                                                                1207
```

<210> SEQ ID NO 242
<211> LENGTH: 976
<212> TYPE: DNA
<213> ORGANISM: Homo sapiens

<400> SEQUENCE: 242

```
gccacctcac agtgcaggaa ctatctcccc gtttgctccc aaatagtctt cttggtgtgg      60
tgctgtctat ggtctgtgac ctgcatctgg agttacccccc aggaccagct tcggaagagg    120
agggatcgct tggaggccgt gcagtgtgag gaacggcagg cagggtgtgg gaccaacatg     180
cacacactcg caggtgctgg ggccaggagg gaatgaggcg ctggctccct ttccctccat     240
ttctccctgg gggtcccagc aacctggcca tccctgactt ccaacagcac agcgtcccca    300
caggtcctgc agtgctctgc aggggtgcag ggagctcccc tcccccagcc cgcaacctca    360
ccttcctcac ccccaccccct ccggcaggaa accacaggct gggttgggga ccctggtgc    420
tccaagagag cagtgagtgc tgggagccgc taaccccgag gcgcctagca cagactcttc    480
tcacccctta tttctgaaat aaagcccttc cttaggtcca gatgaggacc acgtgctcag    540
tgcctcactt tcgtgggagt gtatatcact ttacagtatc aagacaattt tctttcgtta    600
caaatcttta tttagtctct gcgtttagac caaagtagat ttttatgggc tgagtgaaaa    660
aacctcgccc gcattggttt ctgatggaac agctggcagc gccacggccc cgggtggggt    720
ggcctagagg caggggtgct tgggaggaac atctagcacc cgaccacctc caccaggtgg    780
gaaagggacg tttgcaccaa atctccgccg gcaaagcaga ggctttgggg aattacagaa    840
aaactataat gatctaaaag agaacaagtt atcttgaact gtgcgggtat ttgaatcata    900
cagaaaattg tcctgtgtgc ccaatgcact tttgcatgta gagccagggc cttcgaggaa    960
gctttcagga gatccc                                                    976
```

<210> SEQ ID NO 243
<211> LENGTH: 1799
<212> TYPE: DNA
<213> ORGANISM: Homo sapiens

<400> SEQUENCE: 243

```
ggggctcctg cctttggttc agtgctcgcg gcaccaccgc actcaggacg gcagtggggg      60
gctggggctg gggctgggcc tggcccagcg tgggttgggg cggggacgc gccagcagcg     120
cccgcagctc gctccgcagg ggtcgcagcc aggggtcggg agctaggctc gtgggccggg    180
agacgccggg cgcgttgtcc tccggggagg ttggggtgca ggcggtgcac cgaccctcgc    240
catctggcgc tgcagccacc agccacggcg cttagtggag ggtctgcggc caggctcccg    300
gcggaaagat tccggggagg gctcgggggt tgtcccagcc cgcgctaagc gccgcagcct    360
cgcccggctt tcctgcttcc tcggactgtg caggggaagc ctgggtctc gcgggcgca    420
gcagtcaggt cgagggtgca gcaggagggg agtcctgacg ggcaggtccc tctttcccct    480
ggtgcgcaac actggttggt agcttttgcg gaggtggtga agaagggcag gaggcctgtt    540
gagcggagga gtccggggat ccctaattat gtgacaggag acccctttcca gttcggcctg    600
tggcccatcc ctctctcacc gccggcagat tggagtctgc tctcggggag cccccaggta    660
aaccccctcac agggagaagg tttcggattg aaggaggac cgcgctcgtg gggcgcctgt    720
gagagctggg aagcccaagg ggtagcgtgt aggggggttt ttatgcggga ggagctgcct    780
cctgggcggc ggggactttc tgtctcagcc tgtctgcctt tgggaaaaca aggagttgcc    840
```

| | |
|---|---|
| ggagaagcag ggaaagaaag gagggaggga aggagggtcc ttgggggaat atttgcgggt | 900 |
| caaatcgata tccccgtttg gccacgagaa tggcgatttc aaagcagatt agattacttt | 960 |
| gtggcatttc aaataaaacg gcaatttcag ggccatgagc acgtgggcga cccgcgggag | 1020 |
| ctgtgggcct gcaggctcg cacaggcgcc cgggctgccg gccgctgcgg ggatttctcc | 1080 |
| cccagccttt tctttttaac agagggcaaa ggggcgacgg cgagagcaca gatggcggct | 1140 |
| gcggagccgg ggaggcggcg gggagacgcg cgggactcgt ggggagggct ggcagggtgc | 1200 |
| aggggttccg cgtgacctgc ccggctccca ggcatcgggc tgggcgctgc agtttaccga | 1260 |
| tttgctttcg tccctcgtcc aggtttagga gacgcgtggg gacagccgag ccgcgccggg | 1320 |
| cccctggacg gcgtcgccaa ggagctggga tcgcacttgc tgcaggtaga gcggcctcgc | 1380 |
| cgggggagga gcgcagccgc cgcaggctcc cttcccaccc cgccacccca gcctccaggc | 1440 |
| gtcccttccc caggagcgcc aggcagatcc agaggctgcc gggggctggg gatggggtgg | 1500 |
| tccccactgc ggagggatgg acgcttagca tgtcggatgc ggcctgcggc caaccctacc | 1560 |
| ctaaccctac gtctgccccc acaccccgcc gaaggcccca ggactcccca ggccacctga | 1620 |
| gacctacgcc aggggcgcct cccgagcgtg gtcaagtgct ttccaatctc acttccctca | 1680 |
| gcaggttcca cccagcgctt gctctgtgcc aggcgccagg gctggagcag cagaaatgat | 1740 |
| tgggctgctc tgagctctga agcattcggc cgctgtgtgt gtgcaagggg cgcaaggac | 1799 |

<210> SEQ ID NO 244
<211> LENGTH: 1799
<212> TYPE: DNA
<213> ORGANISM: Homo sapiens

<400> SEQUENCE: 244

| | |
|---|---|
| ggggctcctg cctttggttc agtgctcgcg gcaccaccgc actcaggacg gcagtggggg | 60 |
| gctgggctg gggctgggcc tggcccagcg tgggttgggg cggggacgc gccagcagcg | 120 |
| cccgcagctc gctccgcagg ggtcgcagcc aggggtcggg agctaggctc gtgggccggg | 180 |
| agacgccggg cgcgttgtcc tccggggagg ttggggtgca ggcggtgcac cgaccctcgc | 240 |
| catctggcgc tgcagccacc agccacgcg cttagtggag ggtctgcggc caggctcccg | 300 |
| gcggaaagat tccggggagg gctcgggggt tgtcccagcc cgcgctaagc gccgcagcct | 360 |
| cgcccggctt tcctgcttcc tcggactgtg caggggaagc ctgggtctc gcggggcgca | 420 |
| gcagtcaggt cgagggtgca gcaggagggg agtcctgacg ggcaggtccc tctttcccct | 480 |
| ggtgcgcaac actggttggt agcttttgcg gaggtggtga agaagggcag gaggcctgtt | 540 |
| gagcggagga gtccggggat ccctaattat gtgacaggag acccttttcca gttcggcctg | 600 |
| tggcccatcc ctctctcacc gccggcagat tggagtctgc tctcggggag cccccaggta | 660 |
| aaccccctcac agggagaagg tttcggattg gaaggaggac cgcgctcgtg gggcgcctgt | 720 |
| gagagctggg aagcccaagg ggtagcgtgt aggggggtttt ttatgcggga ggagctgcct | 780 |
| cctgggcggc gggggactttc tgtctcagcc tgtctgcctt tgggaaaaca aggagttgcc | 840 |
| ggagaagcag ggaaagaaag gagggaggga aggagggtcc ttgggggaat atttgcgggt | 900 |
| caaatcgata tccccgtttg gccacgagaa tggcgatttc aaagcagatt agattacttt | 960 |
| gtggcatttc aaataaaacg gcaatttcag ggccatgagc acgtgggcga cccgcgggag | 1020 |
| ctgtgggcct gcaggctcg cacaggcgcc cgggctgccg gccgctgcgg ggatttctcc | 1080 |
| cccagccttt tctttttaac agagggcaaa ggggcgacgg cgagagcaca gatggcggct | 1140 |
| gcggagccgg ggaggcggcg gggagacgcg cgggactcgt ggggagggct ggcagggtgc | 1200 |

```
agggggttccg cgtgacctgc ccggctccca ggcatcgggc tgggcgctgc agtttaccga    1260
tttgctttcg tccctcgtcc aggtttagga gacgcgtggg gacagccgag ccgcgccggg    1320
cccctggacg gcgtcgccaa ggagctggga tcgcacttgc tgcaggtaga gcggcctcgc    1380
cgggggagga gcgcagccgc cgcaggctcc cttcccaccc cgccacccca gcctccaggc    1440
gtcccttccc caggagcgcc aggcagatcc agaggctgcc gggggctggg gatggggtgg    1500
tccccactgc ggagggatgg acgcttagca tgtcggatgc ggcctgcggc caaccctacc    1560
ctaaccctac gtctgccccc acaccccgcc gaaggcccca ggactcccca ggccacctga    1620
gacctacgcc aggggcgcct cccgagcgtg gtcaagtgct ttccaatctc acttccctca    1680
gcaggttcca cccagcgctt gctctgtgcc aggcgccagg gctggagcag cagaaatgat    1740
tgggctgctc tgagctctga agcattcggc cgctgtgtgt gtgcaagggg cgcaaggac     1799
```

<210> SEQ ID NO 245
<211> LENGTH: 847
<212> TYPE: DNA
<213> ORGANISM: Homo sapiens

<400> SEQUENCE: 245

```
gagttagccc actggcctag ctctagagcc cacccggata accagaactt ggtgaggcct      60
ccgggctctt gcttggtttg gagccaggtg cttagcgccc cgagcccggg gccattcacc     120
ctgcaggagc tgcacgcgcc cctgacctcg gcttttccct ggcagcagag gggctttgcg     180
ggtcggccgg gtagccctga gcacagctcg ccacttccag gtgggctgtt ggcgctggct     240
ggggacacat cccgatcttt caaatgccct ttacagagcc tcatcaacga cccgattcat     300
tcccccctcc tgtcatttgt ctctgccatc gaaaaatgcc taccgagagc tgctctgcat     360
ttccgccctc tattttgtgt tttactttaa aataataata aaaaaaatgt tggctgcagg     420
acgccatgac ttaggtcagc gagtcagccg ctagctctgc atttccaaaa agcagatctt     480
ttcacaactc tcttgcccca gtgccctgg tgtggtttat tttttaaaat gcatgcctgc     540
ggaagagaag acccgggaa tattcgaaac cccgagcttt tacaacataa agcgcatggt     600
gtggccgcgg cgagtaatgg cgctctggga gccctgccca ggcggcctct gctcgccctc     660
ctccacttcc agctccgagc tgggtgtgtt gcaagtttca tactcctaca tattataagt     720
gacactaata tcagggacaa ctaagtgctg ggaacttca atgaaaacct ggctggtaaa     780
gtcaacaccc ccagacttct ctgtgctaca tttctttaat taattccgga gtggtgtgtg     840
gacgggc                                                              847
```

<210> SEQ ID NO 246
<211> LENGTH: 1478
<212> TYPE: DNA
<213> ORGANISM: Homo sapiens

<400> SEQUENCE: 246

```
gtttcccaaa atgaggtctg taaacaactg atctagaaaa tgttctggaa aaagtaaaaa      60
aggatcagga tctgaggtca actgacctct ccctgcgctc tggacaggca aacaggcaag     120
gttccctctg aggccgtagc ggcttctcgt gggcgagtcc ctgttcgcag gtgacgtgtg     180
gaccacgctc ttccgaagcg tctggcctgt gtgctctcgg ggaggggacg caggtcagcc     240
cacctagccg atggctaaca agtcagtttg ttttctgaac ggaagcttaa acctagaaaa     300
gtaactgggt tggggtgggg gtgtagccac atgcagtaaa agcactgcct gtctgtataa     360
```

| | |
|---|---|
| caacgacctg atgaaaaaag gaacgcgtga aatggggagt gttagggcgt cacaaactcc | 420 |
| agtgtggttg aaatgaaagc agaaagcaaa tggcaagctg gcttcccctt ccagcttttc | 480 |
| acaaccctgc cttgctcatg gtcagcccca agcacgggcg gaagaaagga ctggagggga | 540 |
| gggaaagggg tggggagcga gggtaccaga ggcgtgggag gacggggaca aaggggcagc | 600 |
| aagggaccgg cggaaaggaa agtcggcgtt agctggattg gaaacagtcc agacagaacg | 660 |
| atgggctctg ctgcctccgg gtggggcacc aagcggggag cggggccacg aggcagggga | 720 |
| cagtgaagca ccatgcagcg cccaccagcc ggcagcgccc accagcctgc gctgcgctgc | 780 |
| acatggtacc cgcggcccca gctggccagt gtgtggcgga gatgagaccc tcgtgaagag | 840 |
| actaagcggc cacagcaggg ggaagggttg ctcacataac cccatactgc tcacactacg | 900 |
| aggttaactg ccgtgagatc tgcctgcagc cagcagaaac ccgttctagg aaaacgttgc | 960 |
| ccagtgactt cagtgagtgc cactgacccg ggcgcctccg ccccggcgtc cggcagcagc | 1020 |
| accgattgcg caggaggcac cttgcaaaca accttcctg atccgcgctg cagttcccag | 1080 |
| gccggttgca gccgtttcac agagactgcg cacacaaagc gtctccgtgc cctgccattc | 1140 |
| acctttcgac acagccgcaa cccctctttt cagtgttaaa acctggcgcc aaaaggaaca | 1200 |
| tgcgatgtga cgtgttacct ctgcgcatgc gccgggcatt cccagcgccc cgaacctgat | 1260 |
| gaacgcgcgg tggggacccc aggcttccgt gctttcgttt tcctggaagc tacgtgtcct | 1320 |
| cagtctacat attgttacct ggaaaataaa gttttctcct tttttcttcc tttgttaaca | 1380 |
| ggcagaaggt gtaggctgca ggtttcgggc ctaagagagg gcatggctgg cgacacggag | 1440 |
| tagactccta gatgacataa cggaggcgag tctgcacc | 1478 |

<210> SEQ ID NO 247
<211> LENGTH: 1478
<212> TYPE: DNA
<213> ORGANISM: Homo sapiens

<400> SEQUENCE: 247

| | |
|---|---|
| gtttcccaaa atgaggtctg taaacaactg atctagaaaa tgttctggaa aaagtaaaaa | 60 |
| aggatcagga tctgaggtca actgacctct ccctgcgctc tggacaggca aacaggcaag | 120 |
| gttccctctg aggccgtagc ggcttctcgt gggcgagtcc ctgttcgcag gtgacgtgtg | 180 |
| gaccacgctc ttccgaagcg tctggcctgt gtgctctcgg ggaggggacg caggtcagcc | 240 |
| cacctagccg atggctaaca agtcagtttg ttttctgaac ggaagcttaa acctagaaaa | 300 |
| gtaactgggt tggggtgggg gtgtagccac atgcagtaaa agcactgcct gtctgtataa | 360 |
| caacgacctg atgaaaaaag gaacgcgtga aatggggagt gttagggcgt cacaaactcc | 420 |
| agtgtggttg aaatgaaagc agaaagcaaa tggcaagctg gcttcccctt ccagcttttc | 480 |
| acaaccctgc cttgctcatg gtcagcccca agcacgggcg gaagaaagga ctggagggga | 540 |
| gggaaagggg tggggagcga gggtaccaga ggcgtgggag gacggggaca aaggggcagc | 600 |
| aagggaccgg cggaaaggaa agtcggcgtt agctggattg gaaacagtcc agacagaacg | 660 |
| atgggctctg ctgcctccgg gtggggcacc aagcggggag cggggccacg aggcagggga | 720 |
| cagtgaagca ccatgcagcg cccaccagcc ggcagcgccc accagcctgc gctgcgctgc | 780 |
| acatggtacc cgcggcccca gctggccagt gtgtggcgga gatgagaccc tcgtgaagag | 840 |
| actaagcggc cacagcaggg ggaagggttg ctcacataac cccatactgc tcacactacg | 900 |
| aggttaactg ccgtgagatc tgcctgcagc cagcagaaac ccgttctagg aaaacgttgc | 960 |
| ccagtgactt cagtgagtgc cactgacccg ggcgcctccg ccccggcgtc cggcagcagc | 1020 |

```
accgattgcg caggaggcac cttgcaaaca acctttcctg atccgcgctg cagttcccag    1080
gccggttgca gccgtttcac agagactgcg cacacaaagc gtctccgtgc cctgccattc    1140
acctttcgac acagccgcaa cccctctttt cagtgttaaa acctggcgcc aaaaggaaca    1200
tgcgatgtga cgtgttacct ctgcgcatgc gccgggcatt cccagcgccc cgaacctgat    1260
gaacgcgcgg tggggacccc aggcttccgt gctttcgttt tcctggaagc tacgtgtcct    1320
cagtctacat attgttacct ggaaaataaa gttttctcct ttttcttcc tttgttaaca    1380 ggcagaaggt gtaggctgca ggtttcgggc taagagagg gcatggctgg cgacacggag    1440
tagactccta gatgacataa cggaggcgag tctgcacc                             1478

<210> SEQ ID NO 248
<211> LENGTH: 600
<212> TYPE: DNA
<213> ORGANISM: Homo sapiens

<400> SEQUENCE: 248
gaggagcggg cacgtcagca tcaccctgt caccatcagc aggagaagcg gcggctcctg     60
gaatgacatt ggaaggtcag ccaatcaggc gcggagctgc tcccggagct gccacctccg    120
aggcgcgcgc cacgccgggg ttccctcgcg gctttggaaa gggggtgcaa atgcacccctt   180 ctgcgggccc gctacccgct gcaacacctg tgtttccttt ctgggcacct tctaggtttc    240
tagatattgc tgtgaatacg gtcctccgct gtacagttga aaacaaaggc tgctggacct    300
cgcctgacct gcggttgcct ttgcccggtt cctgttagac gaactctacg acgccggagt    360
ttgggcgcag tgaacttgag agatcgtggg ggaggcgtct tcagaagaaa gcccctgacc    420
atctgcatgg agcagtcctc cctcggtggc ggctgggttt gctggctctg ctgaaggctg    480
gctgcaagag tcttgtgagg tttgccgccc actagtgtcc tatggcgggg acacaatcgg    540
cctgcaggta gcaccacctc cctatctccc aggctgaggg tgcgggcacc aaggcccagc    600

<210> SEQ ID NO 249
<211> LENGTH: 631
<212> TYPE: DNA
<213> ORGANISM: Homo sapiens

<400> SEQUENCE: 249
ctctggttca aacacctctg acagttggac aagttggtga cagccaggag ggcccgatgt     60
ggacatgtga caggcaccct gtggccatca gattctcagg aggaagaaat cccctctga    120 aataaagcac cctgagaacc ggcgggaagg agcggggact ccgtcgggc tttcagggga    180 agcagccagg gacttgccct gattttggtt tctccaggtt ggagccgccc cgcaggctgc    240
ctctgccggc gggaggaagt gagcagctcc tgcggaacct ctggctggca cagagcccgg    300
gggcggggga gccctccctg ccaagagaag ccatcaggtg cagaggacag cactgactgg    360
gccagtgggg cgttctccag ctgggtcagc cgtggccccc gctcgggct ggagtccggc    420 aggcaactgc tgcagaaacg gaggcagagg caggtggagg agccgcctcc aggcggagga    480
gccccagcaa gatggggcgc tggagttgag ctcaggctgt cagccccaga atccaagctc    540
cttgccctcg tgctaaccca gcctcactaa ctggcagctg ggggcaccct cccagcctgc    600
cagggacacc acactgggca cacaccactt c                                   631

<210> SEQ ID NO 250
<211> LENGTH: 1650
<212> TYPE: DNA
```

<213> ORGANISM: Homo sapiens

<400> SEQUENCE: 250

| | | | | | |
|---|---|---|---|---|---|
| ctgggggtaa | cccgtgcatg | catgcattgg | gggtaacagg | ctggagctca | gatccctccc | 60
| ccagccccca | gcaggggga | ctgcaggctc | ctggtctgag | tggggagctg | ggcccctgg | 120
| acagaggact | gggctgcggg | gtcaggaatg | gcacacttc | ctaactgcag | gacactctaa | 180
| gggctttggt | catgcacacg | cagccaagag | aaggtgtcgc | tggcacacag | ccttccagga | 240
| gcggacttgg | agacctcgcc | aaggaccagg | actccccagc | actcacactc | ccttaggcgc | 300
| tgaagtccag | aggacagagg | ttgagggcag | agctcctggg | agcaccagtg | gaagtaggag | 360
| ggctgggctg | gaaaacctcc | cccaacctcc | tattgcaaag | aggctccagc | cagcagcctc | 420
| cacaccccag | tgatctttta | agatgcaaat | ctgcgccatc | atttatttcc | tcagtgcctt | 480
| ctccagctcc | tgggatgcac | actgcccgtc | cccaggccca | gagacctgac | caccctcatt | 540
| cctccctcag | cccaccctgg | ggtctctcca | ccagctgaca | gccttcctgc | agtcccctcc | 600
| ccgaatgctg | ctccctgagg | ccctcctgga | cacctgcagg | gcaggcacag | cccgcgggac | 660
| ctcacagcac | ttgctccggg | cagagctgca | gtttggccaa | gttgccagct | ccgtgtgggc | 720
| aggggccctg | gcctgtggct | gccacatccc | gggtgggggc | acggcctttc | ctggcgtgga | 780
| tgctgagcaa | acgtaggggg | aaggggagtg | aatgaggaga | gccaggtagc | tcagggggctg | 840
| aggcctcact | gagcagggtc | ccgcgtgacc | ggtccccacc | gctgacggtt | cctggggtaa | 900
| cactcaggac | agggagaggc | aatggaaaga | gacgtggccg | ccctcgcatc | ctgcagctcc | 960
| cgcactccca | gcctcccagc | ctcccaccca | gccccccaga | gcccaccagt | gaccccgccc | 1020
| actgggtcct | cagatggctc | ccacgggatc | tcctgccttg | atctcctgtc | cacatggagg | 1080
| tgaagtgggt | tgctctgaat | gaggggtgcc | gagcctaggg | cgcagcccac | tctcctgggt | 1140
| ccgcagcatc | acgcagcccg | gaccacaggc | tccttacaag | aatcggaagg | gtccctgcaa | 1200
| tcgcccttcg | cactgaggct | tcctactgtg | tggtgtaaaa | acacaggctt | gtcctcccct | 1260
| gctgcccacg | gggctggagc | cgcctgaaaa | tcccagccca | caacttcccc | aaagcctggc | 1320
| agtcacttga | atagccaaat | gagtcctaga | aagcgagaga | cgagagggga | atgagcgccg | 1380
| aaaatcaaag | caggttcccc | tcctgacaac | tccagagaag | gcgcatgggc | ccgtggcag | 1440
| acccgaaccc | ccagcctcgc | gaccgcctgt | gacctgcggg | tcaaccaccc | gccgcggctc | 1500
| cacgccgtgg | gcacagactc | agggagcagg | atgagaaagc | tgagacggcg | cagccacggc | 1560
| ccggtgcctt | cacgcgcaca | gcgacacagc | cccagccagc | ggggcccacg | ctaaggcgga | 1620
| atcccacaga | agcctacaga | gcgagcgcgc | | | 1650

<210> SEQ ID NO 251
<211> LENGTH: 669
<212> TYPE: DNA
<213> ORGANISM: Homo sapiens

<400> SEQUENCE: 251

| | | | | | |
|---|---|---|---|---|---|
| ggtgcactct | ggctgggggt | ttgggcagca | ggtccccaca | gtctgctgga | gggtcccaga | 60
| ggcaggtcgg | ggctctgcta | gggggtccta | gaggcaggtc | ggggctctgc | tgtggtgggg | 120
| aggggggtc | ccagaggtag | gtcctgtgct | ctgcgggggg | tgggggtgg | tcctggaggc | 180
| agatcccagg | ctctgctggg | ggtctaggcg | gcaggtcccg | ggctctgctg | gtccccgg | 240
| cggcagcggc | cgtccatccc | caggaggggc | tgggctccct | cggagggctt | tttatctggt | 300
| gcccagccct | cccgagggtg | tgtgggtttg | tcaactgttg | ggtttcagga | atttccctct | 360

```
ggagggaagt cggtccttaa agggaacagc taatgagaag gagtgggtga gtgtccctca    420
gggaaggggc acggccatgg tcactcatcc agagccgagg accctcgcat ctgacctctc    480
gacactgcaa tgggcatgcc actcgagggg agcagctatt aactagaagt attcttttta    540
caaaagtgcc ctgcccccct accctctcca aacagcactg aacgcagcat tcttgcagaa    600
atctccaacg caactgggtg ctgcgtttct gtgcctggtg tggaggccct ggcaaactgg    660
tctgaggcc                                                            669
```

<210> SEQ ID NO 252
<211> LENGTH: 736
<212> TYPE: DNA
<213> ORGANISM: Homo sapiens

<400> SEQUENCE: 252

```
agggctccca ctgctgccca cagacatctc agggtctccc gggccgggtc agcggcgccg     60
gaacagggtc tcccgggccg ggtcagcggc gccggaagtg attctcgtca gcaggaatgc    120
gctggctgcc cggagccctt cagggtgggc tctgggggcc aggtgcggcc tcagcgccgt    180
cccttcccgg gaagcctcct ccctgggggtc cacgccggct cctgctggct cccccattcc    240
gctgaaatct gaggaaaagg ctctgggaac gcagccagac tcccccacag ctcagacggc    300
tgtaaagaaa tattcctgcc agatgttcag aggcggaggc cagcatgagg taacgggaaa    360
ggcttaaccc gtccagcccc gcagcctcgc agccgcctcc ggggcccagc tctagggct     420 gcggcccccg tgccgtgggg gacgtccctg ccgcgtccgt gtcccggggg ccgggcctgc    480
ctgcggcggg agcccacccc gtgcggtcag acgggctcag agcgctcttc tgcagtctcc    540
agccctccct ggagggcgtg ttggaccagc cctgatgggg cgcccgggag ccacgggatg    600
gggcgtgatg ccagcctggg agagggatcc actcgggggt cctcaggagg cggtgccagc    660
ccccggcatg gcttggggga gcctctgtgt tgccagcgct gggcagccct ggacccccccg    720 ccaccctttg cctcac                                                    736
```

<210> SEQ ID NO 253
<211> LENGTH: 659
<212> TYPE: DNA
<213> ORGANISM: Homo sapiens

<400> SEQUENCE: 253

```
cgcgggcggc cggcttcccc caaaccctgt gggaggggca tcccgaggag gcgaccccag     60
agagtggggc gcggacacct tccctgggga gggccagcgc gcttccttcc ttccagatgt    120
tccagaagga gaaggcggtg ctggacgagc tgggccgacg cacggggacc cggctgcagc    180
ccctgacccg gggcctcttc ggaggagct gagggccgcg ttccttctga agcgggacg    240 cgggaggggt ggaggctgcg gggagccggg gtcgcacacg aataaataac gaatgaacgt    300
acgaggggaa cctcctctta tttccttcac gttgcatcgg gtattttttcg ttattgtaaa    360 taaaacggtt ccgagccgtg gcatcgagag ggcgtctgga gttcagggaa cgcgtggccc    420
ccgcccggga gcaccgcgca gcgctcgcct ctcgcccttc aaggggtcc ctgcccggag    480 cctgcgcccc cggagaggaa ggggctcgag ggcttgggt gccgcagcgc gtccttccgt    540
agaaaaggct tgcgtcagta tttcctgctt ttacctcctg agtattggaa tattcgagta    600
aaccctggag tttcagcgcc agcgcacgcc tcttcatcag ggcagcgcgt cgcgagcgc    659
```

<210> SEQ ID NO 254

<211> LENGTH: 659
<212> TYPE: DNA
<213> ORGANISM: Homo sapiens

<400> SEQUENCE: 254

```
cgcgggcggc cggcttcccc caaaccctgt gggaggggca tcccgaggag gcgacccag     60
agagtggggc gcggacacct tccctgggga gggccagcgc gcttccttcc ttccagatgt    120
tccagaagga gaaggcggtg ctggacgagc tgggccgacg cacggggacc cggctgcagc    180
ccctgacccg gggcctcttc ggagggagct gagggccgcg ttccttctga aagcgggacg    240
cgggaggggt ggaggctgcg gggagccggg gtcgcacacg aataaataac gaatgaacgt    300
acgaggggaa cctcctctta tttccttcac gttgcatcgg gtattttcg ttattgtaaa    360
taaaacggtt ccgagccgtg gcatcgagag ggcgtctgga gttcagggaa cgcgtggccc    420
ccgcccggga gcaccgcgca gcgctcgcct ctcgcccttc aaggggtcc ctgcccggag    480
cctgcgcccc cggagaggaa ggggctcgag gggcttgggt gccgcagcgc gtccttccgt    540
agaaaaggct tgcgtcagta tttcctgctt ttacctcctg agtattggaa tattcgagta    600
aaccctggag tttcagcgcc agcgcacgcc tcttcatcag ggcagcgcgt cgcgagcgc    659
```

<210> SEQ ID NO 255
<211> LENGTH: 731
<212> TYPE: DNA
<213> ORGANISM: Homo sapiens

<400> SEQUENCE: 255

```
tcactgcact ccagcctggg tgacagagca caaagacag gcatgacttt gtacttaact      60
gctcagcttt gtaatcactg ggggcccaga tgctcacttg gattctaact ttgttggcat    120
ctgggcctaa aagccgtgat gcaggtgagc aatgatgcag agggctctgt gcgcctggcg    180
ggctctgttt gcctgctggg ctctgtgcgc ctgctgggct ctgtgcgccc gggaaggtgc    240
ggccaccctc acgcggaagg cggccagcgg atcccggtgc gcgcagctcc cagcgctggg    300
gttccagcgc cccgcctctt cctatagcaa ccagcgggac ctgccgtccc ccggggcacc    360
ccgagggtc tgcgcccgct tctttccgaa acgggaaggc gctgggggct cggcagccag    420
agggacgggt tcagggagcg tccggtgagc ctaagacgcg cctttgccgg ggttgccggg    480
tgtctgcctc tcacttaggt attaggaacc gtggcacaaa tctgtaggtt ttcctctggg    540
ggtgggcgga ggctccaaac cggacggttt tctcctggag gactgtgttc agacagatac    600
tggtttcctt atccgcaggt gtgcgcggcg ctcgcaagtg gtcagcataa cgccgggcga    660
attcggaaag cccgtgcgtc cgtggacgac ccacttggaa ggagttggga gaagtccttg    720
ttcccacgcg c                                                         731
```

<210> SEQ ID NO 256
<211> LENGTH: 731
<212> TYPE: DNA
<213> ORGANISM: Homo sapiens

<400> SEQUENCE: 256

```
tcactgcact ccagcctggg tgacagagca caaagacag gcatgacttt gtacttaact      60
gctcagcttt gtaatcactg ggggcccaga tgctcacttg gattctaact ttgttggcat    120
ctgggcctaa aagccgtgat gcaggtgagc aatgatgcag agggctctgt gcgcctggcg    180
ggctctgttt gcctgctggg ctctgtgcgc ctgctgggct ctgtgcgccc gggaaggtgc    240
ggccaccctc acgcggaagg cggccagcgg atcccggtgc gcgcagctcc cagcgctggg    300
```

```
gttccagcgc cccgcctctt cctatagcaa ccagcgggac ctgccgtccc ccggggcacc    360 ccgagggtc tgcgcccgct tctttccgaa acgggaaggc gctgggggct cggcagccag     420
agggacgggt tcagggagcg tccggtgagc ctaagacgcg cctttgccgg ggttgccggg    480
tgtctgcctc tcacttaggt attaggaacc gtggcacaaa tctgtaggtt ttcctctggg    540
ggtgggcgga ggctccaaac cggacggttt tctcctggag gactgtgttc agacagatac    600
tggtttcctt atccgcaggt gtgcgcgcg ctcgcaagtg gtcagcataa cgccgggcga     660
attcggaaag cccgtgcgtc cgtggacgac ccacttggaa ggagttggga aagtccttg     720 ttcccacgcg c                                                         731
```

<210> SEQ ID NO 257
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257

```
gccgaggagg agcagagggc ctaggaggac cccgggcgtg gtccacccgc cctggcagtt    60
gaatggggcg gcaattgcg                                                  79
```

<210> SEQ ID NO 258
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258

```
tggcgatggg gaaggacgcc tgagaaaaca gaccccggcc ccgtgtgcgc gtttgtttga    60
tccttcccca tagggttgtg tgagg                                           85
```

<210> SEQ ID NO 259
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259

```
ctccatgggc aggagggctg gctgcgagag ccccgggttc cctttctga agtcacggtc     60 ttggccaaag ctgttgtttt tgtgactc                                        88
```

<210> SEQ ID NO 260
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260

```
gggaggggc gtccctacct ggaaagctgg ggacgctggg agactcacag cccggtaaac     60
aagggtgacg cacccactcc cacctcgacc cccgct                              96
```

<210> SEQ ID NO 261

```
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261
gtgtgctggg gccacggtgc tggagggctg cgcggtgcgg gaggtcgcgg tgctcgtgcc    60
caggtcgccc aatgggtggg cagaatgaca cggcgcgacc                         100

<210> SEQ ID NO 262
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 262
gtctgcagcg tcgccctgtt cttctatttc agagcgctgg tgagtggcca ccttcccagg    60
ggatcgcggc tgagagcgcc catctccttc ccccgcactt                         100

<210> SEQ ID NO 263
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ccaccttccc aggggatcgc ggctgagagc gcccttctcc ttcccccgca cttggaaact    60
gagtctggcg gcagg                                                    75

<210> SEQ ID NO 264
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gactgggacg ccaaaagctg agaatcctcg atgcccgcgc gtgagccccg tgttatggcg    60
aggtgggaca cccttaggc tg                                             82

<210> SEQ ID NO 265
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gggggcgggc aaggctggga gggaccctcg ccggggtcct ggcctctgga cgccggcgtt    60
tcaaggctgg tttggggact tcac                                          84

<210> SEQ ID NO 266
<211> LENGTH: 99
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 266
cagaggagca aacagcagaa acttcccccg gctgtggtgc cgaaacagga aaccacccag    60
gagccctgtg cagaagcggc cggggattcc cagttcccc                           99

<210> SEQ ID NO 267
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 267 aagaattta ggtttgtcga tagtaatcac caccttctgc gctcctccca ctgctggaga     60
gaccgcggac tgggtgacaa gtcttccagg ctcccag                             97

<210> SEQ ID NO 268
<211> LENGTH: 109
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 268
caccccctcc aaaaccagcc cgcgcagagc tgccgggtcc caagcgcggg ctcgcccgcg    60
gggtctgggt aagtcactga tcctccgtgg ggaccgcgct caggtacgc                109

<210> SEQ ID NO 269
<211> LENGTH: 101
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 269
ggggcacacg acccacagga gccatccacc gcctcgcgcc gcagccgccc tcctctgcgc    60
tgtgggatcc ccagaggcag ggcttgaggt ggggtgggag g                       101

<210> SEQ ID NO 270
<211> LENGTH: 109
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 270 aggggcgac ccggggcgca tctcccgacc atgaccccca cagaccttgg cgccgctacc     60
tgcgcttctt gaggccgaag atgcgcactt tggagaagat atccaccag               109

<210> SEQ ID NO 271
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 271

```
gggcagtgtc agctccattg tctcagaggc cggcggccaa gtgagggacc agtctctccc    60 gggggggcgtc gagcctcagc gcatcgcccc gtcttcc                            97
```

<210> SEQ ID NO 272
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 272

```
gaaggagggc tccccagctg ttgcctcttg cgcggtttct gctgaccct ctgcgcgacc    60 ccagctgggc agtgtcagct ccattgtctc agaggccggc                          100
```

<210> SEQ ID NO 273
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273

```
aactaactgt aagtgtgtct cgaacttgcg cggggcttc agcccgcccg gggctgcgga     60
gctggccggt taaggctctc gggagagggg cgcggtgtct ccacggtgac                110
```

<210> SEQ ID NO 274
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274

```
acgggagggg ggtgacatcc tcccacccgg gggtttgaaa aggtccgggt ggtagttcca    60
ggcgaaaata ggcagccct                                                 79
```

<210> SEQ ID NO 275
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275

```
tgcctaaaca aagaagacgg tcttctgagc gtccgccctc cccgcctcgc cgcgctagga    60
ccccgcgctc ctgggccact tcctcttgca aaccacga                            98
```

<210> SEQ ID NO 276
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276

```
ggccaccggg tccaggcctc taggcaatag gcccggcgcc ccctcctagc accgtttccc    60
gccgaccccg cagtcatcac tgtga                                          85
```

<210> SEQ ID NO 277
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ccgggtgacg cgtgtccccc actcaccttc cccggtgacc ctggcgaccg ccgggcgctg      60
acaccagact tgggttttag actgaacttc                                      90

<210> SEQ ID NO 278
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ggccgaggcc gaacactgcg cccattgtcc cgggcgctct aagcgccgag cagctgcgca      60
gactttctgg gctcgg                                                     76

<210> SEQ ID NO 279
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279
cctgtggtgc ttagggagga cctacctggc tgtgccggtc tgtgaagggg ccagtgaggc      60
ccggtgcggg tacgggcggg tgcagatgca gccaggagga c                         101

<210> SEQ ID NO 280
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tgtgcctggc actttctccg tgcgagaagc accggtgggt gcggacgcgc cacagtctga      60
gccgccgccg aactggctaa gtttaggggc atttatt                              97

<210> SEQ ID NO 281
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
ccagagccct tcactttgtt aagaagtccc ccaccctggc gccccctcg tcctcctcaa       60 gtgccctcgg aaagcggacc agactcacct actgccaggc a                         101

<210> SEQ ID NO 282
<211> LENGTH: 79

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
gccccgaggg cacgctcccg gggctcttgg ccgcccctcg ccctccgggc tctgggtagc    60
ccctcaccag gctcttggc                                                 79

<210> SEQ ID NO 283
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
caatcaggtg gtggtcatta gggcagtgga cccggtggag gccgaggacg cccagcagga    60
gaaccctgcg ctcagctgtg ctacagcccc                                     90

<210> SEQ ID NO 284
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 284
gagtgagggc tgcgcctctc ccgaaagcag ccgcccgccc tgcgcctttg agccccgaag    60
ggcacacggg tcccggatct ctccttcctc ctgggtcctg                         100

<210> SEQ ID NO 285
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gtcaggtacc ctaagggata tatgagggac cccggggctt aagcagcctc tggaagagag    60
tggccgccct gtcacttcag caccaggcgc agaat                               95

<210> SEQ ID NO 286
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gtggcgcggg ttcacctggc agggcaggcg cccggggtcc gccggggtag gacgagggga    60
aggggtgcgc ggactcaggg gcaggcag                                       88

<210> SEQ ID NO 287
<211> LENGTH: 78
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 287
gtttggagcc gtcaggtacc ctaagggata tatgagggtc cccggggcta aagcagcctc    60
tggaagagag tggccgcc                                                  78

<210> SEQ ID NO 288
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
gctggcggac accccagtaa caagtgagag cgctcctccc cgcagtcccc cccgcctctc    60
ctccctgggt ccctcggct ctcgga                                         86

<210> SEQ ID NO 289
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
tgggcagcgc ggagagcgga caggcctcgc cctgcgccgt ggctgcgaga gccgcctgga    60
cccggcgcca ttccgagtgt aggggaagc aagcccca                            99

<210> SEQ ID NO 290
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gttccgagcc agcctcgcac agctcgcttc cggagctgcg agctctggtt tccaccccg    60 atcccccggg ctttcctcgc accgctgagc ccagcttgt                          99

<210> SEQ ID NO 291
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
aaaatgatcc caagcgttgc tgagatgaga aagcgtggct tcccgggggt cctcagcccc    60
acccgcgccc atggtgcaag tctgcaggga caggccc                            97

<210> SEQ ID NO 292
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292

```
caggctgtct ctggtgggtt ttagtacccg ccggcttctt gggctccggg gaccagaagg    60
aacttggcag ctggtcttag g                                              81

<210> SEQ ID NO 293
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
cgcgctagca tctgagcctt agccccatcc actccggtcc ccaagcgcgc acgccggctc    60
cagggaaggg cgcctctg                                                  78

<210> SEQ ID NO 294
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
tcgggccctc ccagatccca gttcctcaac ctgggcgctt tacctggtcc cggacctctg    60
gtaggttgac cttgccggcc agctcc                                         86

<210> SEQ ID NO 295
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
aacccggagc ccatgcgccc cgtcctccgg cccggggagc tccctgcctt gcccgccgag    60
cgcagcccgg gtccggactg tggtcactgg ggacgagaa                           99

<210> SEQ ID NO 296
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
cctggggcat tctgcgattt cggagtgacc ggtggtgccc ccgcccgcgc gcctggctcc    60
cggggtctcc ccacacagca ggggctgcgg gga                                 93

<210> SEQ ID NO 297
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297 cccccctgggg actcagtggt gtcgcctcgc ccgggtccag agattgcgct ggatggattc    60
ccgcgggcag ag                                                        72
```

<210> SEQ ID NO 298
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
ctcctaggcc actggctggg cgtccgaacg tgggtcaccc cgcgcacagt ctagaggttc    60
tgaaagatgc tgtggcccac tttaaaacaa agcccaatt                          99

<210> SEQ ID NO 299
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
agtactaggt ggtatctaat gccatccacc cttccgggtt ctttacggcc cacctctgag    60
tgggtcccac ggggac                                                   76

<210> SEQ ID NO 300
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
cagcagcagc acagagcttc cgactttgcc ttccaggctc tagactcgcg ccttgccaag    60
acgggcccct cgactttcac ccctgactcc caactcca                           98

<210> SEQ ID NO 301
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
acacagacct ccccgacctc ccaagctact ccggcgtcgg gaggatgttg agggaagcct    60
gccaggtgaa gaagggggcca gca                                          83

<210> SEQ ID NO 302
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 302
gcgtgcagct aaaaggaggg ccagagatag tagcgagggg gacgaggagc cacgggccac    60
ctgtgccggg tccccgcgct gtggtactgc ggtgcaggcg ggagca                  106

<210> SEQ ID NO 303
<211> LENGTH: 100
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 303 ggccagggc cacaagttag ttggaagccg gcgttcggta tcagatgcgc tgatggtcat     60
atccaatctc aatatctggg tcaatccaca ccctcttaga                         100

<210> SEQ ID NO 304
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 304
tgctggggcg gcgtccgaac tccccaggtc tgcgctcggc aatgggggca ccgggccttc     60
tgtctgtcct cagaatacgt aggatacccg cgggcgacaa g                       101

<210> SEQ ID NO 305
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
ccagagaggg aggcacaaag tgatggcagc ccggctaaca ctggggcttc gggctgggcc     60
gcgctcgttt aatcccacaa aaatccc                                         87

<210> SEQ ID NO 306
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 306
gggctgagtg aaaaaacctc gcccgcattg gtttctgatg aacagctgg cagcgcctcg     60 gccccgggtg gggtggccta gaggcagggg tgcttgggag gaacatc                 107

<210> SEQ ID NO 307
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 307
cagggagaag gtttcggatt ggaaggagga ccgcgctcgt ggggcgcctg tgtgagctgg     60
gaagcccaag gggtagcgtg taggggggttt tttatgcggg ag                     102

<210> SEQ ID NO 308
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 308
caaaggggcg acggcgagag cacagatggc ggctgcggag ccggggtggc ggcggggaga    60
cgcgcgggac tcgtggggag ggctggcagg gtgcaggg    98

<210> SEQ ID NO 309
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gaacttggtg aggcctccgg gctcttgctt ggtttggtgc caggtgctta gcgccccgag    60
cccggggcca ttcaccctgc aggagctgca cgcgcccc    98

<210> SEQ ID NO 310
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
caggggacag tgaagcacca tgcagcgccc accagccggc agcgcccacc tgcctgcgct    60
gcgctgcaca tggtacccgc ggcccca    87

<210> SEQ ID NO 311
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
cccagtgact tcagtgagtg ccactgaccc gggcgcctcc gccccggcgt ccggctgcag    60
caccgattgc gcaggaggca ccttgcaaac aacc    94

<210> SEQ ID NO 312
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 312
ggctcctgga atgacattgg aaggtcagcc aatcaggcgc ggagctgctc ccggtgctgc    60
cacctccgag gcgcgcgcca cgccggggtt ccctcgcggc    100

<210> SEQ ID NO 313
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ctgccggcgg gaggaagtga gcagctcctg cggaacctct ggctggcaca gtgcccgggg    60 gcggggagc cctccctgcc aagagaagcc atcaggtg                            98

<210> SEQ ID NO 314
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
aaatgagtcc tagaaagcga gagacgagag gggaatgtgc gccgaaaatc aaagcaggtt    60
cccctcctga caact                                                    75

<210> SEQ ID NO 315
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 315
tctgctgggg gtctaggcgg caggtcccgg gctcttctgg gtccccggc ggcagcggcc     60 gtccatcccc aggaggggct gggctccctc ggagggcttt ttatctggtg c            111

<210> SEQ ID NO 316
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
ccactcgggg gtcctcagga ggcggtgcca gcccccggct tggcttgggg gagcctctgt    60
gttgccagcg ctgggcagcc ctggaccccc c                                  91

<210> SEQ ID NO 317
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
gggcatcccg aggaggcgac cccagagagt ggggcgcggt caccttccct ggggagggcc    60
agcgcgcttc cttccttcca gatgttccag aagga                              95

<210> SEQ ID NO 318
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gcctctcgcc cttcaagggg gtccctgccc ggagcctgcg ccccggaga ggtaggggct     60 cgagggcttt gggtgccgca gcgcgtcctt                                    90

<210> SEQ ID NO 319
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
gagggacggg ttcagggagc gtccggtgag cctaagtcgc gcctttgccg gggttgccgg     60
gtgtctgcct ctcacttagg tattaggaac cg                                   92

<210> SEQ ID NO 320
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
agatactggt ttccttatcc gcaggtgtgc gcggcgctcg ctagtggtca gcataacgcc     60
gggcgaattc ggaaagcccg tgcgtccgtg gacga                                95

<210> SEQ ID NO 321
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
gcgtagcaac ctgttacata ttaaagtttt attatactac atttttctac atcctttgtt     60
ttagggtgtt gattgccttt gctcagtatc ttcagcc                              97

<210> SEQ ID NO 322
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gtgtggtcag ctcttccctt catcacatac ttggagaaca aaggacaccg ttatccatgc     60
tttttcaaca cattacatgt gggaggtagg                                      90

<210> SEQ ID NO 323
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gattgacagt ttctccttcc ccagactggc caatcacagg caggaagatg aaggttttgt     60
gggctgcgtt gctggtcaca ttcctggc                                        88

<210> SEQ ID NO 324
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
tctttcccta cacgacgctc ttccgatct                                         29

<210> SEQ ID NO 325
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
gtgactggag ttcagacgtg tgctcttccg atct                                   34

<210> SEQ ID NO 326
<211> LENGTH: 302
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 326
gcgtagcaac ctgttacata ttaaagtttt attatactac attttctac atcctttgtt        60 ttagggtgtt gattgccttt gctcagtatc ttcagccata aagcttgtgt ggtcagctct      120
tcccttcatc acatacttgg agaacaaagg acaccgttat ccatgctttt tcaacacatt     180
acatgtggga ggtaggataa agcttgattg acagtttctc cttccccaga ctggccaatc     240
acaggcagga agatgaaggt tttgtgggct gcgttgctgg tcacattcct ggcataaagc     300
tt                                                                    302

<210> SEQ ID NO 327
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
tctttcccta cacgacgctc ttccgatcta ctacattttt ctacatcc                   48

<210> SEQ ID NO 328
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
gtgactggag ttcagacgtg tgctcttccg atctgatact gagcaaaggc aatc            54

<210> SEQ ID NO 329
<211> LENGTH: 49
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 329
tctttcccta cacgacgctc ttccgatctc tcccacatgt aatgtgttg            49

<210> SEQ ID NO 330
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
gtgactggag ttcagacgtg tgctcttccg atctcatact tggagaacaa aggac      55

<210> SEQ ID NO 331
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
tctttcccta cacgacgctc ttccgatctc caggaatgtg accagcaac            49

<210> SEQ ID NO 332
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
gtgactggag ttcagacgtg tgctcttccg atctcaatca caggcaggaa gatg       54

<210> SEQ ID NO 333
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
aatgatacgg cgaccaccga gatctacact ctttccctac acgacgctc            49

<210> SEQ ID NO 334
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (24)..(25)
<223> OTHER INFORMATION: Nucleotides at these positions are separated by
      an undefined barcode sequence

<400> SEQUENCE: 334
caagcagaag acggcatacg agatgtgact ggagttcaga cgtg                 44
```